(12) United States Patent
Qi et al.

(10) Patent No.: US 12,428,412 B2
(45) Date of Patent: Sep. 30, 2025

(54) ACETYLATION WRITER INHIBITOR DEVELOPMENT AND USES THEREOF

(71) Applicant: DANA-FARBER CANCER INSTITUTE, INC., Boston, MA (US)

(72) Inventors: Jun Qi, Sharon, MA (US); Adam D. Durbin, Memphis, TN (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 910 days.

(21) Appl. No.: 17/289,662

(22) PCT Filed: Nov. 1, 2019

(86) PCT No.: PCT/US2019/059401
§ 371 (c)(1),
(2) Date: Apr. 28, 2021

(87) PCT Pub. No.: WO2020/092907
PCT Pub. Date: May 7, 2020

(65) Prior Publication Data
US 2022/0009916 A1    Jan. 13, 2022

Related U.S. Application Data

(60) Provisional application No. 62/754,934, filed on Nov. 2, 2018.

(51) Int. Cl.
| | |
|---|---|
| C07D 413/14 | (2006.01) |
| A61K 45/06 | (2006.01) |
| A61P 35/00 | (2006.01) |
| C07D 417/14 | (2006.01) |

(52) U.S. Cl.
CPC ............ *C07D 413/14* (2013.01); *A61K 45/06* (2013.01); *A61P 35/00* (2018.01); *C07D 417/14* (2013.01)

(58) Field of Classification Search
CPC ..... C07D 413/14; C07D 417/14; A61P 35/00; A61K 45/06
See application file for complete search history.

(56) References Cited

U.S. PATENT DOCUMENTS

| | | |
|---|---|---|
| 2016/0235716 A1 | 8/2016 | Kesicki et al. |
| 2019/0192668 A1 | 6/2019 | Arhancet et al. |
| 2022/0241425 A1* | 8/2022 | Qi .......................... A61K 31/42 |

FOREIGN PATENT DOCUMENTS

| | | | |
|---|---|---|---|
| WO | 2016044770 A1 | 3/2016 | |
| WO | 2017/197046 A1 | 11/2017 | |
| WO | 2017197036 A1 | 11/2017 | |
| WO | WO-2018081530 A1 * | 5/2018 | ........... A61K 31/444 |

OTHER PUBLICATIONS

Ravindra et al. Targeting of Histone Acetyltransferase p300 . . . , Chem. Res. Toxicol. 2012, 25, 337-347 (Year: 2012).*
U.S. Appl. No. 18/280,877, filed Sep. 7, 2023, Qi; Jun.*
Lasko et al. Nature. Oct. 5, 2017; 550(7674): 128-132. doi:10.1038/nature24028 (Year: 2017).*
Ciske et al. Bromodomain Targeting with PROTACs, Cayman Chemical, Issue 27, Apr. 2017, p. 1-16 (Year: 2017).*
Michaelides et al., "Discovery of spiro oxazolidinediones as selective, orally bioavailable inhibitors of p300/CBP histone acetyltransferases", ACS Med. Chem. Lett., 2018, vol. 9, pp. 28-33.
Bondeson, et al., "Lessons in PROTAC design from selective degradation with a promiscuous warhead", Cell Chem Biol. 25(1):78-87 (2018).
Huang, et al., "A Chemoproteomic Approach to Query the Degradable Kinome Using a Multi-kinase Degrader", Cell Chemical Biology 25:88-99 (2018).
Lai, et al., "Modular PROTAC Design for the Degradation of Oncogenic BCR-ABL", Angew. Chem. Int. 55:807-810 (2016).
Li, et al., "Proteolysis-targeting chimera (PROTAC) for targeted protein degradation and cancer therapy", Journal of Hematology & Oncology 13:50 (2020).
Pettersson, et al., "PROteolysis TArgeting Chimeras (PROTACs)—Past, Present and Future", Drug Discov Today Technol. 31:15-27 (2019).
Tan, et al., "When Kinases Meet PROTACs", Chin J. Chem. 36:971-977 (2018).

* cited by examiner

*Primary Examiner* — Kortney L. Klinkel
*Assistant Examiner* — Richard Grant Peckham
(74) *Attorney, Agent, or Firm* — ArentFox Schiff LLP; Daniel W. Clarke; Shawn P. Foley

(57) ABSTRACT

Disclosed are bifunctional compounds (degraders) that target HAT EP300 for degradation. Also disclosed are pharmaceutical compositions containing the degraders and methods of using the compounds to treat disease.

30 Claims, 28 Drawing Sheets

M = $CH_2$ or O
n = 0-11

Y = O or $H_2$
Z = O, NH, or O-$CH_2$CO

Kelly (500 nM)

ACETYLATION WRITER INHIBITOR DEVELOPMENT AND USES THEREOF

RELATED APPLICATIONS

This application is a national stage application, filed under 35 U.S.C. § 371, of International Application No. PCT/US2019/059401, filed Nov. 1, 2019, which claims the benefit of priority under 35 U.S.C. § 119 (e) to U.S. Provisional Application No. 62/754,934, filed on Nov. 2, 2018, each of which is incorporated herein by reference in its entirety.

BACKGROUND OF THE INVENTION

High-risk neuroblastoma (NB) is a pediatric tumor of the peripheral sympathetic nervous system derived from primitive neural crest cells, and which has a poor survival rate. These neuroendocrine tumors are characterized by high expression of oncogenic MYC family members. (Matthay et al., Nat. Rev. Dis. Primers 2:16078 (2016); Zimmerman et al., Cancer Discov. 8(3):320-35 (2018)). MYCN is an integral member of a positive, feed-forward autoregulatory loop of transcription factors (TFs) that establish cell fate in MYCN-amplified NB. This group of TFs is termed the core-regulatory circuitry (CRC), and each member is regulated by a super-enhancer (SE) gene which is critically required for NB viability. One mechanism by which the MYC family oncogenes drive tumor growth is by invading gene enhancers and recruiting transcriptional and epigenetic machinery (Zeid et al., Nat. Genet. 50(4):515-23 (2018)). Combination pharmacologic inhibition of SE-mediated transcriptional initiation and elongation have been shown to rapidly disrupt the NB CRC in vitro and in vivo, resulting in transcriptional collapse and apoptosis (Durbin et al., Nat. Genet. 50(9):1240-60 (2018)). Since transcriptional inhibition has been insufficient to drive tumor regression in vivo (Morton et al., Mol. Oncol. 7(2):248-58 (2013)), an alternative approach is needed.

EP300, or histone acetyltransferase (HAT) p300, was recently identified as a necessary component in the survival of NB cells (Durbin et al., Nat. Genet. 50(9):1240-60 (2018)). Like its paralog cAMP-response element (CREB)-binding protein (CBP, CREBBP), EP300 catalyzes the H3K27ac mark typical of SE elements (Dancy et al., Chem. Rev. 115(6):2419-52 (2015)). Numerous tumor types display dependency on EP300 and not CBP, suggesting that this finding may be a generalizable property of distinct human cancer subsets. Other EP300-dependent and MYC-family dependent cancers include acute myeloid leukemia (AML), multiple myeloma (MM), melanoma, rhabdomyosarcoma, and diffuse large B cell lymphoma. A recently reported EP300 inhibitor showed highly selective inhibition of EP300/CBP in vitro and in vivo (Lasko et al., Nature 550:128-132 (2017); Michaelides, et al., ACS Med. Chem. Lett. 9:28-33 (2018)). That molecule, however, did not show selectivity as between EP300 and CBP.

SUMMARY OF THE INVENTION

A first aspect of the present invention is directed to a bifunctional compound having a structure represented by formula I:

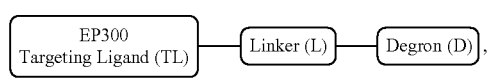

(I)

wherein the targeting ligand represents a moiety that binds histone acetyltransferase (HAT) p300 (also referred to herein as EP300), the degron represents a moiety that that binds an E3 ubiquitin ligase, and the linker represents a moiety that covalently connects the degron and the targeting ligand, or a pharmaceutically acceptable salt or stereoisomer thereof.

In some embodiments, the EP300 targeting ligand is A-485 or an analog thereof as defined herein.

Another aspect of the present invention is directed to a bifunctional compound having a structure represented by formula II:

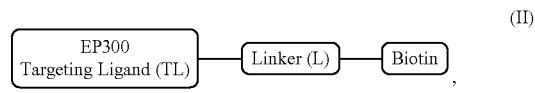

(II)

wherein the targeting ligand represents a moiety that binds histone acetyltransferase p300 (also referred to herein as EP300), the linker represents a moiety that covalently connects biotin and the targeting ligand.

Another aspect of the present invention is directed to a pharmaceutical composition that includes a therapeutically effective amount of the bispecific compound of formula (I) or a pharmaceutically acceptable salt or stereoisomer thereof, and a pharmaceutically acceptable carrier.

A further aspect of the present invention is directed to methods for making bispecific compounds of formula (I) or (II) or pharmaceutically acceptable salts or stereoisomers thereof.

Further aspects of the present invention are directed to methods of treating diseases or disorders involving dysfunctional or dysregulated EP300 activity, that entail administration of a therapeutically effective amount of a bispecific compound of formula (I) or a pharmaceutically acceptable salt or stereoisomer thereof, to a subject in need thereof.

In some embodiments, the disease or disorder is high-risk neuroblastoma (NB).

In some embodiments, the disease or disorder is acute myeloid leukemia (AML), multiple myeloma (MM), or diffuse large B cell lymphoma. In other embodiments, the disease or disorder is a solid tumor. In other embodiments, the disease or disorder is melanoma, rhabdomyosarcoma, colon cancer, rectum cancer, stomach cancer, breast cancer or pancreatic cancer.

Without intending to be bound by any particular theory of operation, the bifunctional compounds of formula (I) of the present invention are believed to cause degradation of EP300 by recruitment of cells' Ubiquitin/Proteasome System, whose function is to routinely identify and remove damaged proteins, into close proximity with p300 as a result of binding between p300 and the targeting ligand. After destruction of an EP300 molecule, the degrader is released and continues to be active. Thus, by engaging and exploiting the body's own natural protein disposal system, the bifunctional compounds of the present invention may represent a potential improvement over current small molecule inhibitors of EP300. Thus, effective intracellular concentrations of the degraders may be significantly lower than for small molecule EP300 inhibitors. Collectively, the present bifunctional compounds may represent an advancement over known EP300 inhibitors and may overcome one or more limitations regarding their use, and may also be selective in targeting EP300 but not CBP.

Further aspects of the present invention are directed to methods using the bifunctional compound of formula (II) as a probe for EP300 protein, comprising contacting lysed cells suspected of containing EP300 with the compound of formula (II) and streptavidin immobilized on a carrier (e.g., beads); isolating complexes formed by molecule and protein binding through biotin-streptavidin binding; and confirming presence of EP300 in the isolated complex. The confirmation can be accomplished by techniques standard in the art such as immunoblotting.

DETAILED DESCRIPTION OF THE INVENTION

Figure 1A:
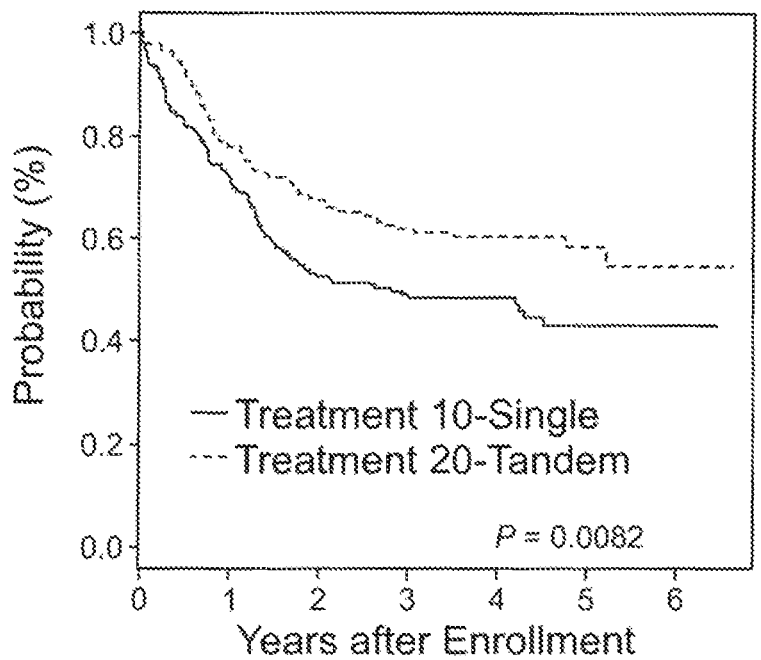
FIG. 1A is a graph that shows low survival rate in high-risk neuroblastoma (NB) patients even with intensive treatment.
Figure 1B:
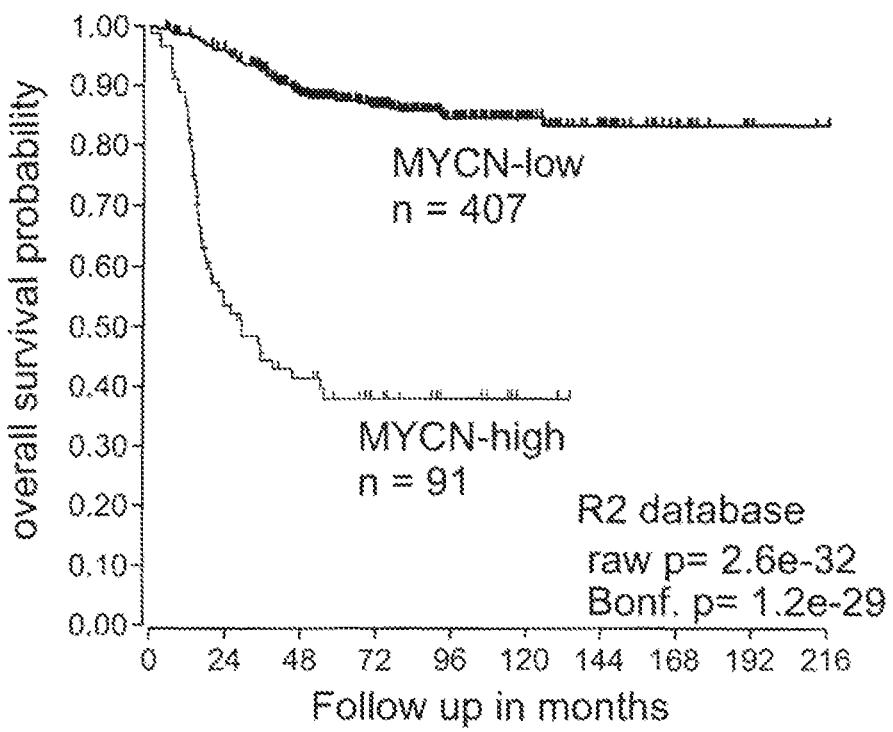
FIG. 1B is a graph that shows a correlation between MYCN amplified NB and high mortality.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "aliphatic" refers to a non-cyclic hydrocarbon group and includes branched and unbranched, alkyl, alkenyl, or alkynyl groups.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "haloalkyl" refers to an alkyl group as defined herein that is substituted with one or more (e.g., 1, 2, 3, or 4) halo groups.

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

As used herein, the term "aldehyde" is represented by the formula-C(O)H. The terms "C(O)" and C=O are used interchangeably herein.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "carboxylic acid" is represented by the formula —C(O)OH, and a "carboxylate" is represented by the formula —C(O)O—.

As used herein, the term "ester" is represented by the formula —OC(O)$Z^1$ or —C(O)O$Z^1$, where $Z^1$ may be an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ether" is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ketone" is represented by the formula $Z^1C(O)Z^2$, where $A^1$ and $A^2$ independently represent alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonyl" refers to the sulfo-oxo group represented by the formula —S(O)$_2$$Z^1$, where $Z^1$ may be hydrogen, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonylamino" (or "sulfonamide") is represented by the formula —S(O)$_2$NH$_2$.

As used herein, the term "thiol" is represented by the formula —SH.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$OH$^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, wherein $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

Representative substituents include halogens, hydroxyl groups, and any other organic groupings containing any number of carbon atoms, e.g., 1-14 carbon atoms, and which may include one or more (e.g., 1 2 3, or 4) heteroatoms such as oxygen, sulfur, and nitrogen grouped in a linear, branched, or cyclic structural format.

Representative examples of substituents may thus include alkyl, substituted alkyl (e.g., C1-C6, C1-5, C1-4, C1-3, C1-2, C1), alkoxy (e.g., C1-C6, C1-5, C1-4, C1-3, C1-2, C1), substituted alkoxy (e.g., C1-C6, C1-5, C1-4, C1-3, C1-2, C1), haloalkyl (e.g., $CF_3$), alkenyl (e.g., C2-C6, C2-5, C2-4, C2-3, C2), substituted alkenyl (e.g., C2-C6, C2-5, C2-4, C2-3, C2), alkynyl (e.g., C2-C6, C2-5, C2-4, C2-3, C2), substituted alkynyl (e.g., C2-C6, C2-5, C2-4, C2-3, C2), cyclic (e.g., C3-C12, C5-C6), substituted cyclic (e.g., C3-C12, C5-C6), carbocyclic (e.g., C3-C12, C5-C6), substituted carbocyclic (e.g., C3-C12, C5-C6), heterocyclic (e.g., C3-C12, C5-C6), substituted heterocyclic (e.g., C3-C12, C5-C6), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., C6-C12, C6), substituted aryloxy (e.g., C6-C12, C6), alkylthio (e.g., C1-C6), substituted alkylthio (e.g., C1-C6), arylthio (e.g., C6-C12, C6), substituted arylthio (e.g., C6-C12, C6), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

The term "binding" as it relates to interaction between the targeting ligand and the targeted protein, which in this invention is EP300 and mutant forms thereof (collectively "EP300"), typically refers to an inter-molecular interaction that may be preferential or substantially specific (also referred to herein as "selective") in that binding of the targeting ligand with other proteinaceous entities present in the cell such as CBP is functionally insignificant. The present bifunctional compounds may preferentially bind and recruit EP300 for targeted degradation, including mutant forms thereof.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the bifunctional compounds of one aspect of the present invention have a structure represented by formula I.

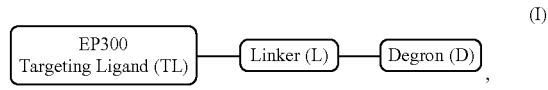
(I)

wherein the targeting ligand represents a moiety that binds histone acetyltransferase (HAT) p300 (EP300), the degron represents a moiety that binds an E3 ubiquitin ligase, and the linker represents a moiety that covalently connects the degron and the targeting ligand, or a pharmaceutically acceptable salt or stereoisomer thereof.

Targeting Ligands

In some embodiments, the EP300 targeting ligand is A-485, or an analog thereof. A-485 is represented by structure TL-1:

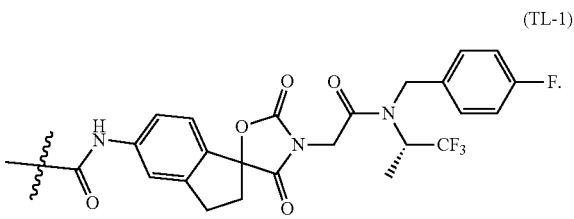 [SMILES: *C(=O)Nc1ccc2c(c1)CCC21OC(=O)N(CC(=O)N(Cc2ccc(F)cc2)[C@@H](C)C(F)(F)F)C1=O]
(TL-1)

A-485, also known as N-[(4-fluorophenyl)methyl]-2-{(1R)-5-[(methylcarbamoyl)amino]-2',4'-dioxo-2,3-dihydro-3'H-spiro[indene-1,5'-[1,3]oxazolidin]-3'-yl}-N-[(2S)-1,1,1-trifluoropropan-2-yl]acetamide, and spirocyclic analogs thereof have been described in U.S. Patent Application Publication 2016/0235716 and Michaelides, et al., ACS Med. Chem. Lett. 9:28-33 (2018).

Thus, in some embodiments, the bifunctional compounds of formula (I) are represented by structure I-1:

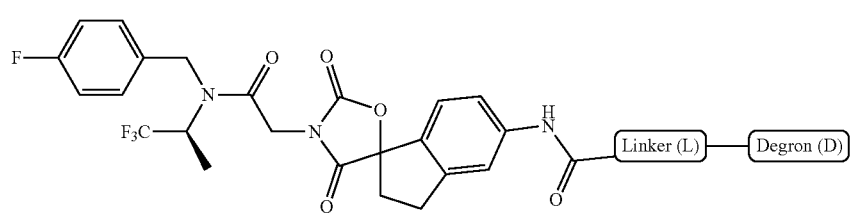
(I-1)

or a pharmaceutically acceptable salt or stereoisomer thereof.

In some embodiments, the EP300 targeting ligand is an A-485 analog and is represented by structure TL-1a:

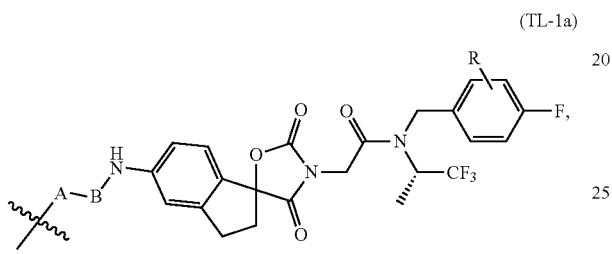
(TL-1a)

wherein A is CH$_2$ or O;
B is CH$_2$ or CO;
and R is H, halo (e.g., Cl or F), CN, CF$_3$, alkyl or alkoxy.

Thus, in some embodiments, the bifunctional compounds of formula (I) are represented by structure I-1a:

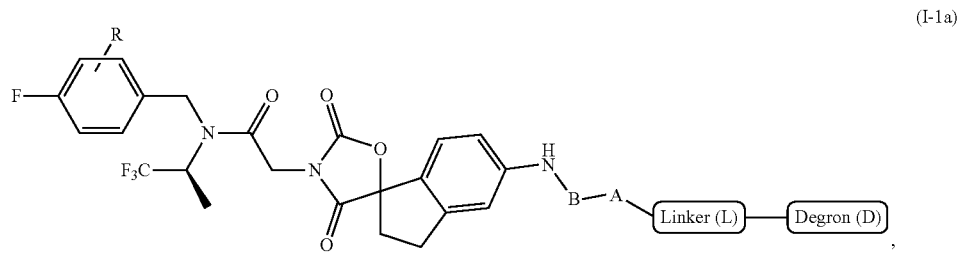
(I-1a)

wherein A is CH$_2$, NH or O;
B is CH$_2$ or CO;
and R is halo (e.g., Cl or F), CN, CF$_3$, alkyl or alkoxy, or a pharmaceutically acceptable salt or stereoisomer thereof.

In some embodiments, the EP300 targeting ligand is an A-485 analog and is represented by structure TL-1b:

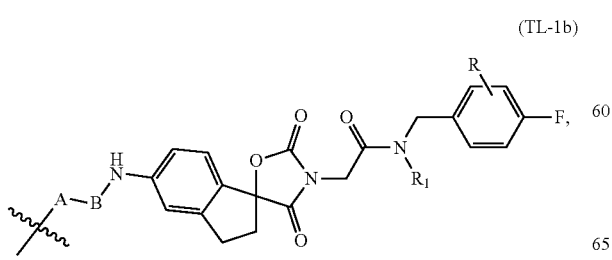
(TL-1b)

wherein A is CH$_2$, NH or O;
B is CH$_2$ or CO;
R is H, halo (e.g., Cl or F), CN, CF$_3$, alkyl or alkoxy;
and R$_1$ is a C3-C5 carbocyclic or alkcarbocyclic group or a 3-5 membered N-heterocyclic or alkN-heterocyclic group (wherein the N is connected to the alkyl group), and wherein the alkyl group is a C1-C10 alkyl (e.g., C1-C3) alkyl group.

In some embodiments, R$_1$ is

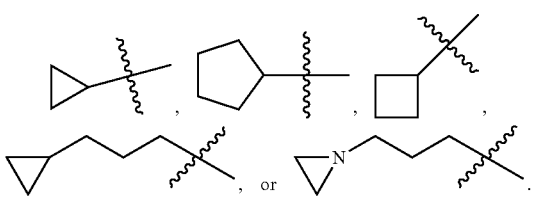

Thus, in some embodiments, the bifunctional compounds of formula (I) are represented by structure I-1b:

(I-1b)

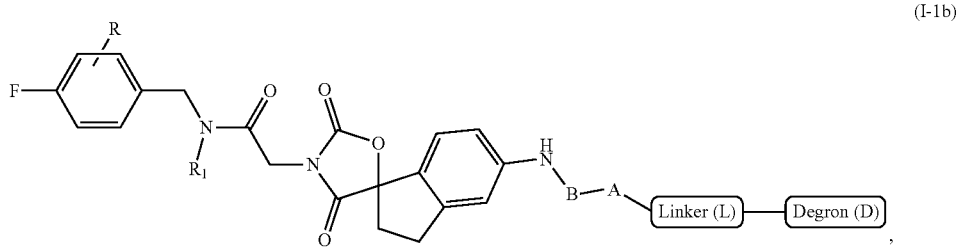

wherein A is CH$_2$, NH or O;
B is CH$_2$ or CO;
R is halo (e.g., Cl or F), CN, CF$_3$, alkyl or alkoxy;
and R$_1$ is a C3-C5 carbocyclic or alkcarbocyclic group or a 3-5 membered N-heterocyclic or alkN-heterocyclic group, and wherein the alkyl group is a C1-C10 alkyl (e.g., C1-C3) alkyl group, or a pharmaceutically acceptable salt or stereoisomer thereof.

In some embodiments, the EP300 targeting ligand is represented by structure TL-1c:

(TL-1c)

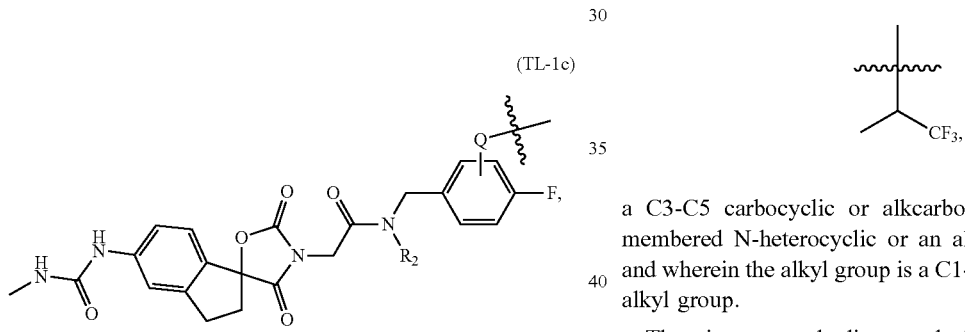

wherein Q is CH$_2$, O, N, CO, C(O)O, C(O)N, CH$_2$N, CH$_2$C(O), CH$_2$C(O)O, CH$_2$C(O)N, or CH$_2$CH$_2$N;

and R$_2$ is a C3-C5 carbocyclic or alkcarbocyclic group or a 3-5 membered N-heterocyclic or an alkN-heterocyclic group, and wherein the alkyl group is a C1-C10 alkyl (e.g., C1-C3) alkyl group.

Thus, in some embodiments, the bifunctional compounds of formula (I) are represented by structure I-c:

(I-1c)

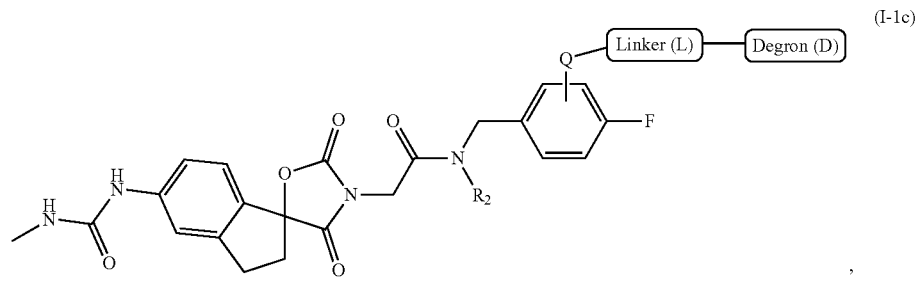

or a pharmaceutically acceptable salt or stereoisomer thereof.

In some embodiments, the targeting ligand is represented by structure TL-1d:

(TL-1d)

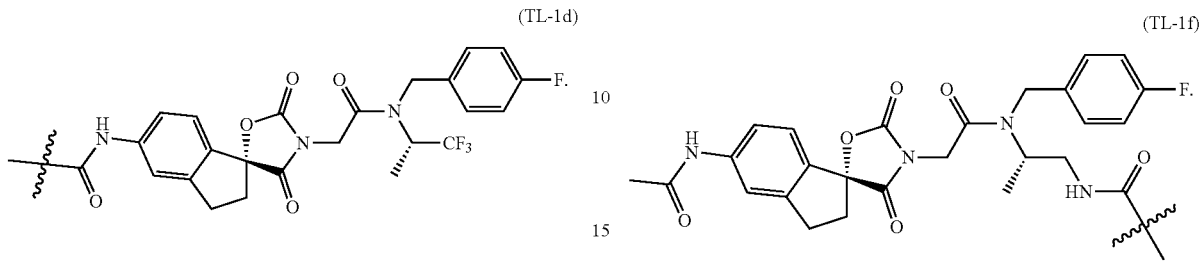

Thus, in some embodiments, the bifunctional compounds of formula (I) are represented by structure I-1d:

(I-1d)

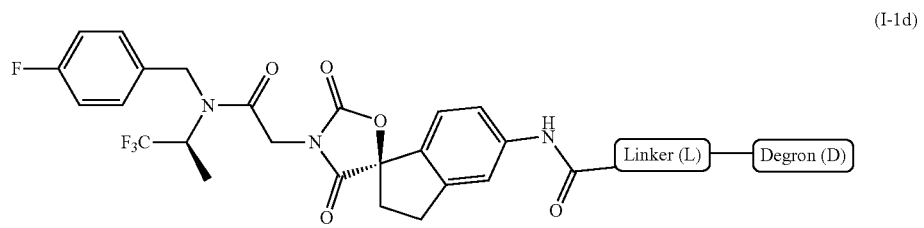

or a pharmaceutically acceptable salt or stereoisomer thereof.

In some embodiments, the EP300 targeting ligand is represented by structure TL-1e:

(TL-1e)

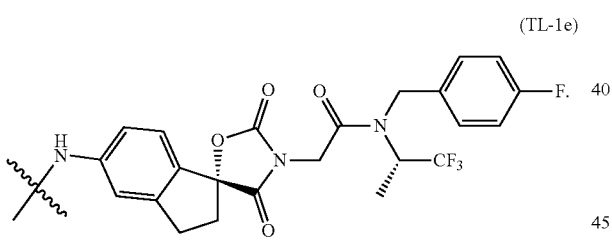

Thus, in some embodiments, the bifunctional compounds of formula (I) are represented by structure I-1e:

(I-1e)

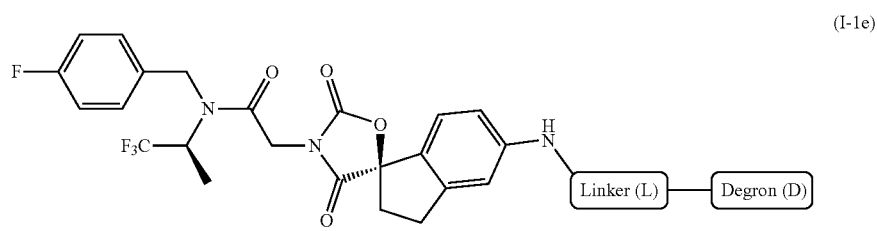

or a pharmaceutically acceptable salt or stereoisomer thereof.

In some embodiments, the EP300 targeting ligand is represented by structure TL-1f:

(TL-1f)

Thus, in some embodiments, the bifunctional compounds of formula (I) are represented by structure I-1f:

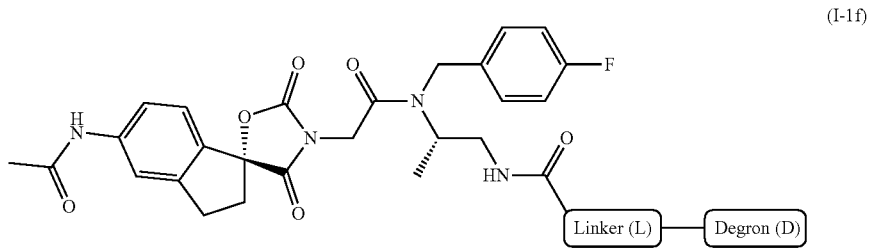

(I-1f)

or a pharmaceutically acceptable salt or stereoisomer thereof.

Linkers

The linker ("L") provides a covalent attachment the targeting ligand and the degron. The structure of linker may not be critical, provided it does not substantially interfere with the activity of the targeting ligand or the degron. In some embodiments, the linker is an alkylene chain (e.g., having 2-20 alkylene units). In other embodiments, the linker may be an alkylene chain or a bivalent alkylene chain, either of which may be interrupted by, and/or terminate (at either or both termini) at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, C$_3$-C$_{12}$ carbocyclene, 3- to 12-membered heterocyclene, 5- to 12-membered heteroarylene or any combination thereof, wherein R' is H or C$_1$-C$_6$ alkyl, wherein the interrupting and the one or both terminating groups may be the same or different.

In other embodiments, the linker may be a polyethylene glycol chain. In other embodiments, the linker may be a polyethylene glycol chain or a bivalent alkylene chain, either of which may be interrupted by, and/or terminate (at either or both termini) at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, C$_{3-12}$ carbocyclene, 3- to 12-membered heterocyclene, 5- to 12-membered heteroarylene or any combination thereof, wherein R' is H or C$_1$-C$_6$ alkyl, wherein the one or both terminating groups may be the same or different.

In some embodiments the linker may be C$_1$-C$_{10}$ alkylene chain terminating in NH-group wherein the nitrogen is also bound to the degron.

In certain embodiments, the linker is an alkylene chain having 1-10 alkylene units and interrupted by or terminating in

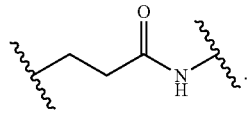

In other embodiments, the linker is a polyethylene glycol chain having 1-8 PEG units and terminating in

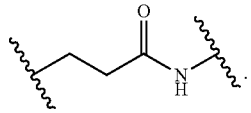 [SMILES: *CCC(=O)N*]

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of linkers that may be suitable for use in the present invention include alkylene chains, e.g.:

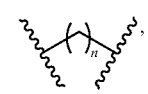

(L1)

wherein n is an integer from 1-10 ("from" meaning inclusive), e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

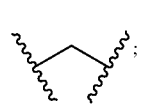

(L1-a)

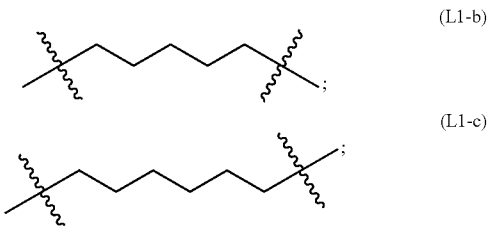

(L1-b)

(L1-c)

(L1-d)
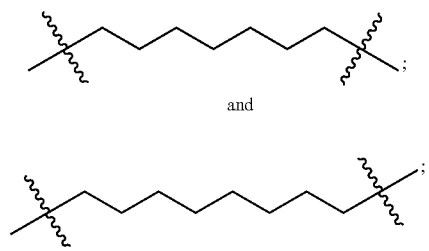
and (L1-e)
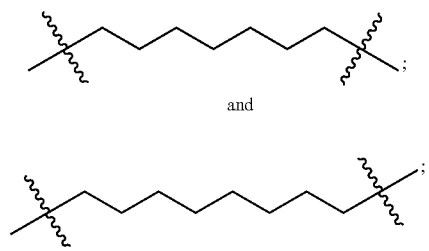

alkylene chains terminating in various functional groups (as described above), examples of which are as follows:

(L2-a)
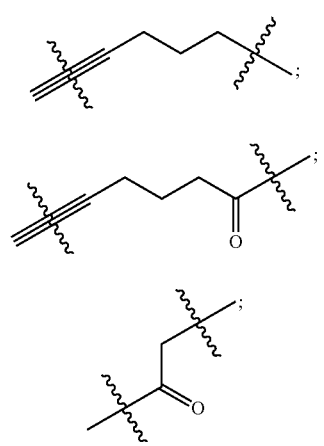

(L2-b)

(L2-c)

(L2-d)
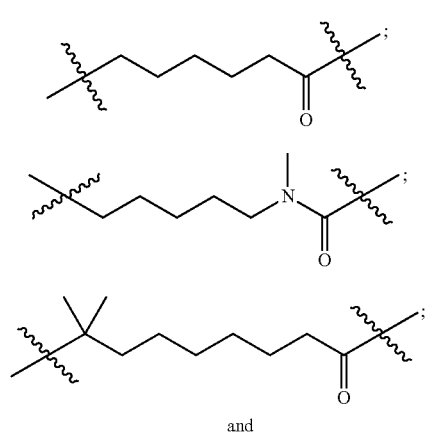

(L2-e)

(L2-f)
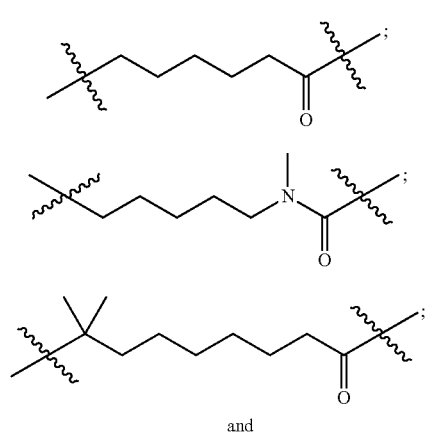

and (L2-g)
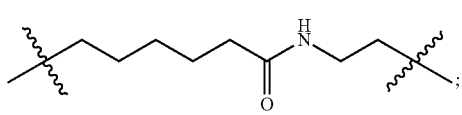

alkylene chains interrupted with various functional groups (as described above), examples of which are as follows:

(L3-a)
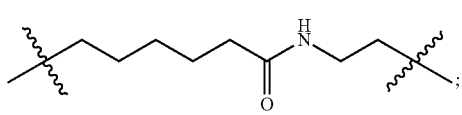

(L3-b)
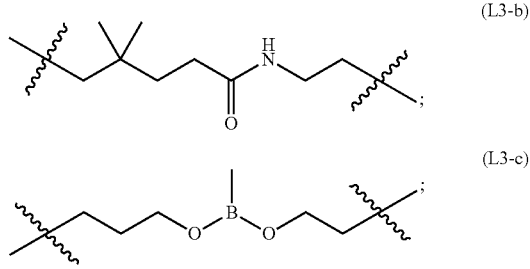

(L3-c)
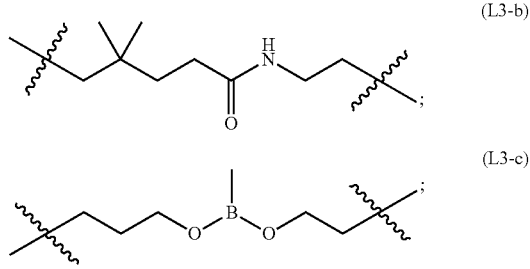

and (L3-d)
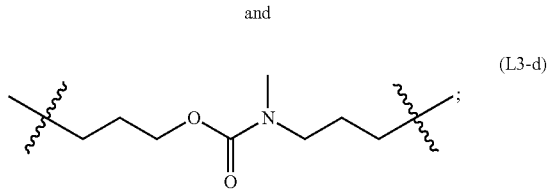

alkylene chains interrupted or terminating with heterocyclene groups, e.g., (L4)
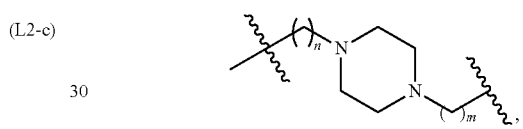

wherein m and n are independently integers from 0-10, examples of which include:

(L4-a)
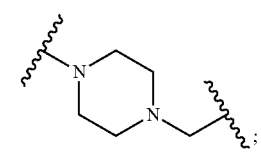

(L4-b)
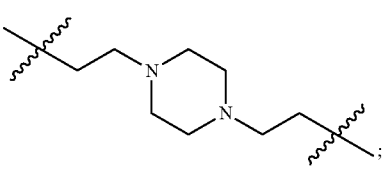

(L4-c)
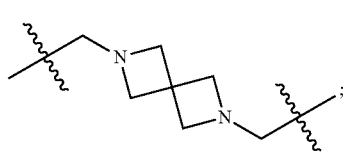

(L4-d)
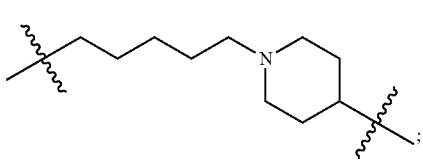

and

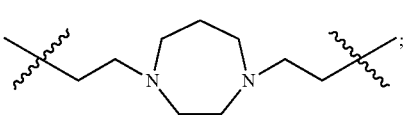
(L4-e)

alkylene chains interrupted by amide, heterocyclene and/or aryl groups, examples of which include:

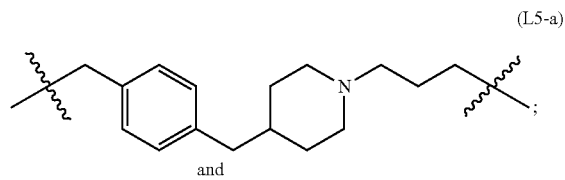
(L5-a)

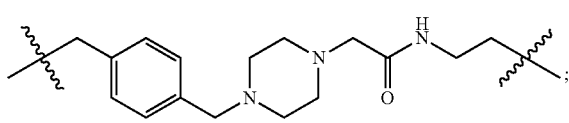
(L5-b)

alkylene chains interrupted by heterocyclene and aryl groups, and a heteroatom, examples of which include:

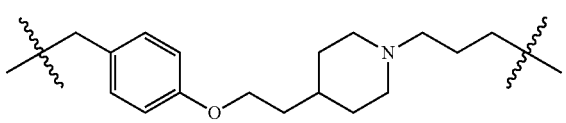
(L6-a)

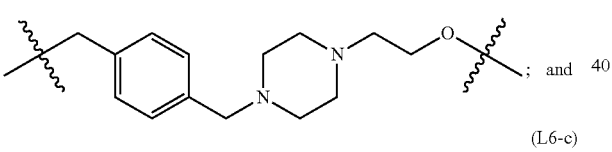
(L6-b)

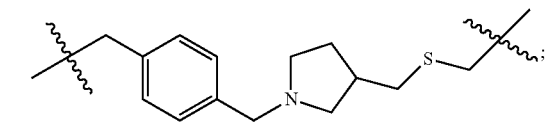
(L6-c)

and
alkylene chains interrupted by or terminating in a heteroatom such as N, O or B, e.g.,

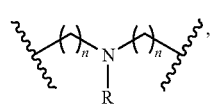
(L7)

wherein each n independently is an integer from 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H, or $C_1$ to $C_4$ alkyl, an example of which is

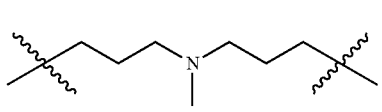
(L7-a)

In some embodiments, the linker is a polyethylene glycol chain, examples of which include:

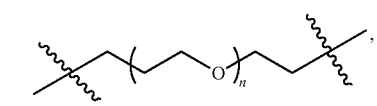
(L8)

wherein n is an integer from 1-10, examples of which include:

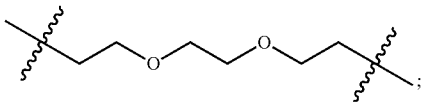
(L8-a)

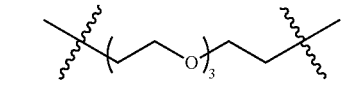
(L8-b)

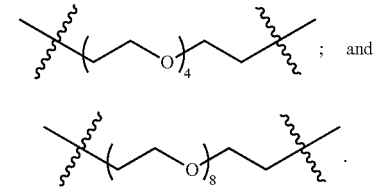
(L8-c)

(L8-d)

In some embodiments, the polyethylene glycol chain may terminate in a functional group, examples of which are as follows:

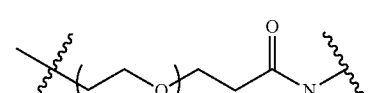
(L9-a)

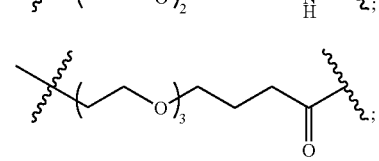
(L9-b)

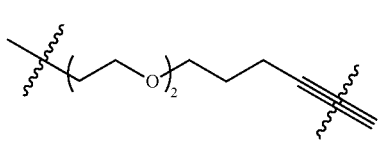
(L9-c)

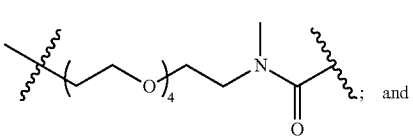
(L9-d)

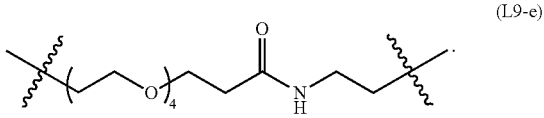
(L9-e)
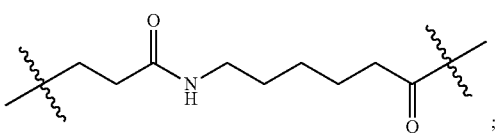
(L10)
wherein X is $CH_2$, NH, NMe, NEt, or O; and n is an integer from 0 to 11.
In some embodiments, the bifunctional compound of formula (I) includes a linker that is represented by structure L10:
In some embodiments, the linker is represented by any one of structures L11 to L26:
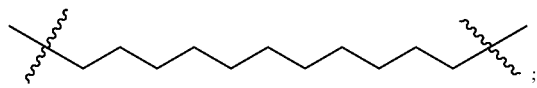
(L11)
(L12)
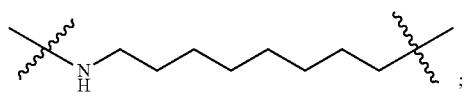
(L13)
(L14)
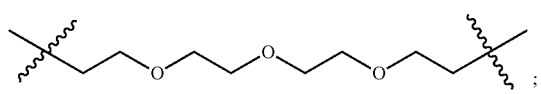
(L15)
(L16)
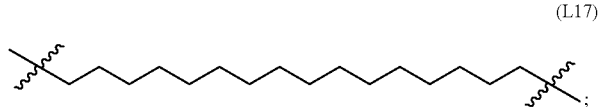
(L17)
(L18)
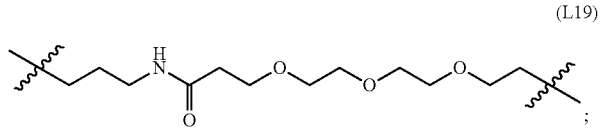
(L19)
(L20)
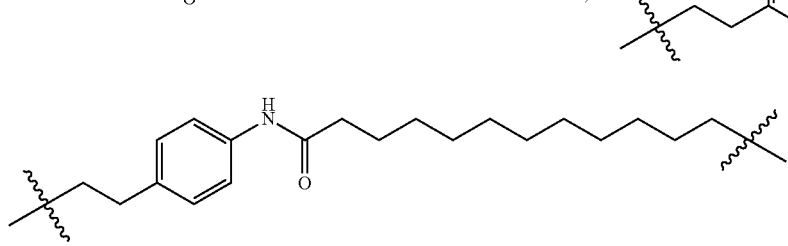
(L21)
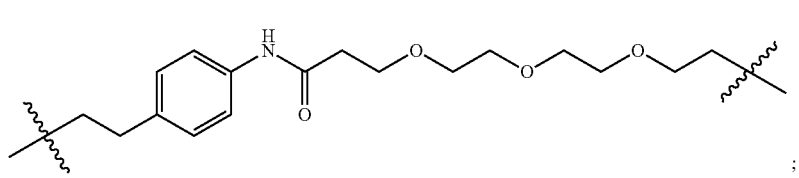
(L22)
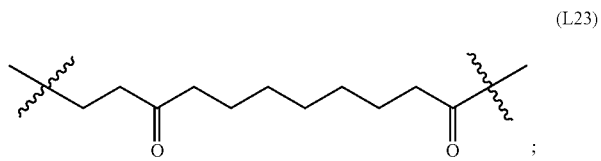
(L23)
(L24)

-continued
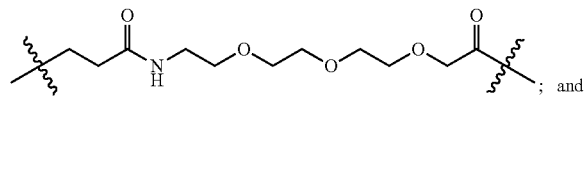
(L25)
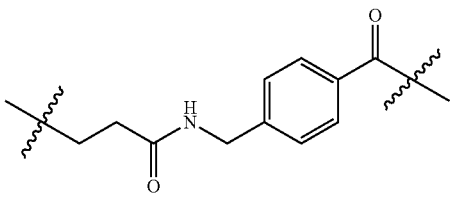
(L26)
; and
.
Thus, in some embodiments, the bifunctional compounds of the present invention are represented by any one of structures I-2 to I-12:
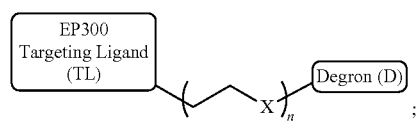
(I-2)
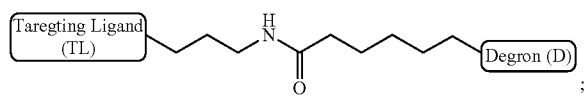
(I-3)
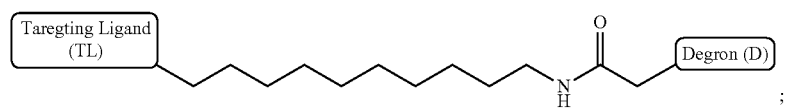
(I-4)
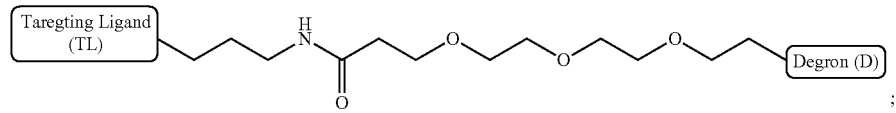
(I-5)
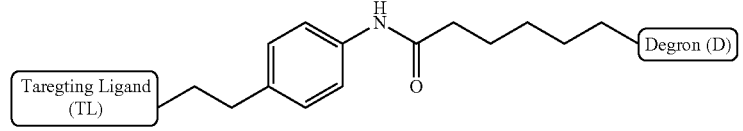
(I-6)
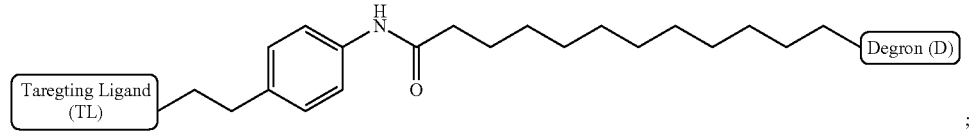
(I-7)
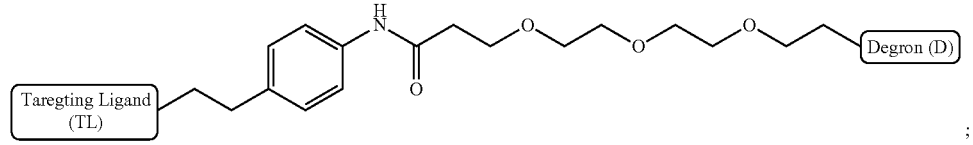
(I-8)
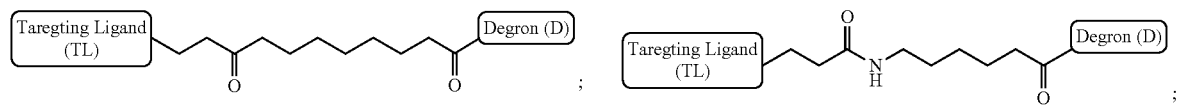
(I-9) (I-10)
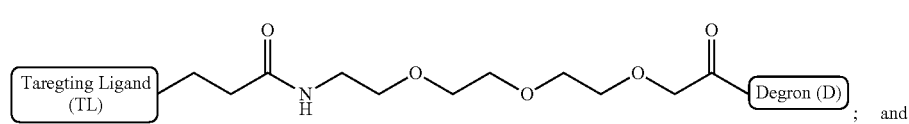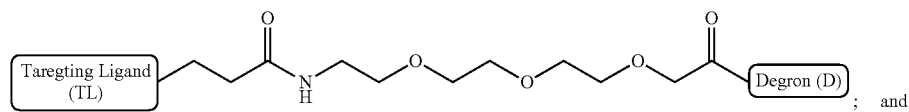
(I-11)
; and -continued
(I-12)
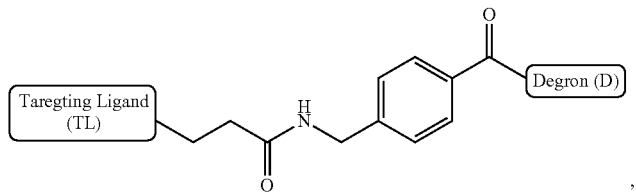
or a pharmaceutically acceptable salt or stereoisomer thereof.
In some embodiments, the bifunctional compounds of the present invention are represented by a structure selected from the group consisting of:
(TL1-L10)
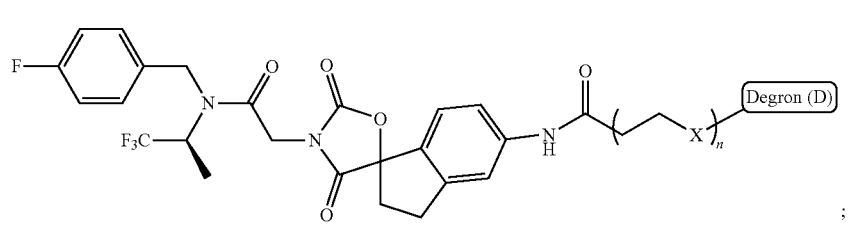
(TL1a-L10)
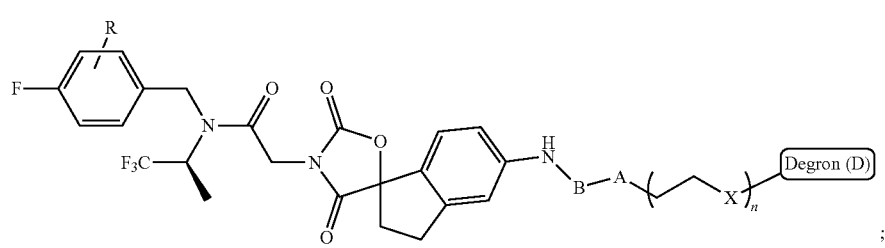
(TL1b-L10)
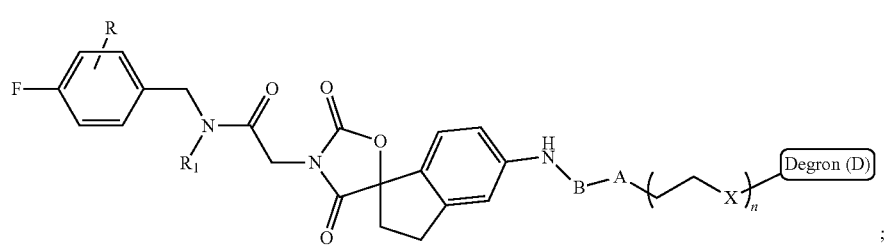
(TL1c-L10)
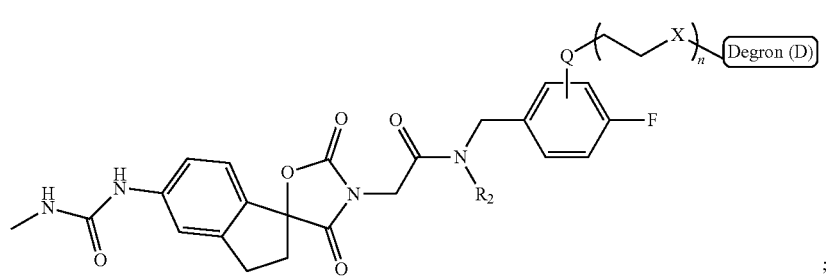
(TL1d-L10)
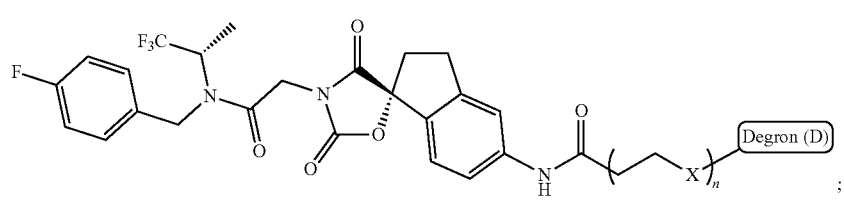

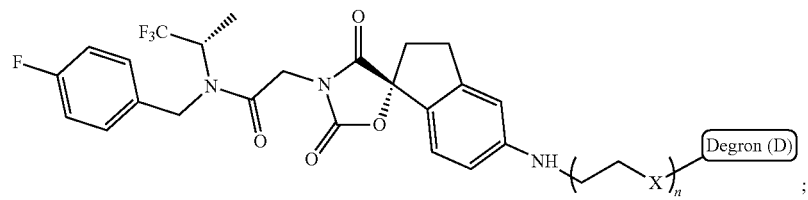
(TL1e-L10)
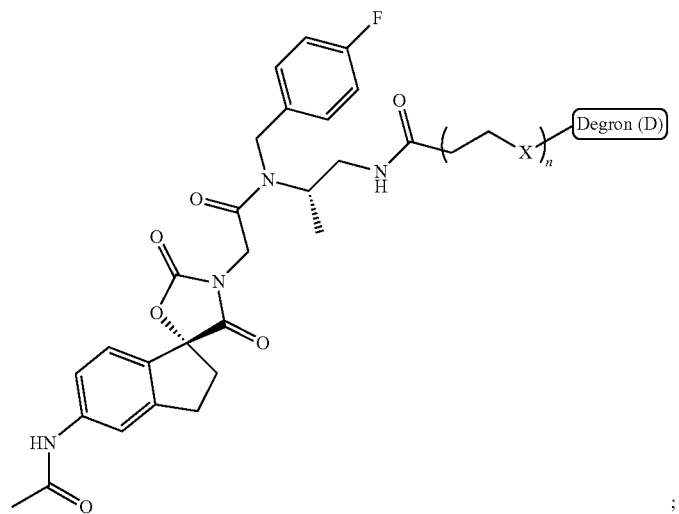
(TL1f-L10)
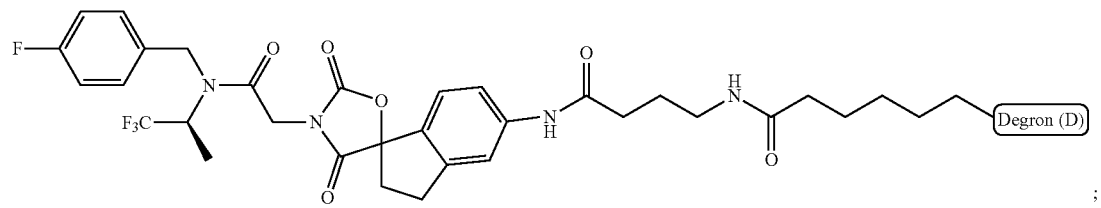
(TL1-L16)
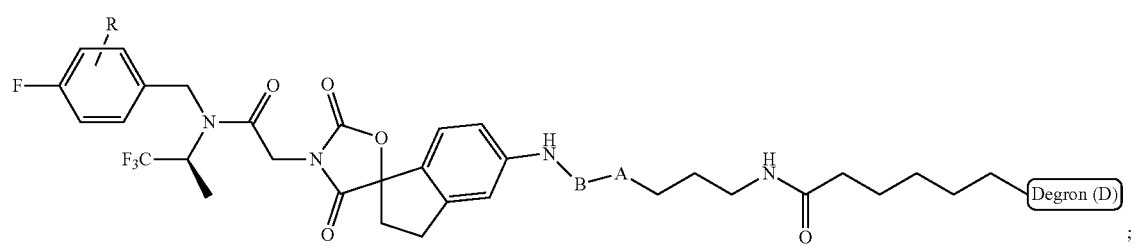
(TL1a-L16)
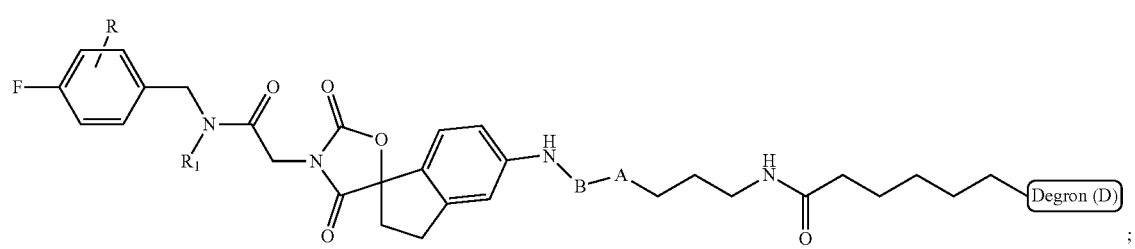
(TL1b-L16)

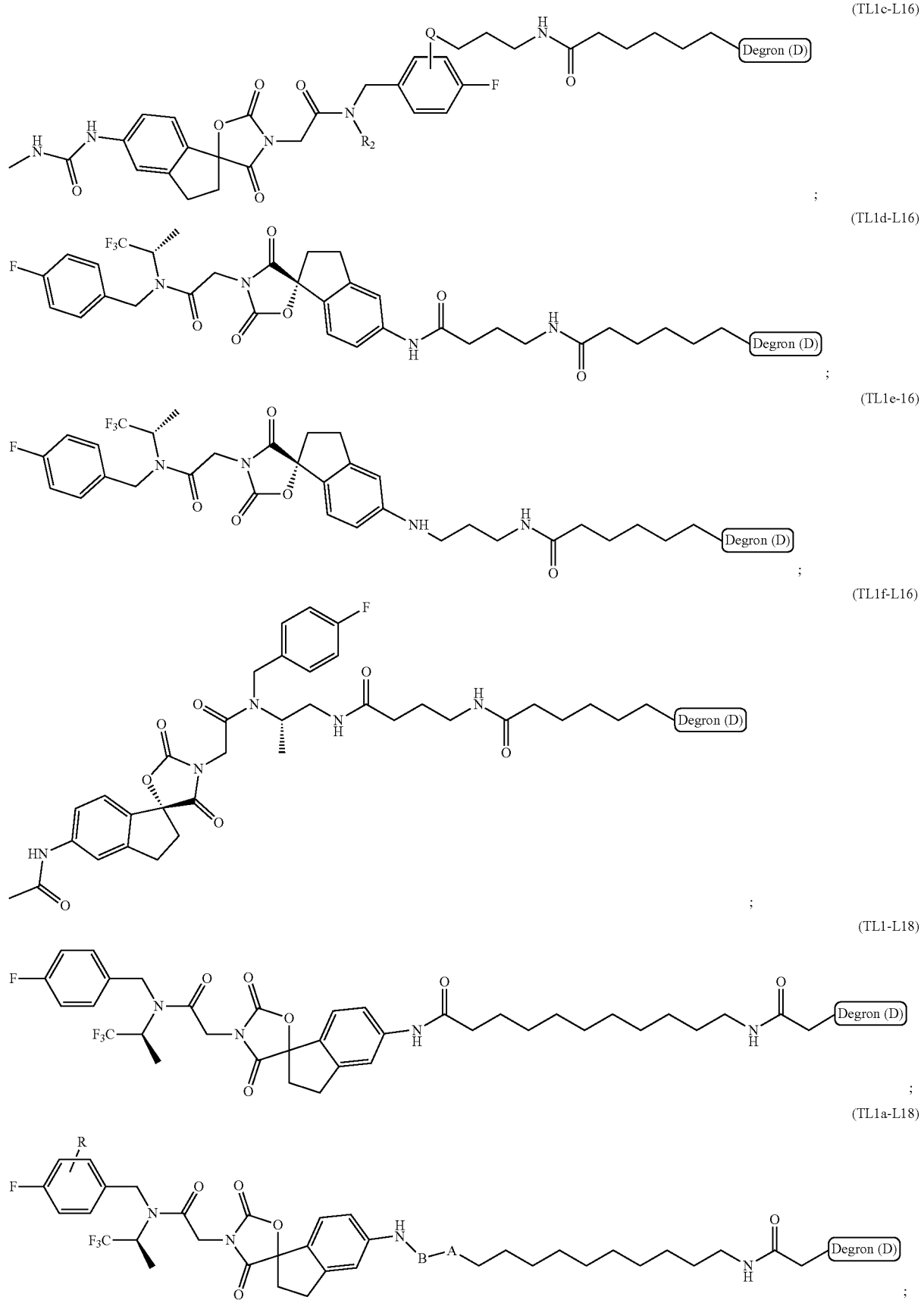

(TL1b-L18)
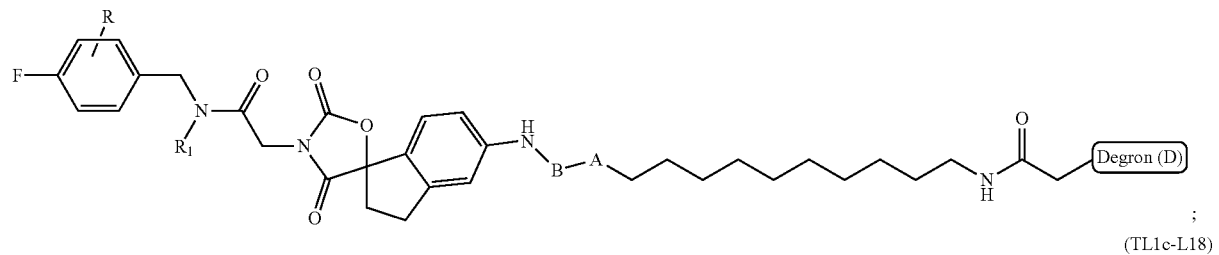
(TL1c-L18)
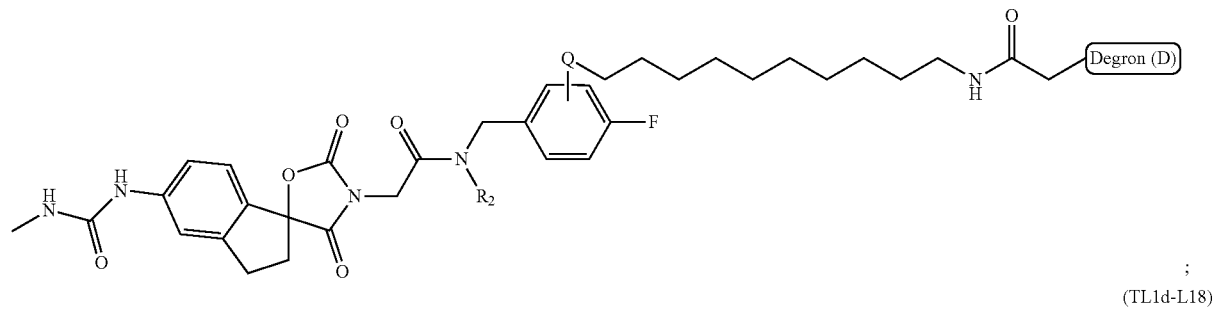
(TL1d-L18)
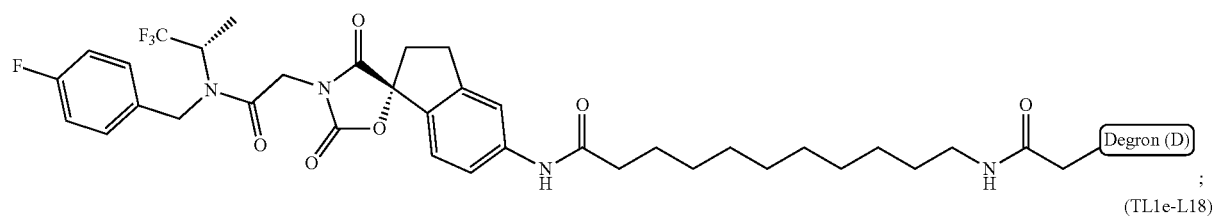
(TL1e-L18)
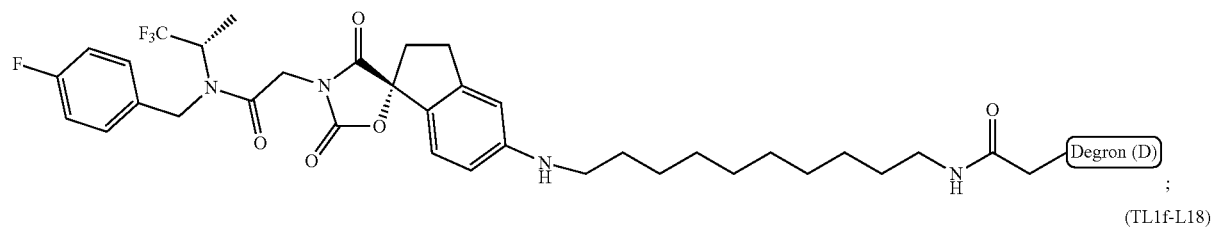
(TL1f-L18)
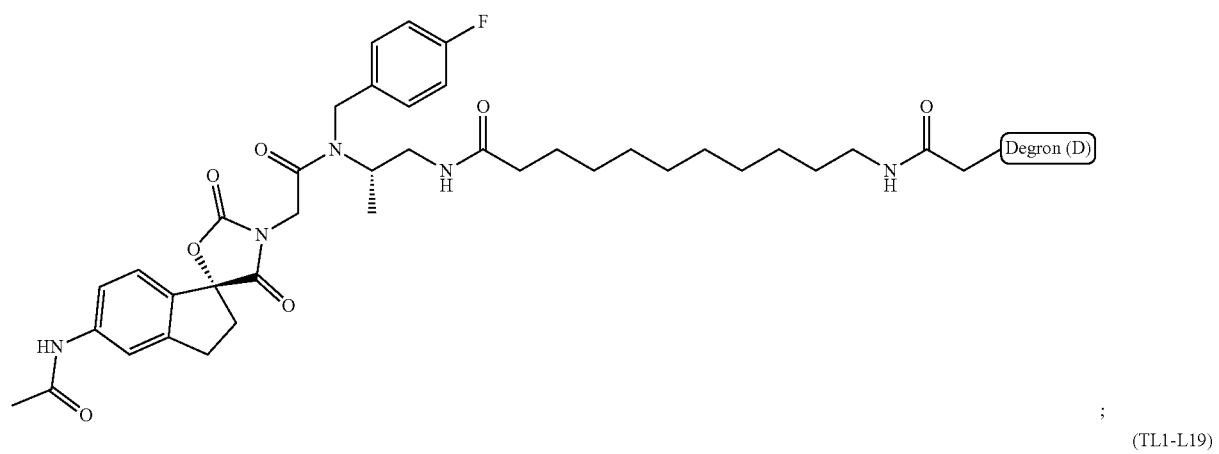
(TL1-L19)
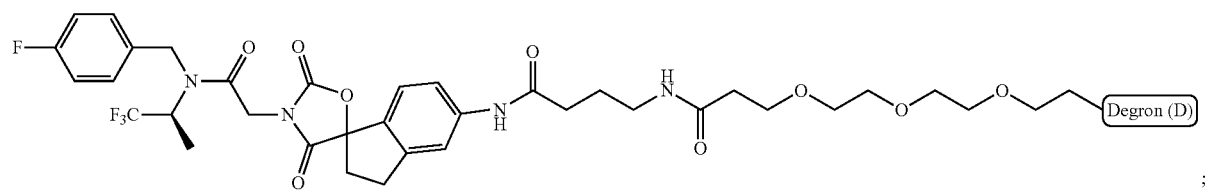

-continued
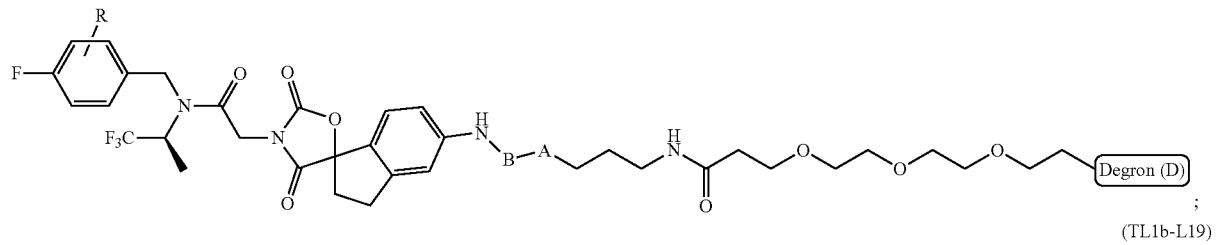
(TL1a-L19)
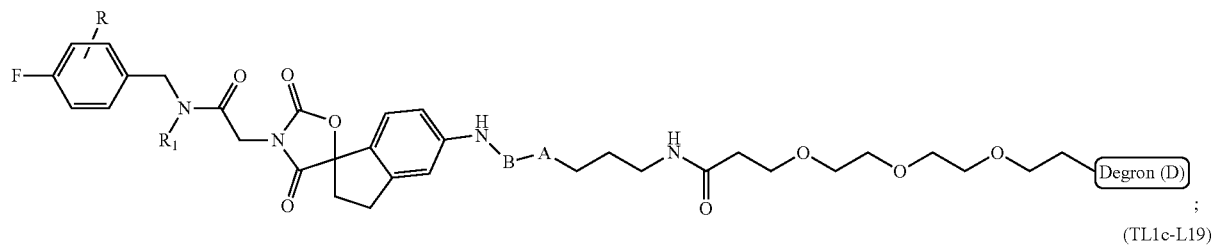
(TL1b-L19)
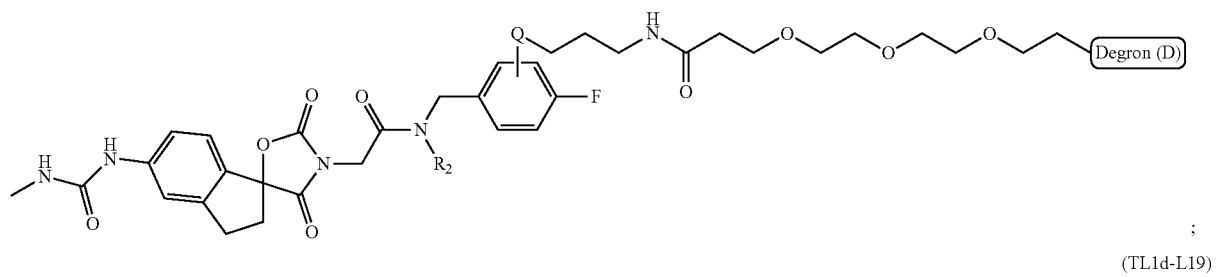
(TL1c-L19)
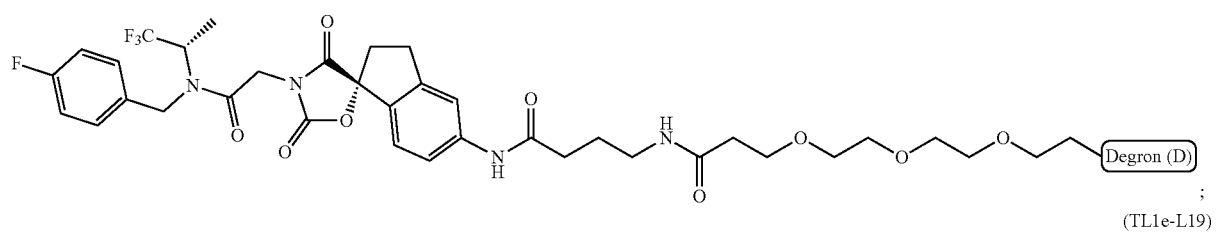
(TL1d-L19)
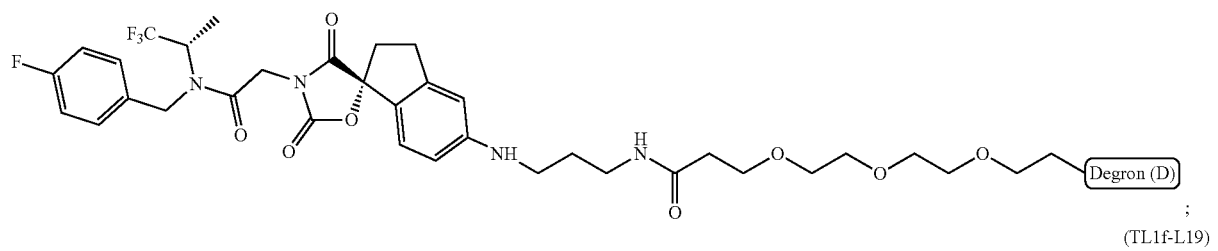
(TL1e-L19)
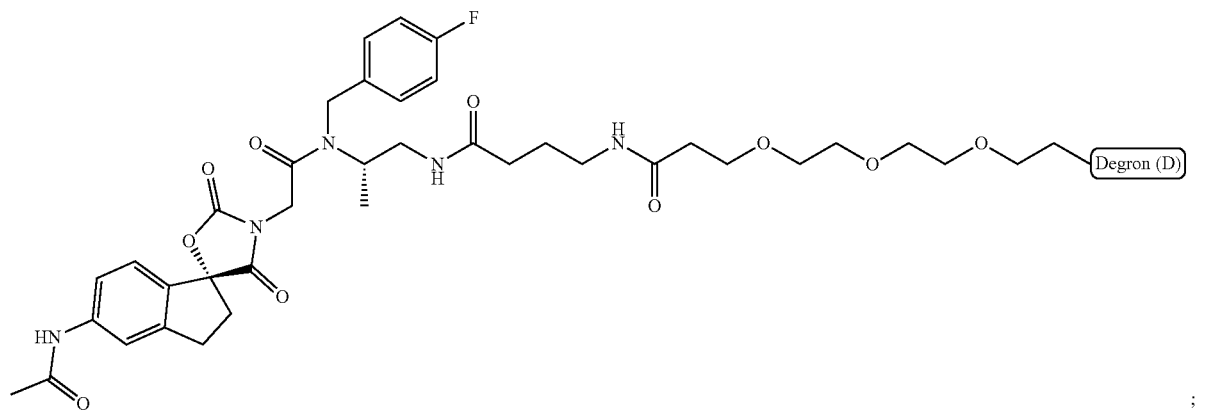
(TL1f-L19)

(TL1-L20)
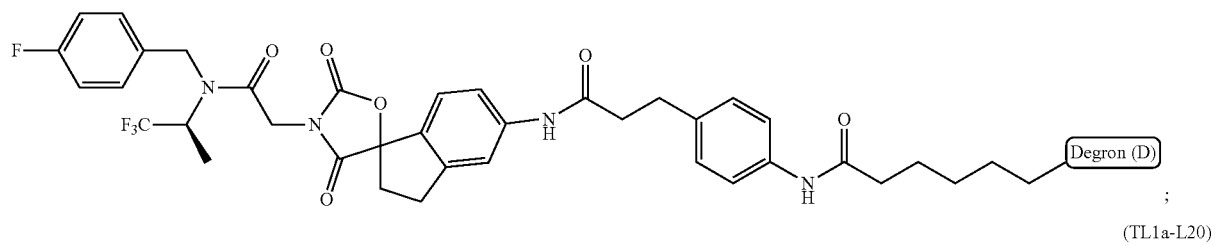
(TL1a-L20)
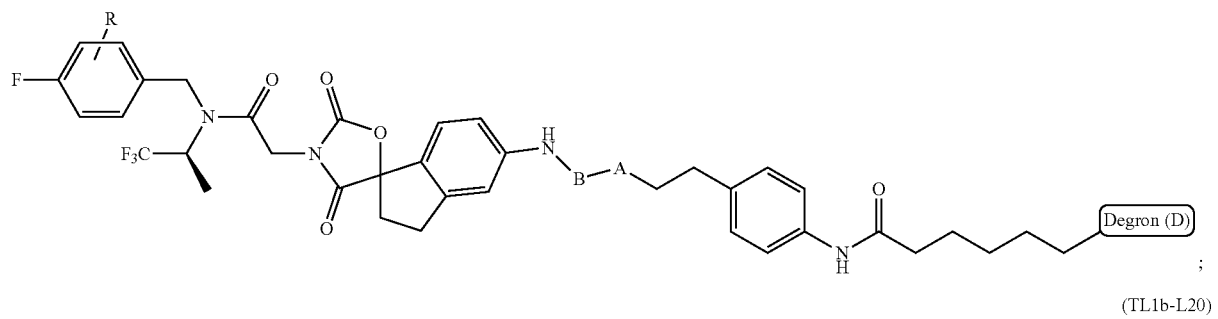
(TL1b-L20)
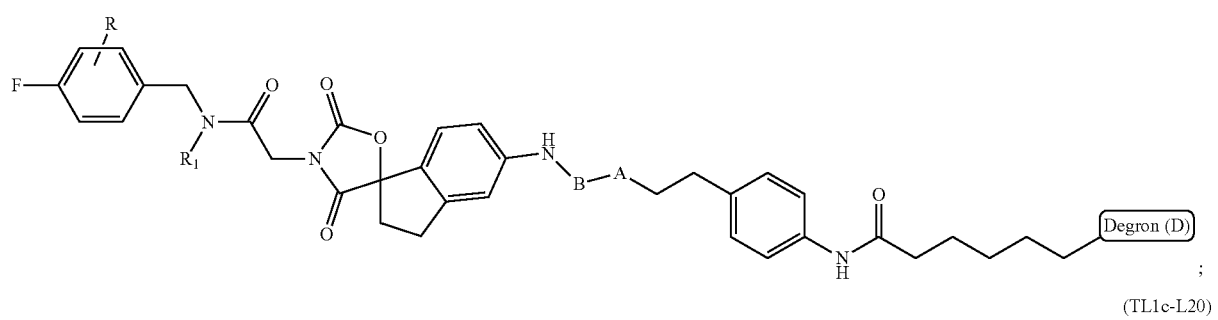
(TL1c-L20)
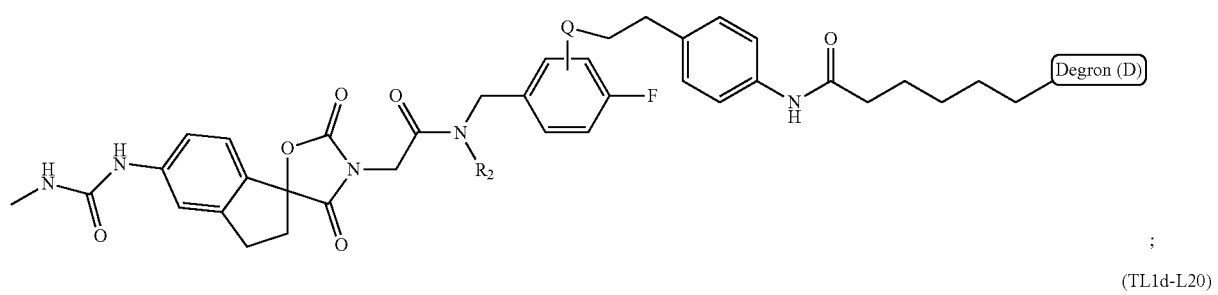
(TL1d-L20)
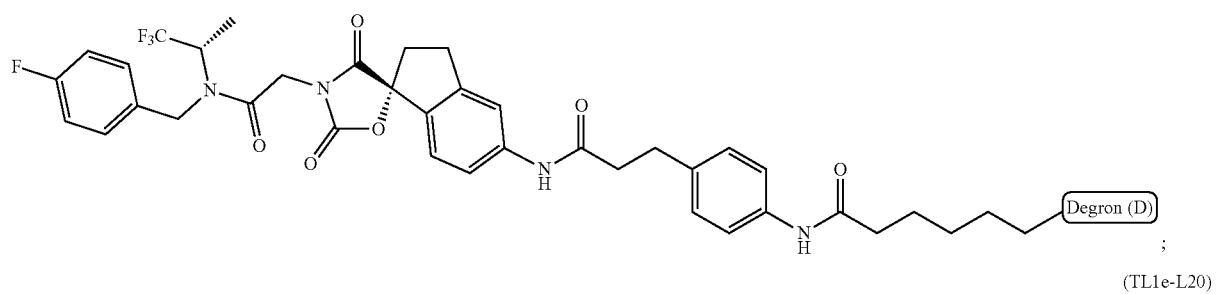
(TL1e-L20)
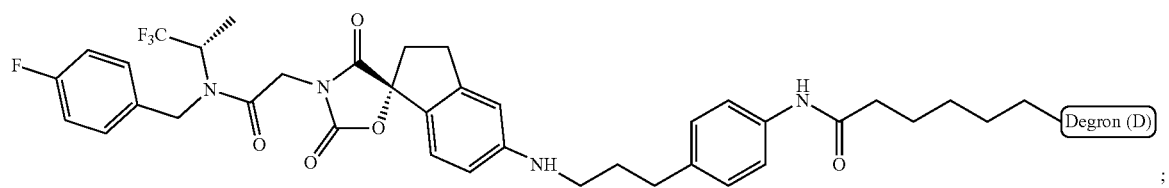

(TL1f-L20)
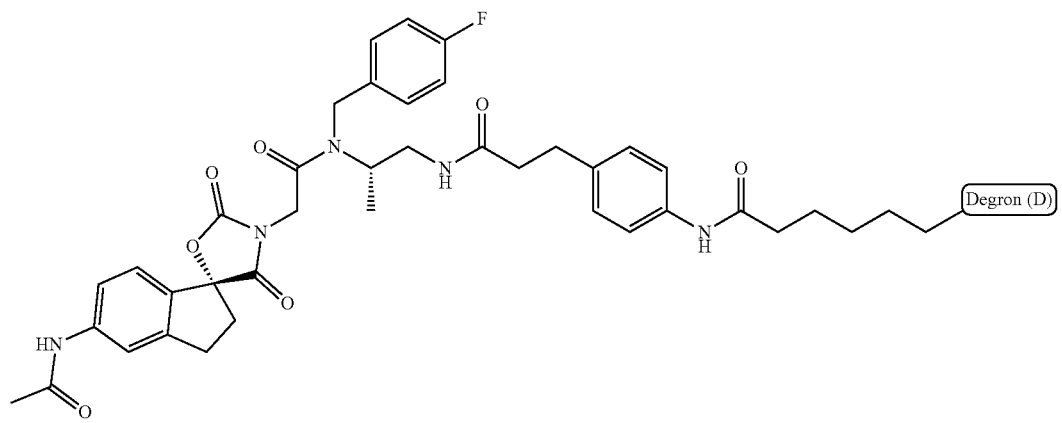
(TL1-L21)
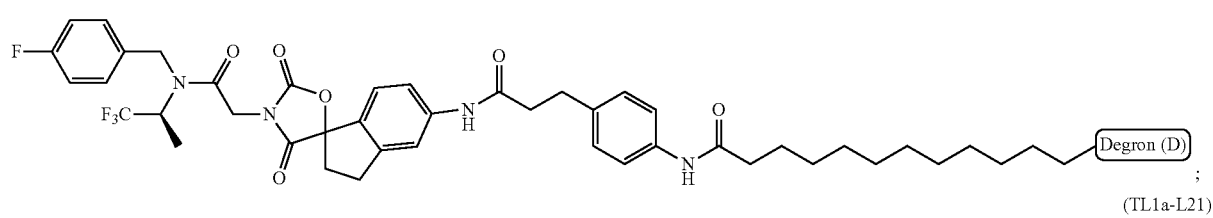
(TL1a-L21)
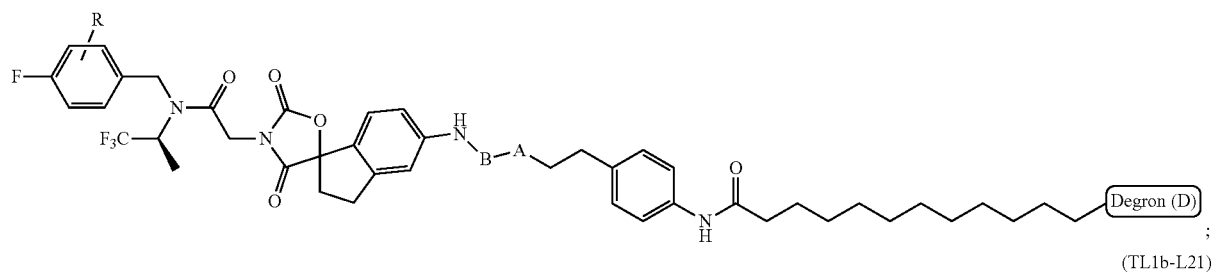
(TL1b-L21)
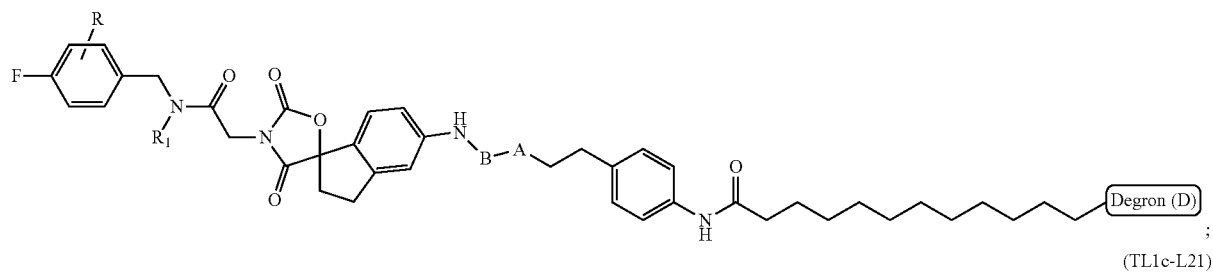
(TL1c-L21)
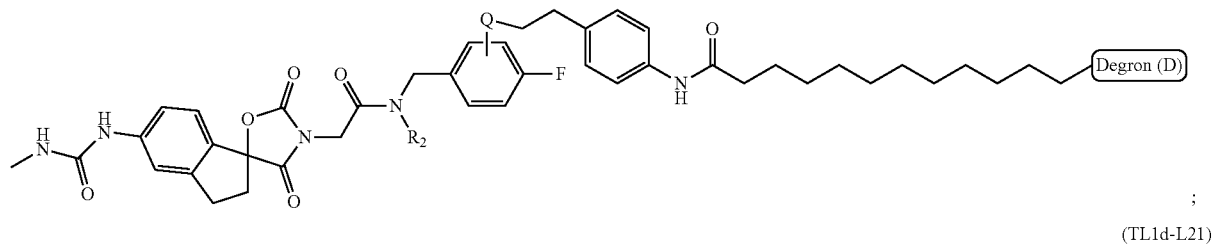
(TL1d-L21)
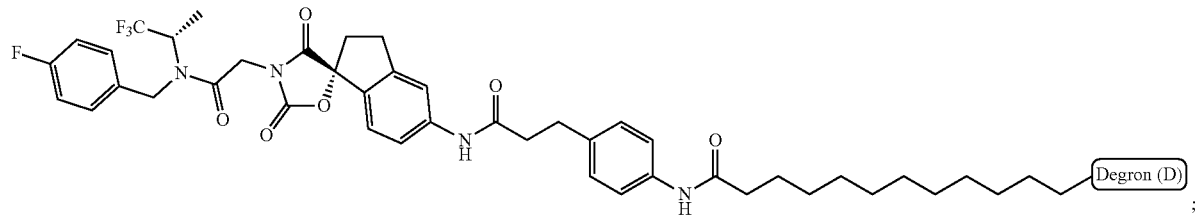

-continued
(TL1e-L21)
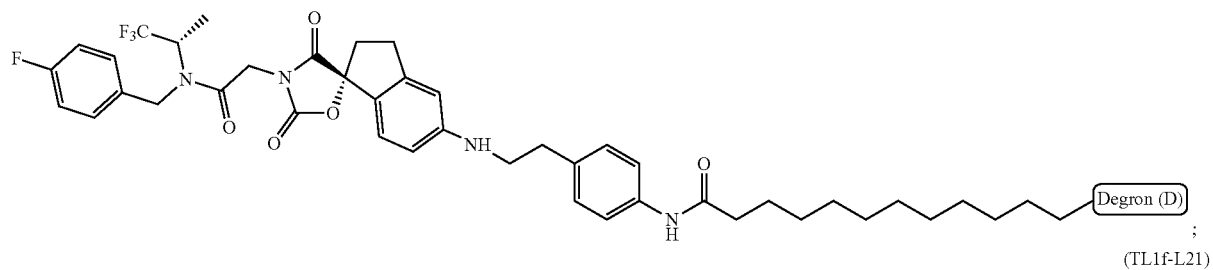
(TL1f-L21)
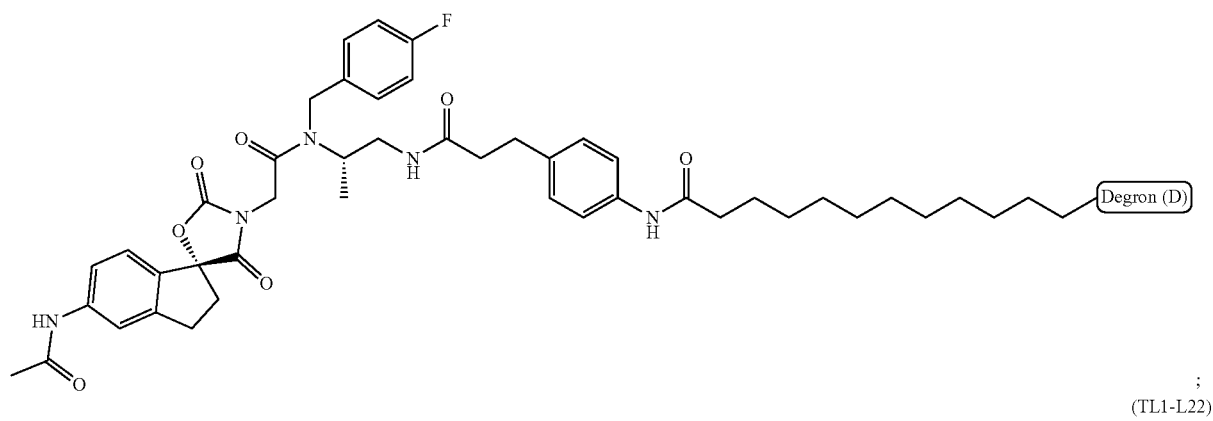
(TL1-L22)
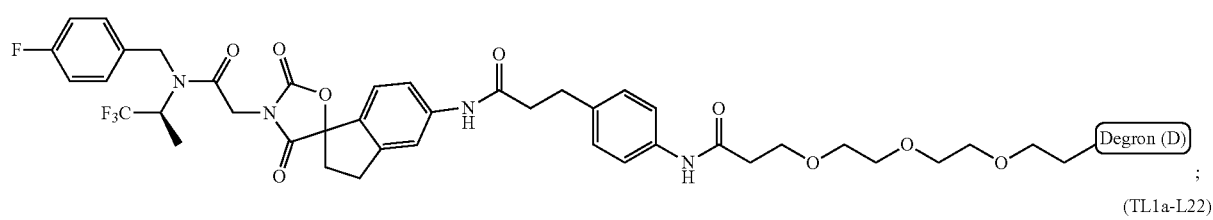
(TL1a-L22)
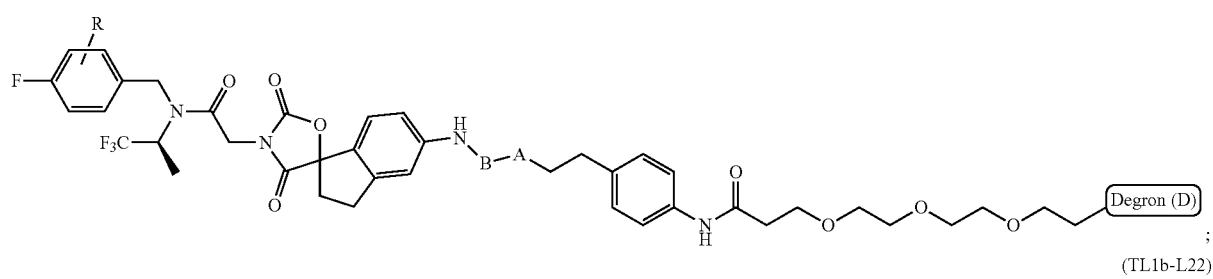
(TL1b-L22)
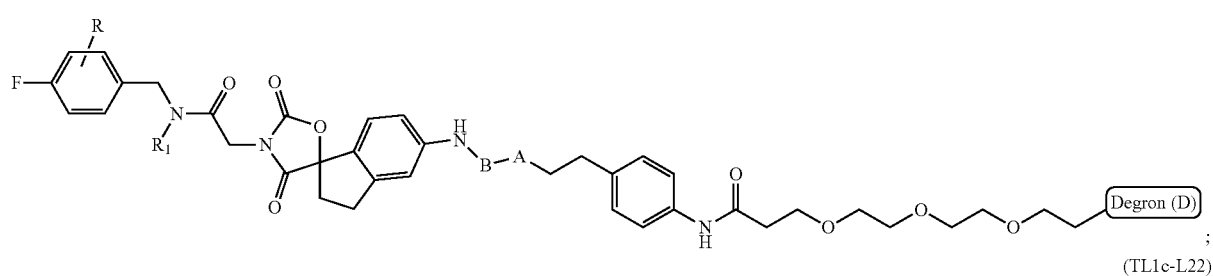
(TL1c-L22)
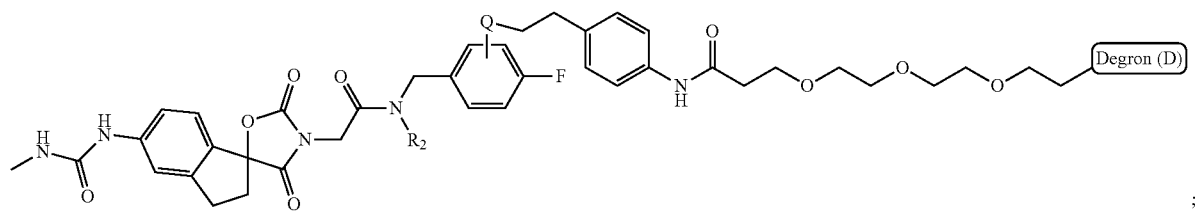

-continued
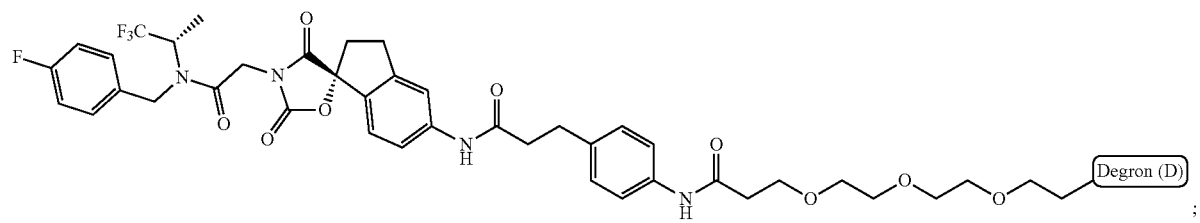
(TL1d-L22)
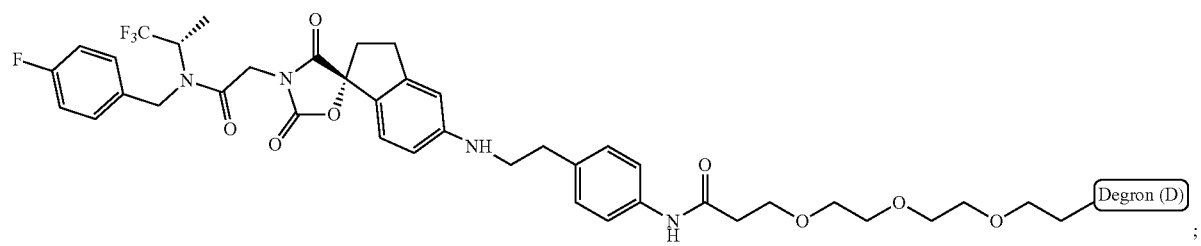
(TL1e-L22)
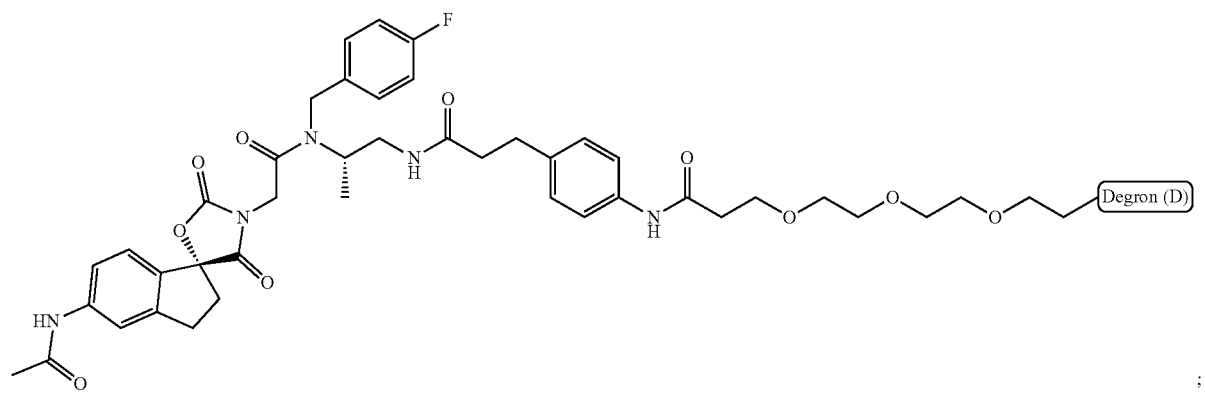
(TL1f-L22)
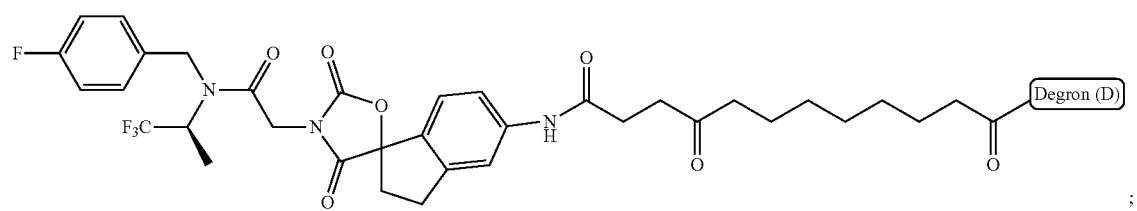
(TL1-L23)
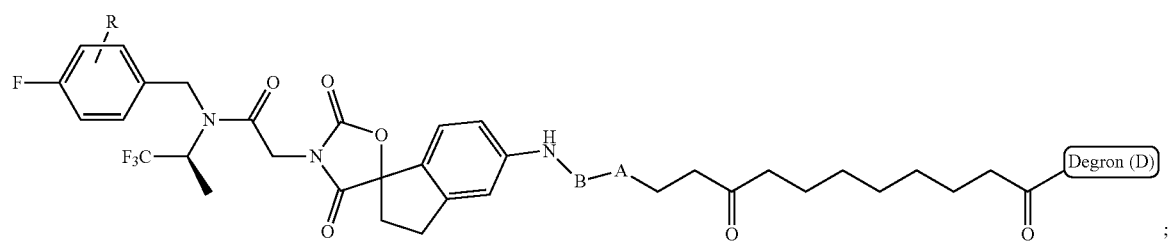
(TL1a-L23)

(TL1b-L23)
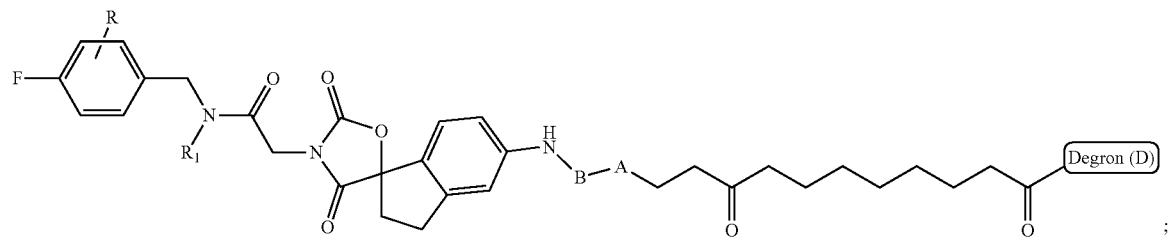
(TL1c-L23)
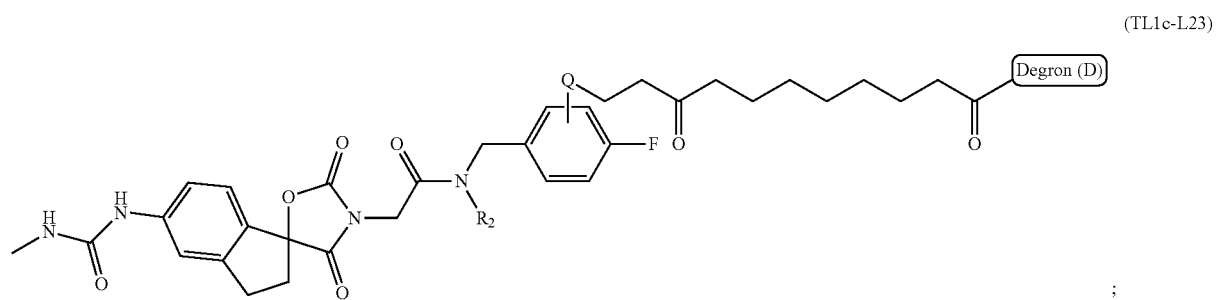
(TL1d-L23)
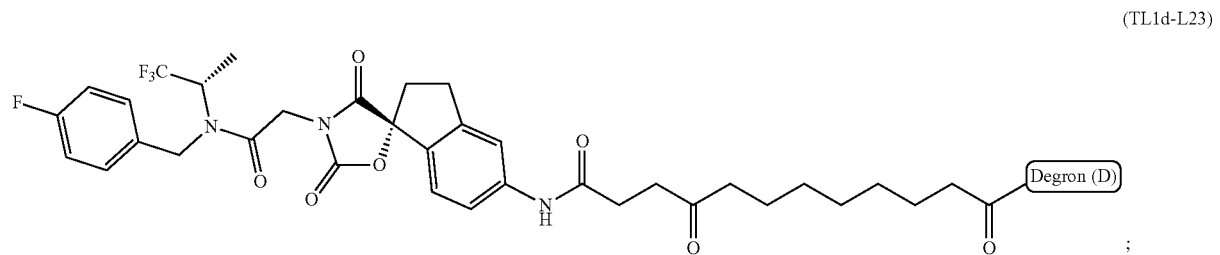
(TL1e-L23)
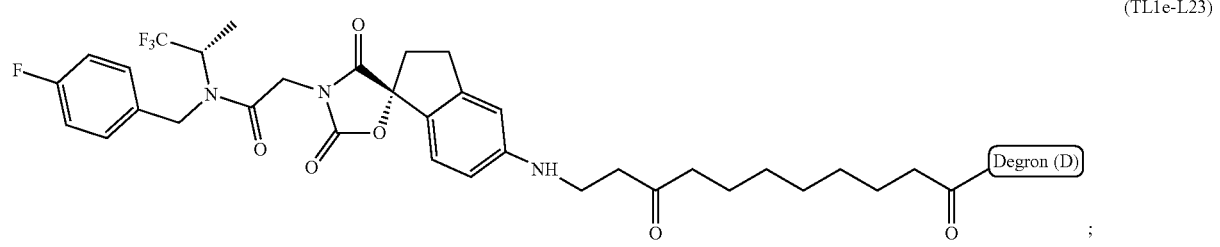
(TL1f-L23)
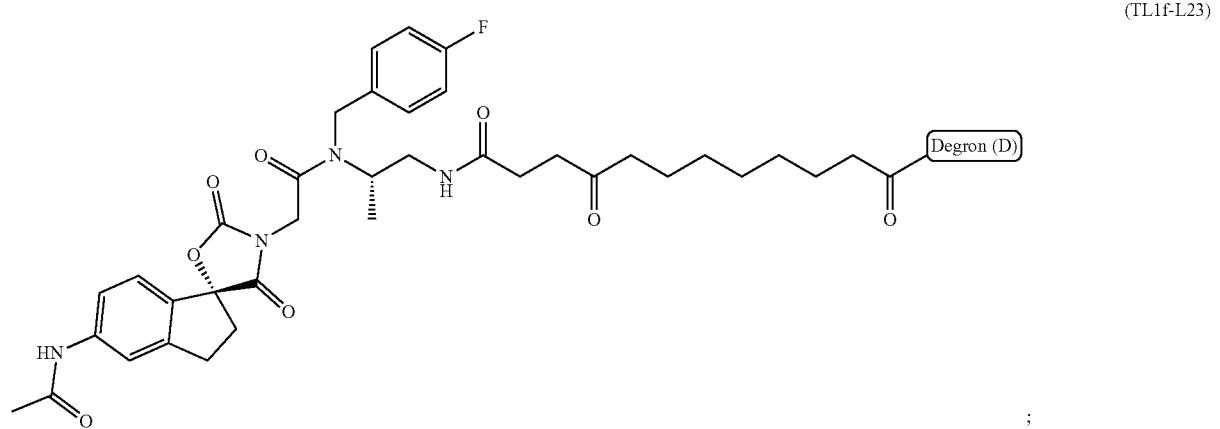

(TL1-L24)
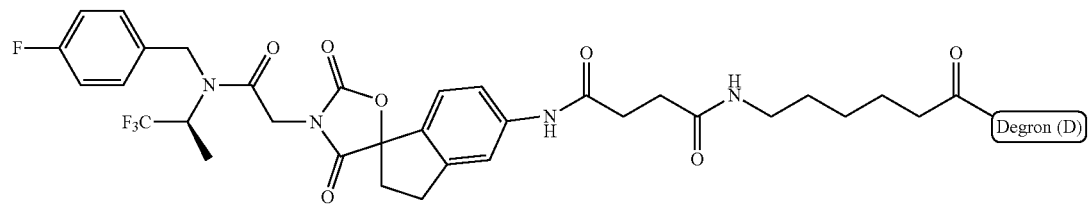
(TL1a-L24)
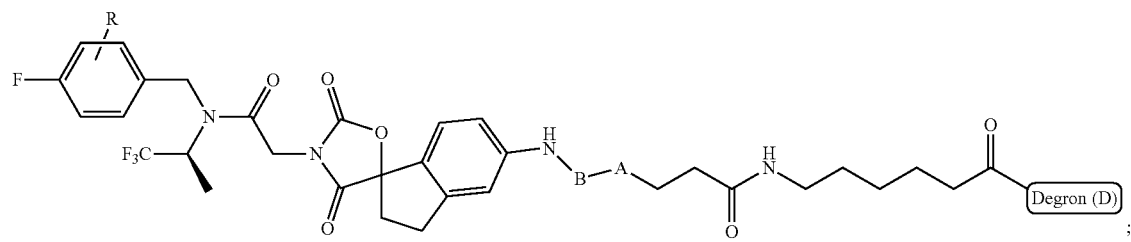
(TL1b-L24)
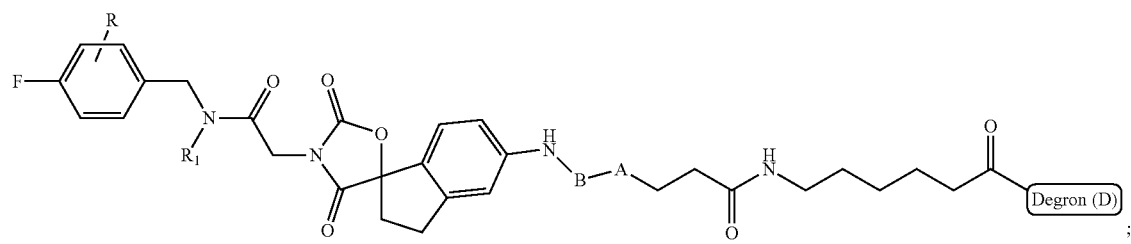
(TL1c-L24)
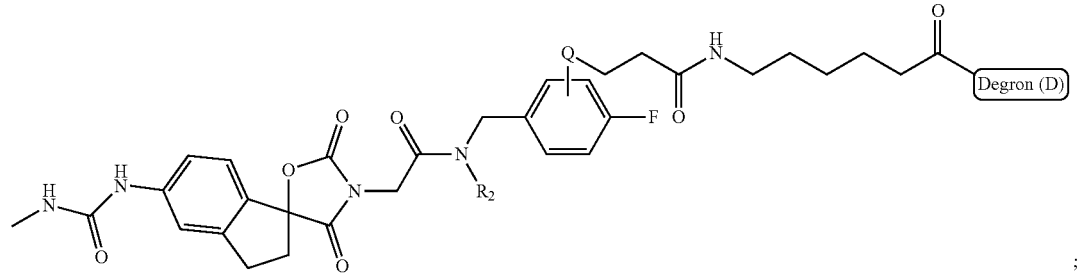
(TL1d-L24)
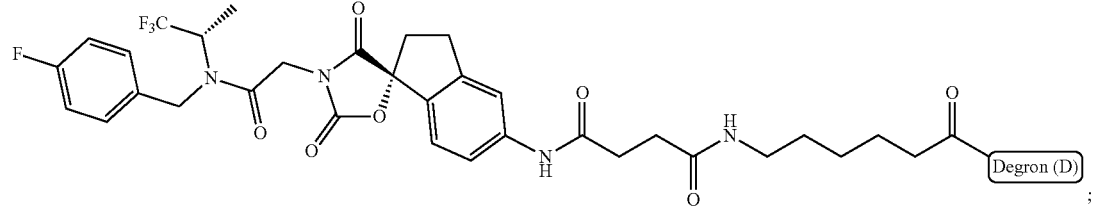
(TL1e-L24)
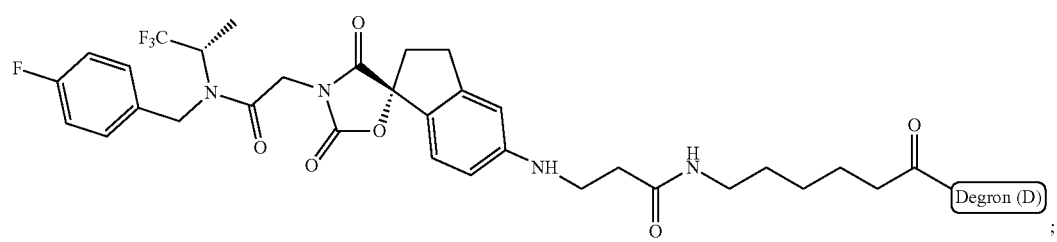

-continued
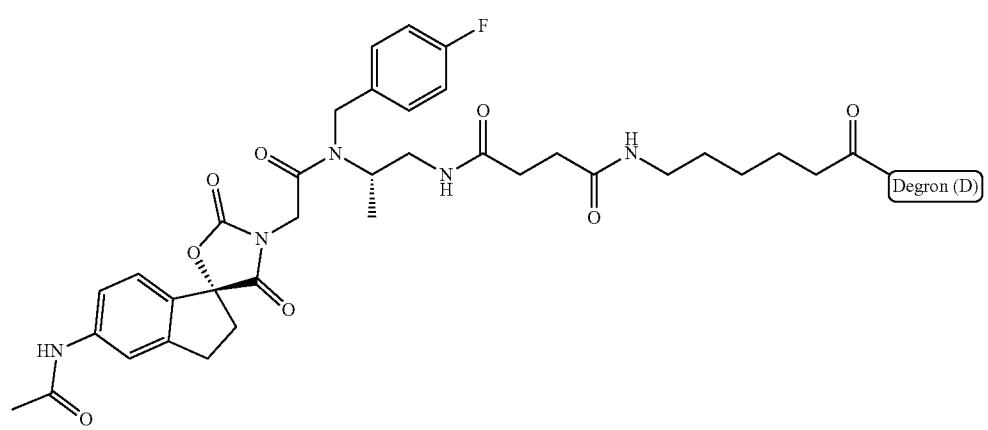
(TL1f-L24)
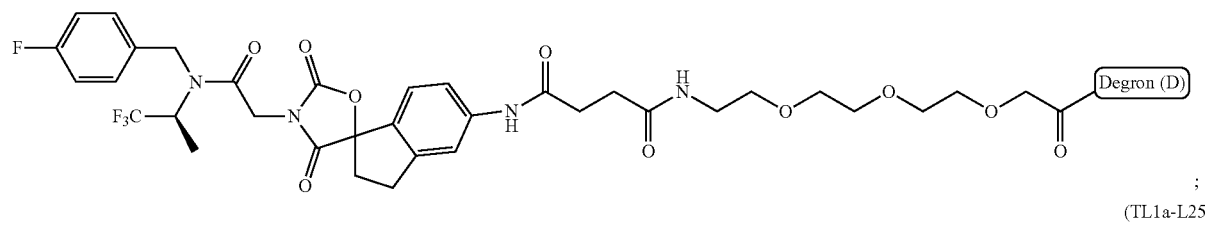
(TL1-L25)
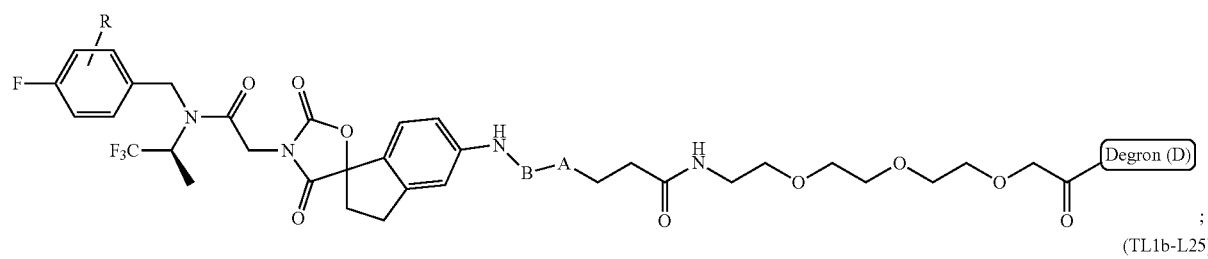
(TL1a-L25)
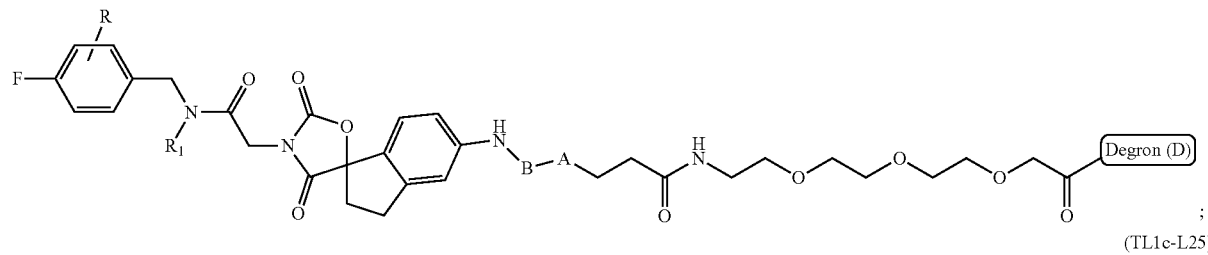
(TL1b-L25)
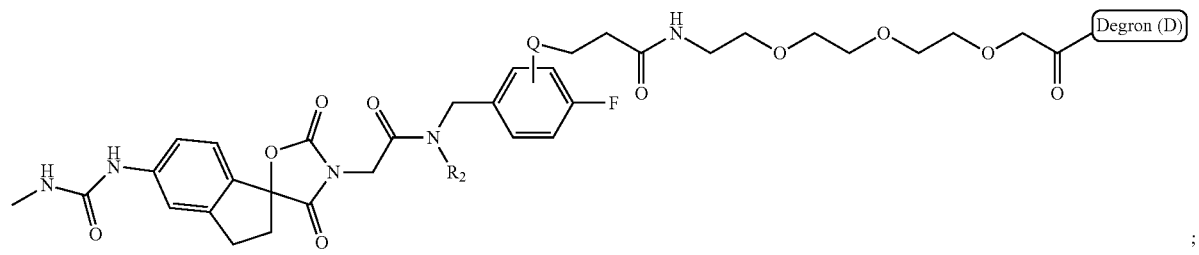
(TL1c-L25)
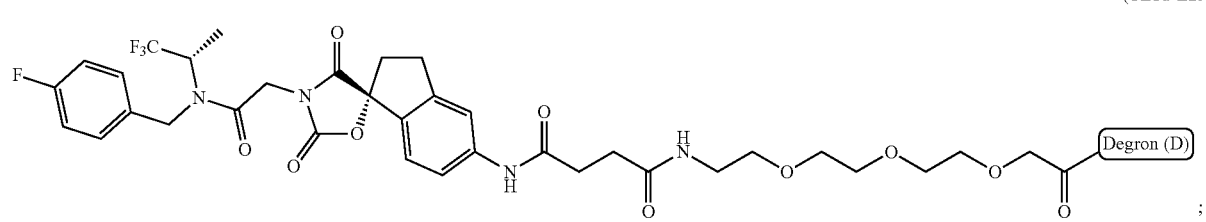
(TL1d-L25)

(TL1e-L25)
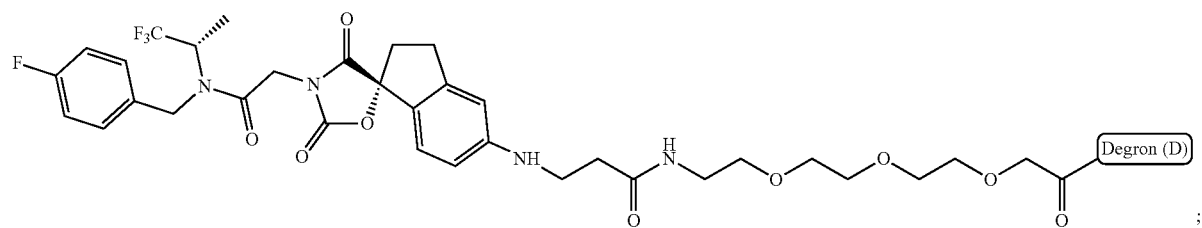
(TL1f-L25)
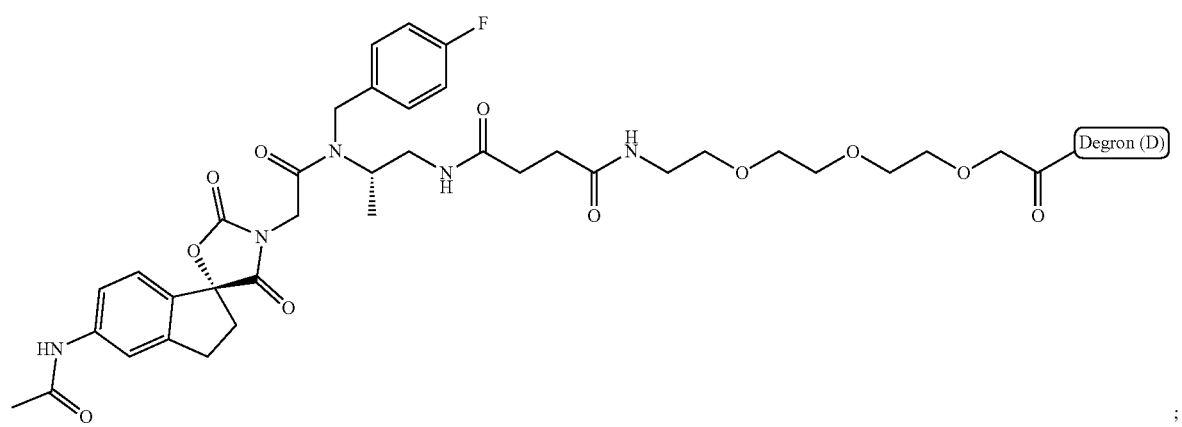
(TL1-L26)
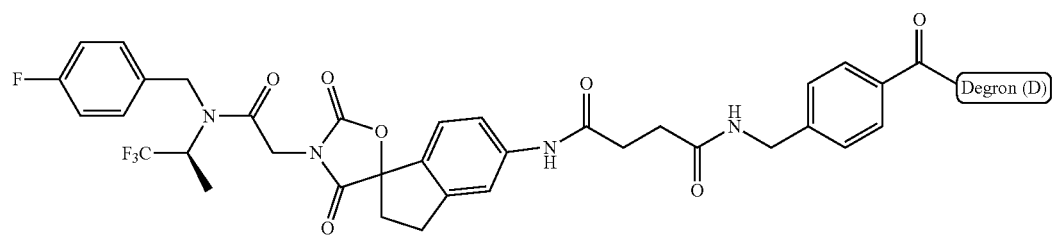
(TL1a-L26)
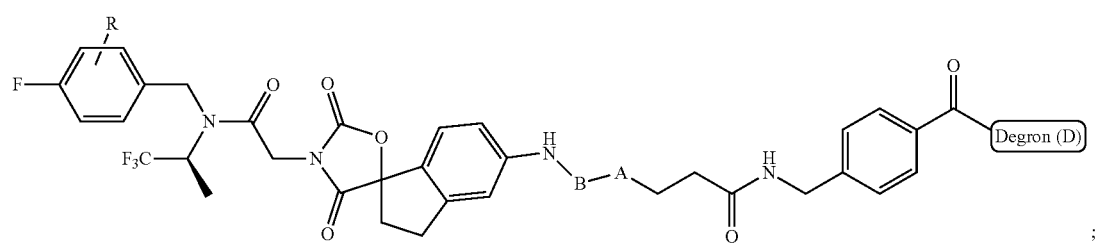
(TL1b-L26)
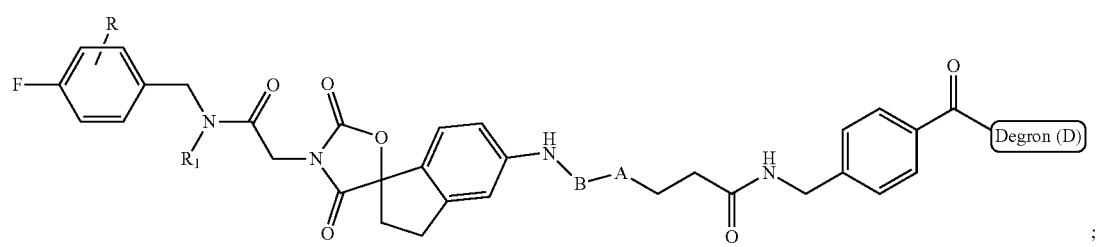

-continued

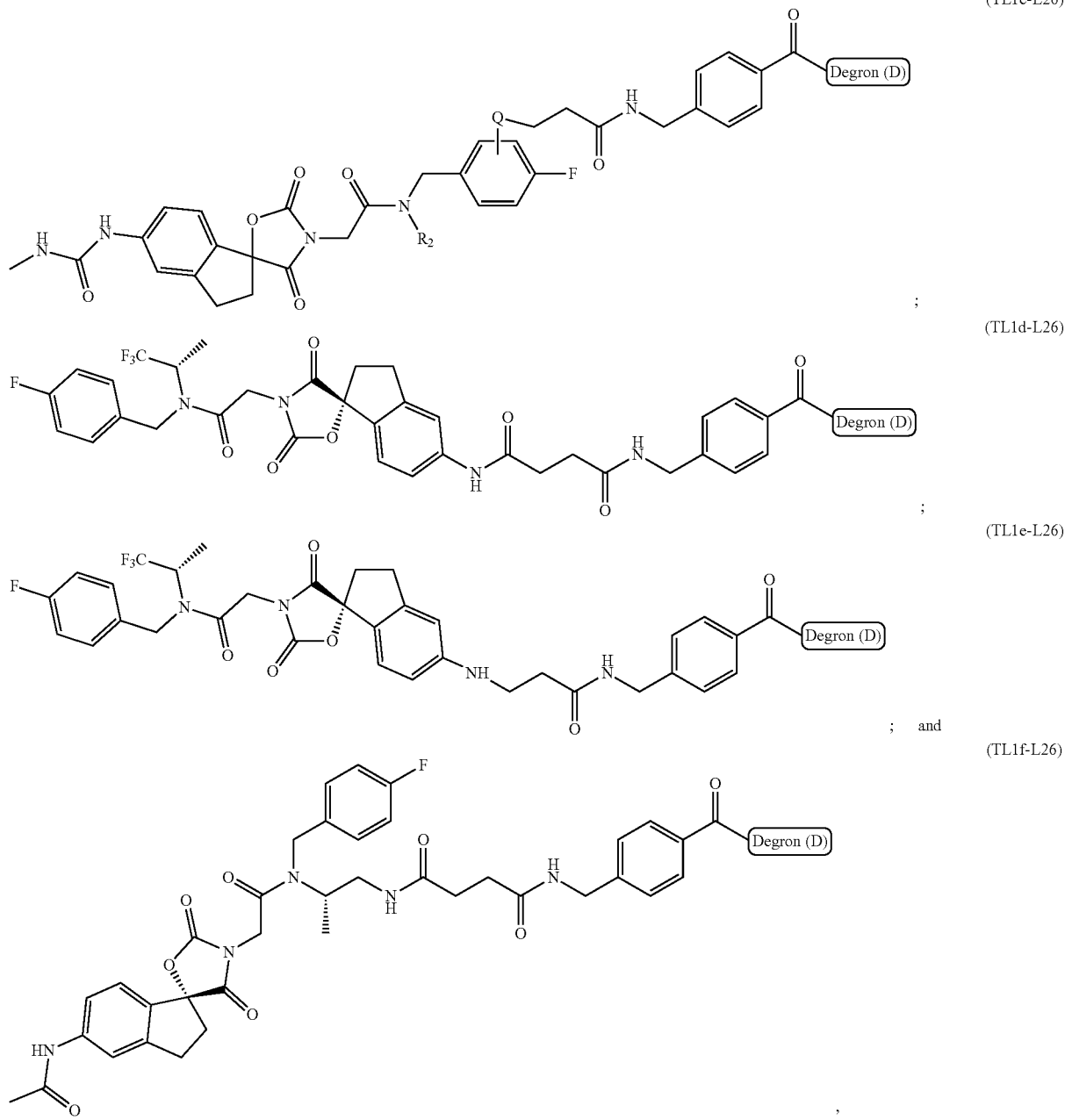

or a pharmaceutically acceptable salt or stereoisomer thereof.

Degrons

The Degron ("D") is a functional moiety that binds an E3 ubiquitin ligase. In some embodiments, the Degron binds cereblon (CRBRN). In some embodiments, the Degron binds a Von Hippel-Lindau (VHL) tumor suppressor.

In some embodiments, the bifunctional compound of formula (I) includes a degron that binds cereblon. Representative examples of degrons that bind cereblon are described in U.S. Patent Application Publication 2018/0015085 (e.g., the indolinones such as isoindolinones and isoindoline-1,3-diones embraced by formulae IA ad IA' therein, and the bridged cycloalkyl compounds embraced by formulae IB and IB' therein).

In some embodiments, the compound of formula (I) includes a degron that binds cereblon, and is represented by structure D1:

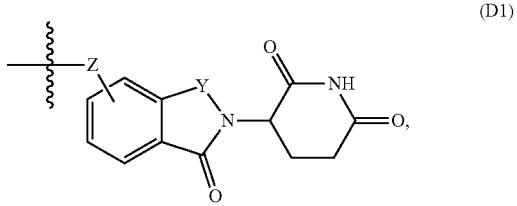

wherein Y is $CH_2$ or CO;

and Z is NH, O, or OCH$_2$CO, and the squiggle ( ⌇ ) represents the point of attachment for the linker and EP300 targeting moiety.

In some embodiments, the degron is represented by structure D1-a:

wherein Y' is a bond, N, O or C;

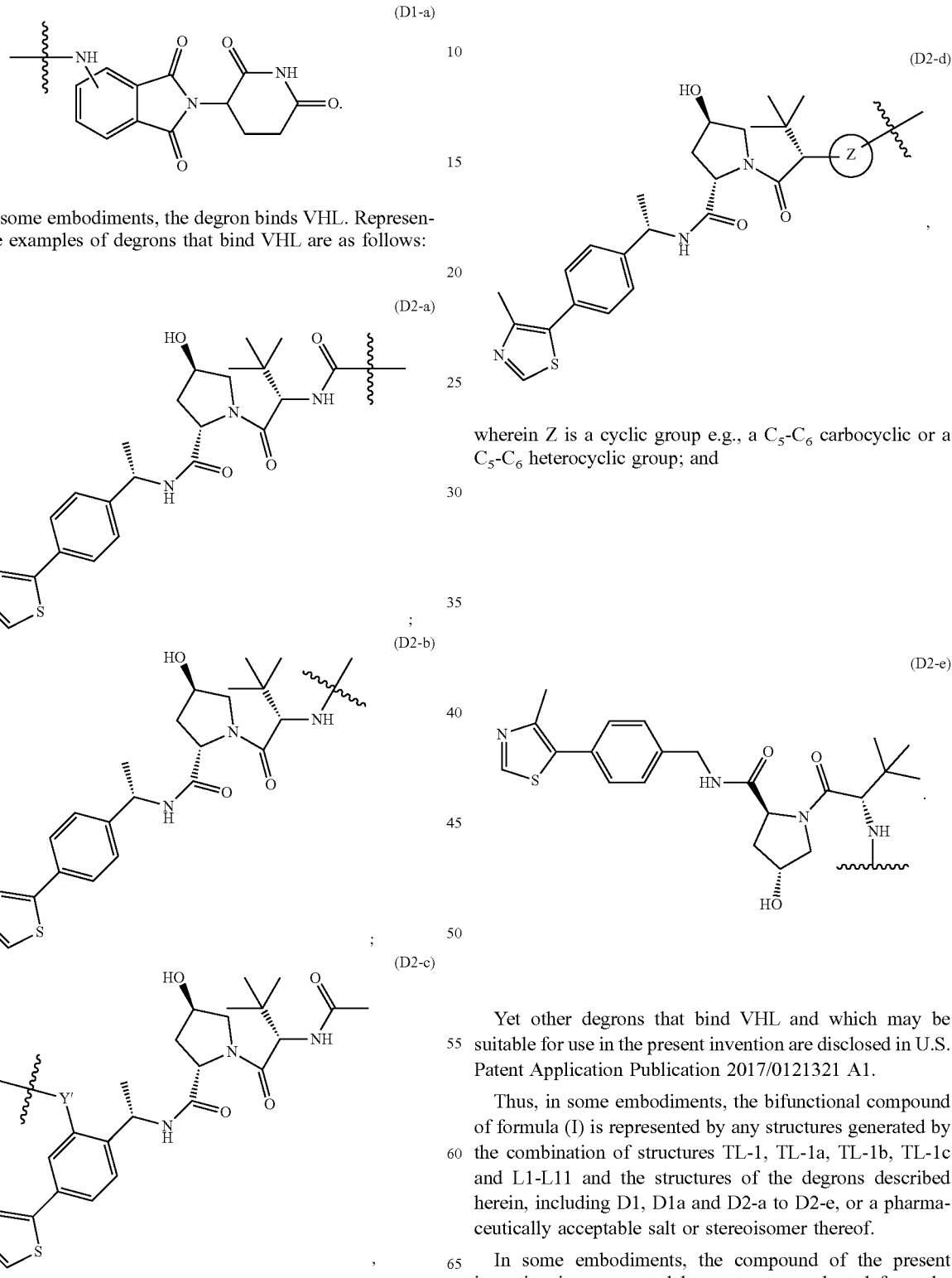

In some embodiments, the degron binds VHL. Representative examples of degrons that bind VHL are as follows:

wherein Z is a cyclic group e.g., a C$_5$-C$_6$ carbocyclic or a C$_5$-C$_6$ heterocyclic group; and Yet other degrons that bind VHL and which may be suitable for use in the present invention are disclosed in U.S. Patent Application Publication 2017/0121321 A1.

Thus, in some embodiments, the bifunctional compound of formula (I) is represented by any structures generated by the combination of structures TL-1, TL-1a, TL-1b, TL-1c and L1-L11 and the structures of the degrons described herein, including D1, D1a and D2-a to D2-e, or a pharmaceutically acceptable salt or stereoisomer thereof.

In some embodiments, the compound of the present invention is represented by a structure selected from the group consisting of:

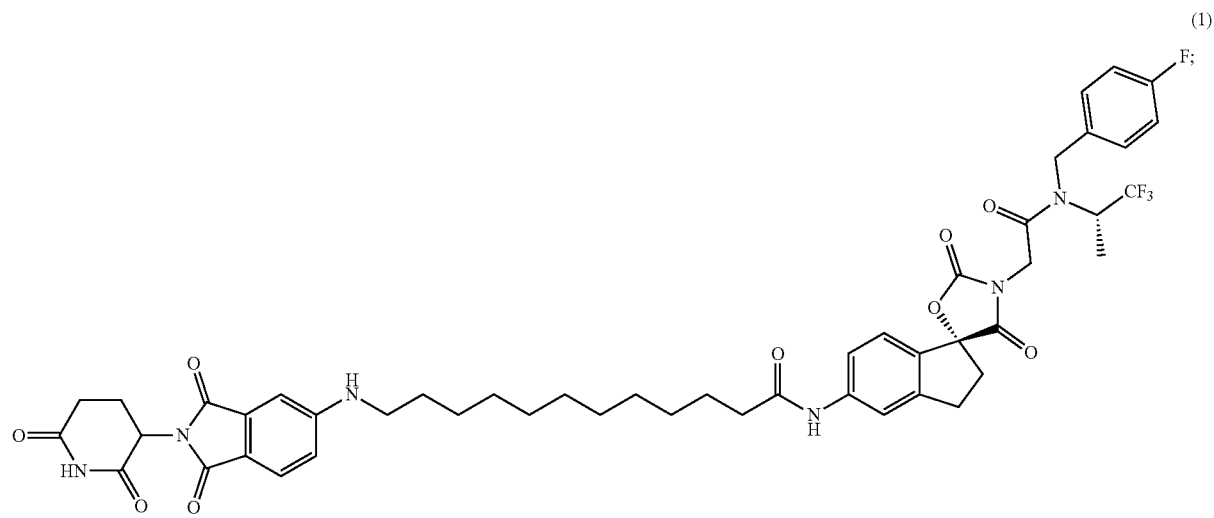
(1)
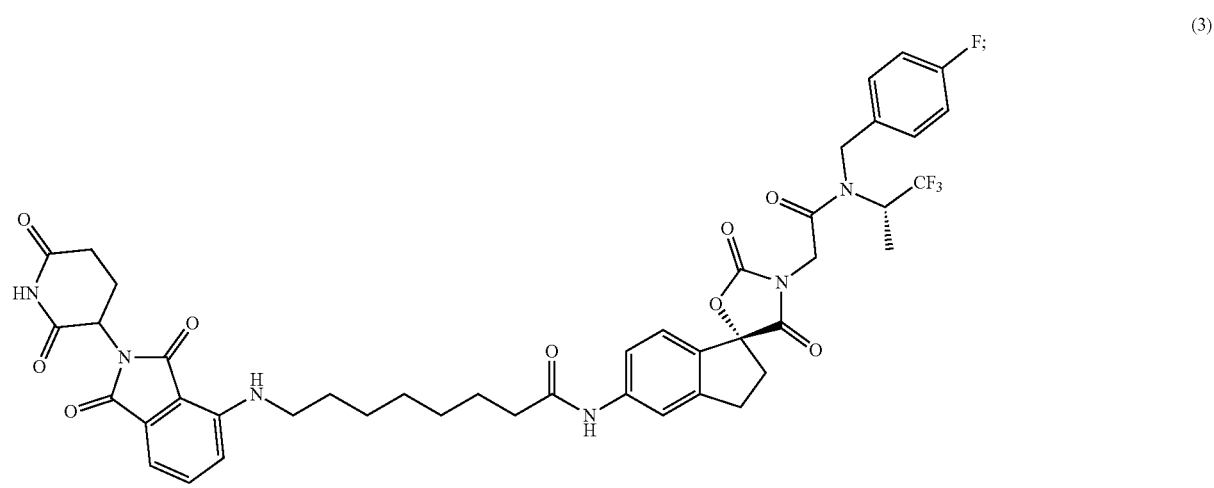
(3)
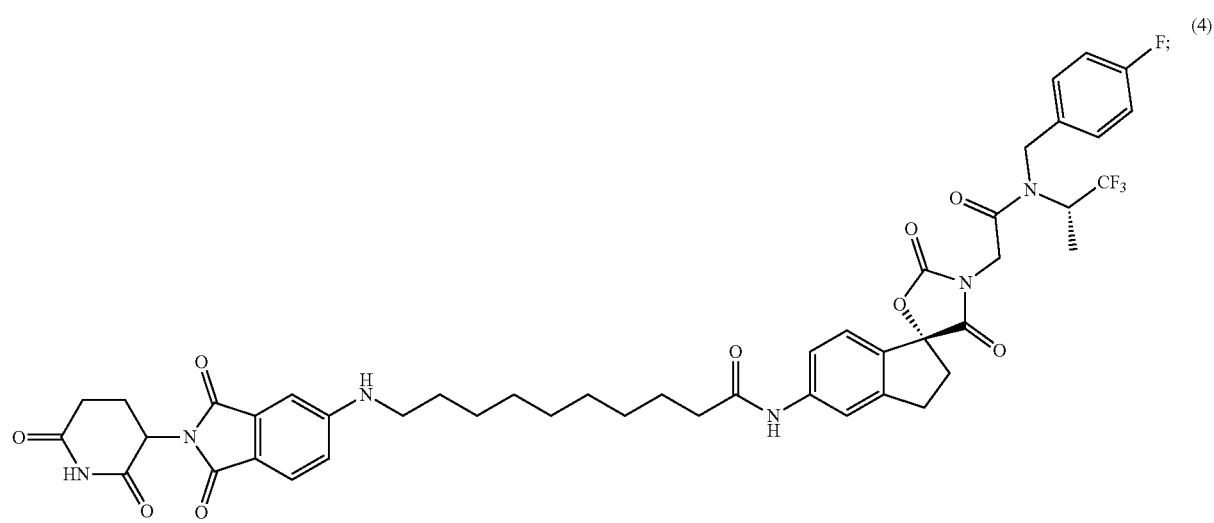
(4)

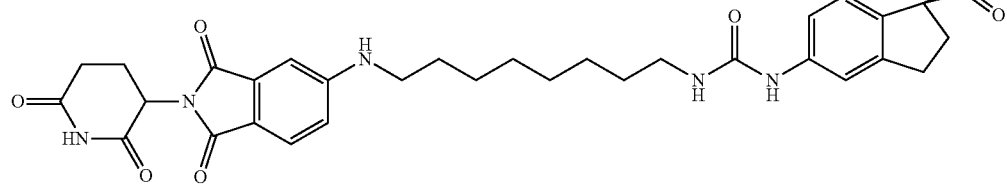
(5)
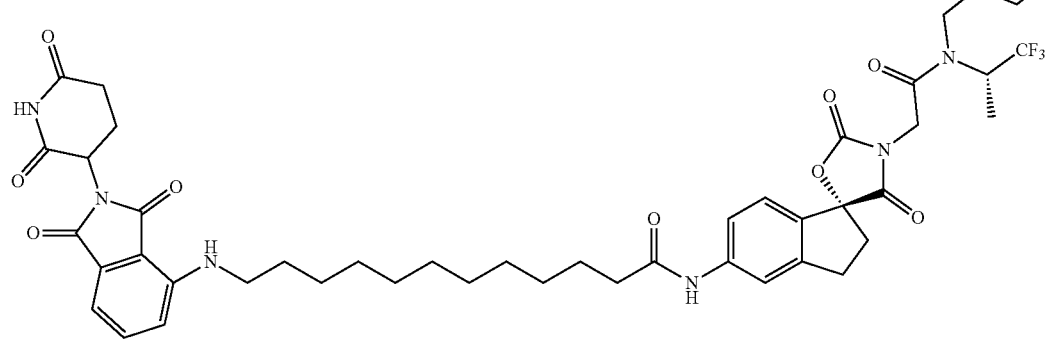
(6)
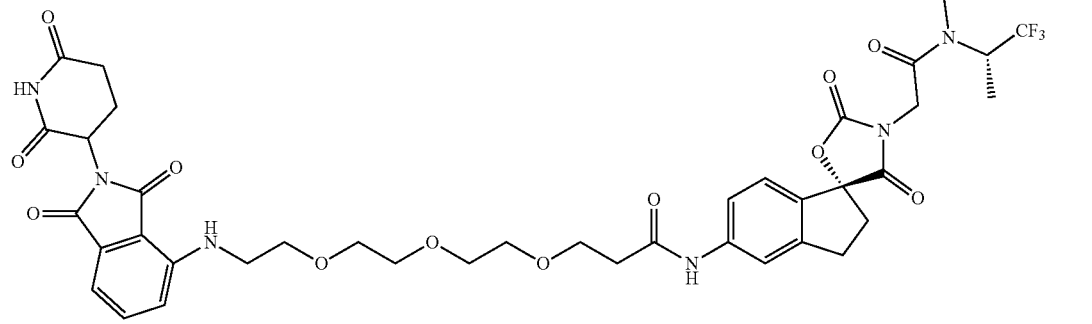
(7)

-continued
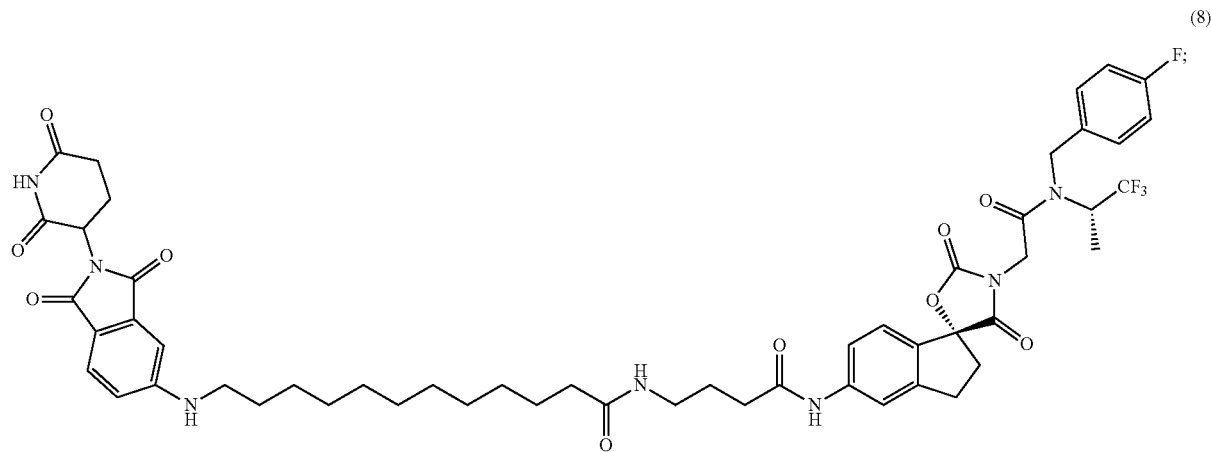
(8)
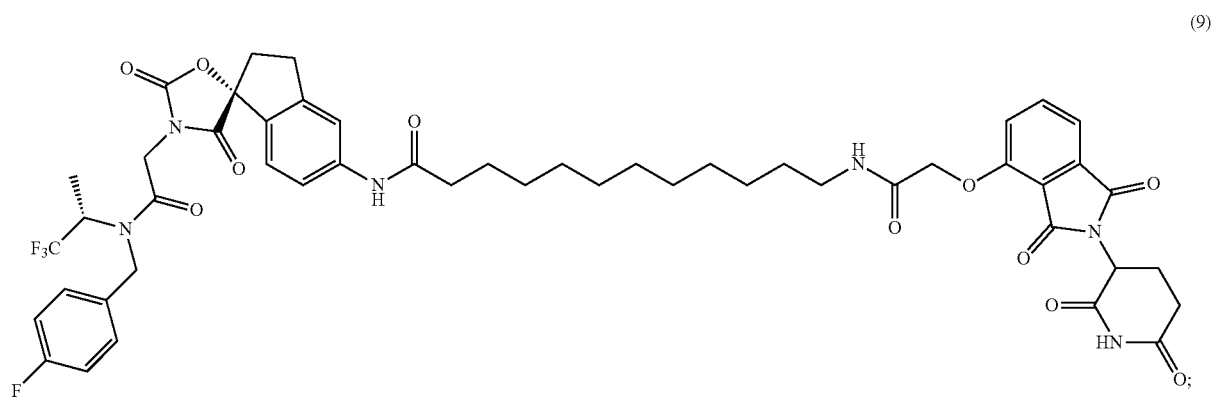
(9)
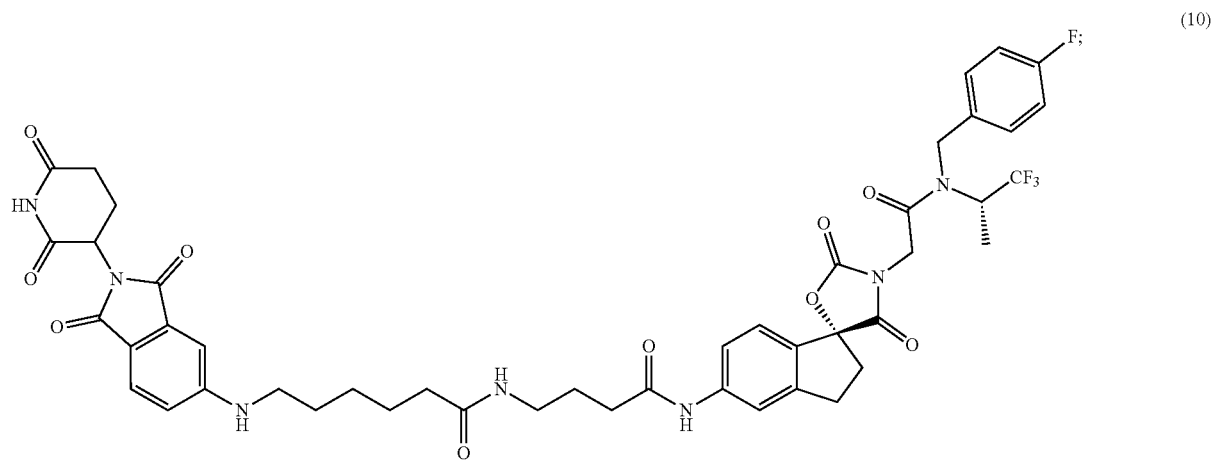
(10)

(11)
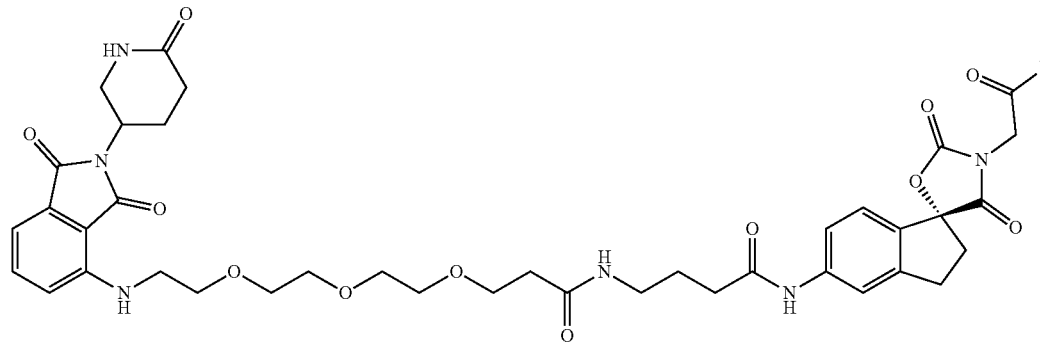
(12)
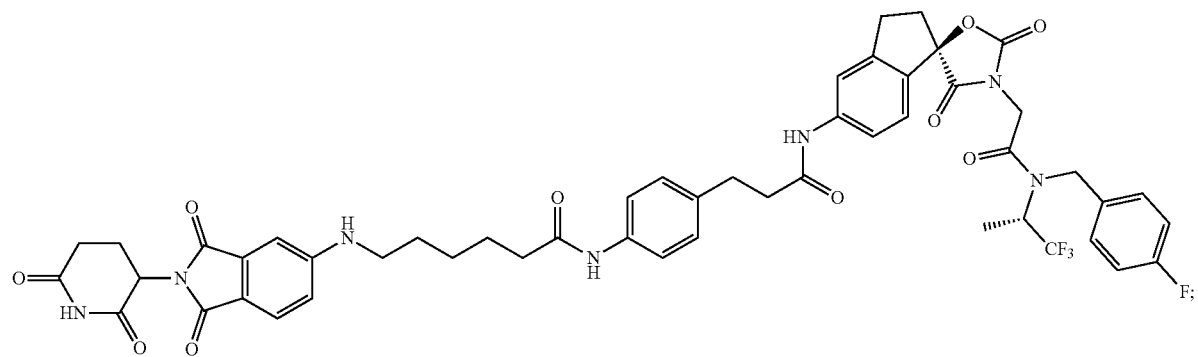
(13)
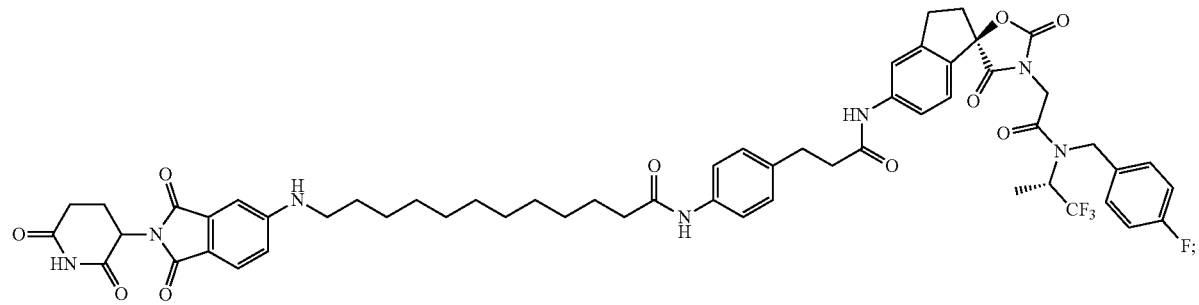
(14)
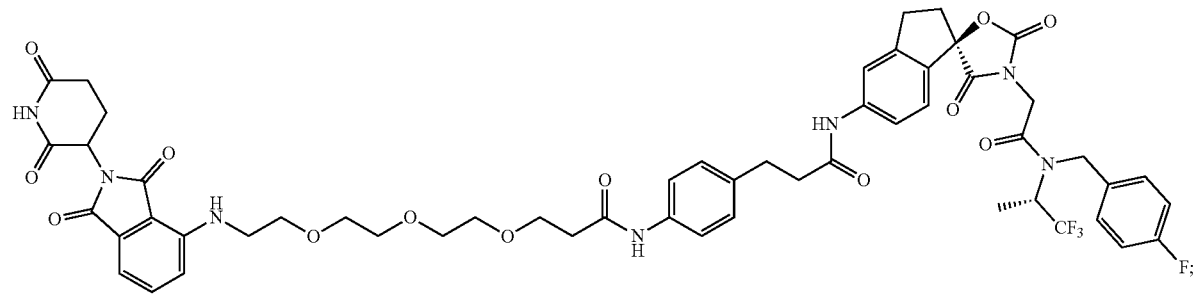

(15)
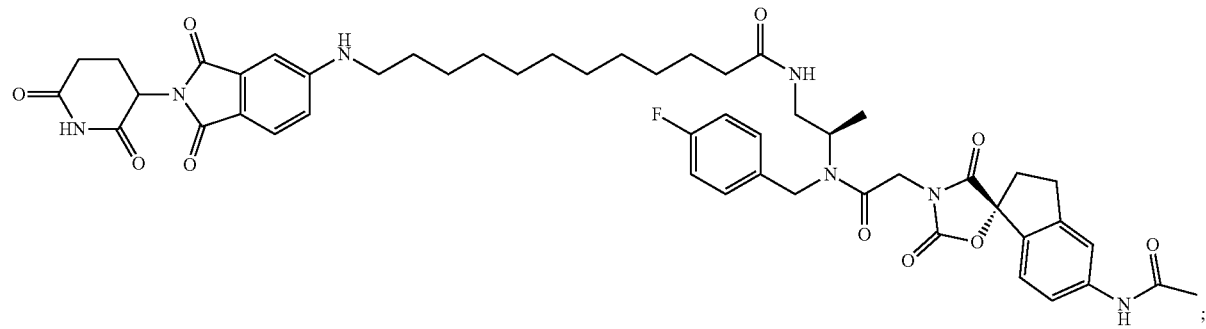
(16)
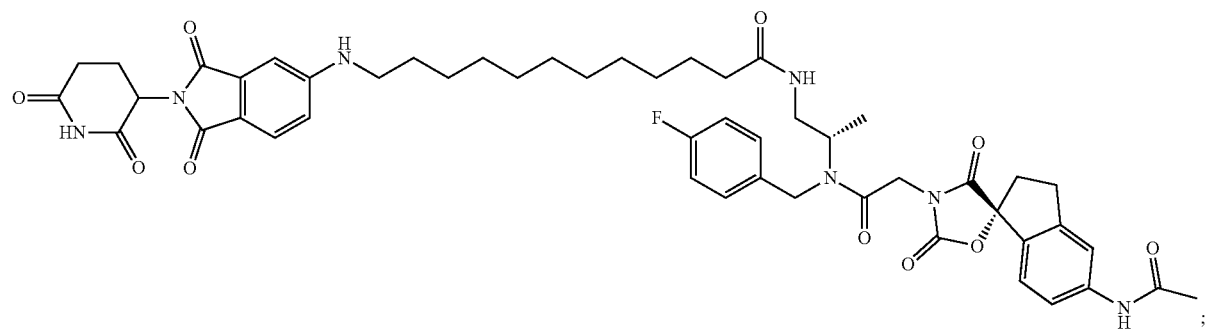
(17)
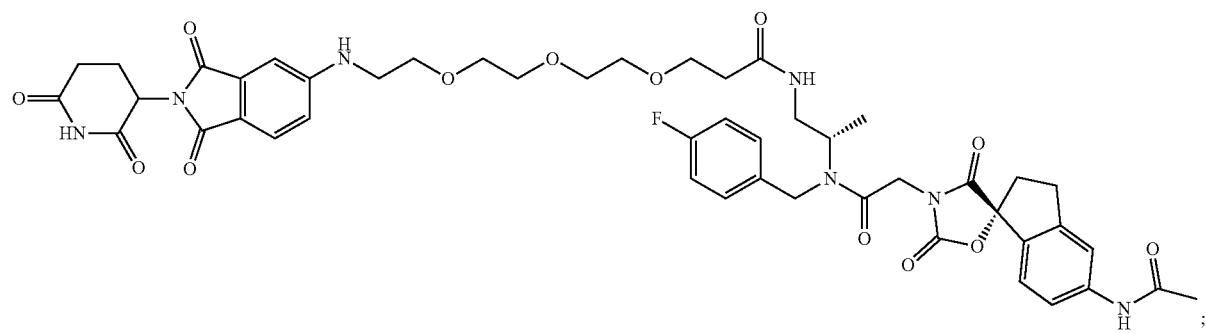
(18)
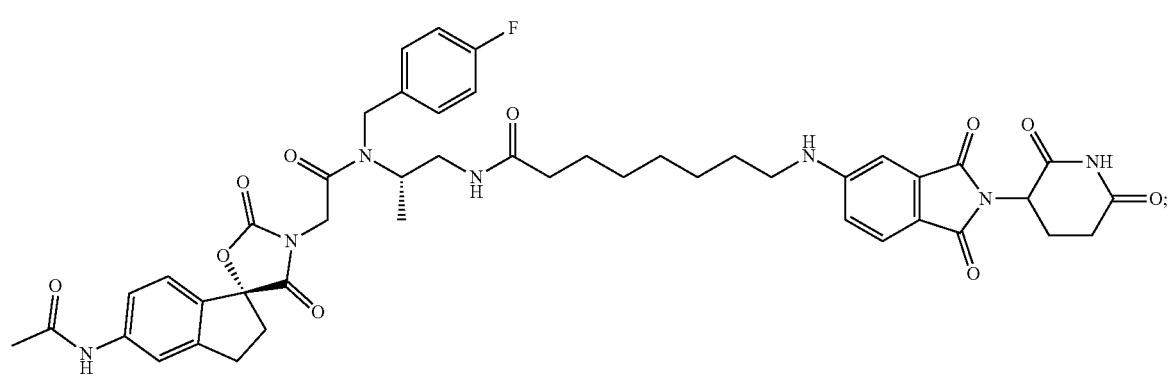

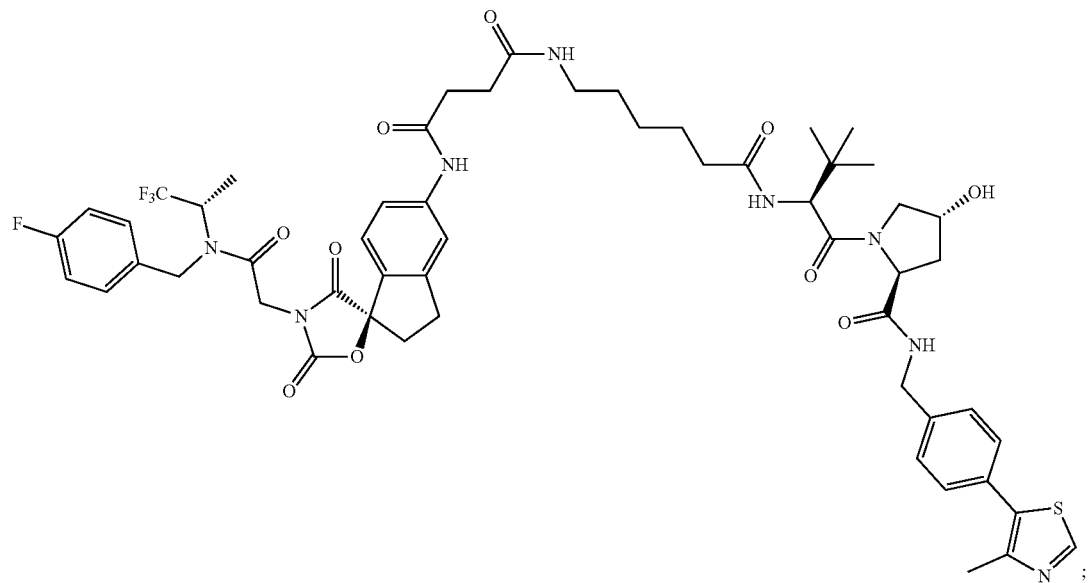
(19)
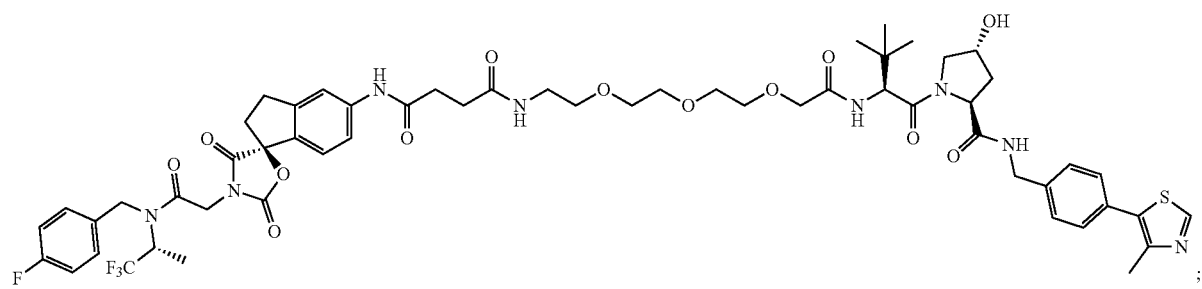
(20)
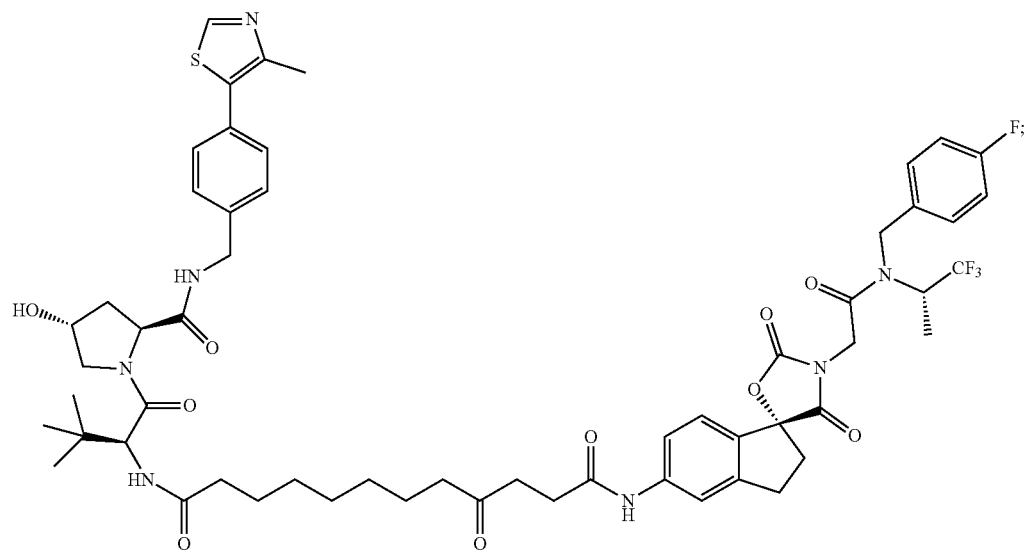
(21)

-continued (22)

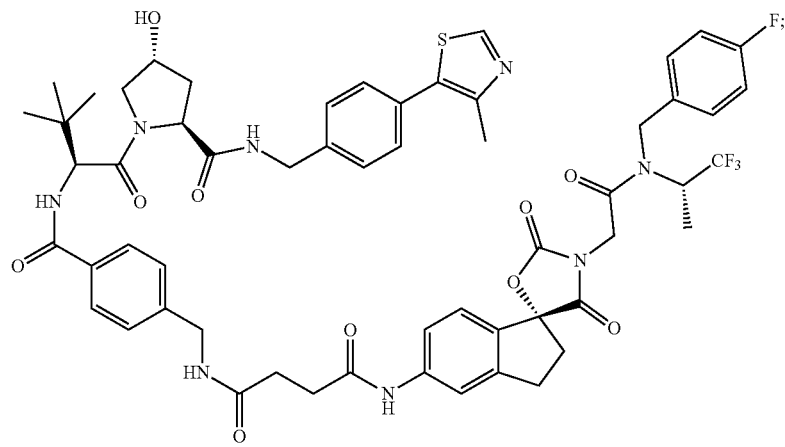

(23)

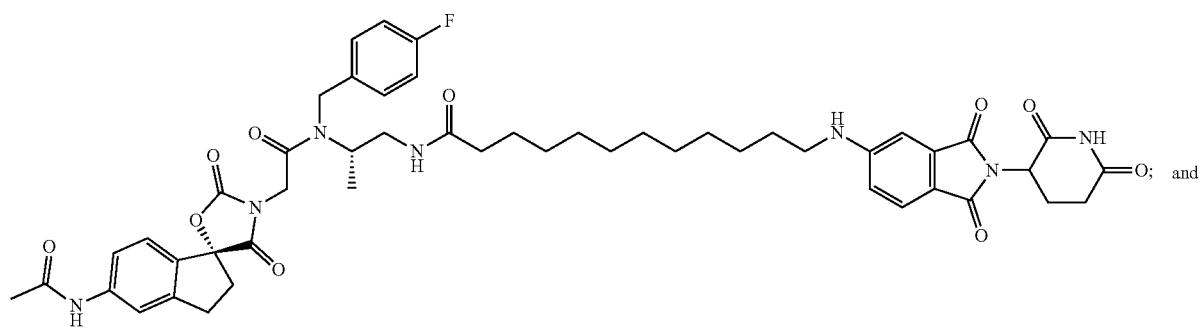
; and (24)

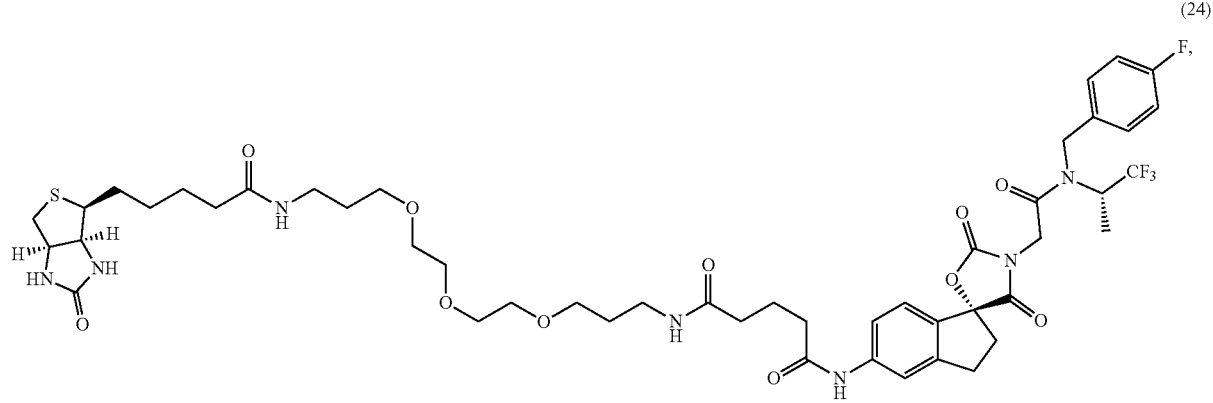

and pharmaceutically acceptable salts and stereoisomers thereof.

Biotinylated Compounds

Another aspect of the present invention is directed to bifunctional compounds that have a structure represented by formula II:

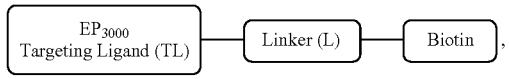,
(II)

wherein the targeting ligand represents a moiety that binds the histone acetyltransferase p300 (also referred to herein as EP300), the linker (which is disclosed above) represents a moiety that covalently connects biotin and the targeting ligand.

Thus in some embodiments, the bifunctional compounds of formula (II) are represented by a structure selected from the group consisting of:

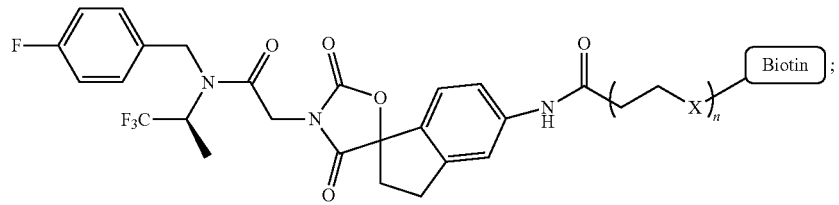
(TL1-L10-1)
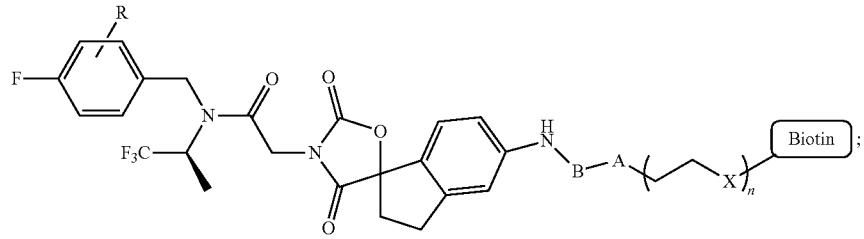
(TL1a-L10-1)
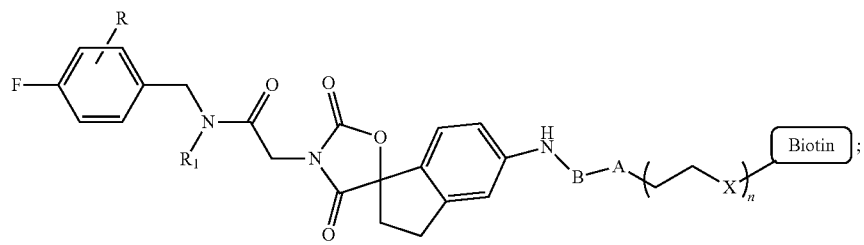
(TL1b-L10-1)
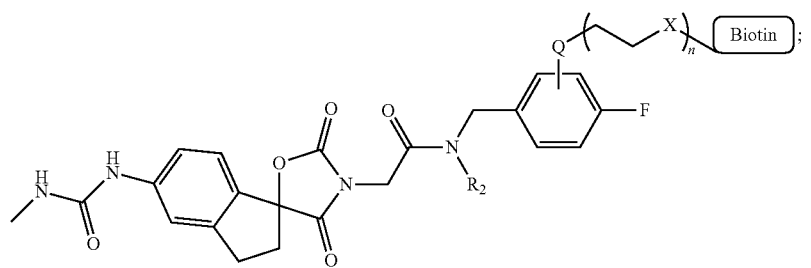
(TL1c-L10-1)
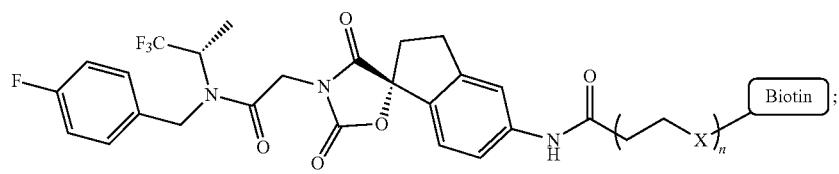
(TL1d-L10-1)
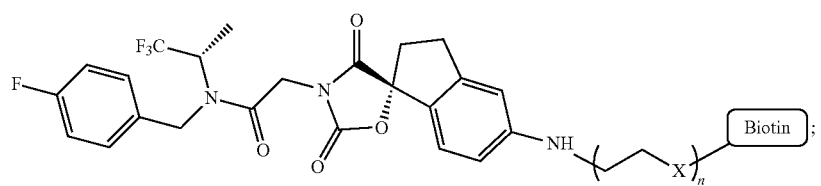
(TL1e-L10-1)

(TL1f-L10-1)
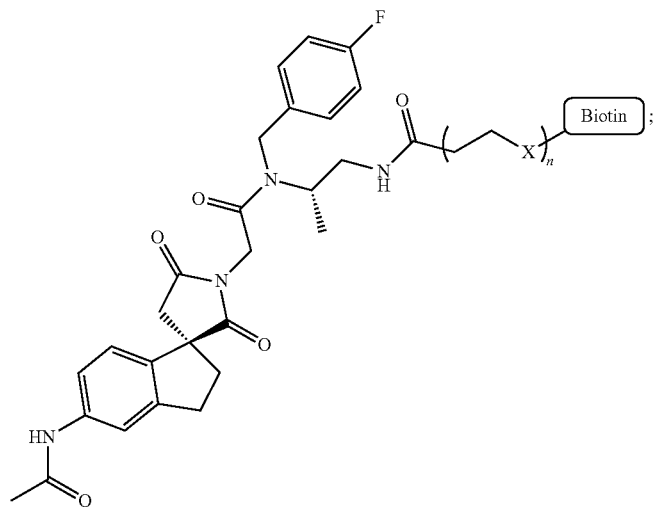
(TL1-L16-1)
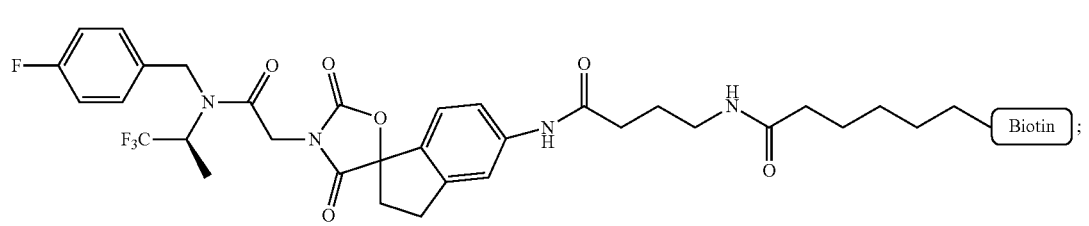
(TL1a-L16-1)
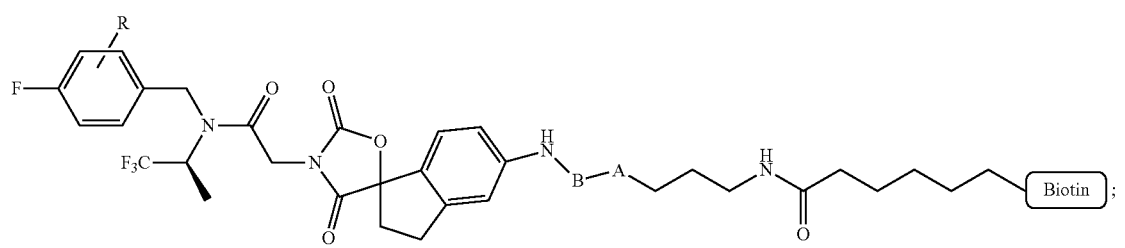
(TL1b-L16-1)
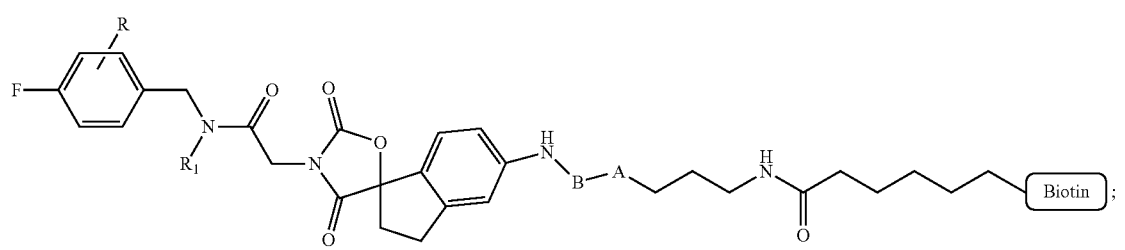
(TL1c-L16-1)
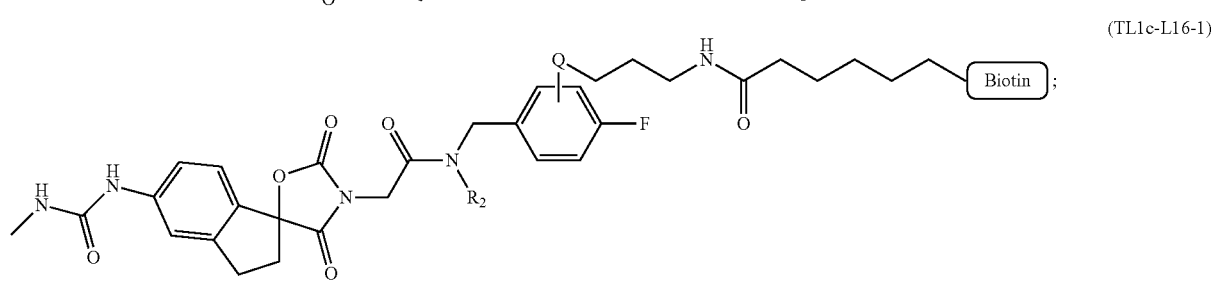

-continued
(TL1d-L16-1)
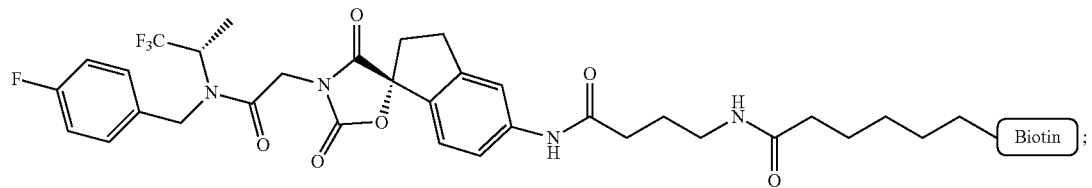
(TL1e-L16-1)
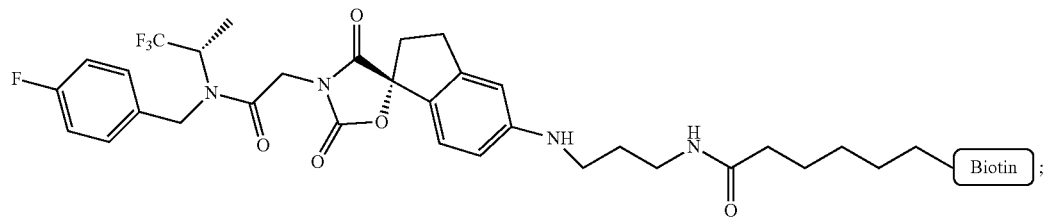
(TL1f-L16-1)
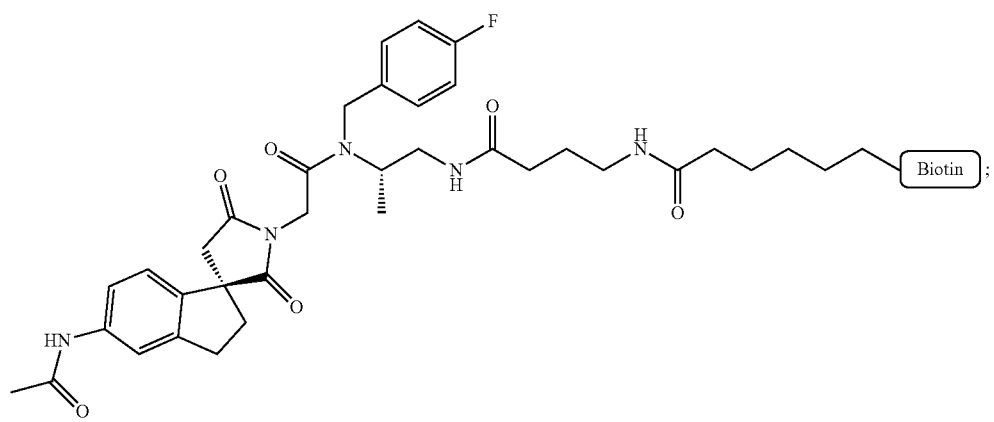
(TL1-L18-1)
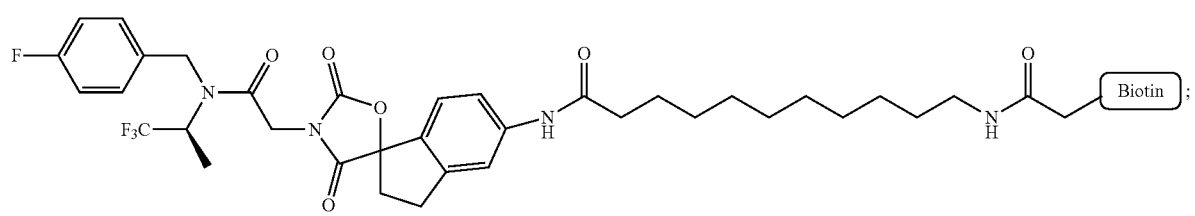
(TL1a-L18-1)
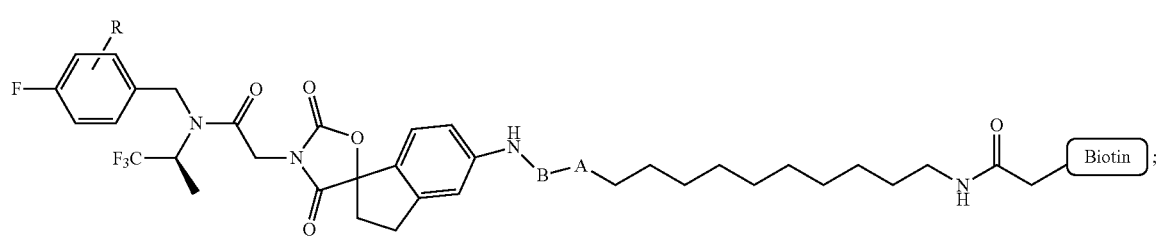
(TL1b-L18-1)
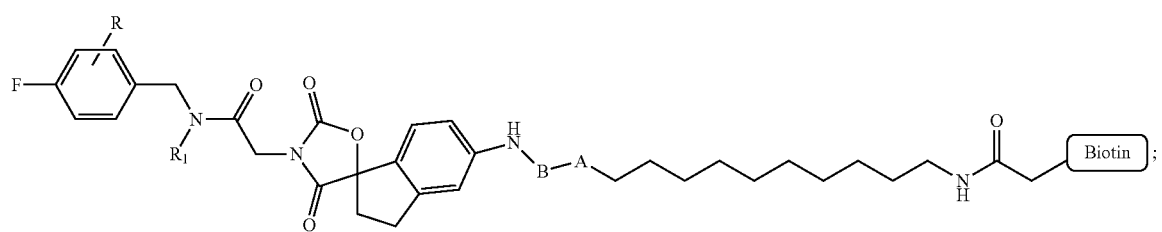

-continued
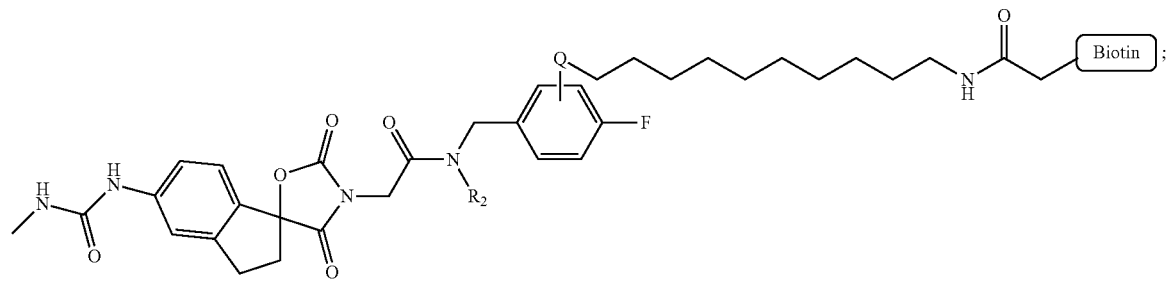
(TL1c-L18-1)
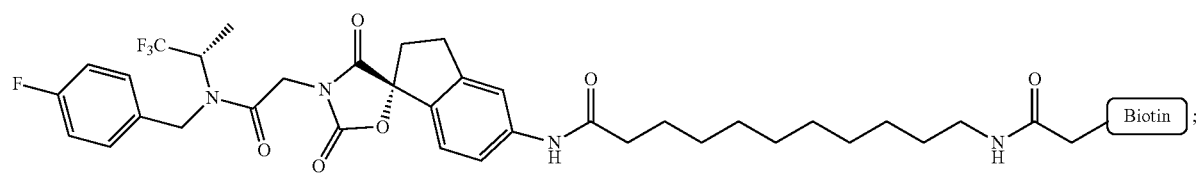
(TL1d-L18-1)
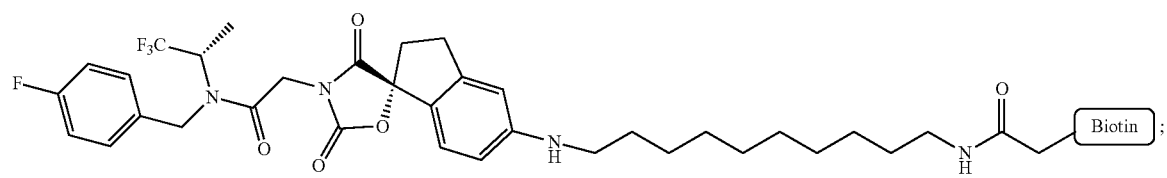
(TL1e-L18-1)
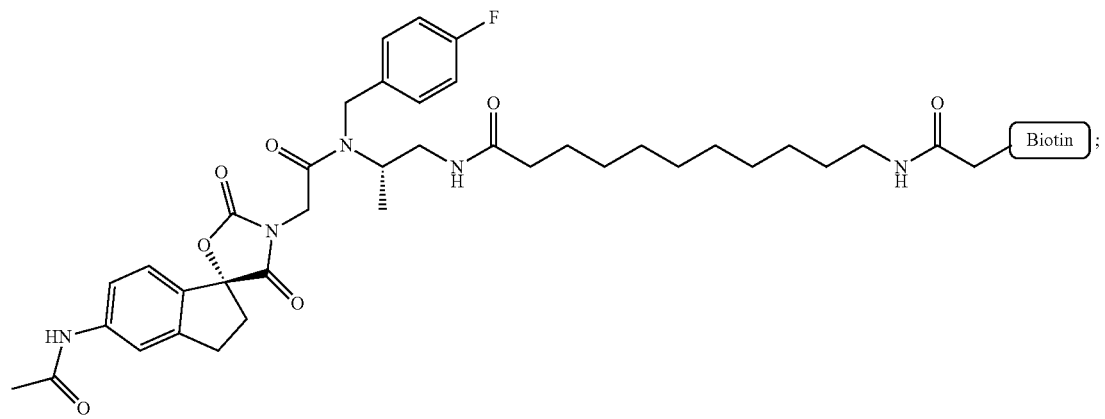
(TL1f-L18-1)
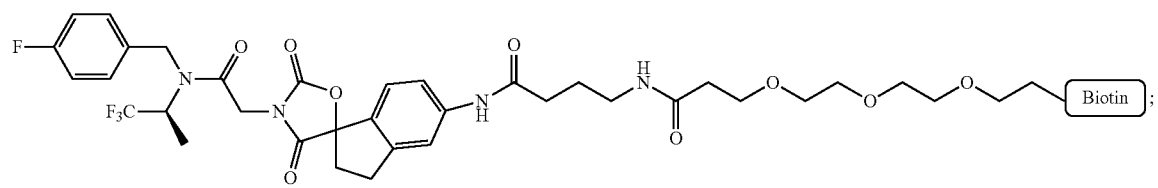
(TL1-L19-1)
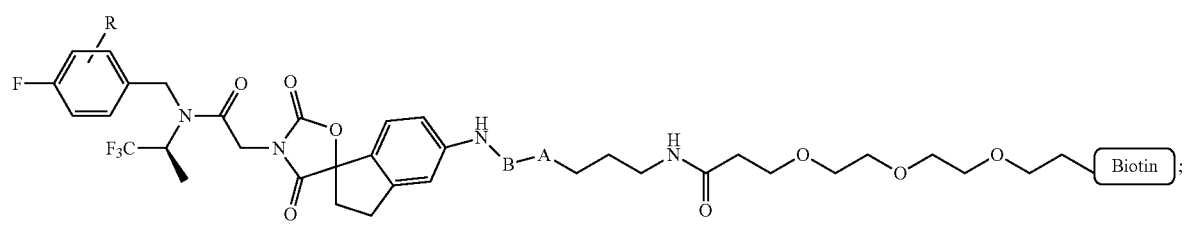
(TL1a-L19-1)

(TL1b-L19-1)
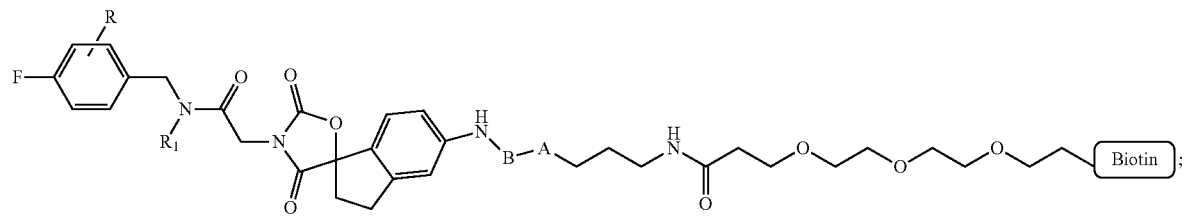
(TL1c-L19-1)
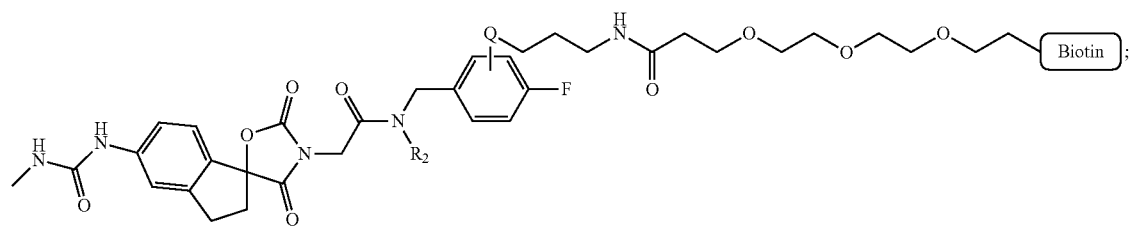
(TL1d-L19-1)
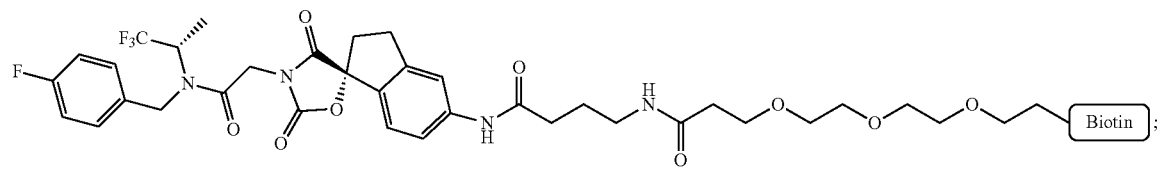
(TL1e-L19-1)
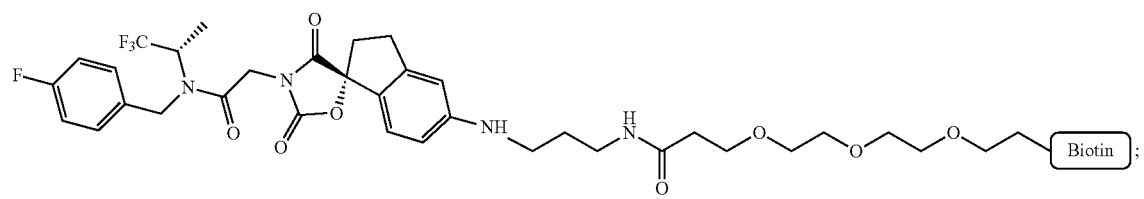
(TL1f-L19-1)
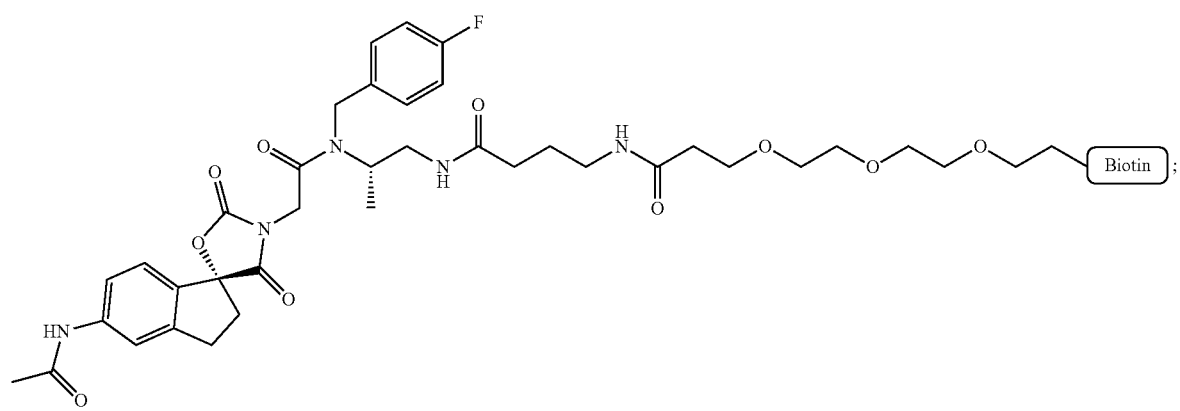
(TL1-L20-1)
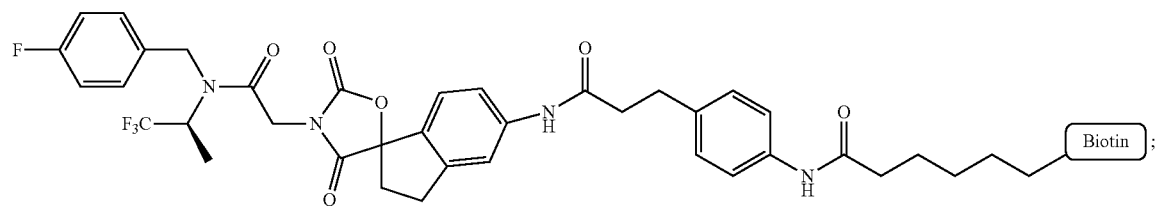

-continued
(TL1a-L20-1)
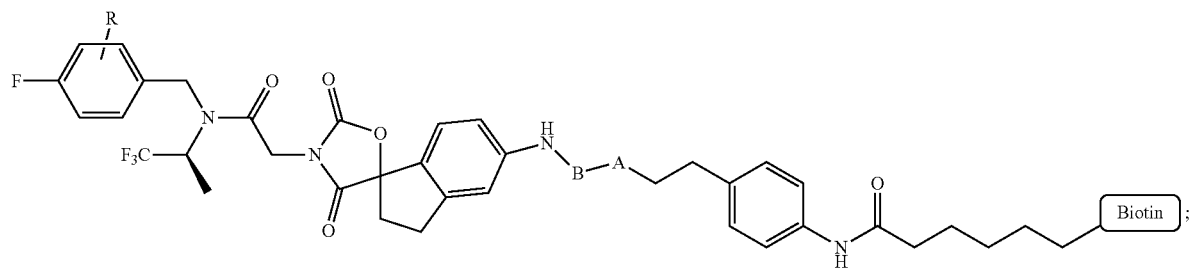
(TL1b-L20-1)
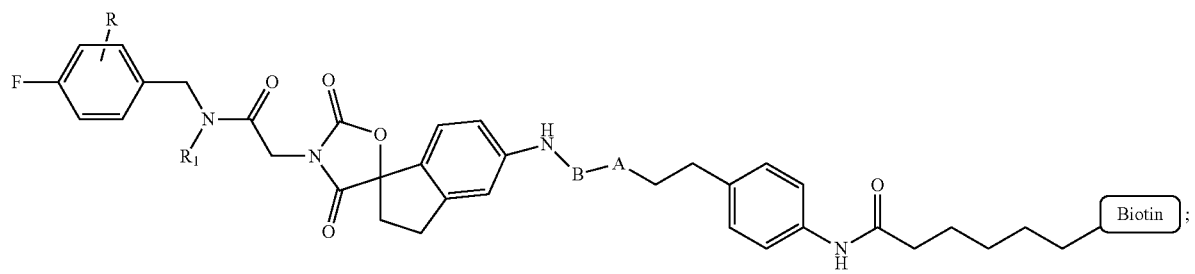
(TL1c-L20-1)
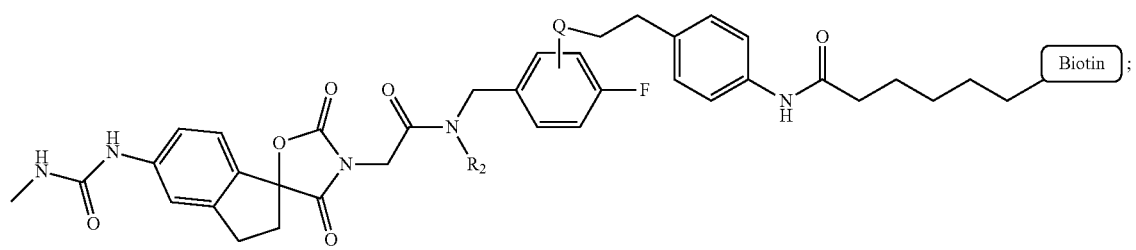
(TL1d-L20-1)
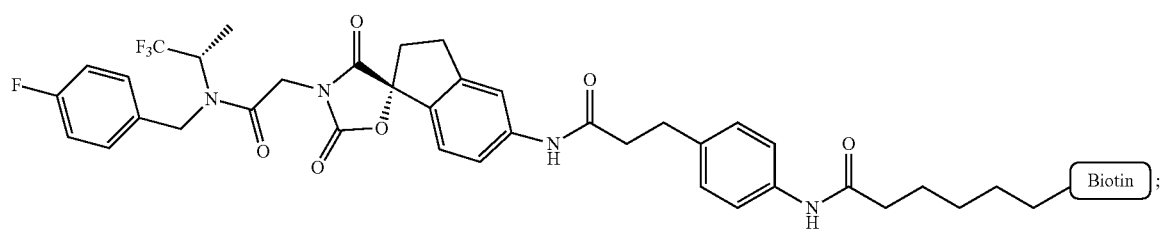
(TL1e-L20-1)
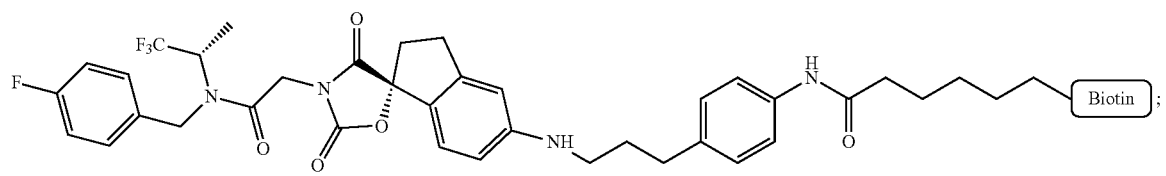

-continued
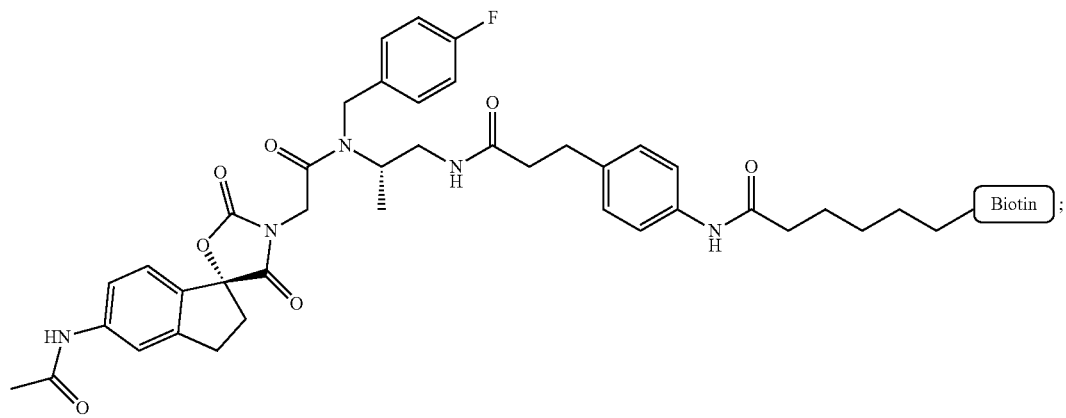
(TL1f-L20-1)
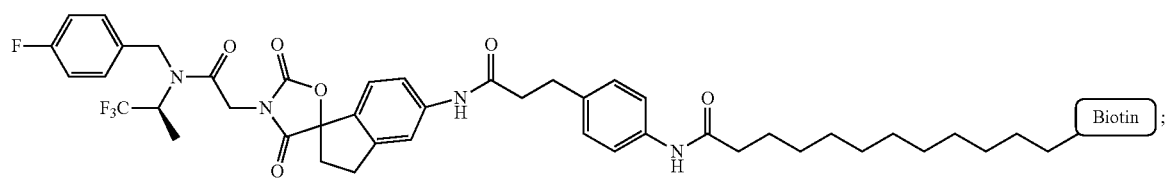
(TL1-L21-1)
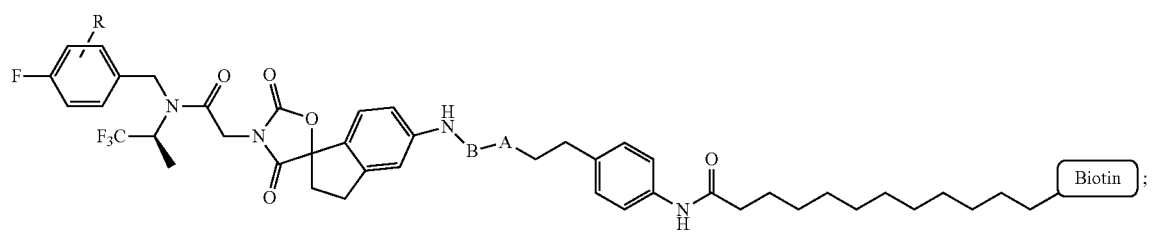
(TL1a-L21-1)
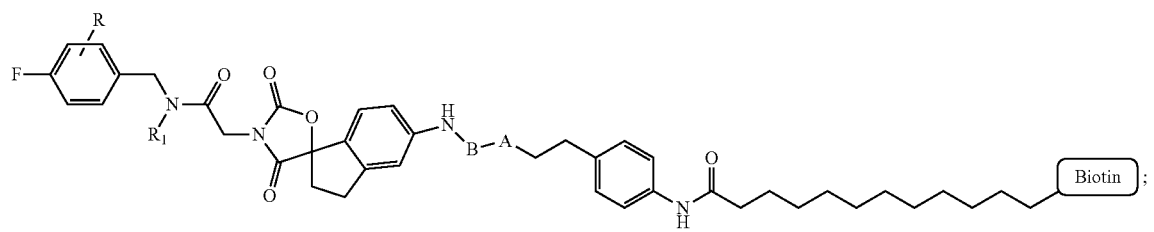
(TL1b-L21-1)
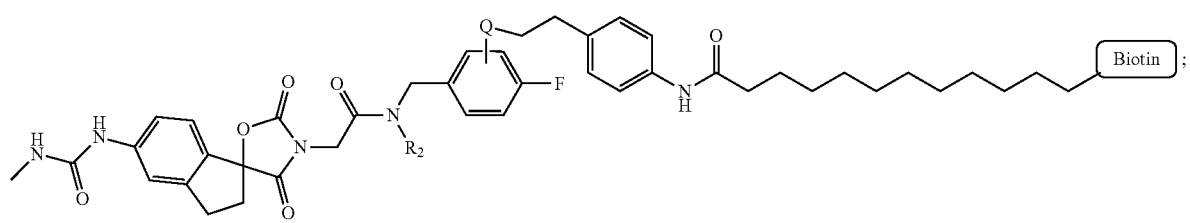
(TL1c-L21-1)
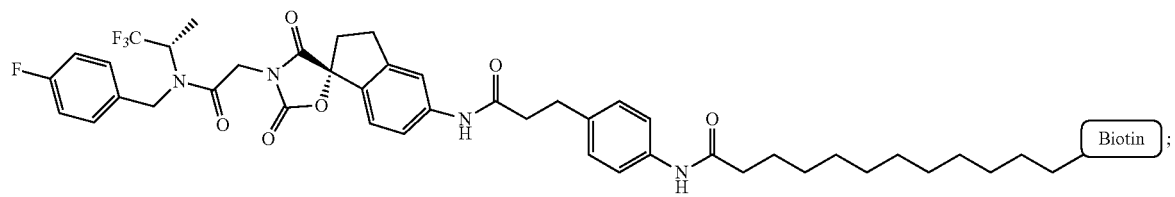
(TL1d-L21-1)

-continued
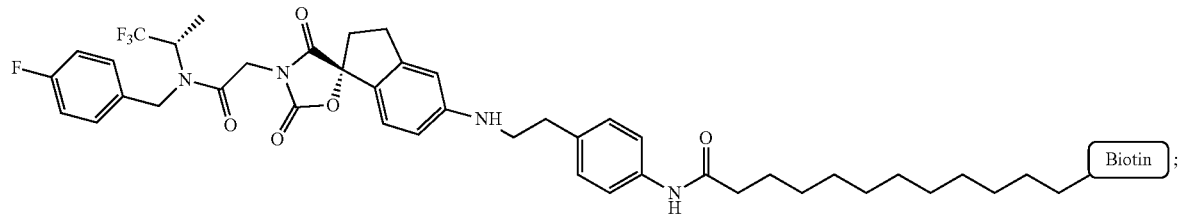
(TL1e-L21-1)
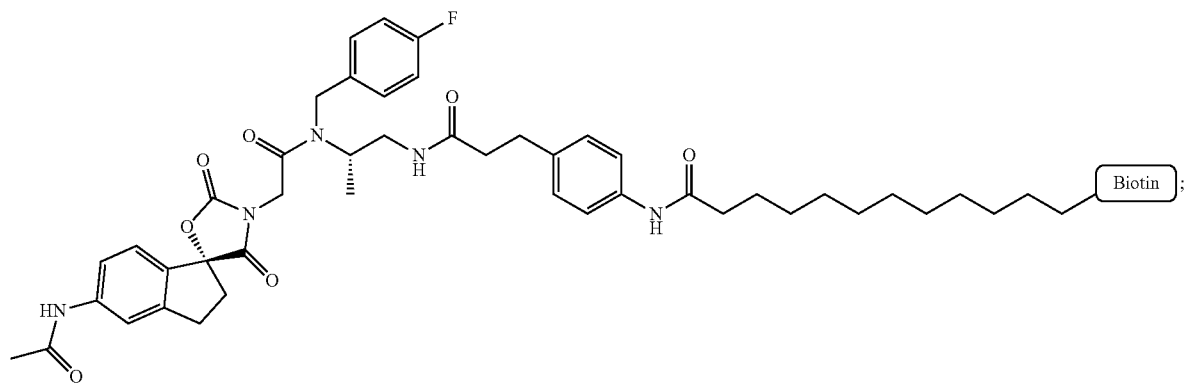
(TL1f-L21-1)
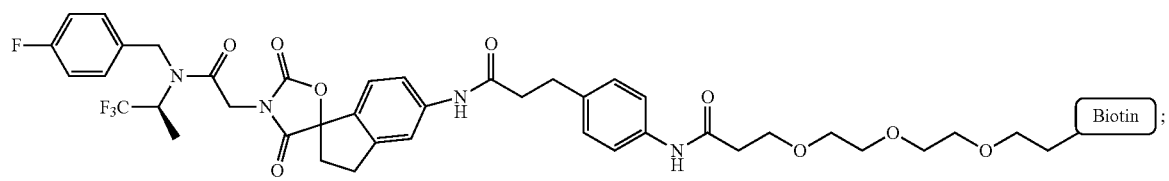
(TL1-L22-1)
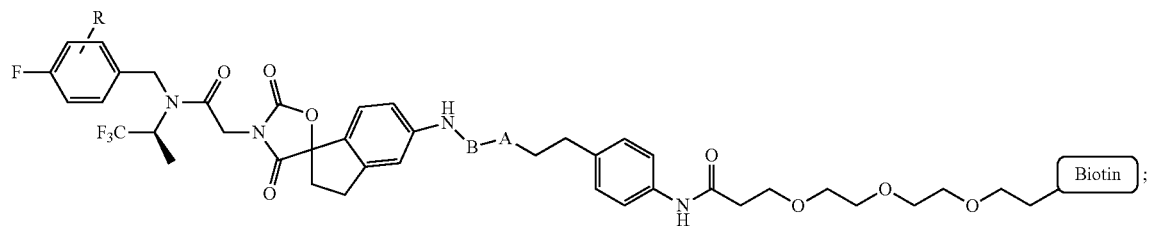
(TL1a-L22-1)
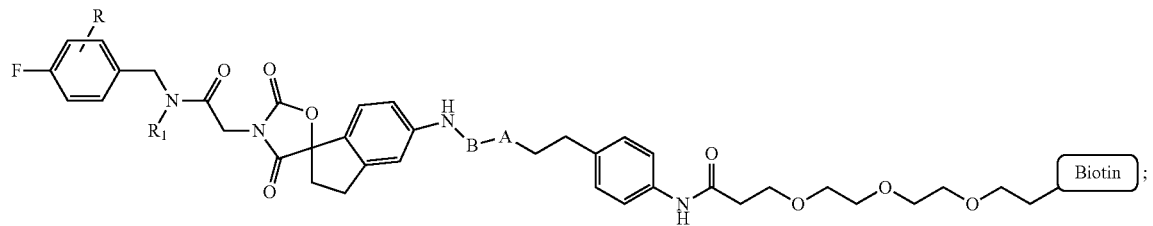
(TL1b-L22-1)
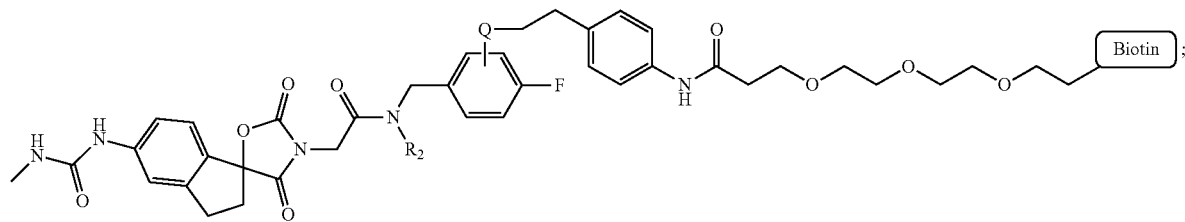
(TL1c-L22-1)

-continued
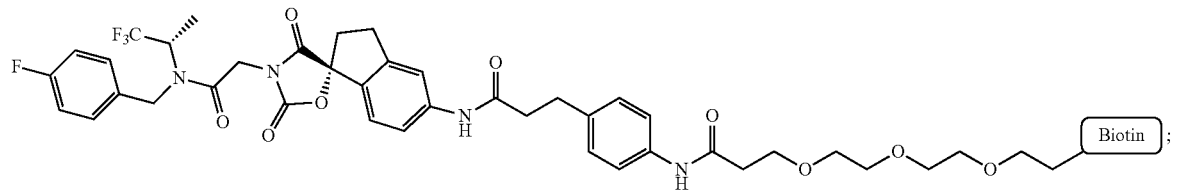
(TL1d-L22-1)
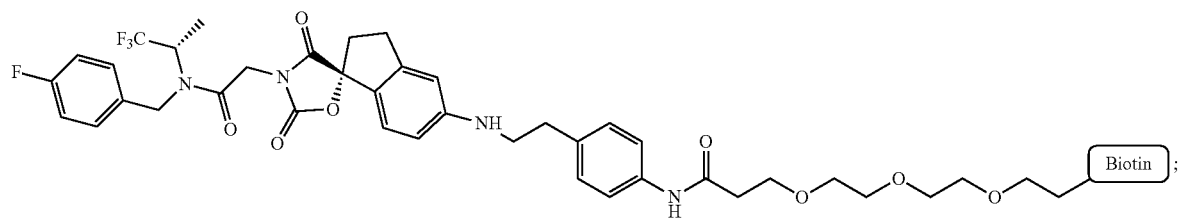
(TL1e-L22-1)
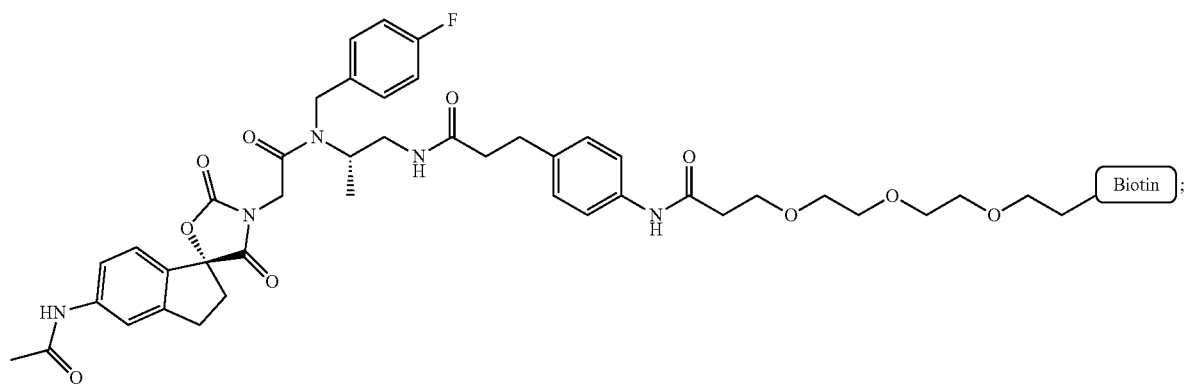
(TL1f-L22-1)
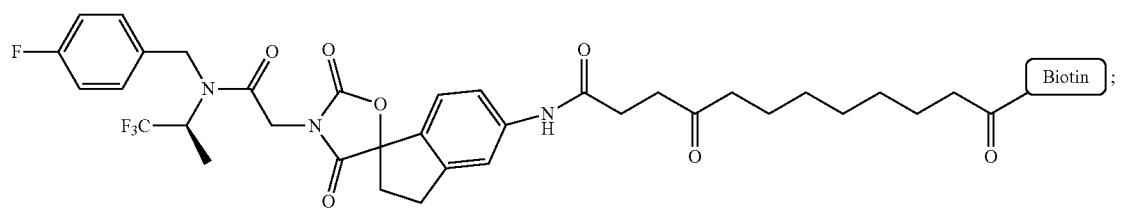
(TL1-L23-1)
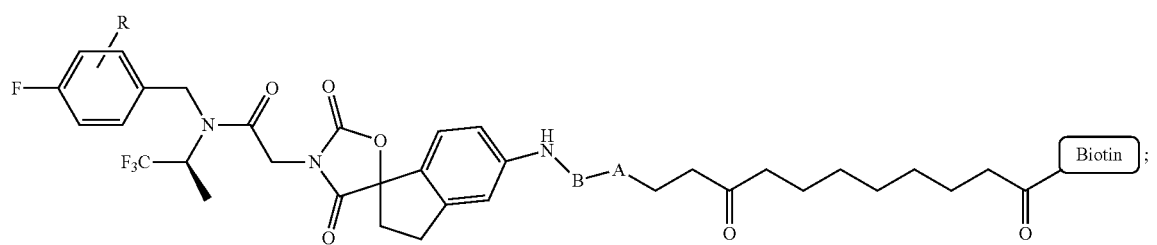
(TL1a-L23-1)
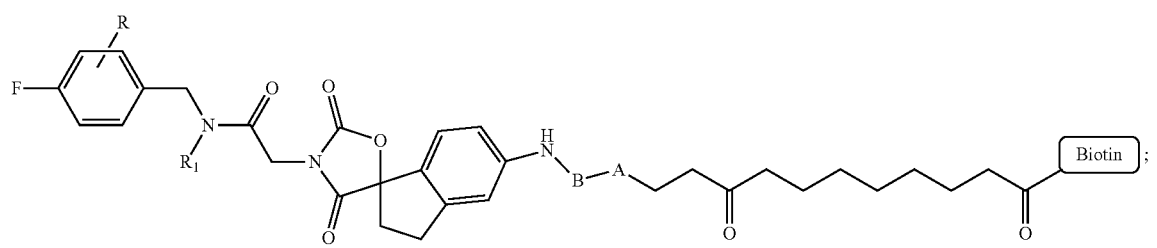
(TL1b-L23-1)

(TL1c-L23-1)
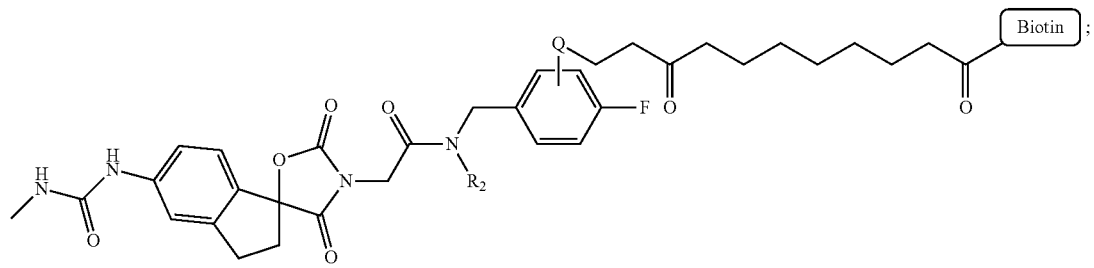
(TL1d-L23-1)
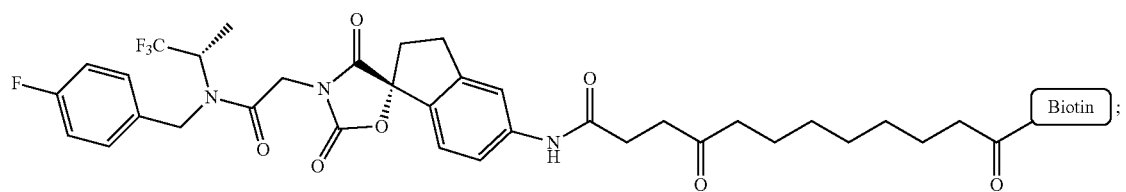
(TL1e-L23-1)
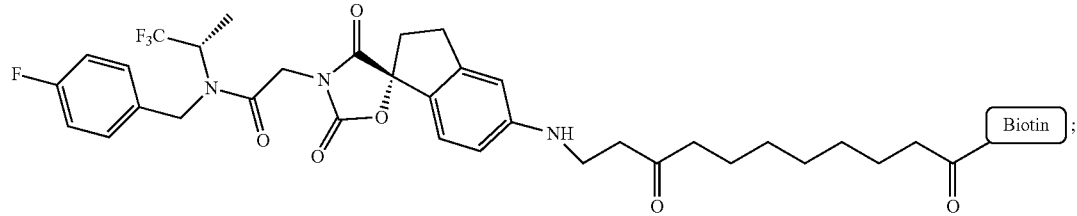
(TL1f-L23-1)
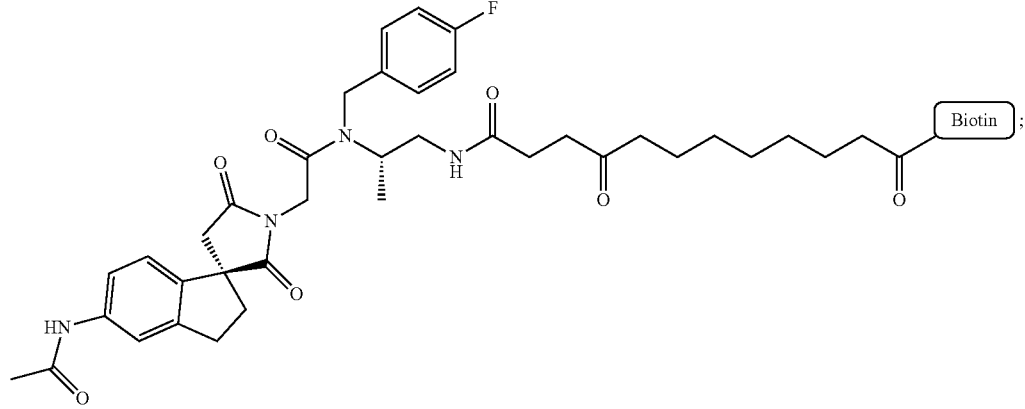
(TL1-L24-1)
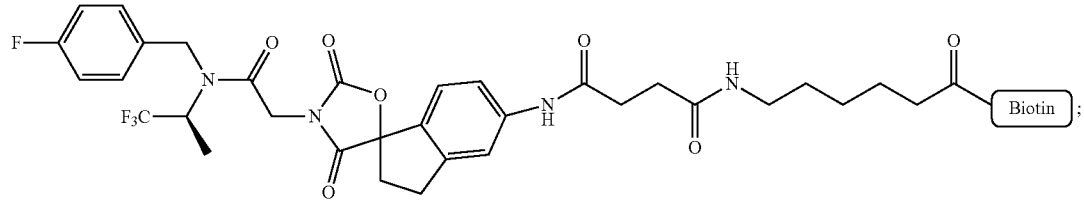
(TL1a-L24-1)
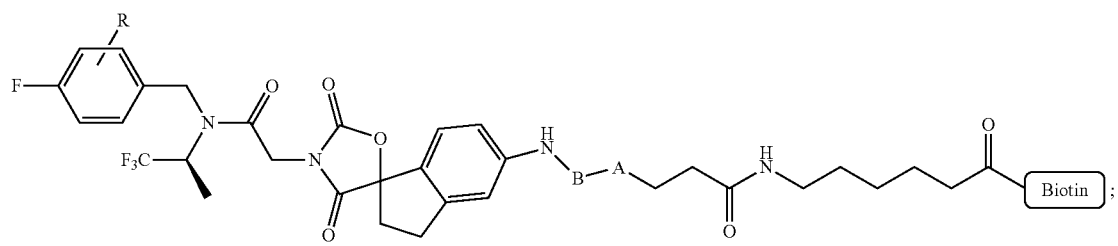

(TL1b-L24-1)
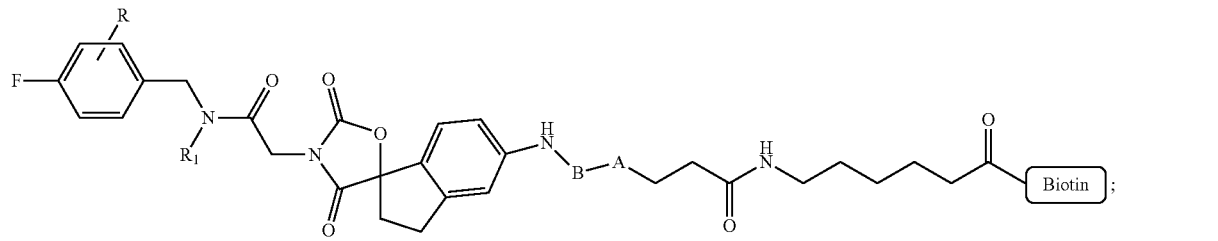
(TL1c-L24-1)
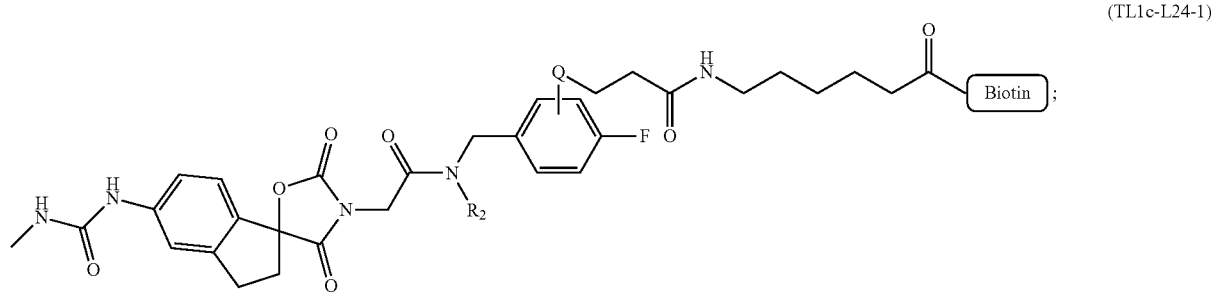
(TL1d-L24-1)
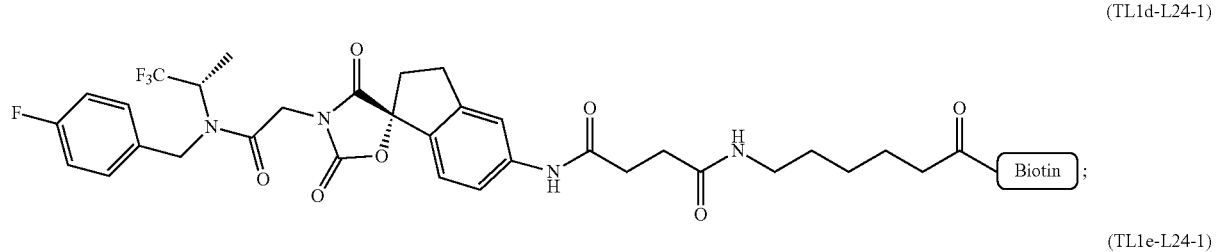
(TL1e-L24-1)
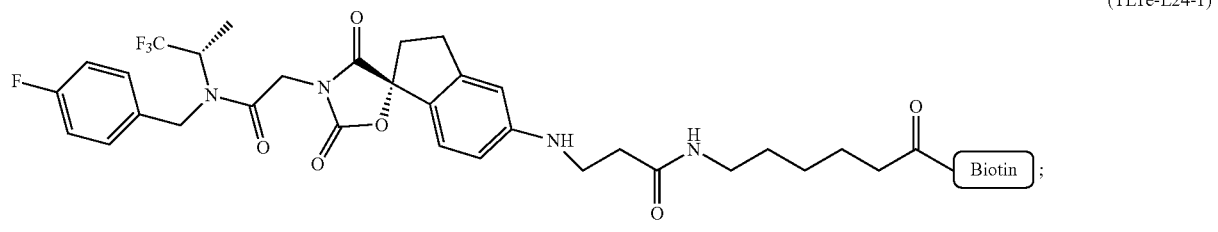
(TL1f-L24-1)
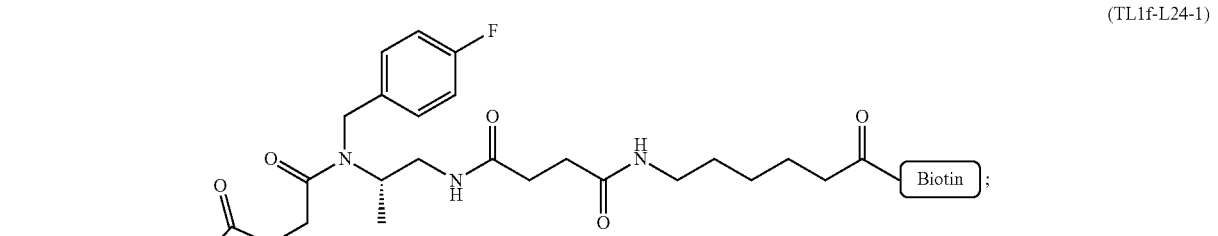
(TL1-L25-1)
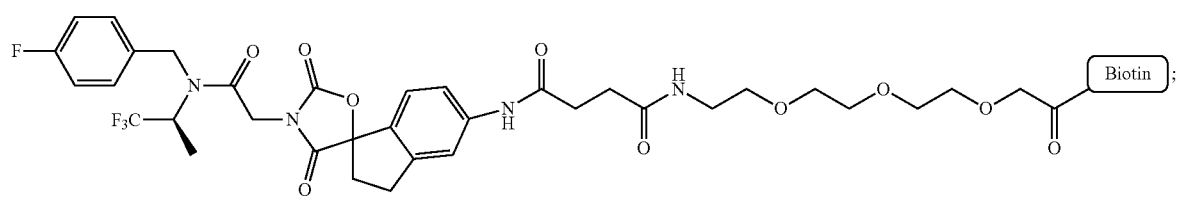

(TL1a-L25-1)
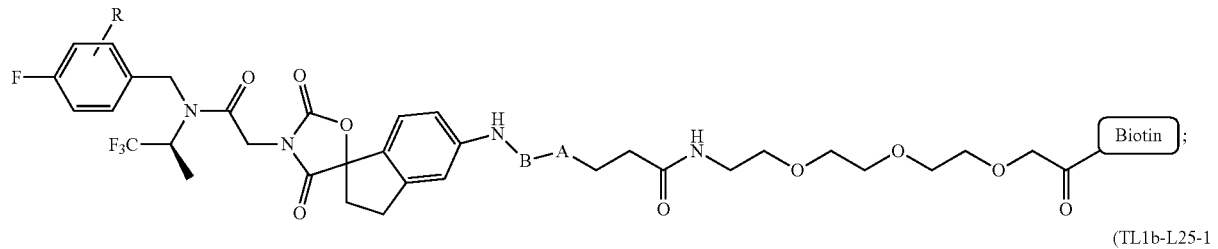
(TL1b-L25-1)
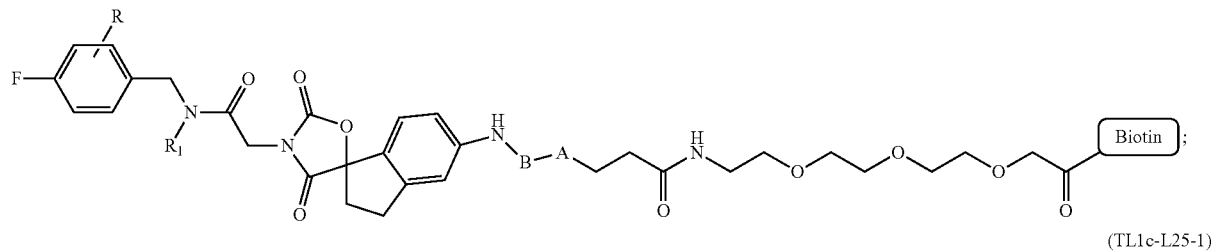
(TL1c-L25-1)
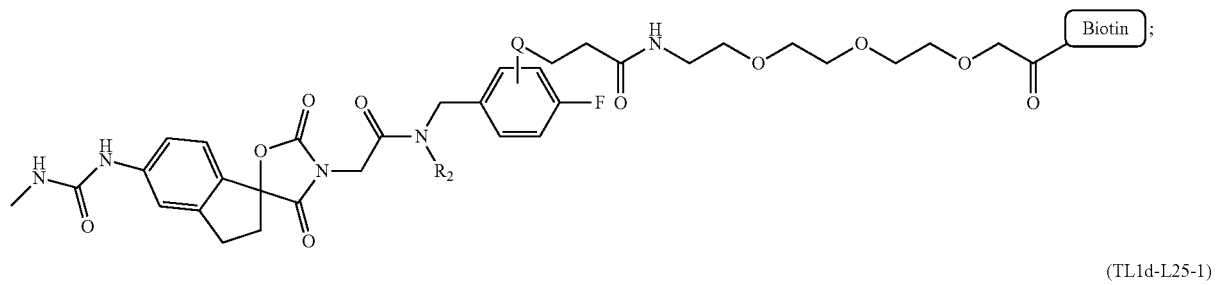
(TL1d-L25-1)
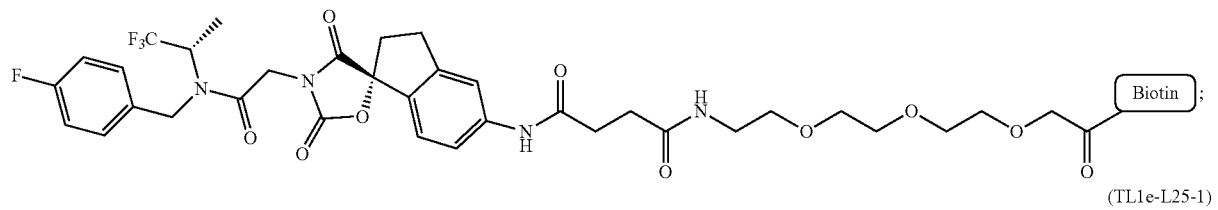
(TL1e-L25-1)
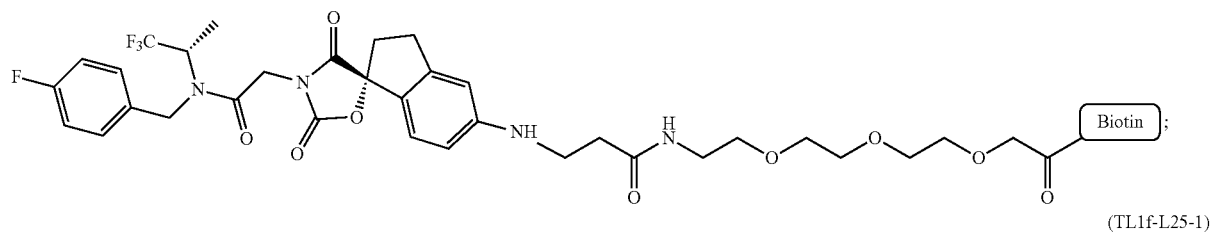
(TL1f-L25-1)
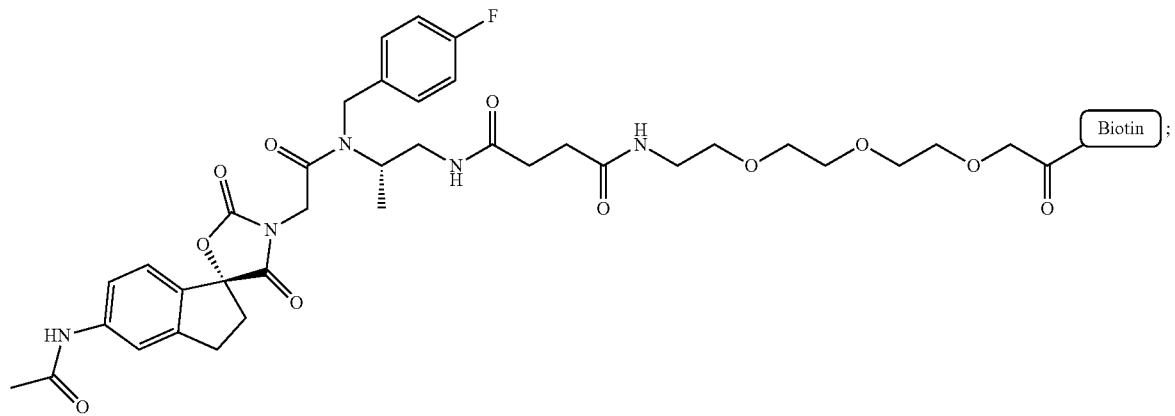

-continued
(TL1-L26-1)
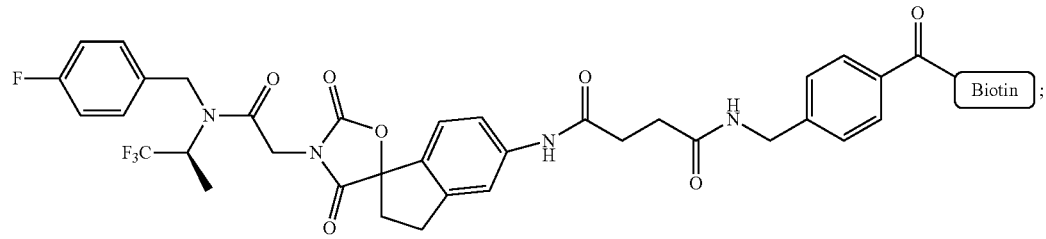
(TL1a-L26-1)
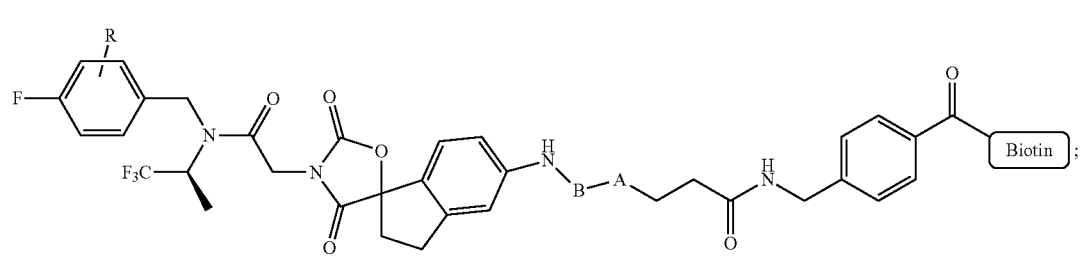
(TL1b-L26-1)
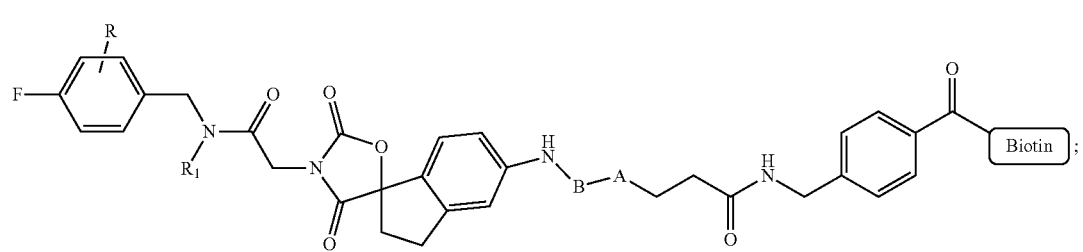
(TL1c-L26-1)
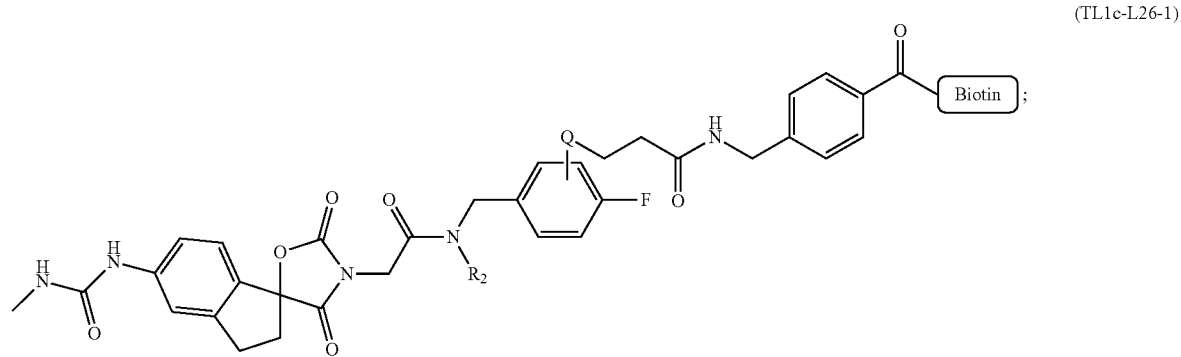
(TL1d-L26-1)
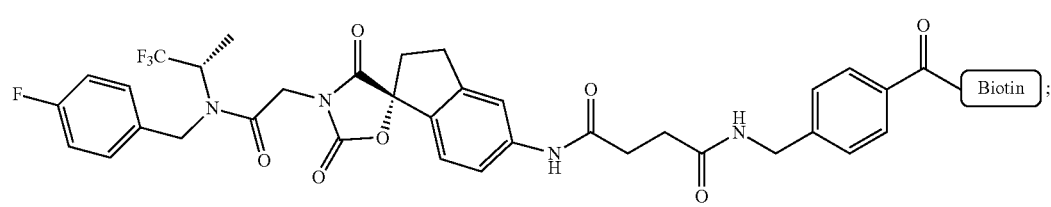
(TL1e-L26-1)
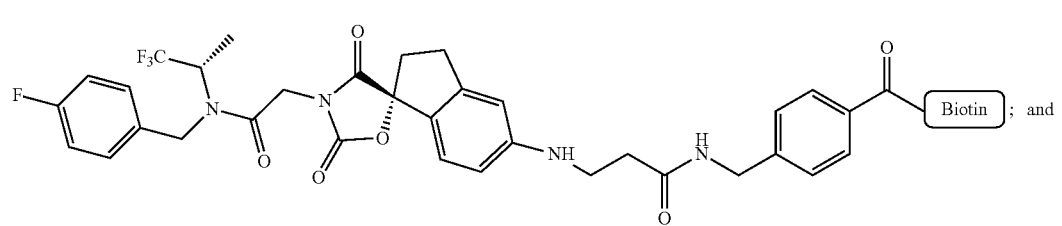
and -continued (TL1f-L26-1)

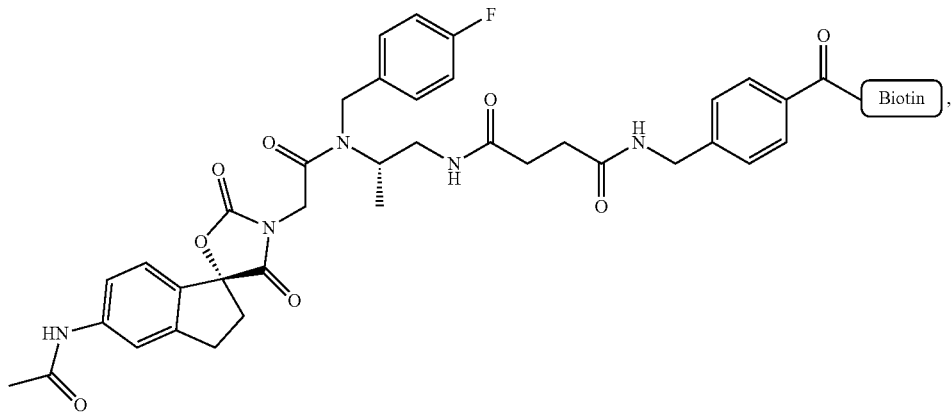

or a salt or stereoisomer thereof.

Bifunctional compounds of formula (I) and formula (II) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

Bifunctional compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R—) or (S—) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R—) form is considered equivalent to administration of the compound in its (S—) form. Accordingly, the compounds of the present invention may be made and used in the form of individual isomers and substantially free of other isomers, or in the form of a mixture of various isomers, e.g., racemic mixtures of stereoisomers.

In some embodiments, the bifunctional compound of formula (I) or formula (II) is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances.

In addition, the compounds of formula (I) embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

In another aspect, the present invention is directed to methods for making the bifunctional compounds of the present invention, or pharmaceutically acceptable salts or stereoisomers thereof. Broadly, the inventive compounds or pharmaceutically-acceptable salts or stereoisomers thereof, may be prepared by any process known to be applicable to the preparation of chemically related compounds. The compounds of the present invention will be better understood in connection with the synthetic schemes that described in various working examples and which illustrate nonlimiting methods by which the compounds of the invention may be prepared.

Pharmaceutical Compositions

Another aspect of the present invention is directed to a pharmaceutical composition that includes a therapeutically effective amount of a bifunctional compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may also include one or more pharmaceutically acceptable excipients.

Broadly, bifunctional compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the bifunctional compounds of formula (I) are formulated for oral or intravenous administration (e.g., systemic intravenous injection).

Accordingly, bifunctional compounds of formula (I) may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bifunctional compounds of formula (I) may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of formula (I) of the present invention may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The bifunctional compounds of formula (I) may be formulated for buccal or sublingual administration, examples of which include tablets, lozenges and gels.

The bifunctional compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bifunctional compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bifunctional compound of formula (I) or a pharmaceutically acceptable salt or a stereoisomer thereof, or a composition including a bifunctional compound of formula (I) or a pharmaceutically acceptable salt or a stereoisomer thereof, effective in producing the desired therapeutic response in a particular patient suffering from a disease or disorder by aberrant EP300 activity. The term "therapeutically effective amount" thus includes the amount of the compound of the invention or a pharmaceutically acceptable salt or a stereoisomer thereof, that when administered, induces a positive modification in the disease or disorder to be treated (e.g., to selectively inhibit/degrade EP300), or is sufficient to prevent development or progression of the disease or disorder, or alleviate to some extent, one or more of the symptoms of the disease or disorder being treated in a subject, or which simply kills or inhibits the growth of diseased (e.g., neuroblastoma) cells, or reduces the amount of EP300 in diseased cells.

The total daily dosage of a bifunctional compound of formula (I) and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, *Goodman and Gilman's The Pharmacological Basis of Therapeutics*, 10th Edition, A. Gilman, J. Hardman and L. Limbird, eds., McGraw-Hill Press, 155-173, 2001).

Bifunctional compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg).

In some embodiments, the amount of a bifunctional compound of formula (I) that is administered will be dependent on the patient being treated, the severity of the disorder, the rate of administration, the disposition of the compound, and the discretion of the prescribing physician. Dosages range from about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, the dosage levels below the lower limit of the aforesaid range may be more than adequate, while in other cases still larger doses may be used without causing any harmful side effect.

Methods of Use

In some aspects, the present invention is directed to methods of treating diseases or disorders involving aberrant (e.g., dysfunctional or dysregulated) EP300 activity, that entails administration of a therapeutically effective amount of a bispecific compound formula (I) or a pharmaceutically acceptable salt or stereoisomer thereof, to a subject in need thereof.

The diseases or disorders may be said to be characterized or mediated by aberrant EP300 or MYC activity (e.g., elevated levels of EP300 or otherwise functionally abnormal EP300 relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health.

In some embodiments, compounds of the application may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g., hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with the bifunctional compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 rearrangement, lung adenocarcinoma, and squamous cell lung carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, the compounds or pharmaceutically acceptable salts or stereoisomers of the present invention are disease or disorder is high-risk neuroblastoma (NB).

In some embodiments, the disease or disorder is acute myeloid leukemia (AML), multiple myeloma (MM), melanoma, rhabdomyosarcoma, or diffuse large B cell lymphoma. In other embodiments, the disease or disorder is small solid tumor. In other embodiments, the disease or disorder is colon cancer, rectum cancer, stomach cancer, breast cancer or pancreatic cancer.

The bifunctional compounds of formula (I) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but who became intolerant to the particular treatment. Therapy may also be given as an adjuvant treatment, i.e., to prevent reoccurrence of cancer in patients with no currently detectable disease or after surgical removal of a tumor. Thus, in some embodiments, the bifunctional compounds may be administered to a patient who has received another therapy, such as chemotherapy, radioimmunotherapy, surgical therapy, immunotherapy, radiation therapy, targeted therapy or any combination thereof.

The methods of the present invention may entail administration of bifunctional compounds of formula (I) or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days) and a 7-day "off" period. In other embodiments, the bifunctional compound may be dosed twice a day (BID) over the course of two and a half days (for a total of 5 doses) or once a day (QD) over the course of two days (for a total of 2 doses). In other embodiments, the bifunctional compound may be dosed once a day (QD) over the course of five days.

In some aspects, the present invention is directed to methods of using the bifunctional compound of formula (II) as a probe for EP300 or CPB. For example, the bifunctional compounds of formula II may be used with streptavidin for identification, isolation, handling, and pulldown of the targeted protein as well as the associated protein for target identification (IP) or Chem-seq (Anders et al., Nat. Biotechnol. 32(1):92-6 (2014)). For example, Dynabeads® M-270 Streptavidin (Thermo Fisher Scientific; catalog number 65305) may be used to exploit the avidin-biotin interaction for direct isolation of any biotinylated molecule. This probe molecule can be used for assay development (See, the AlphaScreen™ assay described in Example 26).

Combination Therapy

Bifunctional compounds of formula (I) of may be used in combination or concurrently with at least one other active agent, e.g., anti-cancer agent or regimen, in treating diseases and disorders. The terms "in combination" and "concurrently in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a compound of formula (I) of the invention in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; *Physician's Desk Reference,* 60th ed., 2006. For example, anti-cancer agents that may be used in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the compound of formula (I) of the invention and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments involving cancer treatment, the bifunctional compound of formula (I) and the additional anti-cancer agent or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, a bifunctional compound of formula (I) may be used in combination with other anti-NB or anti-cancer agents, examples of which include Dinutuximab (e.g., for NB), Cyclophosphamide (e.g., neuroblastoma), Busulfan plus Melphalan Hydrochloride, Carboplatin plus Etoposide Phosphate and Melphalan Hydrochloride (Doxorubicin Hydrochloride, Unituxin (Dinutuximab), Vincristine Sulfate, (Entrectinib (e.g., for brain cancer, central nervous system (CNS) cancer), Hu3F8 plus donated natural killer cells (e.g., for persistent or recurrent neuroblastoma), Hu3F8 plus granulocyte-macrophage colony-stimulating factor (GM-CSF) (e.g., for relapsed/refractory neuroblastoma), Hu3F8/GM-CSF immunotherapy plus isotretinoin (e.g., for consolidation of first remission of patients with NB), Venetoclax (e.g., for persistent or recurrent cancers, including n, leukemia and Non-Hodgkin's lymphoma), bivalent vaccine with the immunological adjuvant OPT-821, in combination with oral ß-glucan (e.g., for NB), Trametinib (e.g., for germ cell tumors, liver cancer, kidney cancer, neuroblastoma, pediatric brain tumors, osteosarcoma, Ewing sarcoma, rhabdomyosarcoma, soft tissue sarcoma, Wilms' tumor), Cobimetinib (e.g., for melanoma, pediatric brain tumors, and soft tissue sarcoma), and intrathecal radioimmunotherapy using 131I-8H9 (e.g., for brain tumors, primary, brain cancer, and CNS cancer).

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the bifunctional compound of formula (I) of the present invention or a pharmaceutical composition. The kits or pharmaceutical systems of the invention may also include printed instructions for using the compounds and compositions.

In some embodiments, the method of using the bifunctional compound of formula (II) as a probe for EP300 comprises contacting lysed cells suspected of containing EP300 with the compound of formula (II) and streptavidin immobilized on a carrier (e.g., beads such as magnetic beads); isolating complexes formed by molecule and protein binding through biotin-streptavidin binding; and confirming presence of EP300 in complex via standard techniques in art (e.g., immunoblotting).

These and other aspects of the present invention will be further appreciated upon consideration of the following Examples, which are intended to illustrate certain particular embodiments of the invention but are not intended to limit its scope, as defined by the claims.

EXAMPLES

Example 1: Synthesis of 12-((2-(2,6-dioxopiperidin-3-yl)-1,3-dioxoisoindolin-5-yl)amino)-N—((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)dodecanamide (Compound (CPD) 1

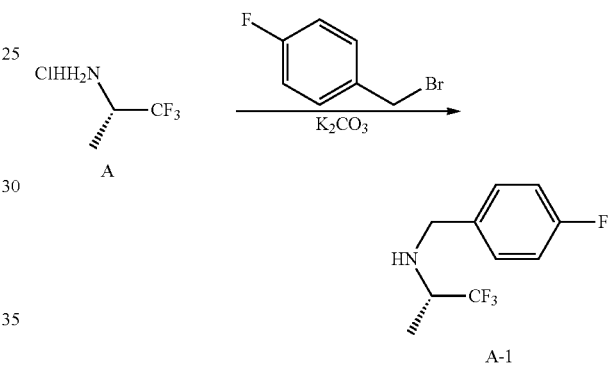

To a solution of compound A (18.5 g, 163.5 mmol) and 1-(bromomethyl)-4-fluorobenzene (37.2 g, 196.5 mmol) in DMF (200 mL) was added $K_2CO_3$ (67.5 g, 490 mmol). The reaction mixture was stirred at room temperature (rt) overnight and then quenched with water. The mixture was extracted with EtOAc and washed with water and brine. The organic extract was dried over $Na_2SO_4$ and concentrated under reduced pressure. The crude product was purified by silica gel chromatography (methanol: $CH_2Cl_2$, 1:20) to afford compound A-1 (15 g, 41.5%).

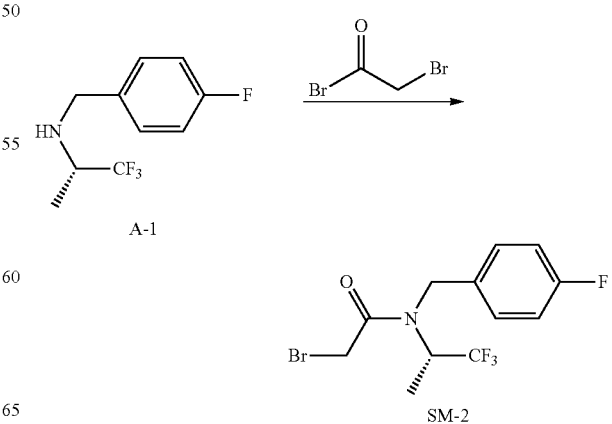

To a stirring solution of compound A-1 (15 g, 67.8 mmol) in dry CH$_2$Cl$_2$ (300 mL) was added 2-bromoacetyl bromide (27.4 g, 135.6 mmol). The resulting mixture was stirred at rt for 2 hours and then quenched with NaHCO$_3$. The reaction was extracted with CH$_2$Cl$_2$. The organic extract was dried over Na$_2$SO$_4$ and concentrated under reduced pressure. The crude product was purified by silica gel chromatography (petroleum ether:ethyl acetate, 1:1) to afford intermediate SM-2 (15.3 g, 66%) as oil.

pressure to give a light yellow solid. The light yellow solid was partitioned between ethyl acetate and aqueous NaHCO$_3$. The organic extract was dried, concentrated and triturated with 1:1 mixture of petroleum ether and ethyl acetate. The crude product int-2 (15 g) was used directly in the subsequent step.

A solution of crude product int-2 (15 g) in THF (300 mL) and triethylamine (12 g, 116 mmol) was cooled to 5° C. and carefully treated with a solution of triphosgene (8.6 g, 29 mmol) in 40 ml THF, so as to maintain temperature below 10° C. The mixture was stirred for 1 hour, treated with 6 N HCl until pH 2, and the resulting mixture was stirred at 5° C. for an additional 30 minutes. About half the volume of the solvent from the reaction mixture was removed under reduced pressure and the remaining mixture was partitioned between water and ethyl acetate. The organic extract was dried over Na$_2$SO$_4$ and concentrated under reduced pressure. The residue was purified by silica gel column chromatography (hexane/ethyl acetate, gradient) to afford intermediate int-4 (8 g) as a yellow solid.

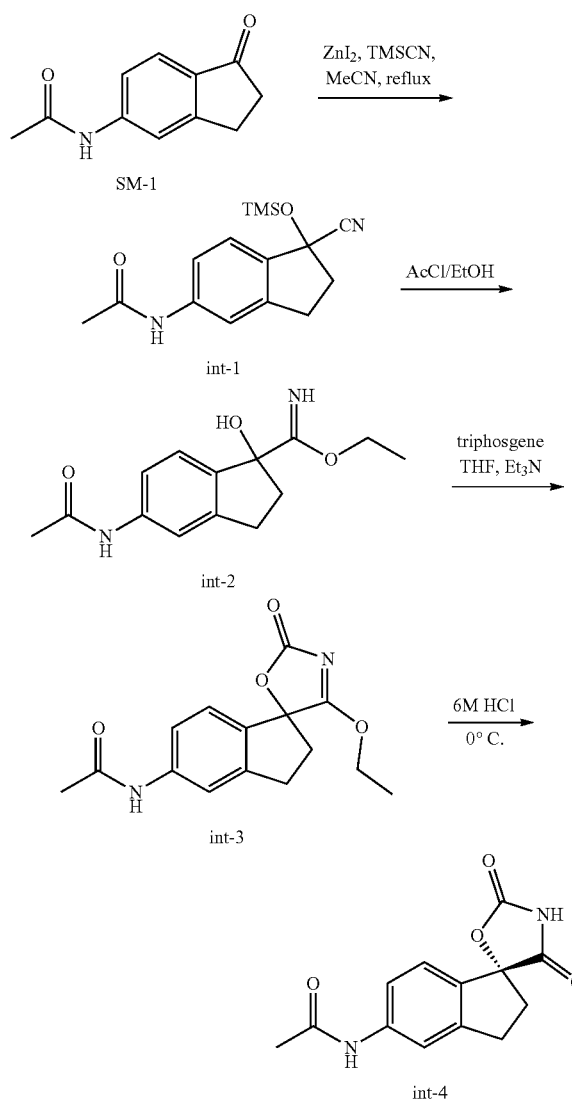

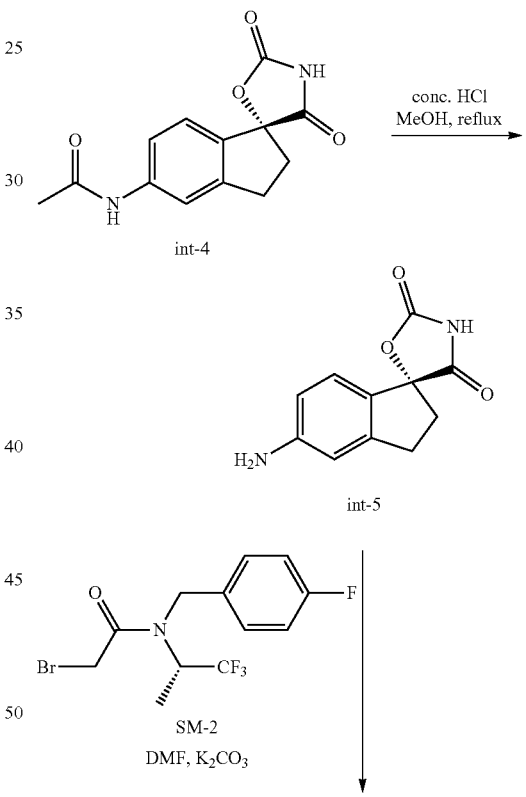

To a stirring solution of SM-1 (31 g, 164 mmol) in 1:1 toluene and MeCN mixture (800 mL) was added ZnI$_2$ (5.2 g, 16.4 mmol) and trimethylsilyl cyanide (TMSCN) (33 g, 328 mmol). The mixture was heated at reflux for 1 hour. The reaction was cooled, and the solvent was removed under reduced pressure. The residue was purified by silica gel column chromatography (hexane/ethyl acetate, gradient) to afford intermediate int-1 (28 g, 60%).

Int-1 (28 g, 97.2 mmol) was taken up in ethanol (400 ml) and cooled to 4° C. Acetyl chloride (280 ml, 3.9 mol) was added drop-wise via addition funnel at a rate so as to keep the temperature below 20° C. The reaction was stirred for 48 hours upon which time it was concentrated under reduced

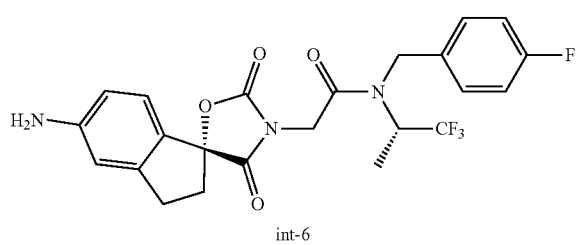

117

2-((R)-5-amino-2',4'-dioxo-2,3-dihydrospiro[indene-1,5'-oxazolidin]-3'-yl)-N-(4-fluorobenzyl)-N—((S)-1,1,1-trifluoropropan-2-yl)acetamide (Int-6

To a stirring suspension of int-4 (8 g, 30.6 mmol) in methanol (80 mL) was added concentrated aqueous HCl (20 mL, 12 M). The mixture was heated to reflux for 3 hours. The resulting precipitate was filtered and dried to afford intermediate int-5 (4 g, 60%) as a yellow solid.

To a solution of int-5 (4 g, 18 mmol) and SM-2 (6.2 g, 18 mmol) in DMF (40 mL) was added $K_2CO_3$ (7.4 g, 54 mmol). The reaction mixture was then stirred at rt for 2 hours, quenched with water, extracted with EtOAc, washed with water and brine, dried, concentrated under reduced pressure, purified by silica gel column chromatography (methanol: $CH_2Cl_2$, 1:20) to afford intermediate int-6 (6 g, 69.5%) as a white solid.

118

2-((R)-5-acetamido-2',4'-dioxo-2,3-dihydrospiro[indene-1,5'-oxazolidin]-3'-yl)-N—((S)-1-aminopropan-2-yl)-N-(4-fluorobenzyl)acetamide (Int-7

Int-7 was synthesized according to Michaelides et al., ACS Med. Chem. Lett. 2018, 9:28-33 (2018).

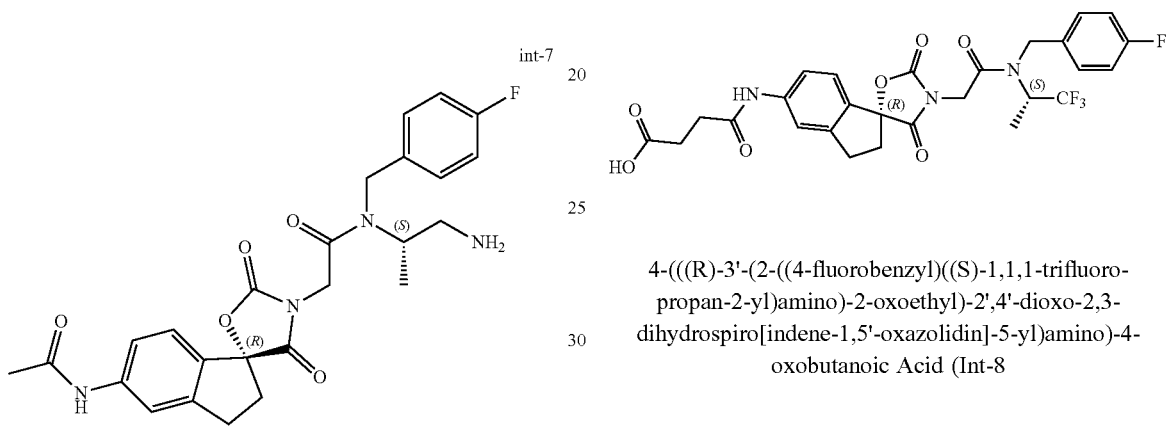

4-(((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)amino)-4-oxobutanoic Acid (Int-8

Int-8 was synthesized according to Michaelides et al., ACS Med. Chem. Lett. 2018, 9:28-33 (2018).

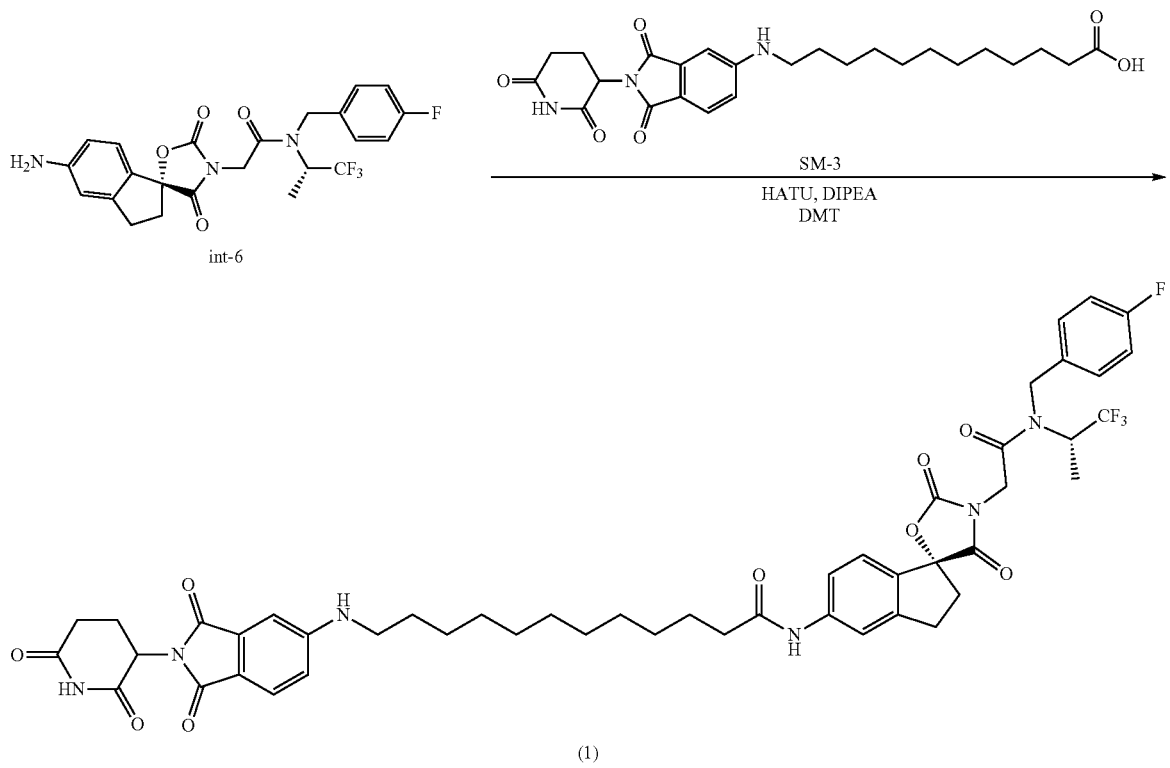

(1)

To a stirring solution of int-6 (6 mg, 0.01 mmol) and compound SM-3 (6 mg, 0.01 mmol) in DMF (1 mL) was added DIPEA (35 µL, 0.1 mmol), followed by 1-[bis(dimethylamino)methylene]-1H-1,2,3-triazolo[4,5-b]pyridinium 3-oxide hexafluorophosphate (HATU) (12 mg, 0.02 mmol) in one portion at rt. The reaction mixture was stirred at rt for 30 min. After consumption of the starting material, which was monitored by thin-layer chromatography (TLC), the reaction mixture was diluted with water and EtOAc. The combined organic extracts were dried over anhydrous $Na_2SO_4$ and concentrated under reduced pressure to obtain the crude product, which was purified by silica gel column chromatography with 1:1 EtOAc/petroleum ether to afford CPD 1 (6.2 mg, 45%) as a yellow solid.

Example 2: Synthesis of 1-((2-(2,6-dioxopiperidin-3-yl)-1,3-dioxoisoindolin-4-yl)amino)-N—((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)-3,6,9,12,15,18-hexaoxahenicosane-21-amide CPD 2

To a stirring solution of int-6 (6 mg, 0.01 mmol) and compound SM-4 (6 mg, 0.01 mmol) in DMF (1 mL) was added DIPEA (17 µL, 0.05 mmol) followed by HATU (11.4 mg, 0.025) in one portion at rt (exothermic reaction). The reaction mixture was stirred at rt for 30 min. After consumption of the starting material (by TLC), the reaction mixture was diluted with water and EtOAc. The combined organic extracts were dried over anhydrous $Na_2SO_4$ and concentrated under reduced pressure to obtain crude product, which was purified by silica gel column chromatography with 1:1 EtOAc/petroleum ether to afford CPD 2 (6 mg, 40%) as a yellow solid.

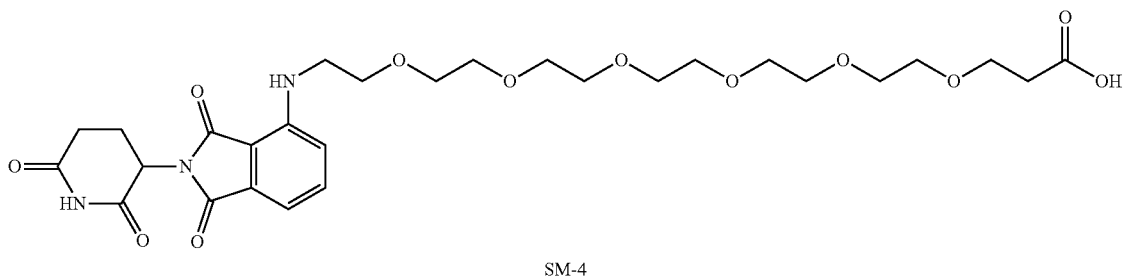

SM-4

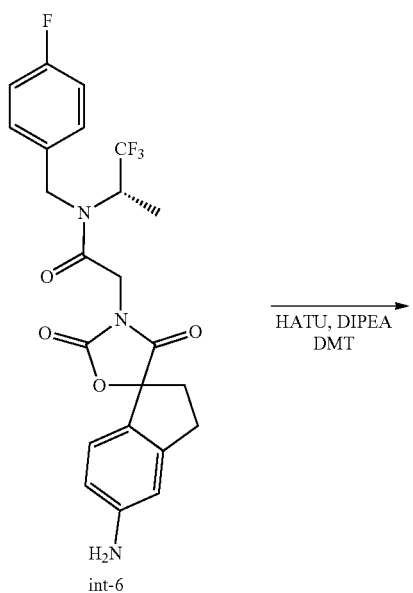

int-6

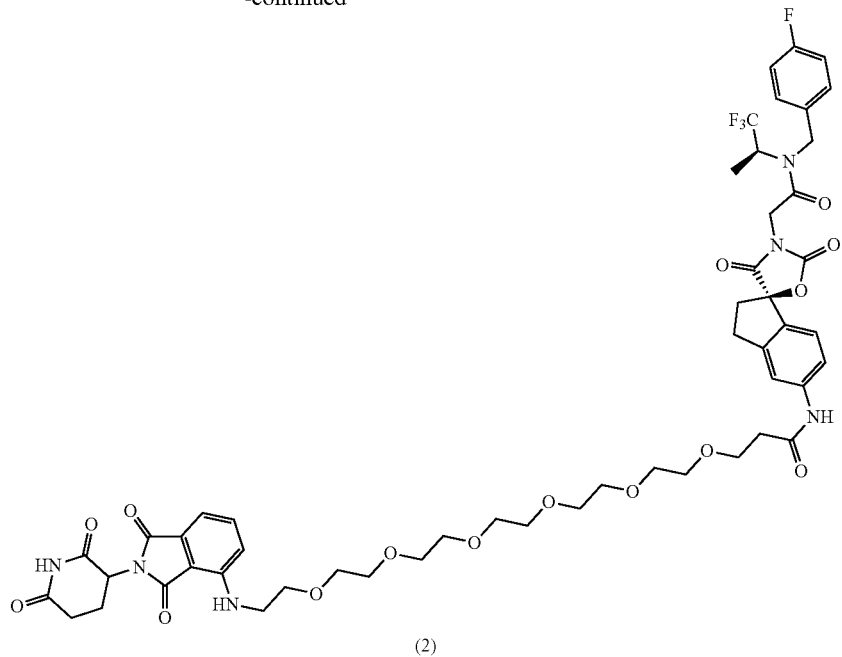

(2)

Example 3: Synthesis of 8-((2-(2,6-dioxopiperidin-3-yl)-1,3-dioxoisoindolin-4-yl)amino)-N—((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)octanamide (CPD 3)

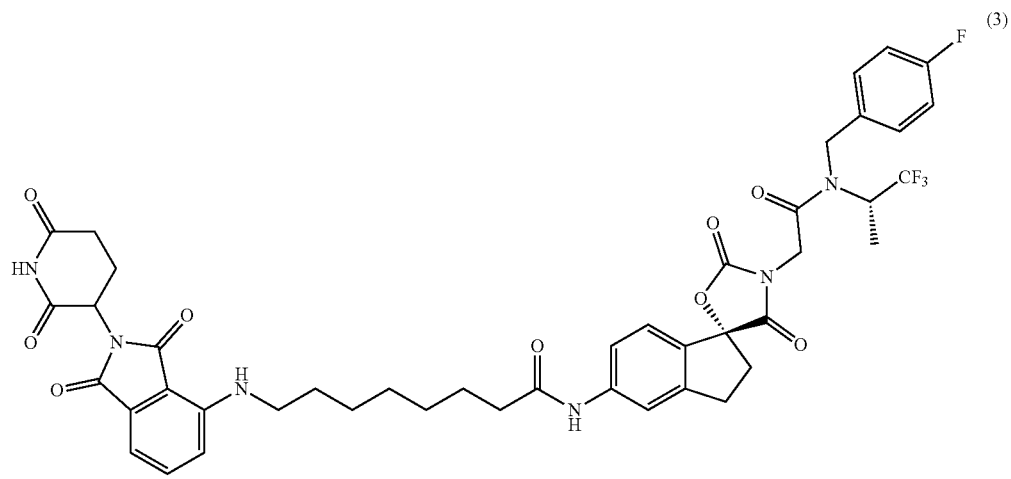 [SMILES: C[C@H](N(Cc1ccc(F)cc1)C(=O)CN1C(=O)O[C@@]2(CCc3cc(NC(=O)CCCCCCCNc4cccc5c4C(=O)N(C4CCC(=O)NC4=O)C5=O)ccc32)C1=O)C(F)(F)F]

(3)

CPD 3 was prepared in an analogous manner to CPD 2 in Example 2 from int-6 and appropriate IMiD intermediate. The crude product was purified by ISCO chromatography (MeOH/DCM, 0-10%) to afford CPD 3 as a yellow powder (53% yield).

Example 4: Synthesis of 10-((2-(2,6-dioxopiperidin-3-yl)-1,3-dioxoisoindolin-5-yl)amino)-N—((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)decanamide (CPD 4)

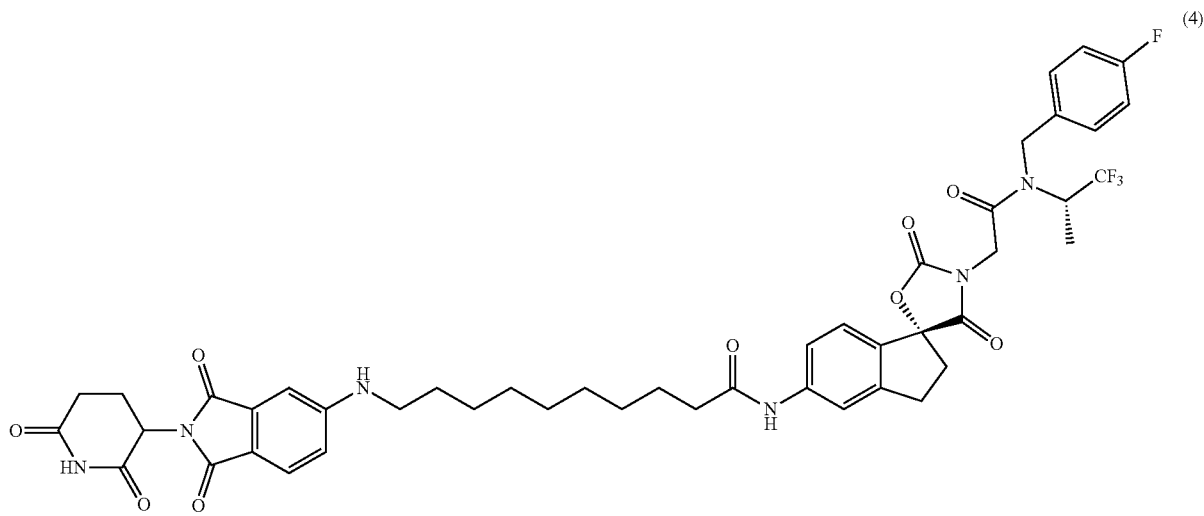 [SMILES: C[C@H](N(Cc1ccc(F)cc1)C(=O)CN1C(=O)O[C@@]2(CCc3cc(NC(=O)CCCCCCCCCNc4ccc5c(c4)C(=O)N(C4CCC(=O)NC4=O)C5=O)ccc32)C1=O)C(F)(F)F]

CPD 4 was prepared in an analogous manner to CPD 2 in Example 2 from int-6 and appropriate IMiD intermediate. The crude product was purified by ISCO chromatography (MeOH/DCM, 0-10%) to afford CPD 4 as a yellow powder (15 mg, 40% yield).

MS (ESI) calcd. for $C_{46}H_{48}F_4N_6O_9$: 904.34; Found: [M+1] 905.54, 906.53.

Example 5: Synthesis of 2-((1R)-5-(3-(8-((2-(2,6-dioxopiperidin-3-yl)-1,3-dioxoisoindolin-5-yl)amino)octyl)ureido)-2',4'-dioxo-2,3-dihydrospiro[indene-1,5'-oxazolidin]-3'-yl)-N-(4-fluorobenzyl)-N—((S)-1,1,1-trifluoropropan-2-yl)acetamide (CPD 5)

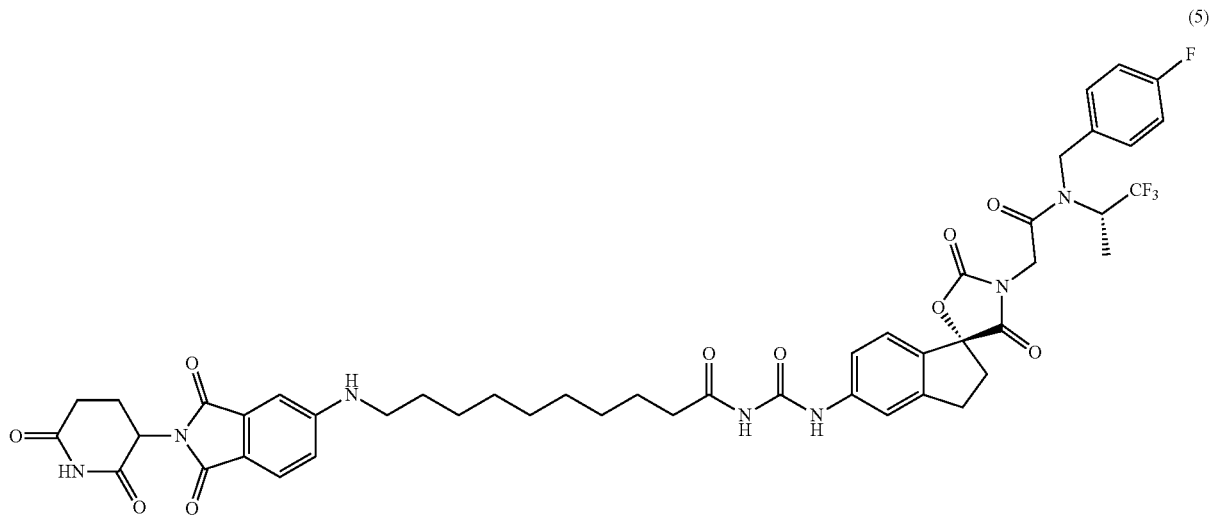 [SMILES: C[C@H](N(Cc1ccc(F)cc1)C(=O)CN1C(=O)O[C@@]2(CCc3cc(NC(=O)NC(=O)CCCCCCCCCNc4ccc5c(c4)C(=O)N(C4CCC(=O)NC4=O)C5=O)ccc32)C1=O)C(F)(F)F]

CPD 5 was prepared in an analogous manner to CPD 2 in Example 2 from int-6 and appropriate IMiD intermediate. The crude product was purified by ISCO chromatography (MeOH/DCM, 0-10%) to afford CPD 5 as a yellow powder (2 mg, 12% yield).

MS (ESI) calcd. for $C_{45}H_{47}F_4N_7O_9$: 905.34; Found: [M+1] 906.60, 907.29.

Example 6: Synthesis of 12-((2-(2,6-dioxopiperidin-3-yl)-1,3-dioxoisoindolin-4-yl)amino)-N—((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)dodecanamide (CPD 6)

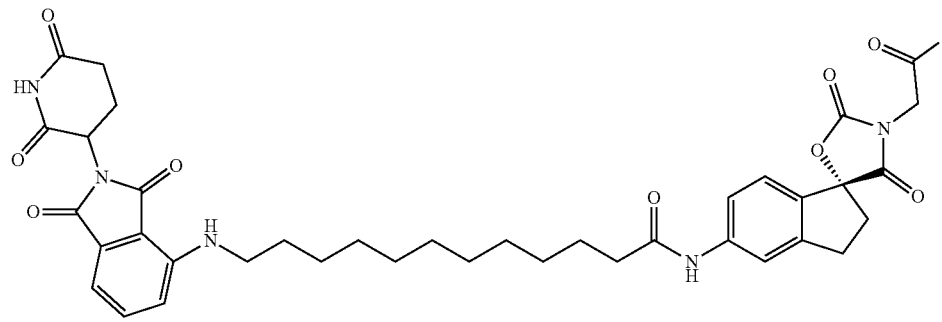

CPD 6 was prepared in an analogous manner to CPD 2 in Example 2 from int-6 and appropriate IMiD intermediate. The crude product was purified by ISCO chromatography (MeOH/DCM, 0-10%) to afford CPD 6 as a yellow powder (7 mg, 72% yield).

$^1$H NMR (500 MHz, Acetone-$d_6$) δ 9.90 (d, J=4.0 Hz, 1H), 9.26 (d, J=5.1 Hz, 1H), 7.90 (d, J=7.7 Hz, 1H), 7.59 (td, J=7.8, 2.7 Hz, 1H), 7.49 (d, J=9.7 Hz, 3H), 7.36-7.31 (m, 1H), 7.22 (t, J=8.6 Hz, 2H), 7.13-7.00 (m, 3H), 6.42 (d, J=5.9 Hz, 1H), 5.51 (p, J=7.8 Hz, 1H), 5.07 (ddd, J=12.1, 7.6, 4.2 Hz, 2H), 4.97-4.81 (m, 1H), 4.67 (dd, J=71.1, 16.7 Hz, 1H), 4.43 (dd, J=90.6, 16.6 Hz, 1H), 3.38 (q, J=6.3 Hz, 2H), 3.28-3.04 (m, 2H), 3.03-2.85 (m, 3H), 2.85-2.70 (m, 4H), 2.56 (dddd, J=14.5, 12.1, 8.6, 4.2 Hz, 1H), 2.39 (t, J=7.2 Hz, 2H), 2.27-2.17 (m, 1H), 2.07 (p, J=2.2 Hz, 2H), 1.73-1.67 (m, 4H), 1.39 (dd, J=38.4, 5.3 Hz, 12H).

MS (ESI) calcd. for $C_{48}H_{52}F_4N_6O_9$: 932.37; Found: [M+1] 933.36, 934.38.

Example 7: Synthesis of 12-((2-(2,6-dioxopiperidin-3-yl)-1,3-dioxoisoindolin-4-yl)amino)-N—((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)dodecanamide (CPD 7)

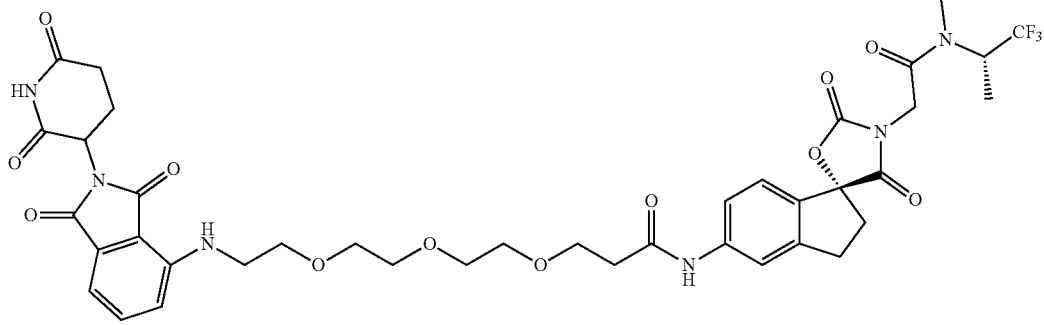

CPD 7 was prepared in an analogous manner to CPD 2 in Example 2 from int-6 and appropriate IMiD intermediate. The crude product was purified by ISCO chromatography (MeOH/DCM, 0-10%) to afford CPD 7 as a yellow powder (14 mg, 72% yield).

$^1$H NMR (500 MHz, Acetone-$d_6$) δ 9.91 (s, 1H), 9.31 (s, 1H), 7.85 (s, 1H), 7.60-7.56 (m, 1H), 7.52-7.47 (m, 3H), 7.34 (dd, J=8.3, 5.3 Hz, 1H), 7.22 (t, J=8.8 Hz, 2H), 7.12-7.00 (m, 3H), 6.60 (t, J=5.9 Hz, 1H), 5.51 (p, J=7.7 Hz, 1H), 5.12-5.04 (m, 2H), 4.96-4.84 (m, 1H), 4.67 (dd, J=69.9, 16.7 Hz, 1H), 4.43 (dd, J=91.2, 16.6 Hz, 1H), 3.80 (t, J=5.9 Hz, 2H), 3.71 (t, J=5.1 Hz, 2H), 3.51-3.47 (m, 2H), 3.22 (dt, J=15.3, 7.3 Hz, 1H), 3.09 (ddd, J=15.2, 8.8, 4.0 Hz, 1H), 3.00-2.95 (m, 2H), 2.84 (d, J=16.7 Hz, 4H), 2.78-2.75 (m, 2H), 2.63-2.50 (m, 4H), 2.22 (ddt, J=12.8, 5.4, 2.5 Hz, 1H), 2.07 (t, J=2.2 Hz, 2H), 1.50 (d, J=6.8 Hz, 1H), 1.43 (d, J=7.2 Hz, 2H).

MS (ESI) calcd. for $C_{45}H_{46}F_4N_6O_{12}$: 938.31; Found: [M+1] 939.40, 940.50.

Example 8: Synthesis of 3-(2-(2-(2-((2-(2,6-dioxopiperidin-3-yl)-1,3-dioxoisoindolin-4-yl)amino)ethoxy)ethoxy)ethoxy)-N—((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)propanamide (CPD 8)

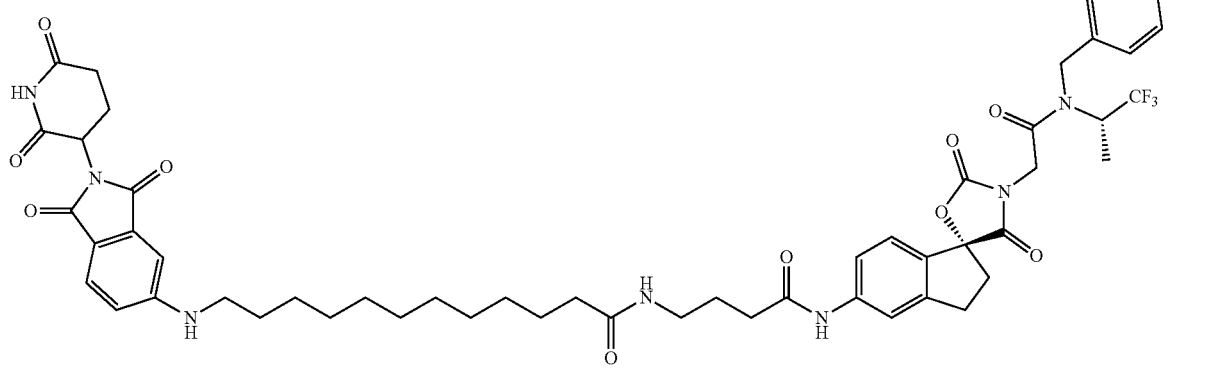

(8)

CPD 8 was prepared in an analogous manner to CPD 2 in Example 2 from int-6 and appropriate IMiD intermediate. The crude product was purified by ISCO chromatography (MeOH/DCM, 0-10%) to afford CPD 8 as a yellow powder (10.8 mg, 66% yield).

$^1$H NMR (500 MHz, Acetone-$d_6$) δ 9.88 (s, 1H), 9.65 (d, J=7.3 Hz, 1H), 7.87 (s, 1H), 7.59-7.49 (m, 4H), 7.32 (dt, J=22.6, 5.7 Hz, 2H), 7.21 (d, J=8.8 Hz, 1H), 7.01 (d, J=2.1 Hz, 1H), 6.93 (dd, J=8.3, 2.2 Hz, 1H), 6.32 (t, J=5.5 Hz, 1H), 5.51 (p, J=7.7 Hz, 1H), 5.06 (dd, J=12.6, 5.4 Hz, 2H), 4.96-4.84 (m, 1H), 4.67 (dd, J=70.8, 16.7 Hz, 1H), 4.43 (dd, J=88.2, 16.6 Hz, 1H), 3.99 (h, J=6.6 Hz, 2H), 3.48 (q, J=7.4 Hz, 2H), 3.25 (dq, J=36.5, 7.5, 6.9 Hz, 6H), 3.09 (ddd, J=16.3, 8.8, 3.9 Hz, 2H), 3.01-2.91 (m, 2H), 2.82-2.73 (m, 4H), 2.55 (ddd, J=14.4, 8.2, 3.9 Hz, 1H), 2.40 (t, J=7.0 Hz, 2H), 2.22-2.14 (m, 4H), 2.07 (p, J=2.2 Hz, 2H), 1.89-1.83 (m, 2H), 1.68 (p, J=7.2 Hz, 2H), 1.62-1.57 (m, 2H), 1.48-1.41 (m, 7H).

MS (ESI) calcd. for $C_{52}H_{59}F_4N_7O_{10}$: 1017.43; Found: [M+1] 1018.67, 1019.62.

Example 9: Synthesis of 12-(2-((2-(2,6-dioxopiperidin-3-yl)-1,3-dioxoisoindolin-4-yl)oxy)acetamido)-N—((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)dodecanamide (CPD 9)

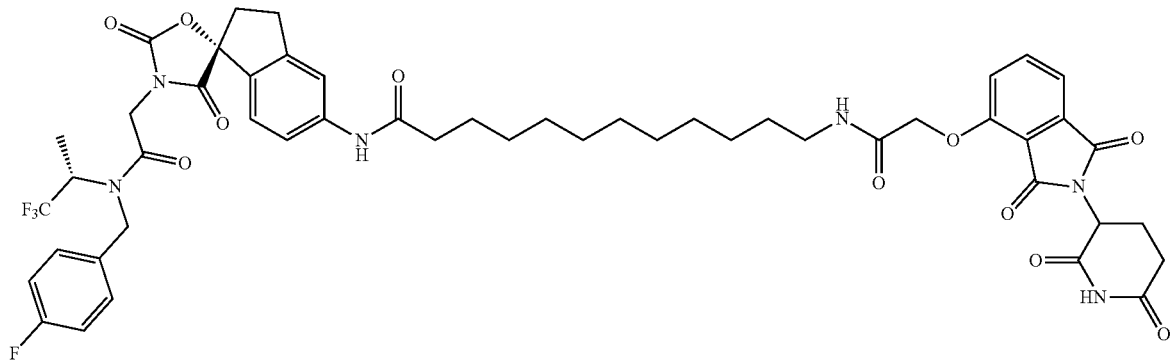

CPD 9 was prepared in an analogous manner to CPD 2 in Example 2 from int-6 and appropriate IMiD intermediate. The crude product was purified by ISCO chromatography (MeOH/DCM, 0-10%) to afford CPD 9 as a white powder (2 mg, 20% yield).

$^1$H NMR (500 MHz, Acetone-$d_6$) δ 9.96 (s, 1H), 9.28 (s, 1H), 7.98 (s, 1H), 7.90-7.85 (m, 3H), 7.53 (d, J=2.0 Hz, 2H), 7.49 (d, J=3.0 Hz, 2H), 7.22 (t, J=8.7 Hz, 2H), 5.51 (p, J=7.8 Hz, 1H), 5.20-5.13 (m, 2H), 5.10-5.00 (m, 2H), 4.96-4.83 (m, 2H), 4.56 (dd, J=42.2, 16.6 Hz, 2H), 4.33 (d, J=16.8 Hz, 1H), 3.37-3.19 (m, 6H), 3.14-2.97 (m, 4H), 2.78-2.71 (m, 2H), 2.54 (ddd, J=14.5, 8.3, 3.8 Hz, 2H), 2.38 (t, J=7.4 Hz, 2H), 2.29-2.24 (m, 2H), 1.69 (t, J=7.3 Hz, 3H), 1.59-1.47 (m, 7H), 1.43 (d, J=7.3 Hz, 4H).

MS (ESI) calcd. for $C_{50}H_{54}F_4N_6O_{11}$: 990.38; Found: [M+1] 991.57, 992.37.

Example 10: Synthesis of 6-((2-(2,6-dioxopiperidin-3-yl)-1,3-dioxoisoindolin-5-yl)amino)-N-(4-(((R)-3'-(2-((4-fluorobenzyl)((R)-1,1,1-trifluoropropan-2-yl)amino)-2-oxoethyl)-2',4'-dioxo-2,3-dihydrospiro[indene-1,5'-oxazolidin]-5-yl)amino)-4-oxobutyl)hexanamide (CPD 10)

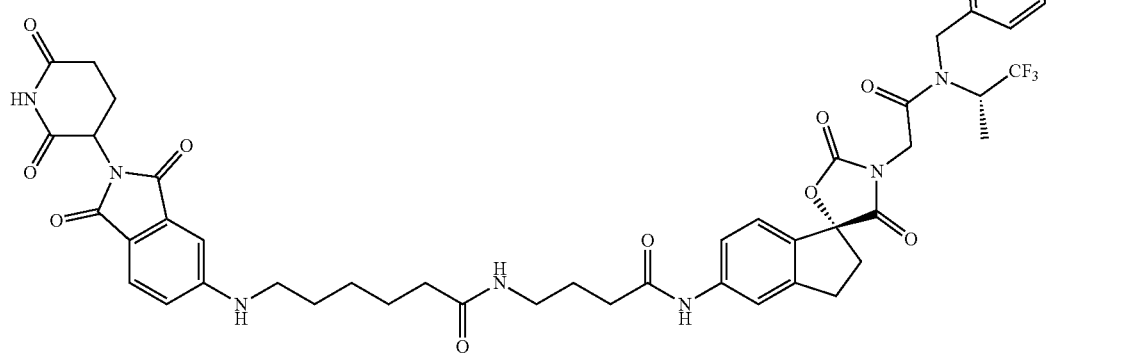

CPD 10 was prepared in an analogous manner to CPD 2 in Example 2 from int-6 and appropriate IMiD intermediate. The crude product was purified by ISCO chromatography (MeOH/DCM, 0-10%) to afford CPD 10 as a yellow powder (12 mg, 71% yield).

$^1$H NMR (500 MHz, Acetone-$d_6$) δ 9.87 (s, 1H), 9.62 (d, J=5.5 Hz, 1H), 7.87 (d, J=5.6 Hz, 1H), 7.58-7.43 (m, 6H), 7.22 (t, J=8.7 Hz, 2H), 7.01 (d, J=2.2 Hz, 1H), 6.92 (dd, J=8.4, 2.2 Hz, 1H), 6.35 (t, J=5.5 Hz, 1H), 5.51 (p, J=7.8 Hz, 1H), 5.06 (dt, J=10.7, 3.3 Hz, 2H), 4.96-4.84 (m, 1H), 4.67 (dd, J=70.1, 16.7 Hz, 1H), 4.43 (dd, J=90.3, 16.6 Hz, 1H), 3.25 (dq, J=39.8, 7.6, 7.0 Hz, 6H), 3.10 (ddt, J=16.1, 8.7, 3.9 Hz, 2H), 3.01-2.92 (m, 2H), 2.80-2.71 (m, 4H), 2.54 (ddd, J=14.4, 8.3, 3.9 Hz, 1H), 2.40 (t, J=7.0 Hz, 2H), 2.25-2.13 (m, 4H), 1.84 (q, J=6.9 Hz, 2H), 1.70-1.64 (m, 4H).

Example 11: Synthesis of 4-(3-(2-(2-(2-((2-(2,6-dioxopiperidin-3-yl)-1,3-dioxoisoindolin-4-yl)amino)ethoxy)ethoxy)ethoxy)propanamido)-N—((R)-3'-(2-((4-fluorobenzyl)((R)-1,1,1-trifluoropropan-2-yl)amino)-2-oxoethyl)-2',4'-dioxo-2,3-dihydrospiro[indene-1,5'-oxazolidin]-5-yl)butanamide (CPD 11)

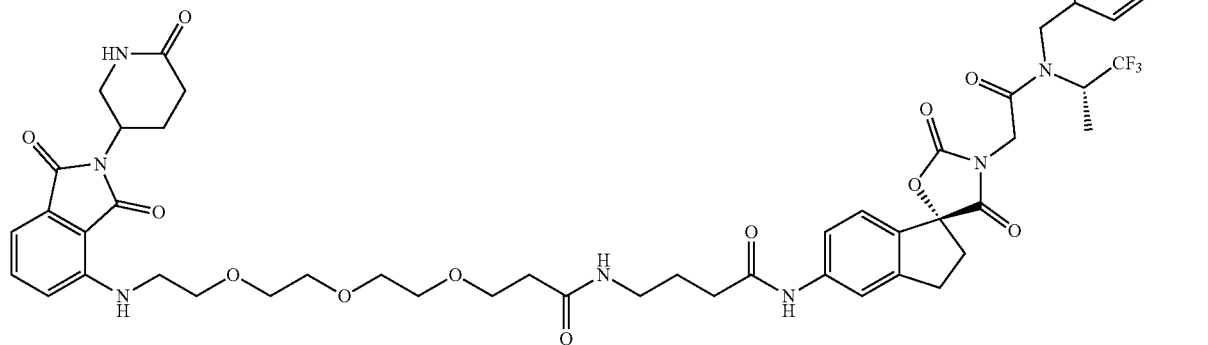

(11)

CPD 11 was prepared in an analogous manner to CPD 2 in Example 2 from int-6 and appropriate IMiD intermediate. The crude product was purified by ISCO chromatography (MeOH/DCM, 0-10%) to afford CPD 11 as a yellow powder (10 mg, 56% yield).

$^1$H NMR (500 MHz, Acetone-$d_6$) δ 9.98 (s, 1H), 9.57 (s, 1H), 7.87 (s, 1H), 7.62-7.57 (m, 1H), 7.51-7.45 (m, 3H), 7.25 (dt, J=31.7, 7.3 Hz, 3H), 7.13-7.01 (m, 3H), 6.62 (q, J=5.9 Hz, 1H), 5.51 (p, J=7.8 Hz, 1H), 5.13-4.86 (m, 4H), 4.67 (dd, J=69.4, 16.7 Hz, 1H), 4.43 (dd, J=92.2, 16.6 Hz, 1H), 3.73 (tt, J=13.1, 6.0 Hz, 6H), 3.60-3.48 (m, 6H), 3.33-3.18 (m, 4H), 3.10 (ddd, J=20.1, 9.9, 5.5 Hz, 2H), 3.05-2.92 (m, 2H), 2.75 (ddd, J=16.4, 7.2, 4.7 Hz, 4H), 2.59-2.51 (m, 1H), 2.40 (q, J=7.4, 6.8 Hz, 4H), 2.23 (dtd, J=10.4, 5.5, 2.8 Hz, 1H), 1.84 (t, J=6.8 Hz, 2H).

MS (ESI) calcd. for $C_{49}H_{53}F_4N_7O_{13}$: 1023.36; Found: [M+1] 1024.67, 1025.62.

Example 12: Synthesis of 6-((2-(2,6-dioxopiperidin-3-yl)-1,3-dioxoisoindolin-5-yl)amino)-N-(4-(3-(((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)amino)-3-oxopropyl)phenyl)hexanamide (CPD 12)

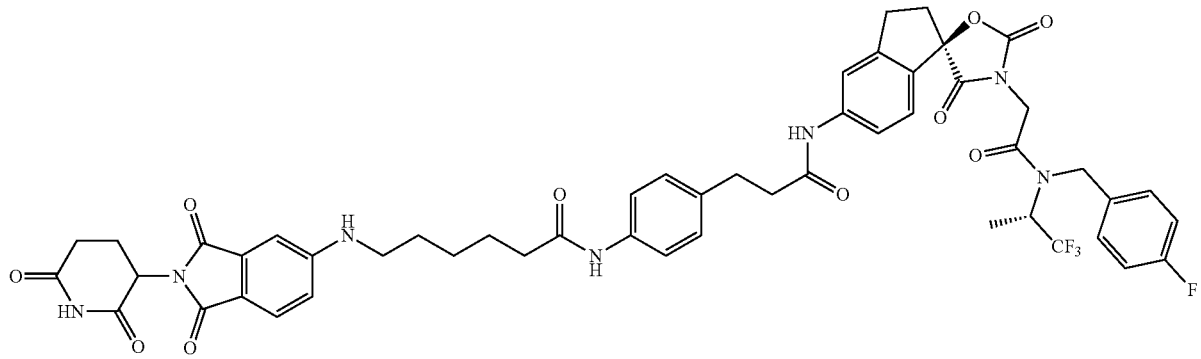

(12)

CPD 12 was prepared in an analogous manner to CPD 2 in Example 2 from int-6 and appropriate IMiD intermediate. The crude product was purified by ISCO chromatography (MeOH/DCM, 0-10%) to afford CPD 12 as a yellow powder (12.5 mg, 79% yield).

$^1$H NMR (500 MHz, Acetone-$d_6$) δ 9.86 (s, 1H), 9.30 (d, J=4.8 Hz, 1H), 9.03 (s, 1H), 7.98 (s, 1H), 7.86 (s, 1H), 7.56 (d, J=8.1 Hz, 4H), 7.47 (s, 2H), 7.21 (d, J=10.9 Hz, 3H), 7.06-6.91 (m, 3H), 6.35 (t, J=5.6 Hz, 1H), 5.51 (p, J=7.9 Hz, 1H), 5.11-5.01 (m, 3H), 4.88 (t, J=13.7 Hz, 1H), 4.67 (dd, J=70.4, 16.8 Hz, 1H), 4.53-4.31 (m, 1H), 3.32-3.18 (m, 4H), 3.14-3.04 (m, 2H), 2.54 (ddd, J=13.3, 8.1, 3.7 Hz, 2H), 2.38 (t, J=7.4 Hz, 2H), 2.18 (dt, J=11.2, 5.4 Hz, 2H), 1.73 (q, J=8.0 Hz, 6H), 1.51 (d, J=6.8 Hz, 6H).

MS (ESI) calcd. for $C_{51}H_{49}F_4N_7O_{10}$: 995.35; Found: [M+1] 996.70, 997.73.

Example 13: Synthesis of 12-((2-(2,6-dioxopiperidin-3-yl)-1,3-dioxoisoindolin-5-yl)amino)-N-(4-(3-(((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)amino)-3-oxopropyl)phenyl)dodecanamide (CPD 13)

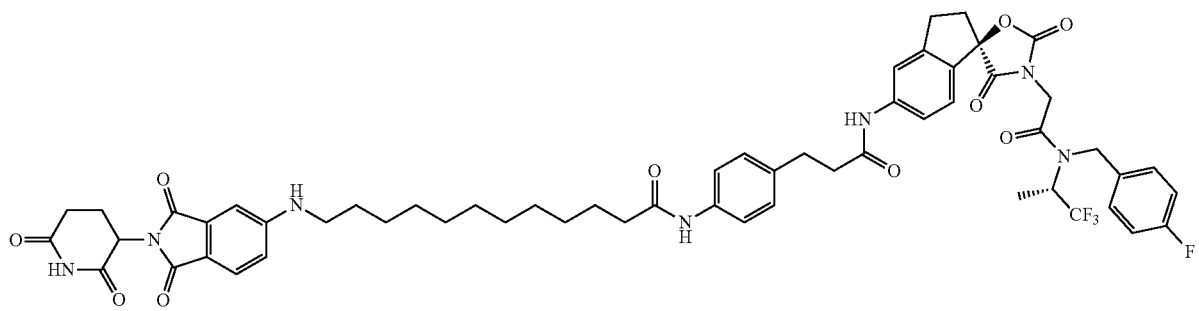

(13)

CPD 13 was prepared in an analogous manner to CPD 2 in Example 2 from int-6 and appropriate IMiD intermediate. The crude product was purified by ISCO chromatography (MeOH/DCM, 0-10%) to afford CPD 13 as a yellow powder (15 mg, 88% yield).

$^1$H NMR (500 MHz, Acetone-$d_6$) δ 9.86 (s, 1H), 9.30 (d, J=4.8 Hz, 1H), 9.01 (s, 1H), 8.73 (d, J=4.4 Hz, 1H), 8.42 (d, J=8.3 Hz, 1H), 7.98 (s, 1H), 7.86 (s, 1H), 7.57 (d, J=8.2 Hz, 2H), 7.52-7.48 (m, 2H), 7.22-7.17 (m, 3H), 7.09-6.90 (m, 3H), 6.32 (t, J=5.6 Hz, 1H), 5.51 (p, J=7.7 Hz, 1H), 5.11-5.01 (m, 3H), 4.88 (t, J=13.9 Hz, 1H), 4.67 (dd, J=70.0, 16.7 Hz, 1H), 4.42 (dd, J=91.7, 16.6 Hz, 1H), 3.25 (dq, J=43.4, 7.4, 6.9 Hz, 4H), 3.09 (ddd, J=16.3, 8.6, 3.8 Hz, 2H), 2.96 (s, 4H), 2.79 (s, 4H), 2.68 (t, J=7.4 Hz, 3H), 2.54 (ddd, J=14.1, 8.1, 3.7 Hz, 2H), 2.34 (t, J=7.4 Hz, 3H), 2.18 (t, J=3.7 Hz, 1H), 1.68 (q, J=7.5 Hz, 5H), 1.50-1.41 (m, 9H).

MS (ESI) calcd. For $C_{57}H_{61}F_4N_7O_{10}$: 1079.44, Found: [M+1]1080.65, 1081.48.

Example 14: Synthesis of 3-(2-(2-(2-((2-(2,6-di-oxopiperidin-3-yl)-1,3-dioxoisoindolin-4-yl)amino)ethoxy)ethoxy)ethoxy)-N-(4-(3-(((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)amino)-3-oxopropyl)phenyl)propenamide (CPD 14)

(14)

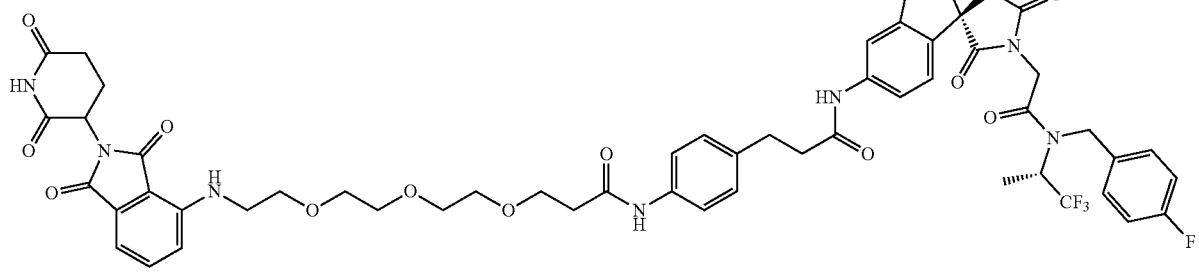

CPD 14 was prepared in an analogous manner to CPD 2 in Example 2 from int-6 and appropriate IMiD intermediate. The crude product was purified by ISCO chromatography (MeOH/DCM, 0-10%) to afford CPD 14 as a yellow powder (12 mg, 70% yield).

$^1$H NMR (500 MHz, Acetone-$d_6$) δ 9.93 (s, 1H), 9.28 (d, J=4.7 Hz, 1H), 9.06 (s, 1H), 7.86 (s, 1H), 7.57 (dd, J=7.7, 3.7 Hz, 3H), 7.49 (ddd, J=8.6, 4.6, 1.7 Hz, 3H), 7.24-7.15 (m, 4H), 7.07 (dd, J=29.3, 7.8 Hz, 3H), 6.60 (t, J=5.7 Hz, 1H), 5.51 (p, J=7.8 Hz, 1H), 5.13-5.01 (m, 3H), 4.96-4.86 (m, 1H), 4.67 (dd, J=70.3, 16.7 Hz, 1H), 4.42 (dd, J=91.8, 16.6 Hz, 1H), 3.78 (t, J=6.0 Hz, 2H), 3.70 (t, J=5.3 Hz, 2H), 3.61-3.53 (m, 2H), 3.49 (q, J=5.0 Hz, 3H), 3.24-3.19 (m, 1H), 3.12-3.06 (m, 1H), 2.97-2.92 (m, 4H), 2.79 (p, J=1.9 Hz, 2H), 2.76 (dd, J=6.5, 4.1 Hz, 2H), 2.67 (t, J=7.5 Hz, 2H), 2.56 (t, J=6.0 Hz, 3H), 2.22 (ddt, J=9.5, 5.2, 2.6 Hz, 1H), 1.50 (d, J=6.6 Hz, 4H), 1.43 (d, J=7.3 Hz, 2H).

Example 15: Synthesis of N—((R)-2-(2-((R)-5-acetamido-2',4'-dioxo-2,3-dihydrospiro[indene-1,5'-oxazolidin]-3'-yl)-N-(4-fluorobenzyl)acetamido)propyl)-12-((2-(2,6-dioxopiperidin-3-yl)-1,3-dioxoisoindolin-5-yl)amino)dodecanamide (CPD 15)

(15)

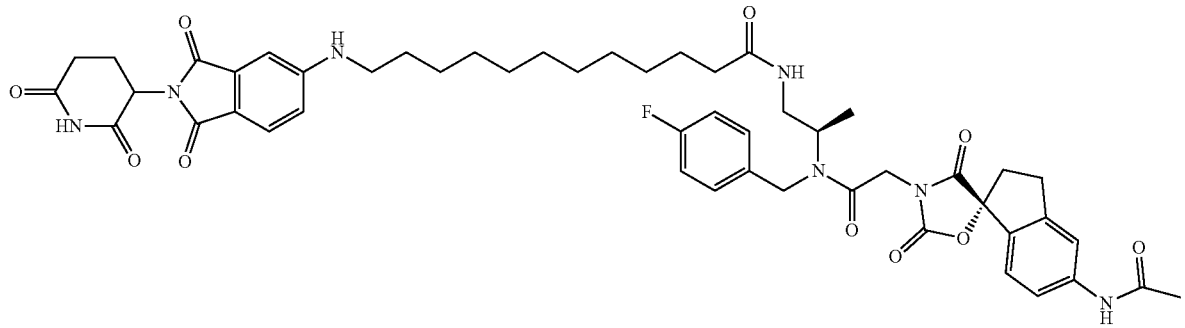

CPD 15 was prepared in an analogous manner to CPD 2 in Example 2 from (R,R)-isomer of int-7 and appropriate IMiD intermediate. The crude product was purified by ISCO chromatography (MeOH/DCM, 0-10%) to afford CPD 15 as a yellow powder (10 mg, 6900 yield).

$^1$H NMR (500 MHz, Acetone-$d_6$) δ 9.86 (s, 1H), 9.32 (s, 1H), 7.86 (s, 1H), 7.57 (dd, J=8.3, 1.4 Hz, 1H), 7.52-7.40 (m, 4H), 7.36-7.31 (m, 2H), 7.25-7.16 (m, 2H), 7.08-7.01 (m, 3H), 6.93 (ddd, J=8.3, 3.3, 2.1 Hz, 2H), 6.32 (q, J=6.1 Hz, 1H), 5.06 (dd, J=12.6, 5.4 Hz, 1H), 4.84 (d, J=16.0 Hz, 1H), 4.77 (d, J=16.5 Hz, 1H), 4.72 (d, J=7.3 Hz, 1H), 4.65 (d, J=16.5 Hz, 1H), 4.52 (d, J=16.5 Hz, 1H), 4.44 (d, J=16.0 Hz, 1H), 4.37 (dt, J=8.4, 6.3 Hz, 1H), 4.27 (d, J=16.4 Hz, 1H), 4.00 (p, J=6.6 Hz, 1H), 3.52-3.39 (m, 3H), 3.28 (dt, J=10.2, 4.1 Hz, 5H), 3.25-3.18 (m, 2H), 3.10 (ddd, J=16.4, 8.7, 4.1 Hz, 2H), 3.01-2.92 (m, 2H), 2.82-2.74 (m, 6H), 2.57 (dddd, J=17.6, 14.2, 8.2, 3.7 Hz, 2H), 2.28-2.14 (m, 4H), 1.68 (td, J=7.4, 4.2 Hz, 3H), 1.61-1.53 (in, 3H).

MS (ESI) calcd. for $C_{50}H_{58}FN_7O_{10}$: 935.42; Found: [M+1] 936.74, 937.65.

Example 16: Synthesis of N—((S)-2-(2-((R)-5-acetamido-2',4'-dioxo-2,3-dihydrospiro[indene-1,5'-oxazolidin]-3'-yl)-N-(4-fluorobenzyl)acetamido)propyl)-12-((2-(2,6-dioxopiperidin-3-yl)-1,3-dioxoisoindolin-5-yl)amino)dodecanamide (CPD 16)

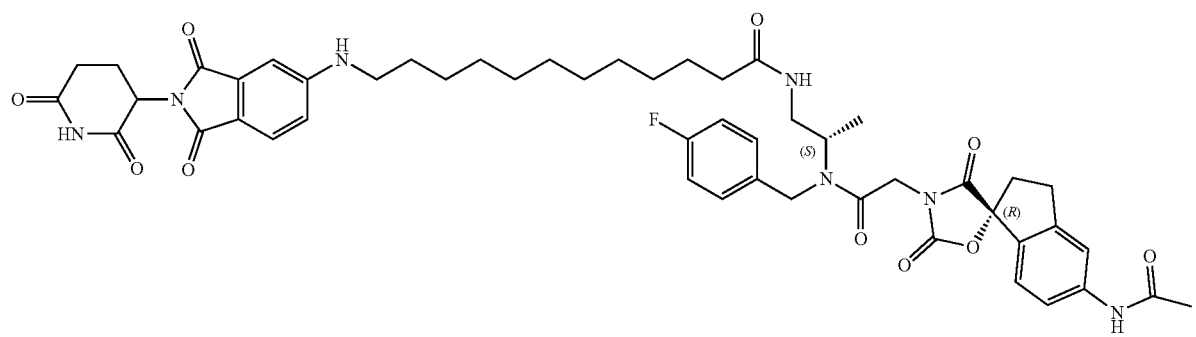

(16)

CPD 16 was prepared in an analogous manner to CPD 2 in Example 2 from int-7 and appropriate IMiD intermediate. The crude product was purified by ISCO chromatography (MeOH/DCM, 0-10%) to afford CPD 16 as a yellow powder (9.6 mg, 68% yield).

$^1$H NMR (500 MHz, Acetone-$d_6$) δ 9.86 (s, 1H), 9.33 (d, J=4.0 Hz, 1H), 7.87 (s, 1H), 7.55 (dd, J=18.0, 8.4 Hz, 3H), 7.51-7.45 (m, 2H), 7.42 (dd, J=8.4, 2.0 Hz, 1H), 7.38-7.32 (m, 2H), 7.28 (s, 1H), 7.19 (t, J=8.8 Hz, 1H), 7.11-7.03 (m, 2H), 7.02 (d, J=2.2 Hz, 2H), 6.93 (dt, J=8.4, 1.6 Hz, 1H), 6.33 (d, J=5.7 Hz, 1H), 5.06 (dd, J=12.6, 5.4 Hz, 1H), 4.88 (d, J=16.1 Hz, 1H), 4.79 (d, J=16.6 Hz, 1H), 4.72 (d, J=6.3 Hz, 1H), 4.61 (d, J=16.6 Hz, 1H), 4.48 (d, J=16.5 Hz, 1H), 4.40 (d, J=16.0 Hz, 1H), 4.30 (d, J=16.5 Hz, 1H), 4.01 (p, J=6.6 Hz, 1H), 3.53-3.39 (m, 2H), 3.32-3.19 (m, 6H), 3.10 (ddt, J=17.0, 8.7, 4.3 Hz, 2H), 3.01-2.93 (m, 2H), 2.83-2.72 (m, 6H), 2.57 (dddd, J=18.5, 14.4, 8.2, 3.7 Hz, 2H), 2.29-2.13 (m, 4H), 1.68 (p, J=7.2 Hz, 3H), 1.58 (p, J=7.3 Hz, 3H).

MS (ESI) calcd. for $C_{50}H_{58}FN_7O_{10}$: 935.42; Found: [M+1] 936.74, 937.65.

Example 17: Synthesis of N—((S)-2-(2-((R)-5-acetamido-2',4'-dioxo-2,3-dihydrospiro[indene-1,5'-oxazolidin]-3'-yl)-N-(4-fluorobenzyl)acetamido)propyl)-3-(2-(2-(2-((2-(2,6-dioxopiperidin-3-yl)-1,3-dioxoisoindolin-5-yl)amino)ethoxy)ethoxy)ethoxy)propanamide (CPD 17)

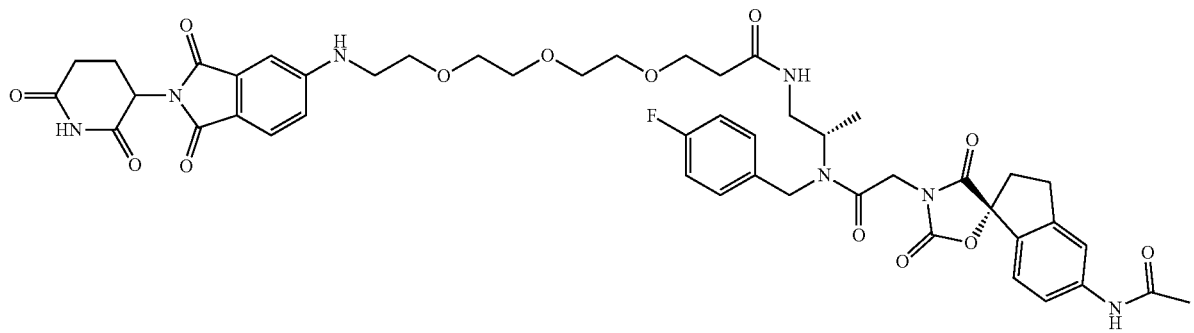

(17)

CPD 17 was prepared in an analogous manner to CPD 2 in Example 2 from int-7 and appropriate IMiD intermediate. The crude product was purified by ISCO chromatography (MeOH/DCM, 0-10%) to afford CPD 17 as a yellow powder (8.4 mg, 86% yield).

$^1$H NMR (500 MHz, Acetone-$d_6$) δ 9.96 (s, 1H), 9.31 (s, 1H), 7.85 (d, J=15.6 Hz, 1H), 7.61-7.57 (m, 1H), 7.53 (d, J=8.3 Hz, 1H), 7.47 (dt, J=8.5, 4.2 Hz, 1H), 7.43-7.38 (m, 1H), 7.36-7.30 (m, 1H), 7.21-6.99 (m, 5H), 6.62 (t, J=5.8 Hz, 1H), 5.09 (ddd, J=12.8, 5.5, 1.7 Hz, 1H), 4.89 (d, J=16.0 Hz, 1H), 4.80 (d, J=16.5 Hz, 1H), 4.70 (d, J=9.4 Hz, 1H), 4.61 (d, J=16.5 Hz, 1H), 4.42-4.35 (m, 1H), 3.76-3.73 (m, 2H), 3.70 (td, J=6.2, 1.4 Hz, 3H), 3.65-3.62 (m, 4H), 3.59-3.57 (m, 2H), 3.56-3.51 (m, 4H), 3.48-3.37 (m, 2H), 3.25 (dtt, J=18.2, 9.8, 4.1 Hz, 2H), 3.10 (ddt, J=12.6, 8.8, 3.9 Hz, 1H), 3.02-2.91 (m, 2H), 2.80-2.75 (m, 4H), 2.61-2.37 (m, 4H), 2.22 (ddt, J=13.0, 5.7, 2.1 Hz, 2H).

MS (ESI) calcd. for $C_{47}H_{52}FN_7O_{13}$: 941.36; Found: [M+1] 942.67, 943.65.

Example 18: Synthesis of N—((S)-2-(2-((R)-5-acetamido-2',4'-dioxo-2,3-dihydrospiro[indene-1,5'-oxazolidin]-3'-yl)-N-(4-fluorobenzyl)acetamido)propyl)-8-((2-(2,6-dioxopiperidin-3-yl)-1,3-dioxoisoindolin-5-yl)amino)octanamide (CPD 18)

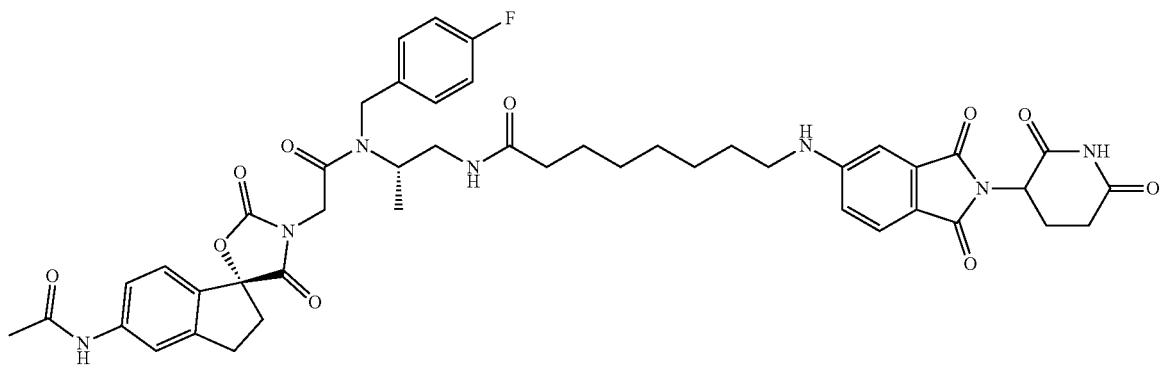

(18)

CPD 18 was prepared in an analogous manner to CPD 1 in Example 1 from int-7 and appropriate IMiD intermediate. The crude product was purified by ISCO chromatography (MeOH/DCM, 0-10%) to afford CPD 18 as a yellow powder (7.2 mg, 82% yield).

$^1$H NMR (500 MHz, Acetone-$d_6$) δ 9.87 (s, 1H), 9.28 (d, J=4.3 Hz, 1H), 7.81 (d, J=2.9 Hz, 1H), 7.53-7.48 (m, 3H), 7.35-7.32 (m, 2H), 7.18 (t, J=8.8 Hz, 1H), 7.07 (t, J=8.8 Hz, 2H), 6.95 (t, J=2.6 Hz, 1H), 6.85 (dt, J=8.3, 1.8 Hz, 1H), 6.31-6.17 (m, 1H), 5.06 (dd, J=12.6, 5.4 Hz, 1H), 4.92 (d, J=16.1 Hz, 1H), 4.80 (d, J=16.5 Hz, 1H), 4.72 (d, J=4.1 Hz, 1H), 4.62 (d, J=16.6 Hz, 1H), 4.49 (d, J=16.5 Hz, 1H), 4.43-4.34 (m, 2H), 4.28 (dd, J=16.5, 1.4 Hz, 1H), 3.51 (ddq, J=9.3, 4.6, 2.2 Hz, 1H), 3.28-3.21 (m, 4H), 3.10 (dt, J=8.3, 4.0 Hz, 1H), 2.98-2.92 (m, 1H), 2.80-2.71 (m, 4H), 2.56 (ddt, J=9.9, 7.6, 4.2 Hz, 1H), 2.28-2.16 (m, 4H), 1.67-1.62 (m, 4H), 1.48-1.37 (m, 4H).

MS (ESI) calcd. for $C_{44}H_{46}FN_7O_{10}$: 851.33; Found: [M+1] 852.53, 853.44.

Example 19: Synthesis of N1-((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)-N4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)succinimide (CPD 19)

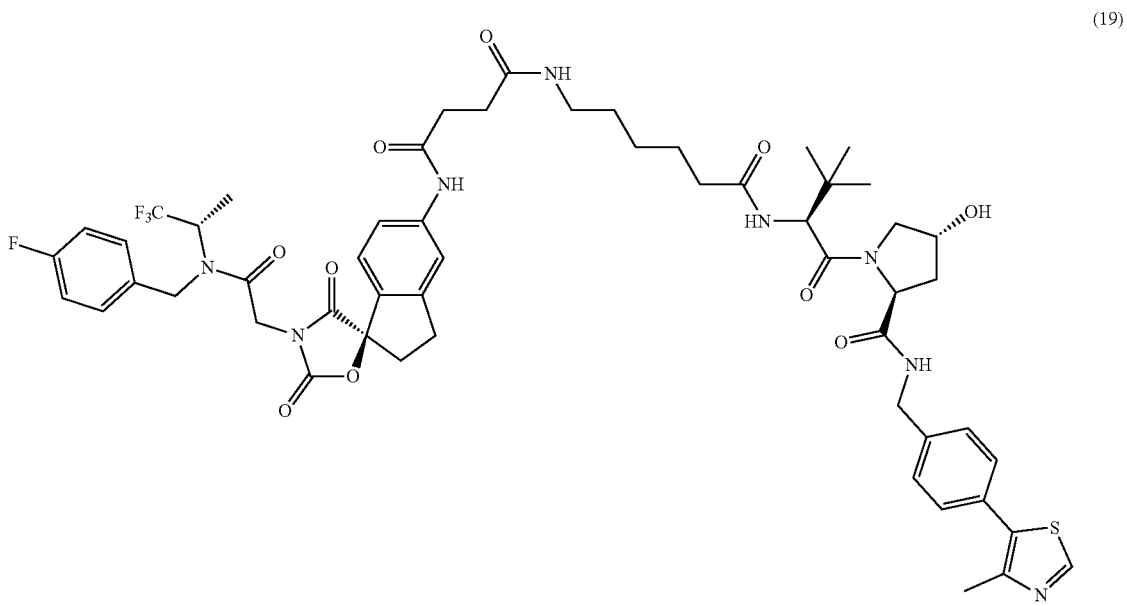 [SMILES: Cc1ncsc1-c1ccc(CNC(=O)[C@@H]2C[C@@H](O)CN2C(=O)[C@@H](NC(=O)CCCCCNC(=O)CCC(=O)Nc2ccc3c(c2)CC[C@@]32OC(=O)N(CC(=O)N(Cc3ccc(F)cc3)[C@@H](C)C(F)(F)F)C2=O)C(C)(C)C)cc1]

(19)

CPD 19 was prepared in an analogous manner to CPD 2 in Example 2 from int-8 and an appropriate VHL-N$_2$ intermediate. The crude product was purified by ISCO chromatography (MeOH/DCM, 0-15%) to afford CPD 19 as a white powder (11 mg, 58 yield).

MS (ESI) calcd. for $C_{55}H_{64}F_4N_8O_{10}S$: 1104.44; Found: [M+1] 1105.73, 1106.72.

Example 20: Synthesis of N1-((S)-3'-(2-((4-fluorobenzyl)((R)-1,1,1-trifluoropropan-2-yl)amino)-2-oxoethyl)-2',4'-dioxo-2,3-dihydrospiro[indene-1,5'-oxazolidin]-5-yl)-N4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)succinam (CPD 20)

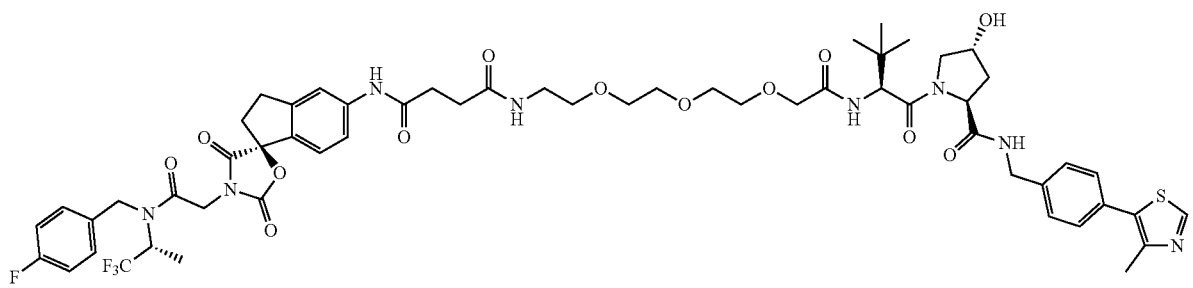

(20)

CPD 20 was prepared in an analogous manner to CPD 2 in Example 2 from int-8 and appropriate VHL-N$_2$ intermediate. The crude product was purified by ISCO chromatography (MeOH/DCM, 0-15%) to afford CPD 20 as a yellow powder (12 mg, 59 yield).

MS (ESI) calcd. For $C_{57}H_{68}F_4N_8O_{13}S$: 1180.46; Found: [M+1]1181.77, 1182.68.

Example 21: Synthesis of N1-((S)-3'-(2-((4-fluorobenzyl)((R)-1,1,1-trifluoropropan-2-yl)amino)-2-oxoethyl)-2',4'-dioxo-2,3-dihydrospiro[indene-1,5'-oxazolidin]-5-yl)-N4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)succinamide (CPD 21)

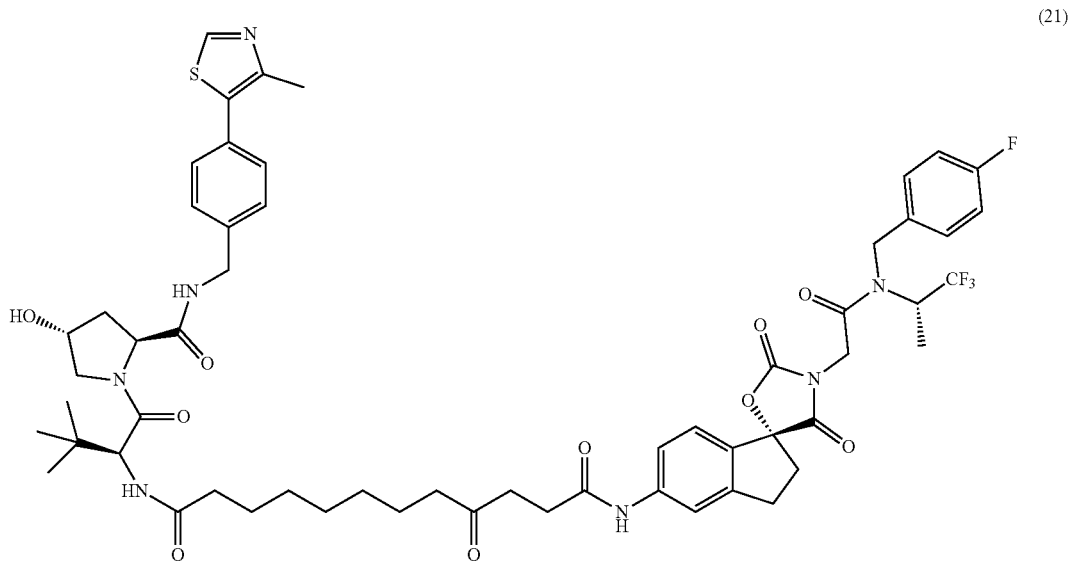 [SMILES: Cc1ncsc1-c1ccc(CNC(=O)[C@@H]2C[C@@H](O)CN2C(=O)[C@@H](NC(=O)CCCCCCCC(=O)CCC(=O)Nc2ccc3c(c2)CC[C@@]32OC(=O)N(CC(=O)N(Cc3ccc(F)cc3)[C@@H](C)C(F)(F)F)C2=O)C(C)(C)C)cc1]

(21)

CPD 21 was prepared in an analogous manner to CPD 2 in Example 2 from int-8 and appropriate VHL-N$_2$ intermediate.

Example 22: Synthesis of N1-((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)-N4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamoyl)benzyl)succinamide (CPD 22)

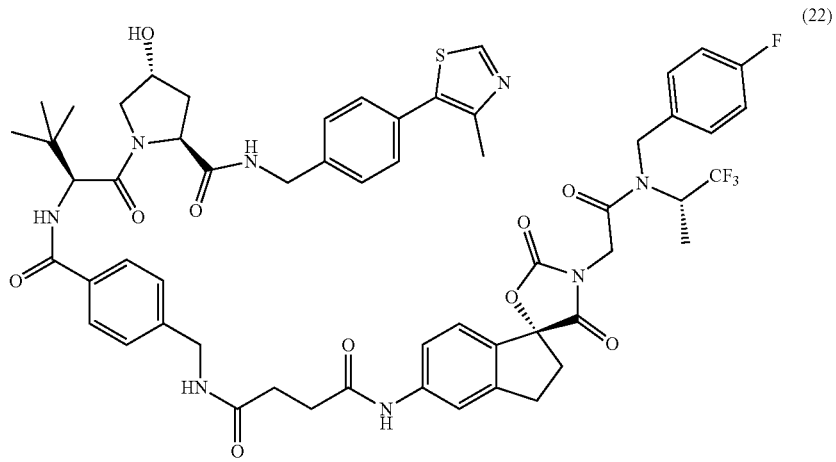 [SMILES: Cc1ncsc1-c1ccc(CNC(=O)[C@@H]2C[C@@H](O)CN2C(=O)[C@@H](NC(=O)c2ccc(CNC(=O)CCC(=O)Nc3ccc4c(c3)CC[C@@]43OC(=O)N(CC(=O)N(Cc4ccc(F)cc4)[C@@H](C)C(F)(F)F)C3=O)cc2)C(C)(C)C)cc1]

(22)

CPD 22 was prepared in an analogous manner to CPD 2 in Example 2 from int-8 and appropriate VHL-N₂ intermediate.

Example 23: Synthesis of N1-((R)-3'-(2-((4-fluorobenzyl)((S)-1,1,1-trifluoropropan-2-yl)amino)-2-oxoethyl)-2',4'-dioxo-2,3-dihydrospiro[indene-1,5'-oxazolidin]-5-yl)-N5-(15-oxo-19-((3aS,4S,6aR)-2-oxohexahydro-1H-thieno[3,4-d]imidazol-4-yl)-4,7,10-trioxa-14-azanonadecyl)glutaramide (CPD 23)

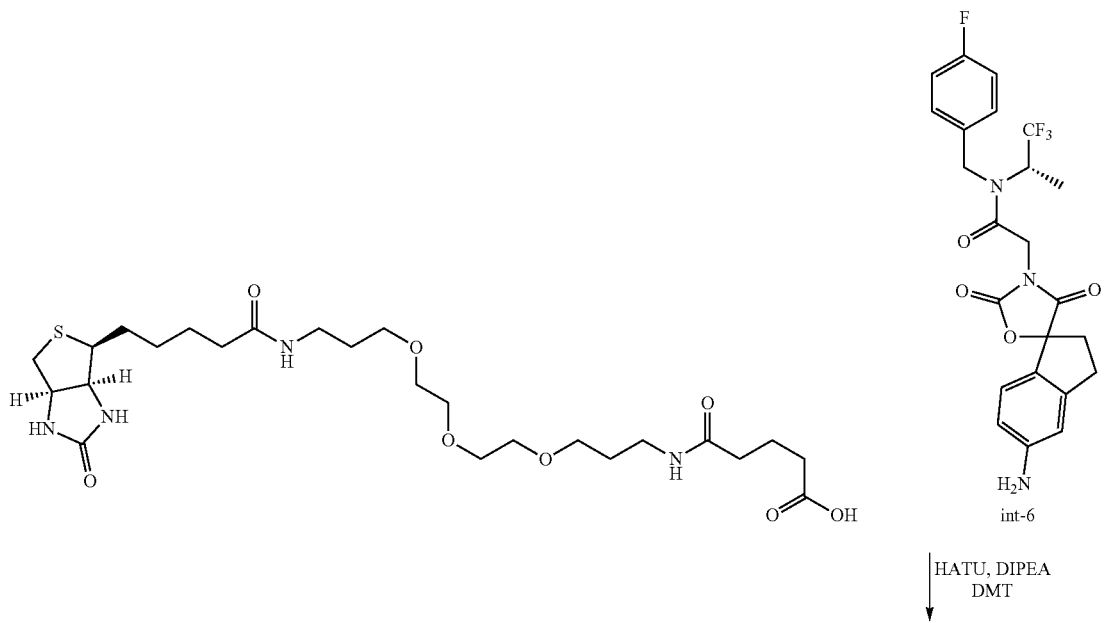

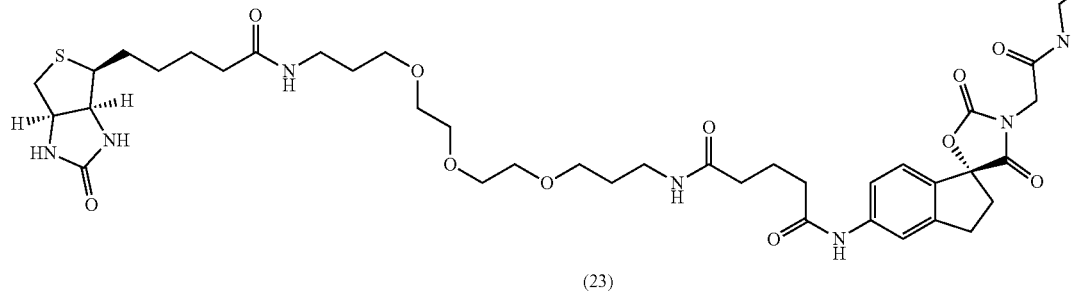

(23)

Compound 3 (30 mg, >95% yield by LCMS) was obtained in analogous manner to compounds 1 and 2 from int-6 (30 mg, 0.06 mmol) and biotin-PEG3-20 atoms-acid (47.5 mg, 0.08 mmol).

Figure 2A:
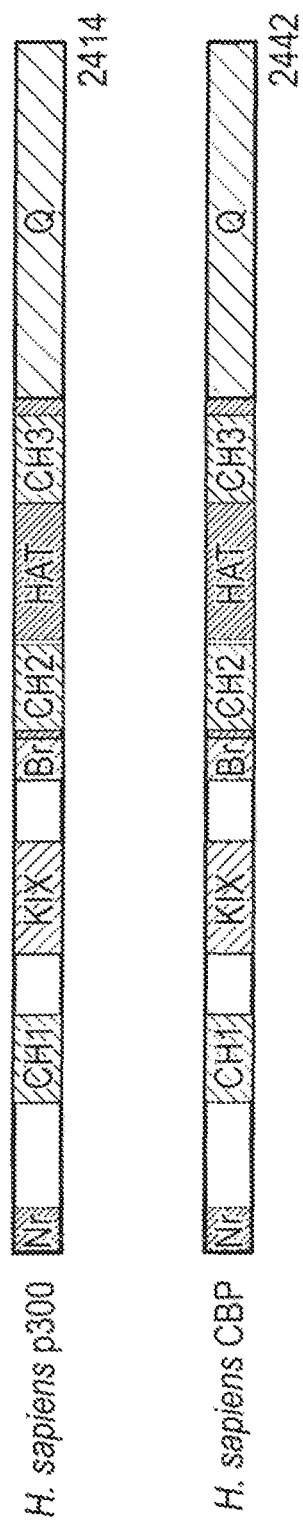
FIG. 2A is an image that shows EP300 and cAMP-response element binding protein (CREB)-binding protein (CBP) as multidomain proteins.

Example 24: Cellular Degradation of p300/CBP in Kelly High-Risk Neuroblastoma (NB) Cells EP300 and CBP are multi-domain proteins containing a kinase-inducible domain (KID) interacting domain (KIX), bromo-, zinc-finger, and acetyltransferase (HAT) domains. The encoded epigenetic modifying domains enable both EP300 and CBP to couple transcription factor recognition to chromatin remodeling, critically mediating gene expression. The studies on developing small molecules to target EP300/CBP have been focusing on the bromodomain, KIX domain and HAT domain (FIG. 2A).

Figure 2B:
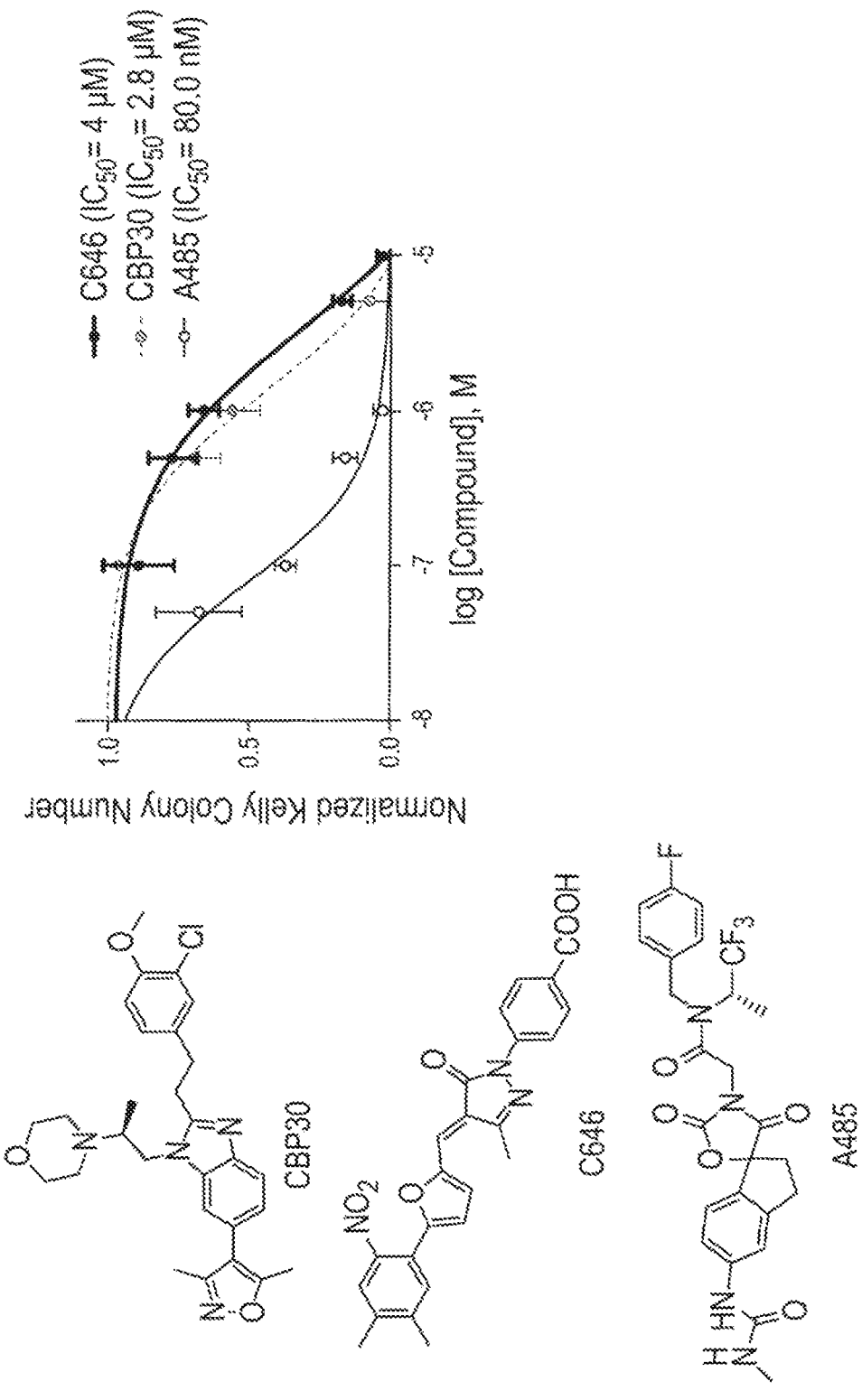
FIG. 2B is a graph that shows the effects of EP300/CBP inhibitors C646, CBP30 and A485 in Kelly NB cells in 7-day colony formation assays. The structures of the inhibitors and $IC_{50}$ values are also shown.
Figure 2C:
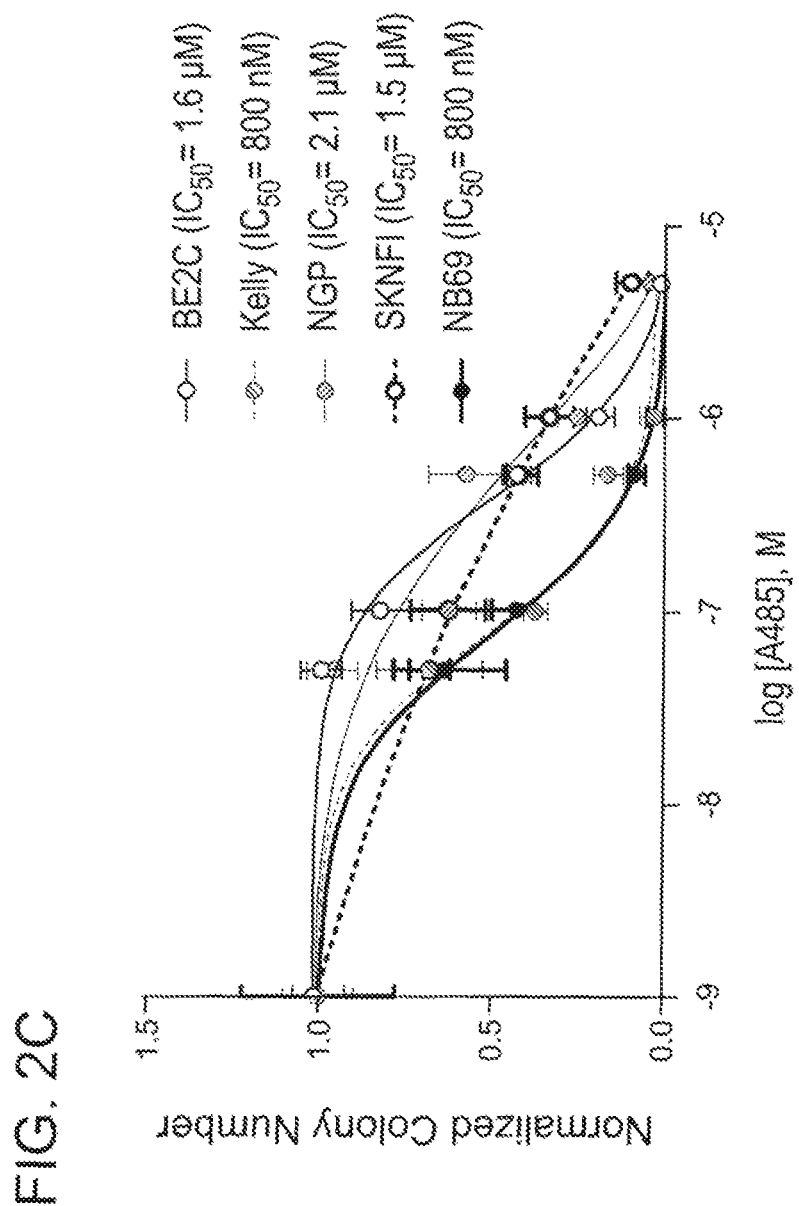
FIG. 2C is a graph that shows the effects of inhibitor A485 in five NB cell lines in colony formation assays. $IC_{50}$ values are also shown.
Figure 2D:
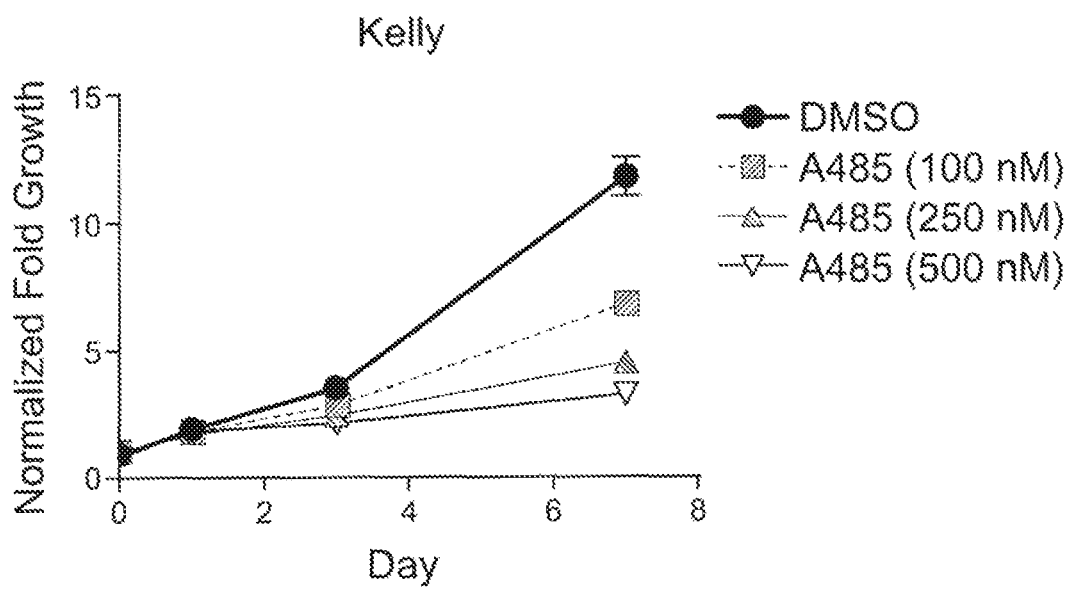
FIG. 2D is a graph that shows growth inhibition in Kelly NB cells that were treated with increasing doses of A485 in CellTiter-Glo® growth assay.
Figure 2E:
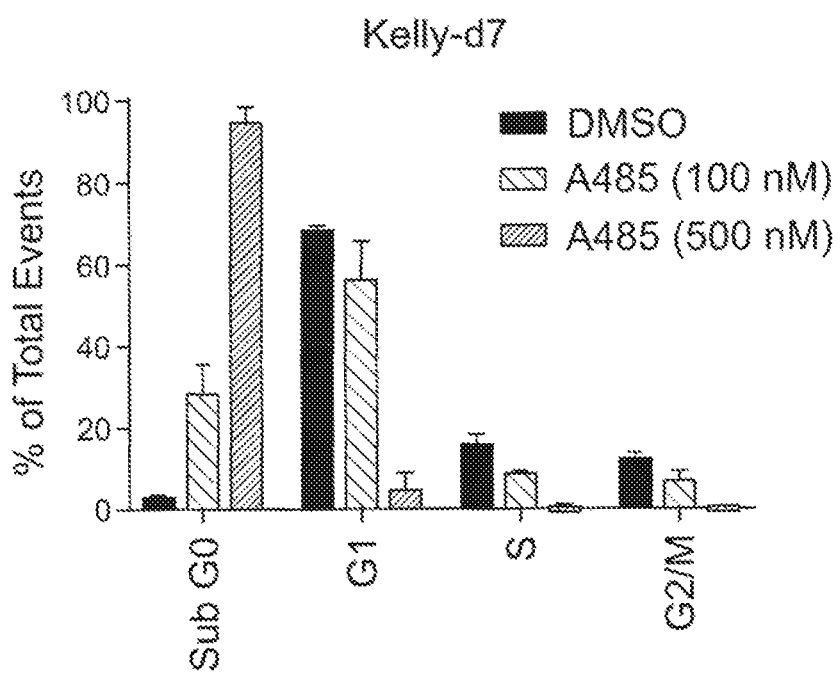
FIG. 2E is a graph that shows induction of apoptosis in Kelly NB cells that were treated with increasing doses of A485 in CellTiter-Glo® growth assay.

The effects of several EP300/CBP inhibitors, C646, CBP30 and A485 were tested in Kelly NB cells. (FIG. 2B). The results indicate that pan-HAT inhibitor A485 was superior to other known EP300/CBP inhibitors in driving growth changes in cellular models of NB at submicromolar levels (FIG. 2C, FIG. 2D). Kelly NB cells treated with increasing doses of A485 in CellTiter-Glo® growth assays demonstrated growth inhibition (FIG. 2E) and induction of apoptosis (FIG. 2F).

Cellular Degradation Assay

Kelly Neuroblastoma cells were seeded at 1,000,000 cells per well in 6 well plates and were treated in a dose-dependent manner for 24 to 72 hours. Whole cell lysates were collected using ice cold lysis buffer [300 mM NaCl, 50 mM Tris-HCl, pH 7.5, 0.5% Triton X-100, 1% SDS, 1 mM dithiothreitol (DTT), Roche® protease inhibitor cocktail (1:000), 25 units/mL Benzonase] and blotted at a protein concentration of 20 µg. Histone extraction was performed using the EpiQuik™ Total Histone Extraction Kit (OP-0006-100, Epigentek) and blotted at a protein concentration of 4 µg.

Compounds CPD 1 to CPD 22 were tested via ATPlite™ assay (ATPlite™ 1000 assay kit, PerkinElmer®, USA) using standard protocol. The Kelly cell lines were treated with compounds for 72 hours and ATPlite™ assay kit was used to measure cell growth inhibition. The signal is normalized to DMSO treated cells.

Figure 15A:
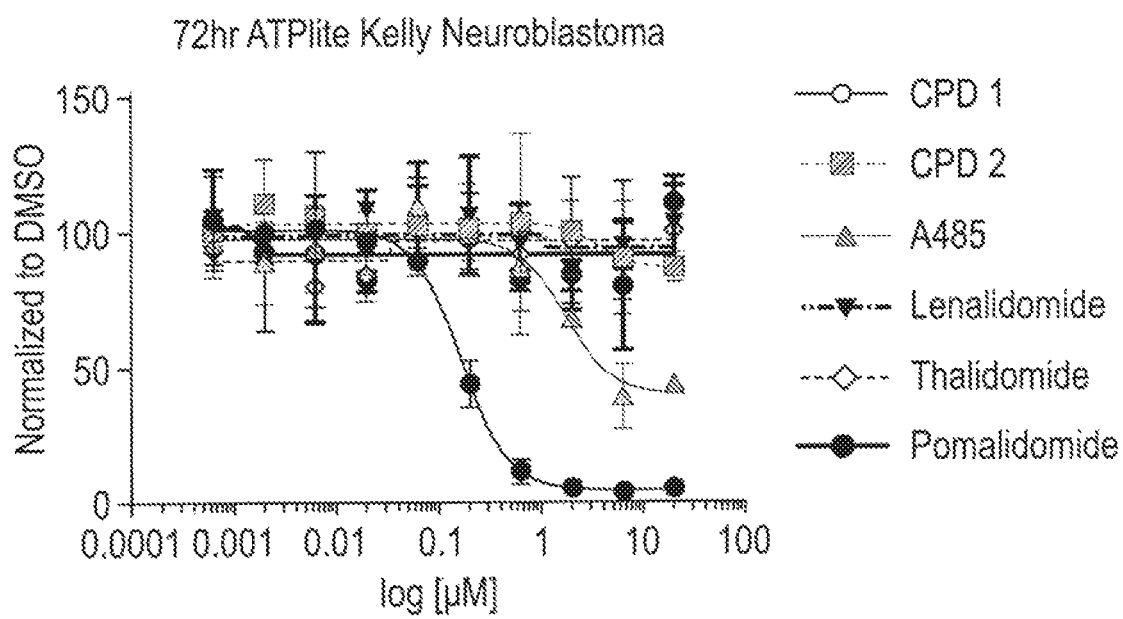
FIG. 15A-FIG. 15G are a set of graphs that show growth inhibition in Kelly cells after treatment with different concentrations (μM) of inventive degraders CPD 1 to CPD 22 and A485 by ATPlite™ assay.
Figure 15B:
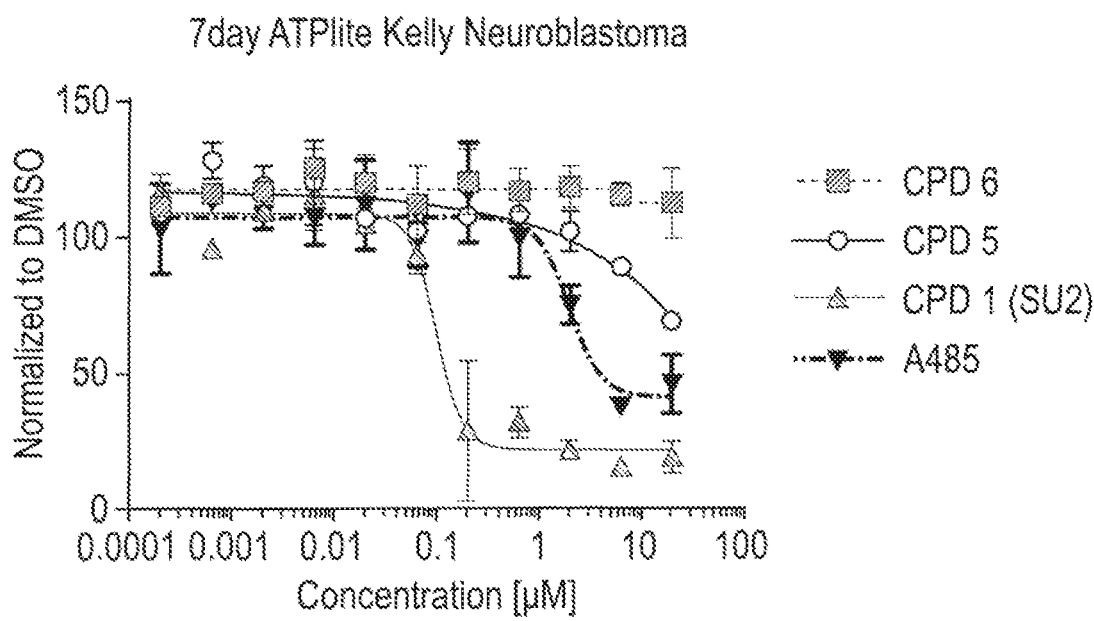
Figure 15C:
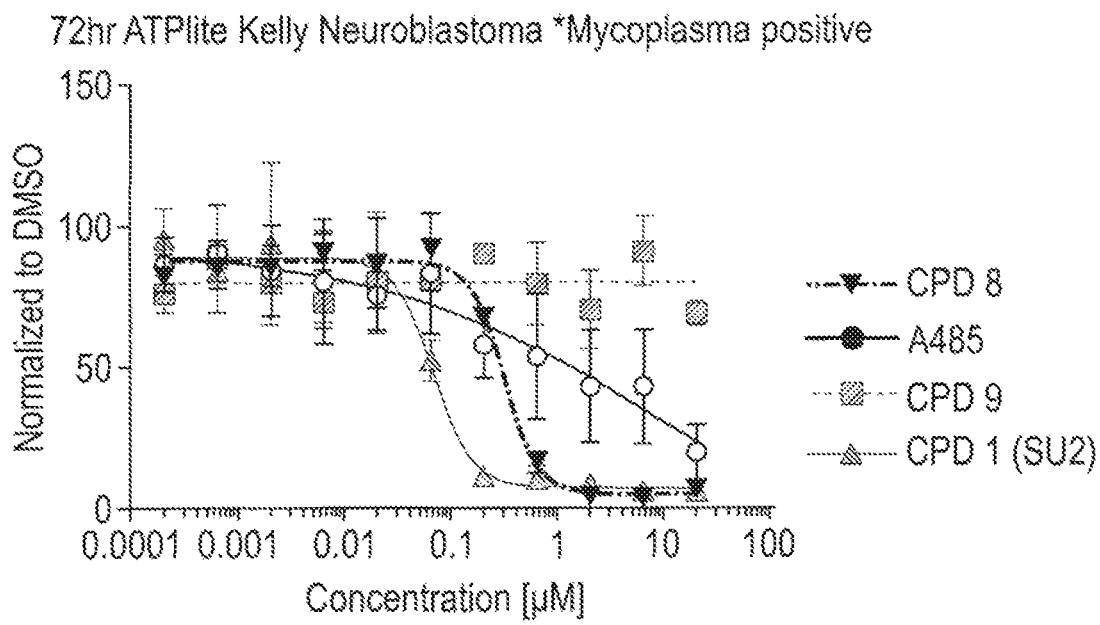
Figure 15D:
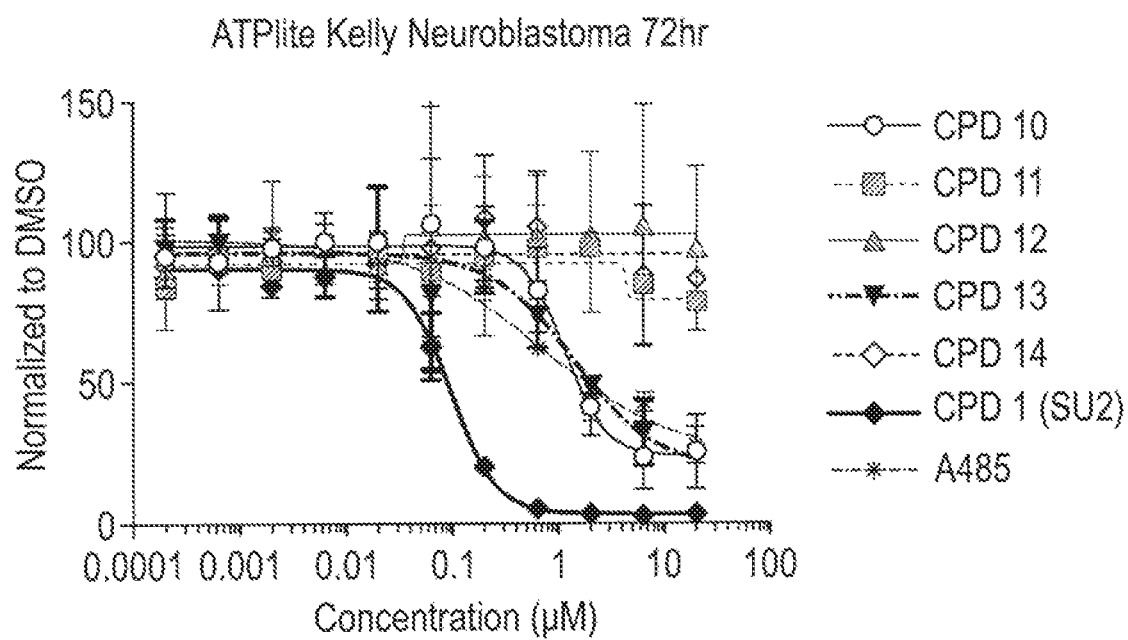
Figure 15E:
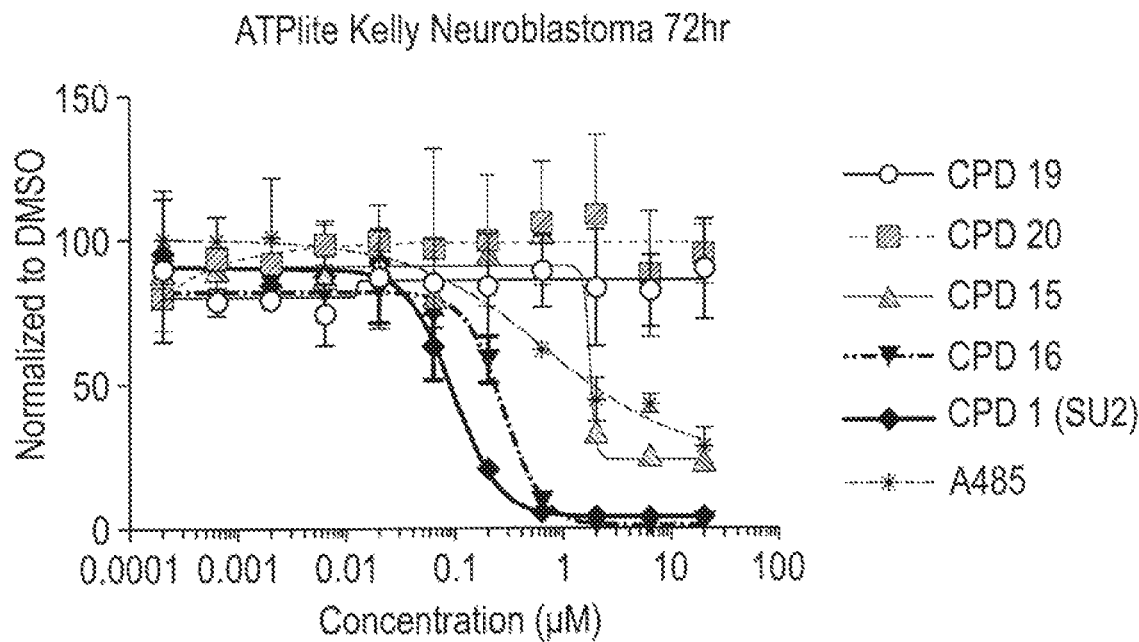
Figure 15F:
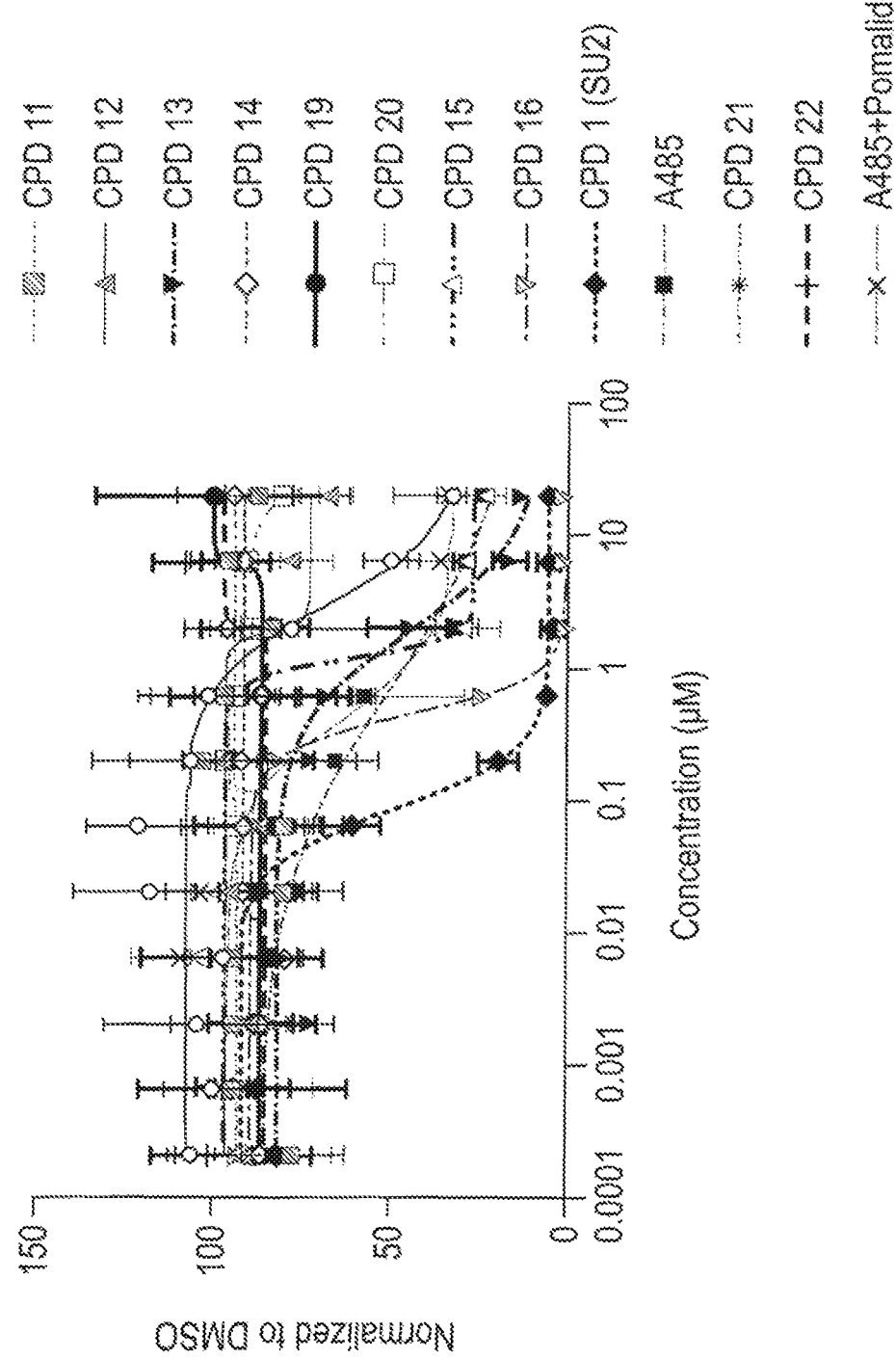
Figure 15G:
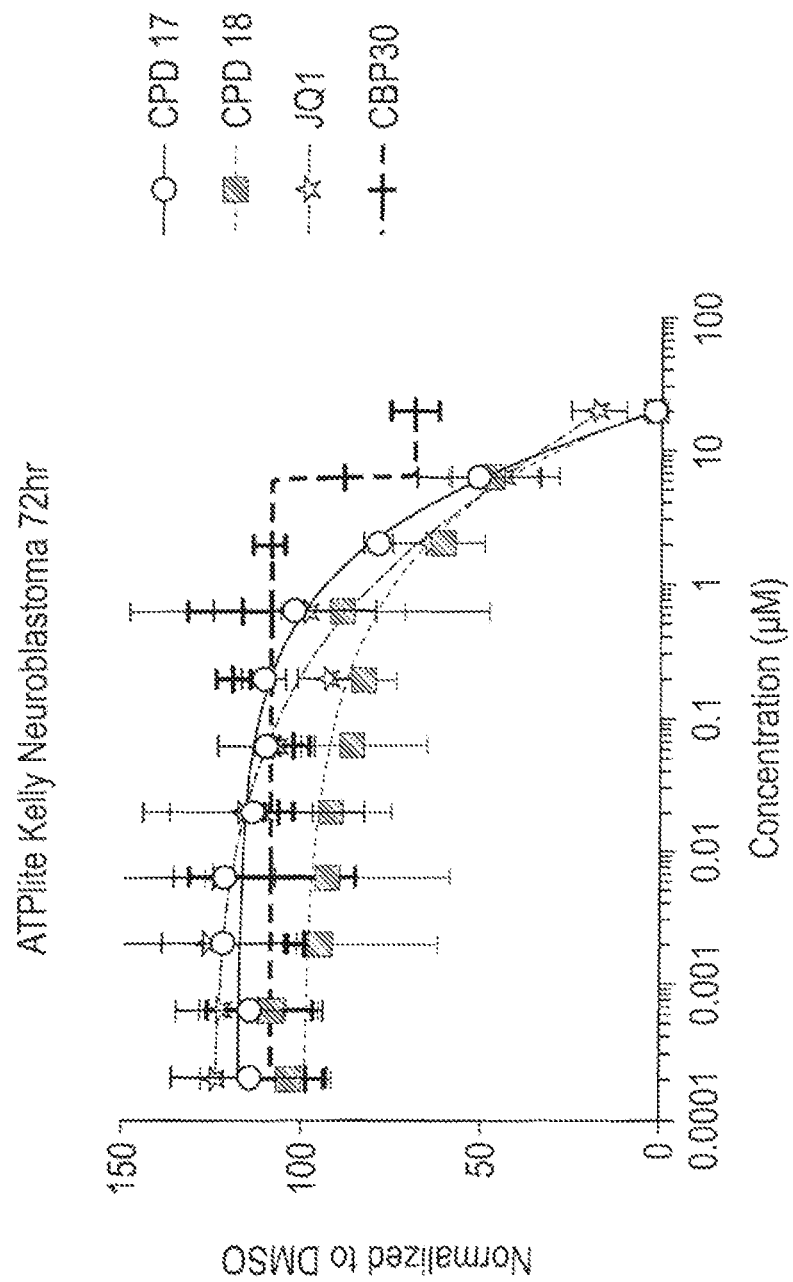

The results, illustrated in FIG. 15A-FIG. 15G, show that inventive compounds caused Kelly NB cell inhibition. CPD 1 (FIG. 15A), CPD 8 (FIG. 15C) and CPD 16 (FIG. 15E) outperformed positive control A485. CPD 2 (negative control), which is not cell permeable, did not inhibit cellular growth (FIG. 15A).

Blotting

Figure 3A:
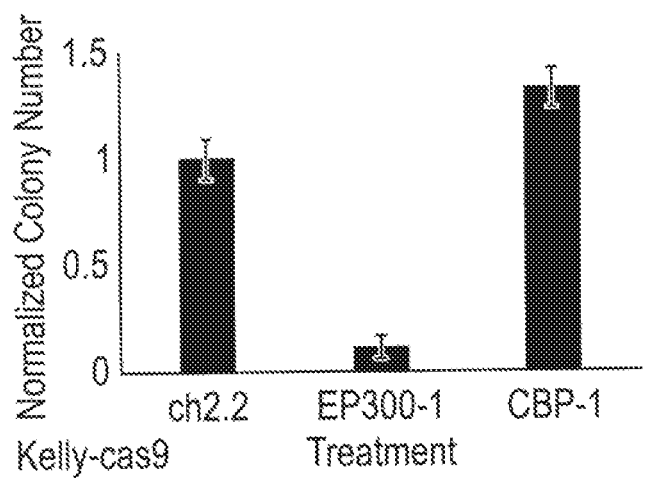
FIG. 3A is a graph that shows a colony formation assay of Kelly NB cells genetically edited to lack EP300 or CBP. The results confirm that NB cells do not require CBP but do require EP300 for cell growth. Ch2.2 is a control sgRNA targeting a gene desert.
Figure 3B:
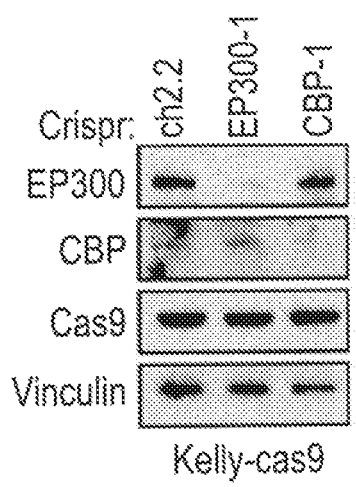
FIG. 3B is an immunoblot that shows successful specific CRISPR-editing of EP300 and CBP.
Figure 4A:
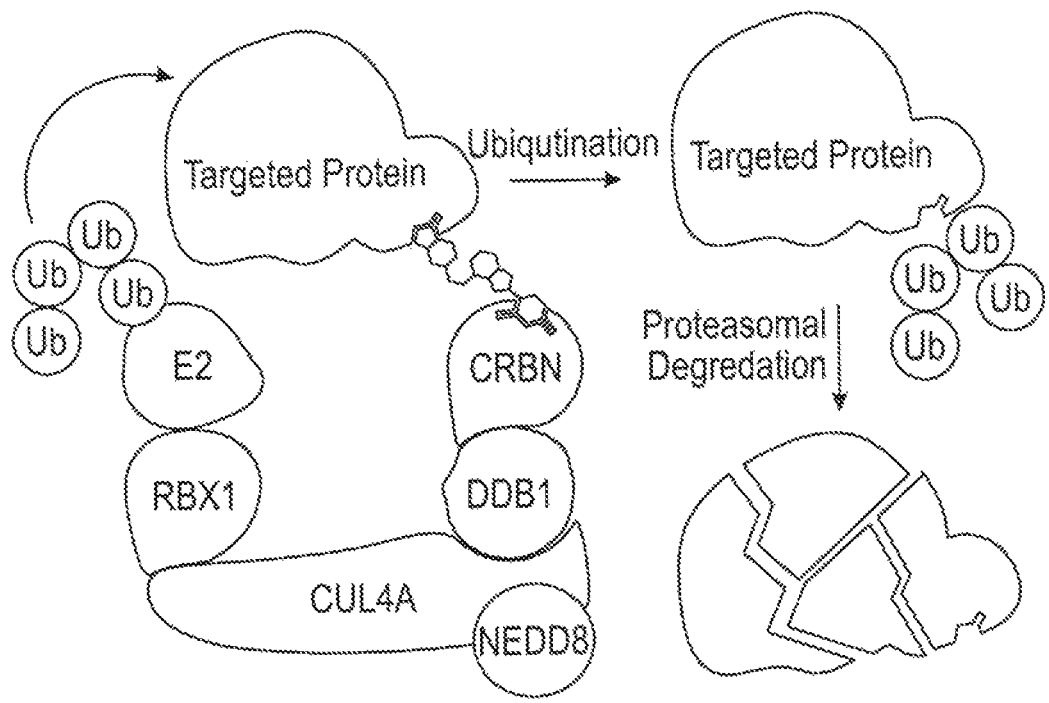
FIG. 4A is a schematic of CRBN based P300 degrader design principles.
Figure 4B:
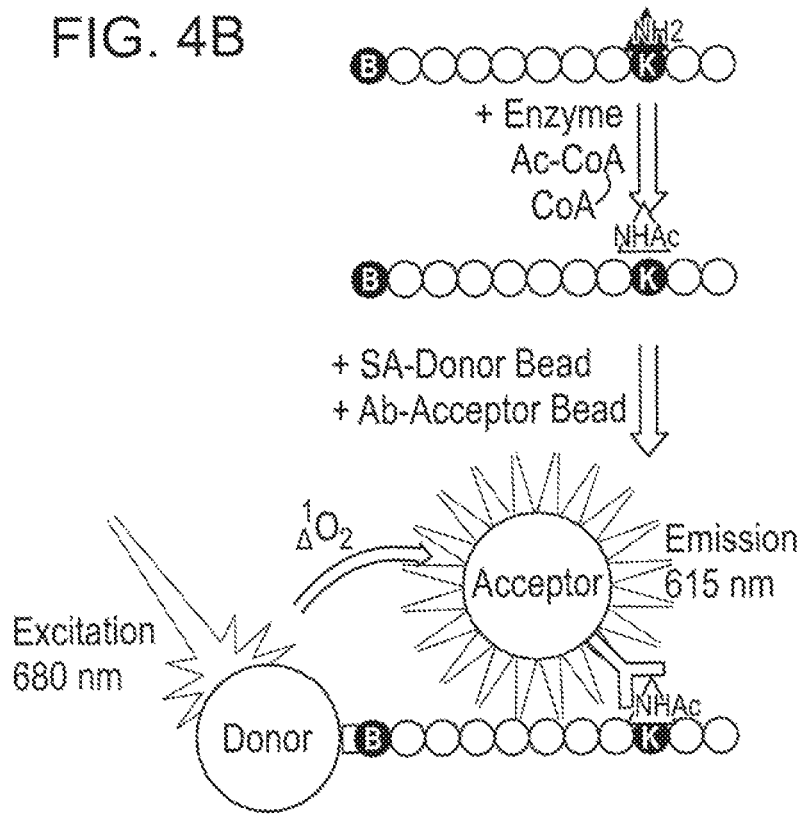
FIG. 4B is an image that shows AlphaLISA® assay for HAT domain of EP300 for evaluating the catalytic function inhibition from degrader.
Figure 4C:
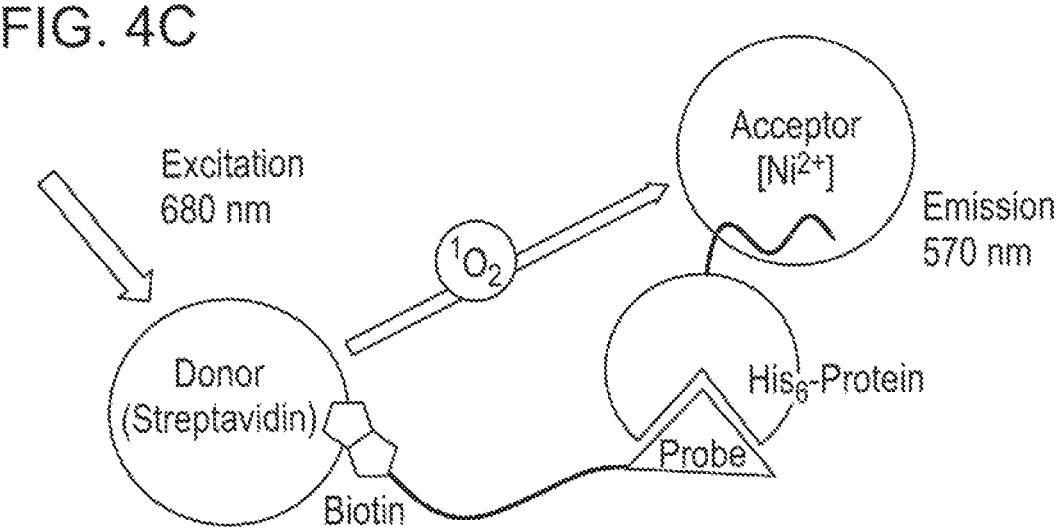
FIG. 4C is an image that shows AlphaScreen™ Assay for both EP300 bromodomain and CRBN.
Figure 4D:
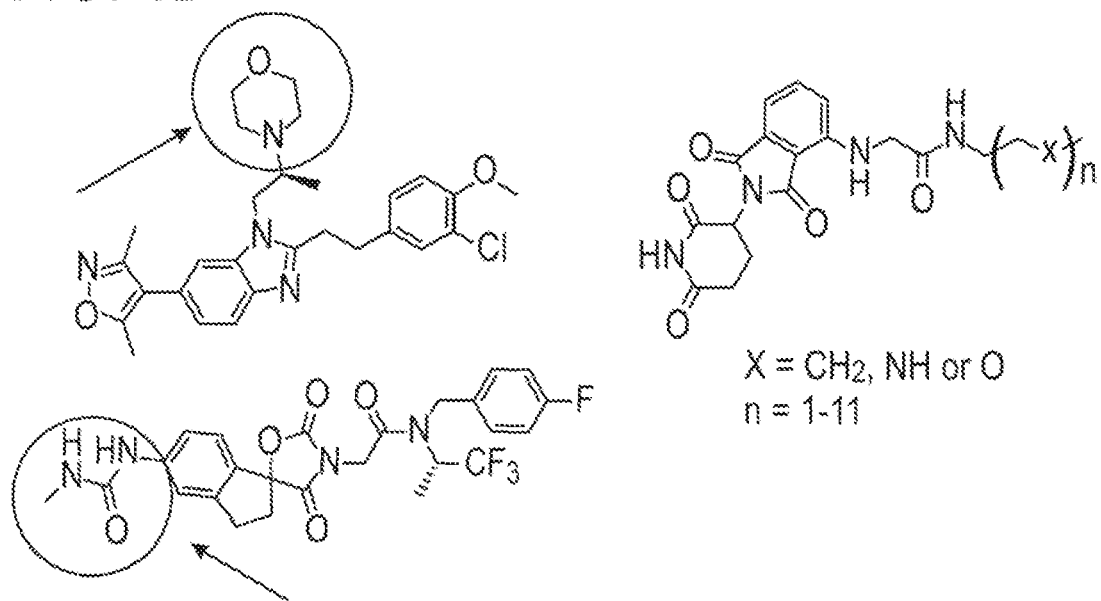
FIG. 4D is an image that shows structure guided design of EP300 degrader based on EP300/CBP bromodomain inhibitor and EP300 inhibitor by linking IMiDs to the different modification sites with different linkers.
Figure 4E:
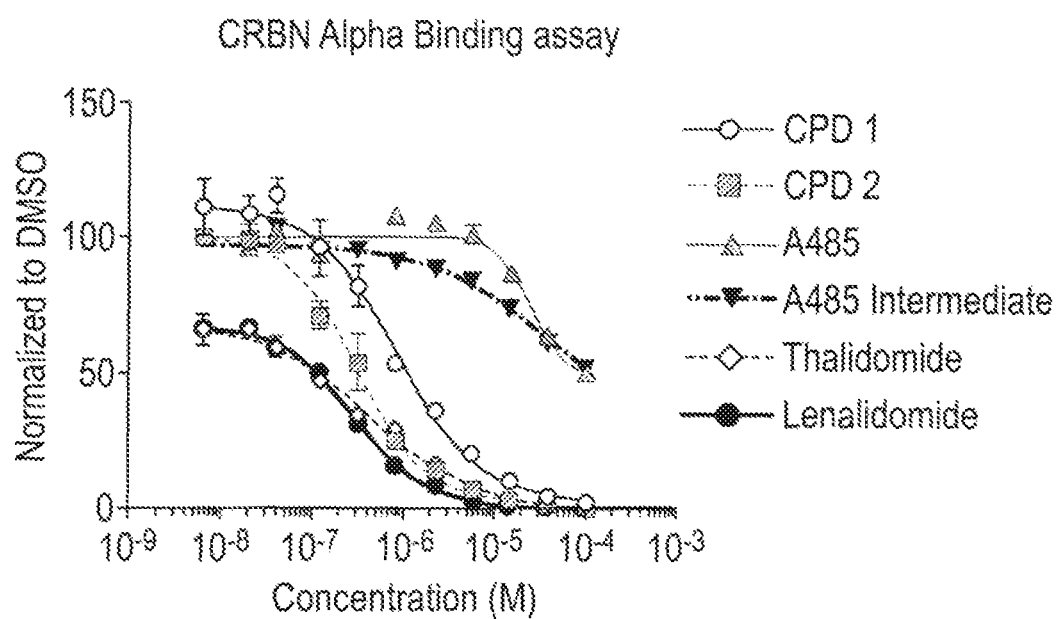
FIG. 4E is a graph that shows evaluation of inventive degrader compound (CPD) 1 and CPD 2 (Negative control compound) in a CRBN AlphaScreen™ assay.
Figure 4F:
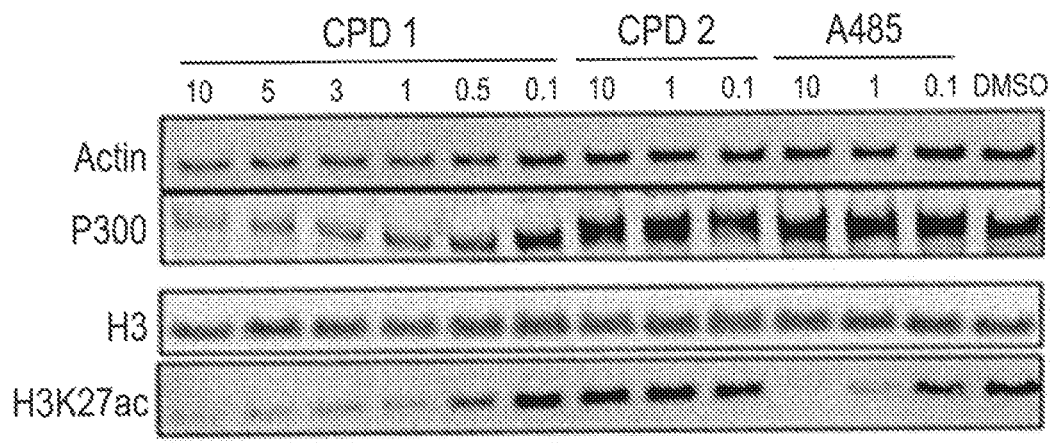
FIG. 4F is an immunoblot that shows EP300 degradation and H3K27Ac level after treating Kelly NB cells with CPD 1, CPD 2, and A485 at different doses at 24 hours.
Figure 4G:
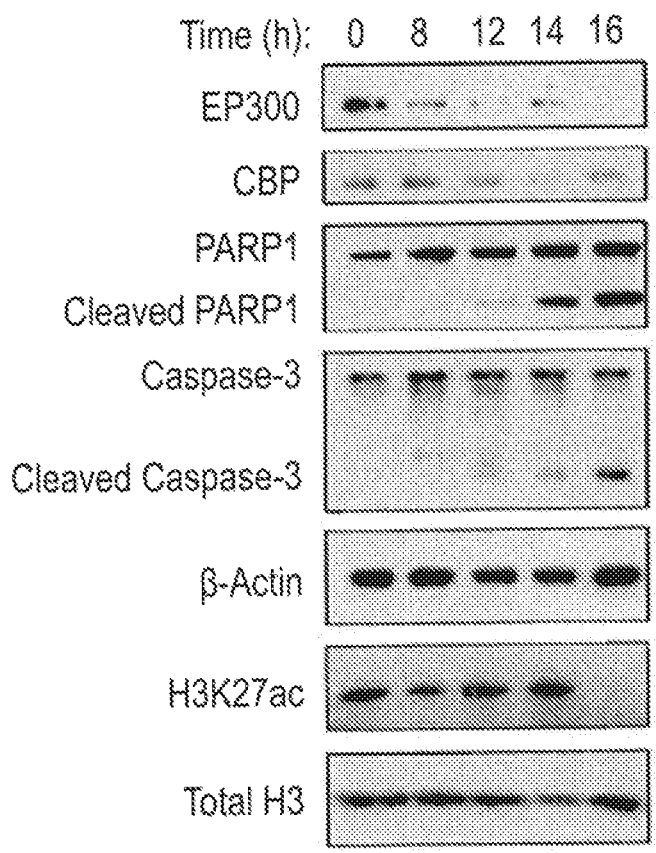
FIG. 4G is an immunoblot that shows EP300 and CBP degradation along with PARP1, cPARP1, Caspase-4 and cCaspase-3 levels after treatment of Kelly NB cells with CPD 1 at 1 µM within 0, 8, 12, 14 and 16 hour. The results confirmed the selective degradation of EP300 by CPD 1.
Figure 4H:
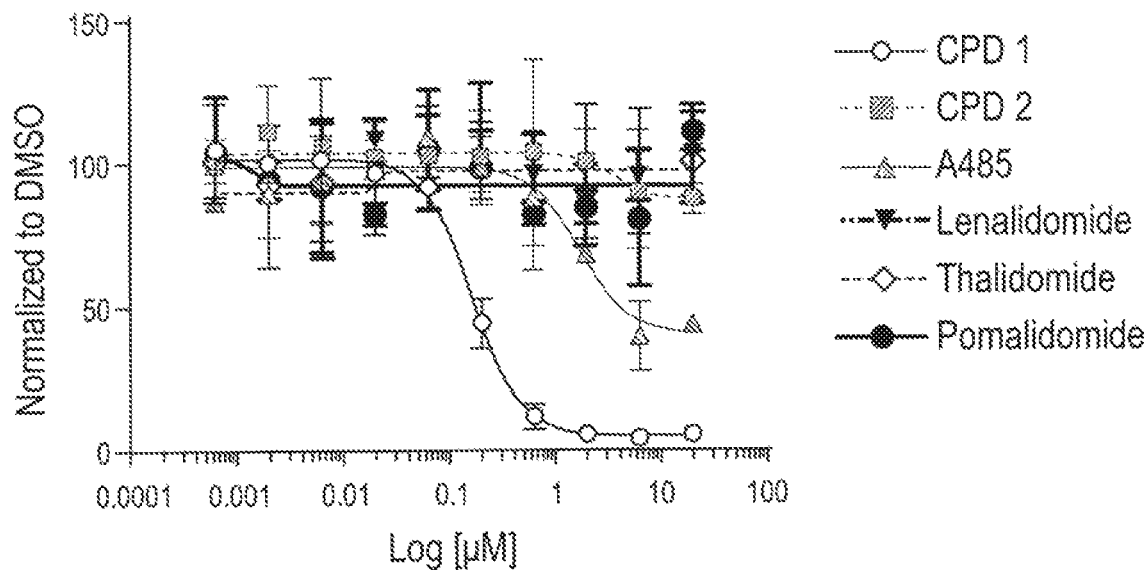
FIG. 4H is a graph that shows relative cell growth after treatment of Kelly cell lines with CPD 1 by CellTiter-Glo®.

Whole cell lysates were resolved in NuPAGE® 3-8% Tris-Acetate polyacrylamide gels (EA03785BOX, Invitrogen™) and histone extraction lysates in Bolt 4-12% Bis-Tris polyacrylamide gels (NWO4125BOX, Invitrogen™). Afterwards, gels were transferred to nitrocellulose membranes (LC2001, Invitrogen™). Primary and secondary antibodies used included anti-p300 at 1:500 dilution (ab10485, Abcam®), anti-CBP at 1:1000 dilution (ab2832, Abcam®), anti-Actin at 1:5000 dilution (3700S, Cell Signaling Technology), anti-H3 at 1:1000 dilution (4499S, Cell Signaling Technology®), anti-H3K27ac at 1:1000 dilution (ab4729, Abcam®), IRDye® 800 goat anti-rabbit at 1:5000 dilution (926-32211, LiCor® Biosciences) and IRDye® 680 goat anti-mouse at 1:5000 dilution (926-68070, LiCor®). Visualization was performed on an Odyssey infrared imaging system (LiCor® Biosciences) (FIG. 3B, FIG. 4F and FIG. 4G).

Example 25: EP300 Dependency in NB Cells

Screening and low throughput data have suggested that EP300, but not CBP, is selectively required for NB cell growth. The experimental method for the colony formation assay is as described in Durbin et al., Nat Genet. 50(9): 1240-60 (2018). The results are shown in FIG. 3A.

Example 26: AlphaLISA® and AlphaScreen™ Assays

An AlphaLISA® assay for EP300 catalytic function (FIG. 3B) and an AlphaScreen™ assay for EP300 bromodomain and cereblon (CRBN) using biotinylated tagged small molecules as a probe for EP300 bromodomain and CRBN, respectively, were developed (FIG. 3C).

The AlphaScreen™ assay was performed in 384-well plate format using white AlphaPlate (PerkinElmer®, USA), and transfer of pre-diluted compound (100 nL) was performed using a Janus Workstation (PerkinElmer®, USA). All subsequent steps were carried out in assay buffer (50 mM 4-(2-hydroxyethyl)-1-piperazineethanesulfonic acid (HEPES), pH 7.5, 0.1% (wt/vol) bovine serum albumin (BSA) and 0.01% (vol/vol) Tween-20). In brief, 10 µL of assay buffer containing enzyme (2 nM Final) was pre-incubated for 15 min with dilutions of compound. The enzyme reaction was initiated by the addition of substrate (5 μL) consisting of acetyl Co-A 2-OG (5 μM Final).

FAS final concentration was 10 μM. Histone tail-GGK Biotin final concentration was 100 nM Final. The enzyme reaction was allowed to proceed for 30 minutes and was stopped by the addition of 5 μL of assay buffer containing ethylenediaminetetraacetic acid (EDTA) (40 mM) and NaCl (1200 mM). The final concentration of dimethyl sulfoxide (DMSO) was 1%. Streptavidin donor beads (0.08 mg/mL) and protein-A-conjugated acceptor beads (0.08 mg/mL) were preincubated for 1 h with antibody to methyl mark (300 ng/mL Final), and the presence of histone H3 product acetylation mark was detected using the preincubated AlphaScreen™ beads (5 μL). Detection was allowed to proceed for 2 hours at rt, and the assay plates were read on the Envision™ 2104 plate reader. Data were normalized to the (no-enzyme) control, and the $IC_{50}$ values were determined via nonlinear regression curve fit using GraphPad Prism (FIG. 4E-FIG. 4H).

The $IC_{50}$ values for CDP 1 to CPD 22 that were generated from the assay are reported in Table 1.

TABLE 1

$IC_{50}$ values in Kelly cells.

| Compound | $IC_{50}$ (μM) |
| --- | --- |
| 1 | 0.166 |
| 2 | 3.42 |
| 3 | ND |
| 4 | ND |
| 5 | ND |
| 6 | ND |
| 7 | ND |
| 8 | 0.310 |
| 9 | ND |
| 10 | 1.149 |
| 11 | ND |
| 12 | ND |
| 13 | 1.388 |
| 14 | ND |
| 15 | 1.76 |
| 16 | 0.27 |
| 17 | ND |
| 18 | ND |
| 19 | ND |
| 20 | ND |
| 21 | TBD |
| 22 | TBD |

ND: not detected
TBD: to-be-determined

Cell growth inhibition was observed with inventive degraders CPD 1, CPD 8, CPD 10, CPD 13, CPD 15, and CPD 16. Cell growth inhibition was not detected or determined with the rest of the compounds.

EP300 is important for NB cancer cell survival (FIG. 3A). The inventive compound CPD 1 selectively dimerized the targeted protein (EP300) to E3 ligase (CRBN) without affecting CBP. CPD 1 induced the selective degradation of EP300 in NB cancer cells, and kill NB cells with much higher potency compared to inhibitor alone.

Example 27: Adaptor Function of Putative EP300 Degrader Assessment

Figure 5A:
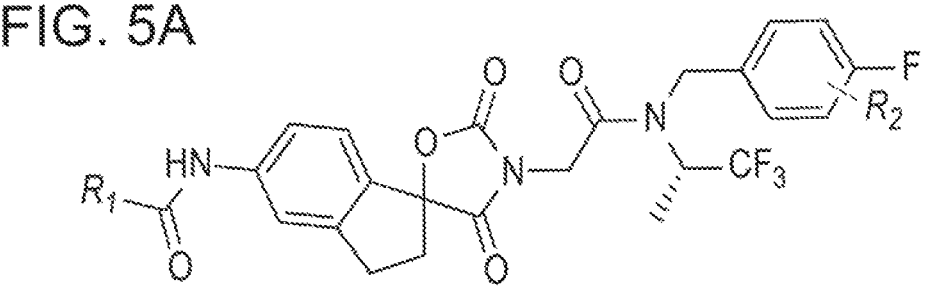
FIG. 5A is an image that shows medicinal chemistry plan to develop a focused EP300 degrader compound library.
Figure 5A:
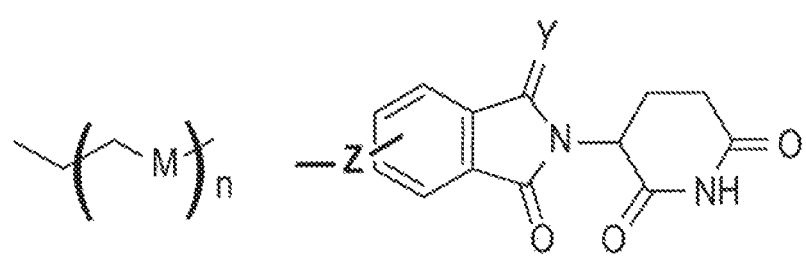
Figure 5B:
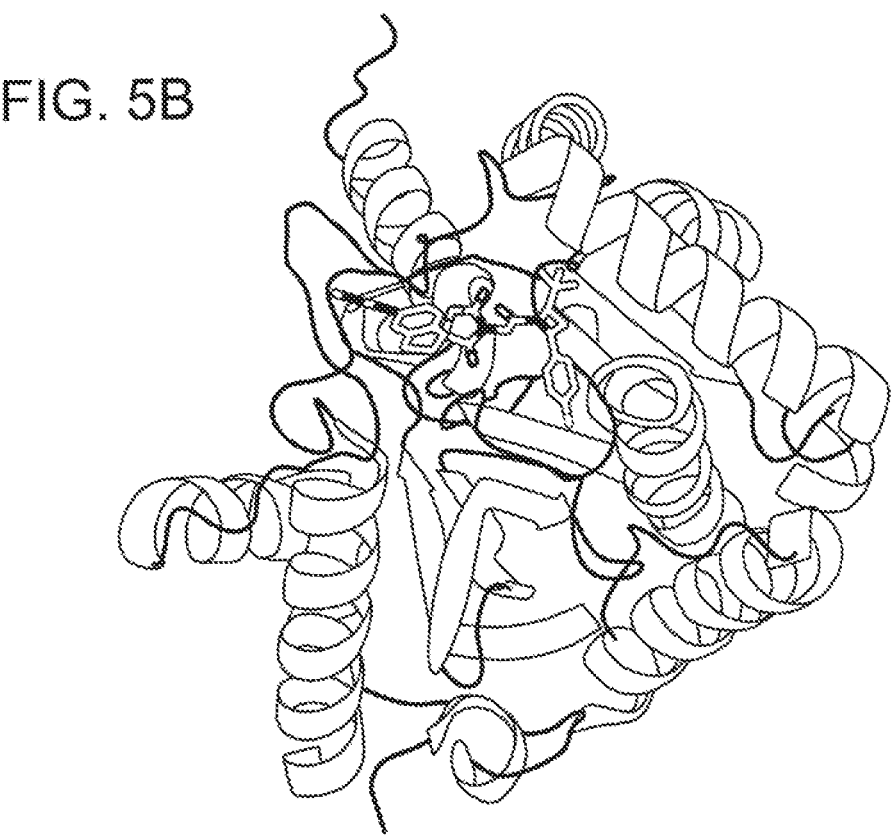
FIG. 5B is an image of computational docking model of inventive compound CPD 1 with EP300 and CRBN.
Figure 5C:
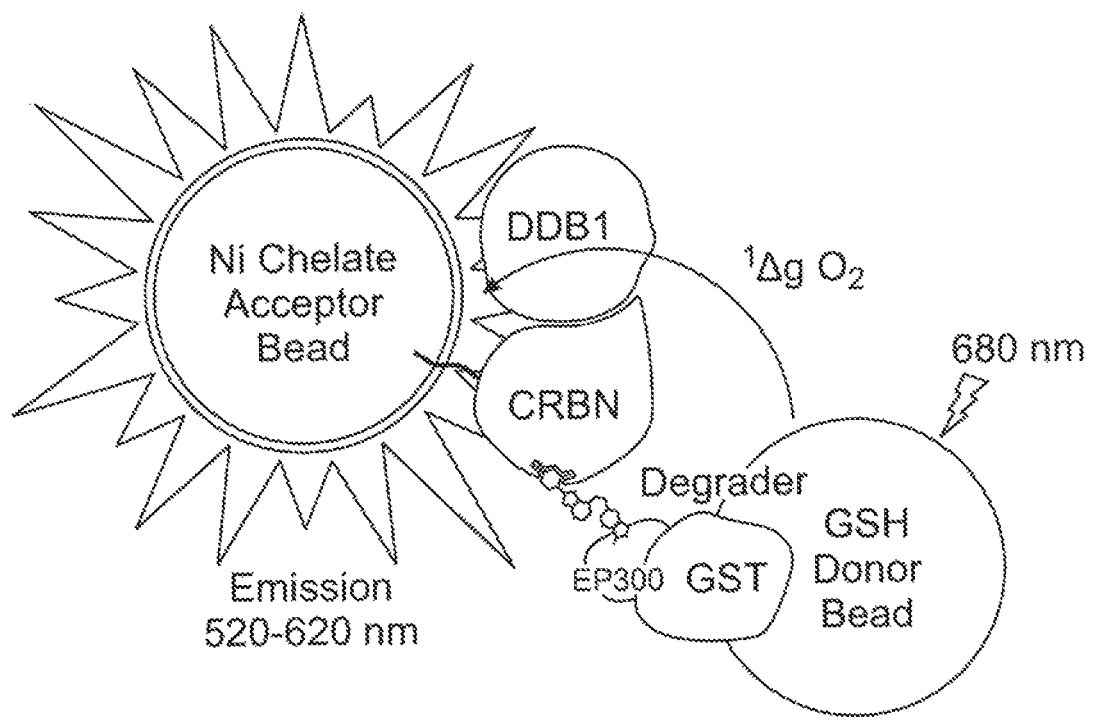
FIG. 5C is a graph that shows schematic illustration of dimerization assay to assess the EP300 and CRBN dimerization induced by degrader.

To experimentally assess the adaptor function of putative EP300 degraders, luminescence proximity assay (AlphaScreen™, PerkinElmer®) for human recombinant EP300 and CRBN-DDB1 proteins is used as was previously reported for BRD4/CRBN-DDB1 (FIG. 5E) (Winter, et al. Science 348(6241):1376-81 (2015)).

Figure 7A:
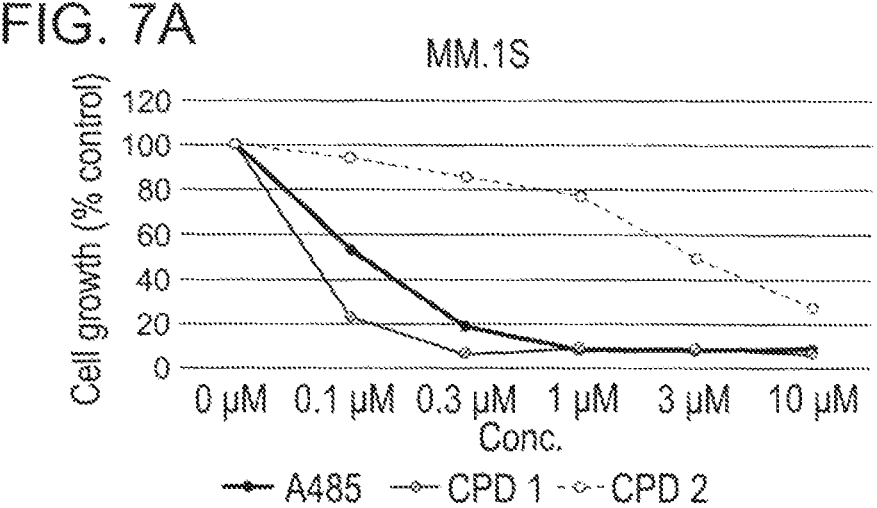
FIG. 7A is a graph that shows growth inhibition in MM.1S cells after treatment with 0-10 µM CPD 1, CPD 2 and A-485 by a 4-day cell counting kit (CCK) assay.
Figure 7B:
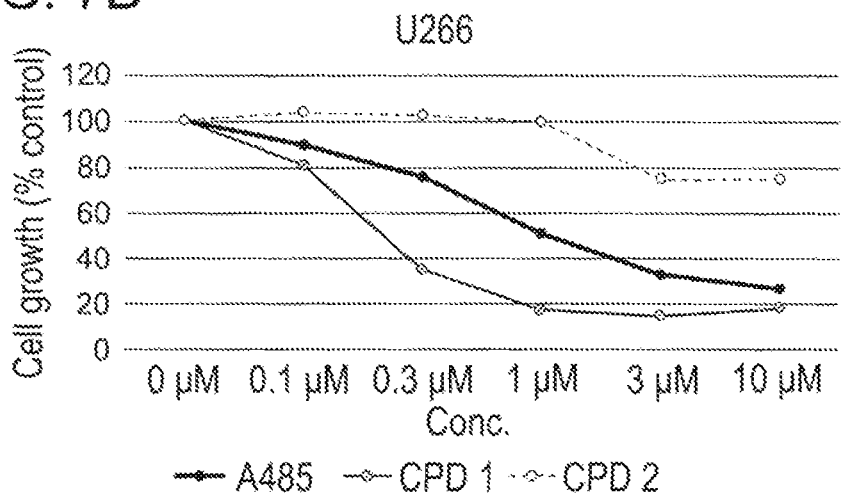
FIG. 7B is a graph that shows growth inhibition in U266 cells after treatment with 0-10 µM CPD 1, CPD 2 and A-485 by a 4-day cell counting kit (CCK) assay.
Figure 7C:
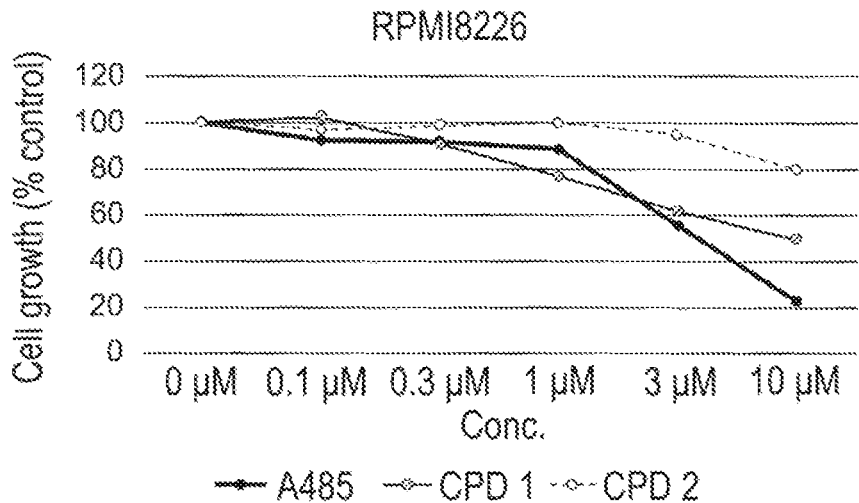
FIG. 7C is a graph that shows growth inhibition in RPMI8226 cells after treatment with 0-10 µM CPD 1, CPD 2 and A-485 by a 4-day cell counting kit (CCK) assay.

Example 28: Cellular Growth Inhibition with CPD 1, CPD 2 and A-485 Using 4-Day ATPlite™ Assay An aliquot of the ATP standard solution (ATPlite™ 1000 assay kit, PerkinElmer®, USA) was used to prepare a dilution series in water. A series of 100 μL of complete culture medium was pipetted without cells into the wells of the plate. To each well was added 50 μL of the mammalian cell lysis solution, and the plate was shaken for 5 minutes in an orbital shaker at 700 rpm. 10 μL of the ATP dilution series was added to the wells, and the plate was shaken for 5 minutes in an orbital shaker at 700 rpm. 50 μL of the substrate solution was added and the plate was shaken for 5 minutes in an orbital shaker at 700 rpm. The plate dark adapted the plate for 10 minutes prior to measuring the luminescence and then preparing a standard curve. The results are summarized in FIG. 7A-FIG. 7C. Inventive compound CPD 1 outperformed inhibitor A485 in MM.1S and U266 cells.

Example 29: Cellular Growth Inhibition with CPD 1, CPD 2 and A-485 Using 6-Day 3-(4,5-Dimethyl-thiazol-2-Yl)-2,5-diphenyltetrazolium Bromide (MTT) Assay Media from cell cultures was discarded. For adherent cells, the media was carefully aspirated. For suspension cells, the 96 well plate at 1,000×g, 4° C., was spun for 5 minutes in a microplate-compatible centrifuge and the media was carefully aspirated. The volume of existing media has to be the same for each sample. Fifty (50) μL of serum-free media and 50 μL of MTT solution were added into each well. The plate was incubated at 37° C. for 3 hours.

Figure 8A:
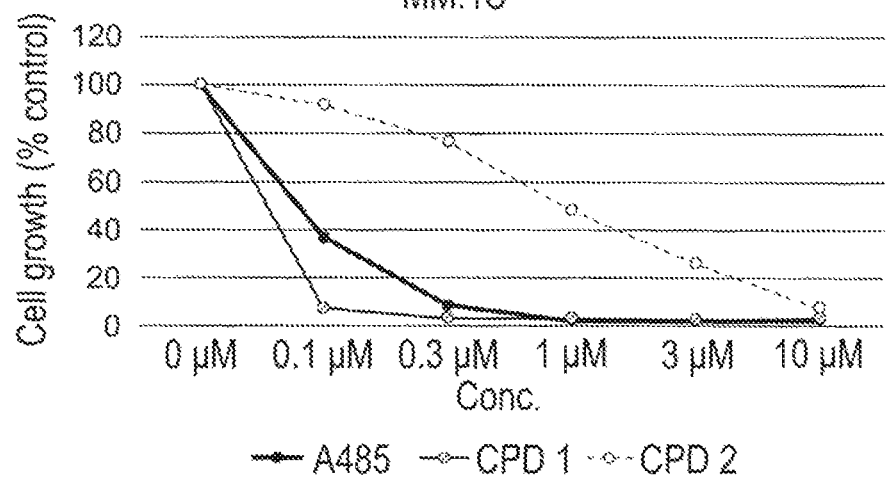
FIG. 8A is a graph that shows growth inhibition in MM.1S cells after treatment with 0-10 µM CPD 1, CPD 2 and A-485 by a 6-day 3-(4,5-dimethylthiazol-2-yl)-2,5-diphenyltetrazolium bromide (MTT) assay.
Figure 8B:
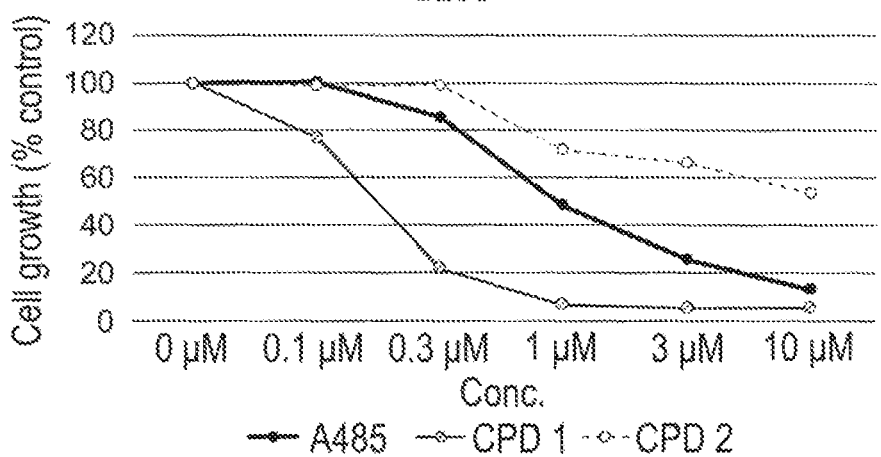
FIG. 8B is a graph that shows growth inhibition in U266 cells after treatment with 0-10 µM CPD 1, CPD 2 and A-485 by a 6-day MTT assay.
Figure 8C:
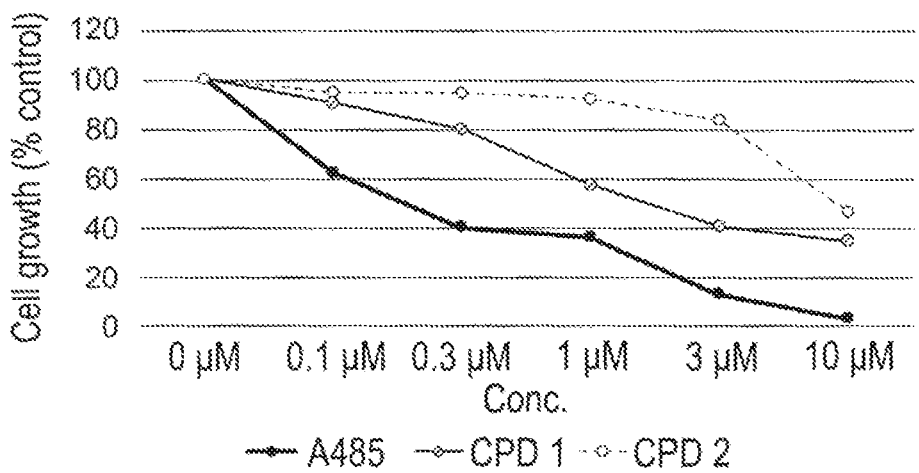
FIG. 8C is a graph that shows growth inhibition in RPMI8226 cells after treatment with 0-10 µM CPD 1, CPD 2 and A-485 by a 6-day MTT assay.

After incubation, 150 μL of MTT solvent were added into each well. The plate was wrapped in foil and shaken on an orbital shaker for 15 minutes. Absorbance was read at OD=590 nm. Reading was performed within 1 hour. The results are summarized in FIG. 8A-FIG. 8C. The inventive compound CPD 1 outperformed inhibitor A485 in MM.1S and U266 cells.

Example 30: Selective Degradation of EP300 by CPD1

The experimental protocol is the same as in Example 24. The protein level was determined by immunoblot using EP300 antibody, CBP antibody or H3K27ac antibody. The total H3 was used as loading control. The protein level was measure in either dose dependent manner or time dependent manner.

Figure 9A:
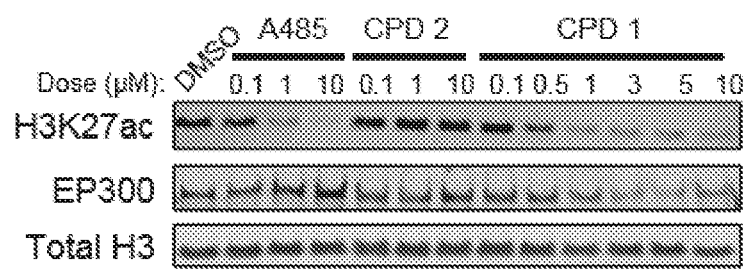
FIG. 9A is an immunoblot that shows EP300 degradation and H3K27Ac level after treating Kelly NB cells with CPD 1, CPD 2, and A485 at different doses at 24 hours.
Figure 9B:
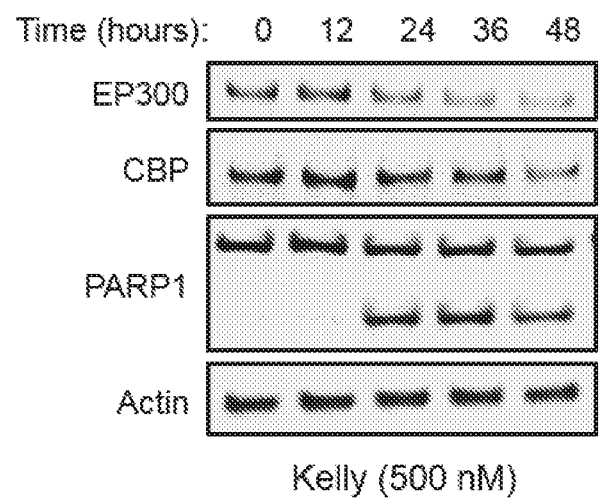
FIG. 9B is an immunoblot that shows EP300 degradation and CBP and PAP1 levels after treating Kelly NB cells with CPD 1 (500 nM) in a time-course experiment.

The results illustrated in FIG. 9A-FIG. 9D show clear degradation of EP300 without affecting the CBP level in first the 36 hours, which confirmed the selectivity of CPD 1 toward EP300 over CBP. The degradation of CBP was observed after 48 hour (FIG. 9B).

Figure 9C:
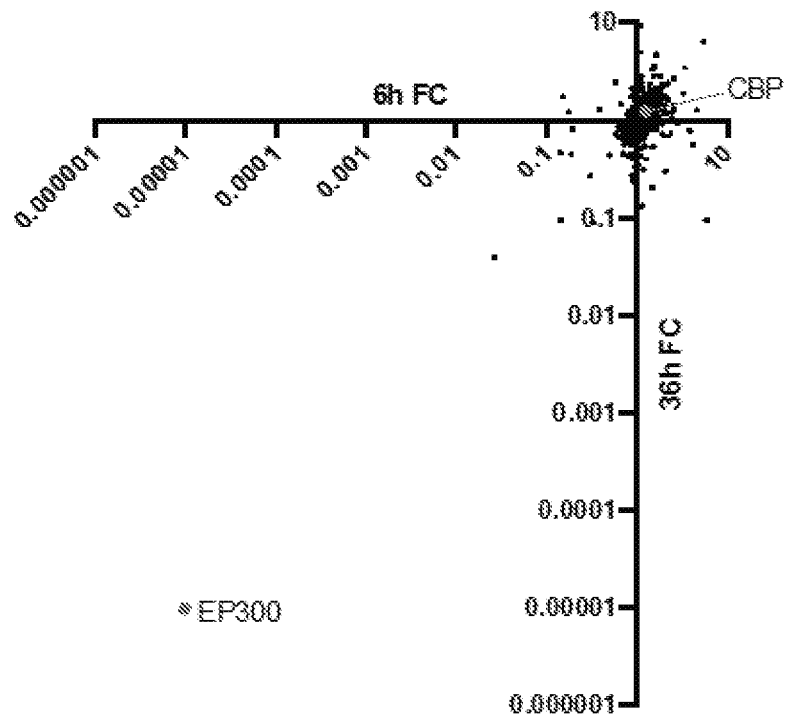
FIG. 9C is a plot of the proteomics analysis results after treating Kelly NB cells with CPD 1 (500 nM) at 6 hours and 36 hours.
Figure 9D:
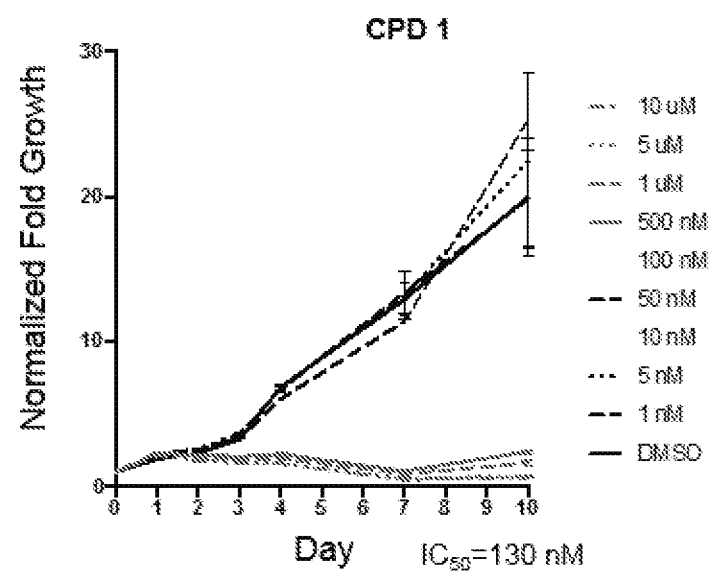
FIG. 9D is a graph that shows Kelly cell growth in a dose dependent manner at 10 days with CPD 1 using colony formation assay.
Figure 10A:
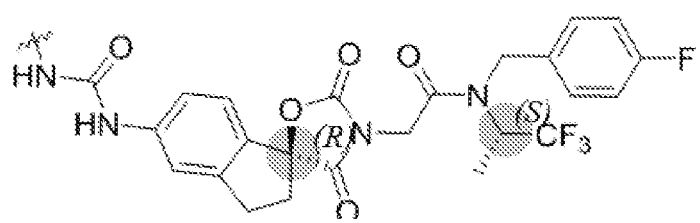
FIG. 10A is an image that shows the chiral centers (R, S) in the targeting ligand in CPD 1.
Figure 10B:
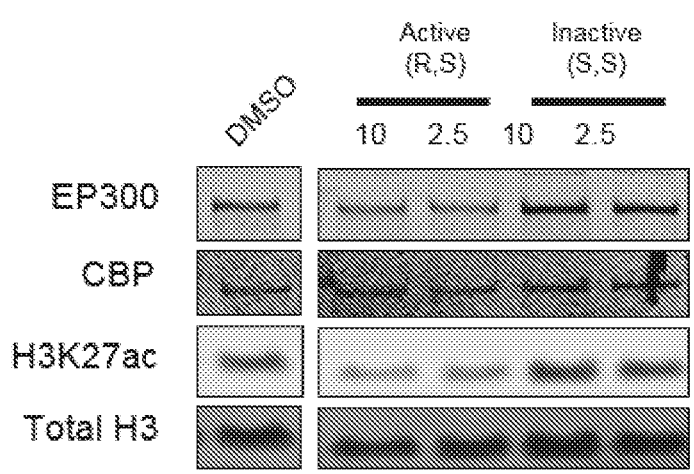
FIG. 10B is an immunoblot that shows EP300 degradation and CBP, H3K27Ac, and total H3 levels after treating Kelly NB cells with CPD 1 and its S,S-isomer.
Figure 10C:
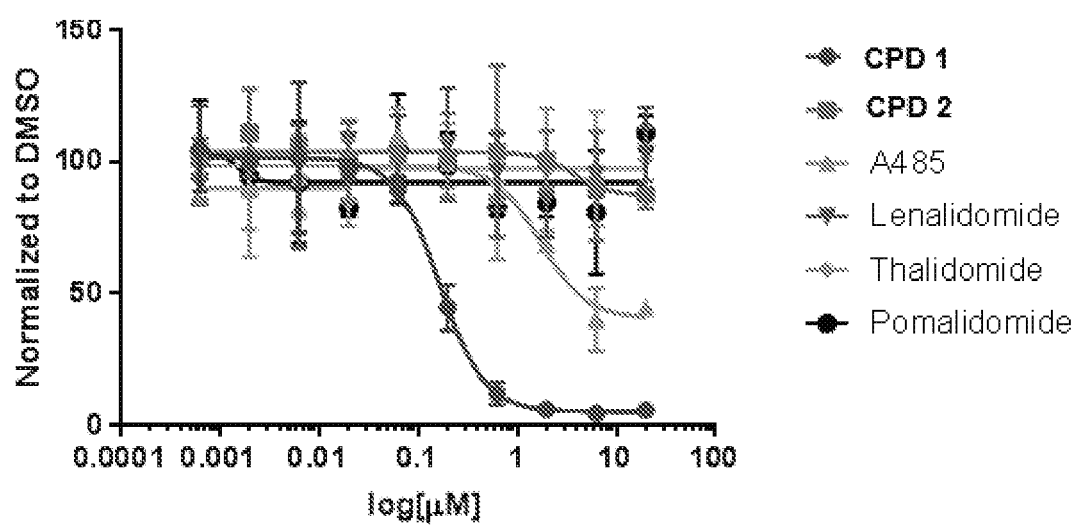
FIG. 10C is a graph that shows growth inhibition in Kelly cells after treatment with different concentrations (µM) of CPD 1, CPD 2 (cell impermeable negative control), lenalidomide, thalidomide, and pomalidomide by ATPlite™ assay.
Figure 10D:
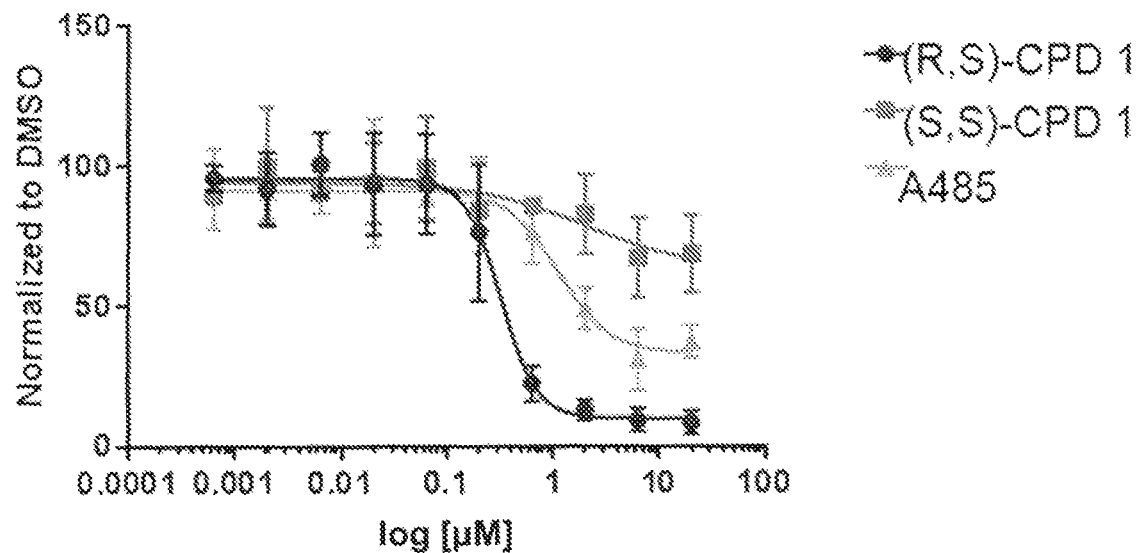
FIG. 10D is a graph that shows growth inhibition in Kelly cells after treatment with different concentrations (µM) of CPD 1, its (S,S)-isomer and A485 by ATPlite™ assay.

The proteomics study showed that EP300 was selectively and significantly degraded by inventive degrader CPD 1 (FIG. 9C). No changes in the CBP level were observed. The results in FIG. 9D showed that CPD 1 inhibited the Kelly cell growth in a dose dependent manner at 10 days using colony formation assay.

Example 31: Biological Activity Assessment of CPD 1 and Isomer (S,S)-CPD 1

The results, illustrated in FIG. 10A-FIG. 10D, show that the chiral centers in the targeting ligand of CPD 1 (R,S) play an important role in the potency of the compound. No cellular degradation of EP300 was observed with (S,S) isomer.

Example 32: Defining Substrate Specificity for Inventive Compounds

AlphaScreen™ assay was used to determine the binding of inventive degrader compound toward both CRBN and HAT domain. The experimental protocol is the same as in Example 26.

Figure 11A:
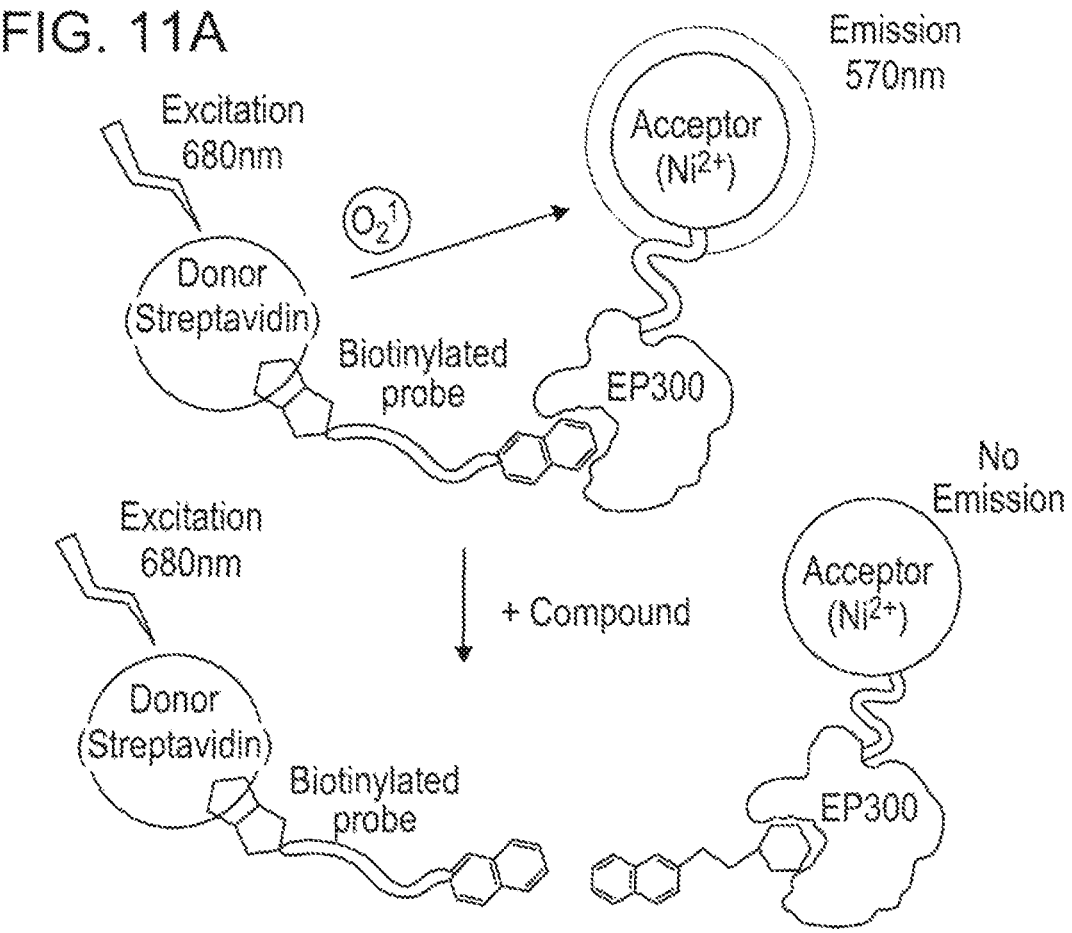
FIG. 11A is a diagram that describes the mechanism of the AlphaScreen™ assay used to determine substrate specificity for inventive compounds.
Figure 11B:
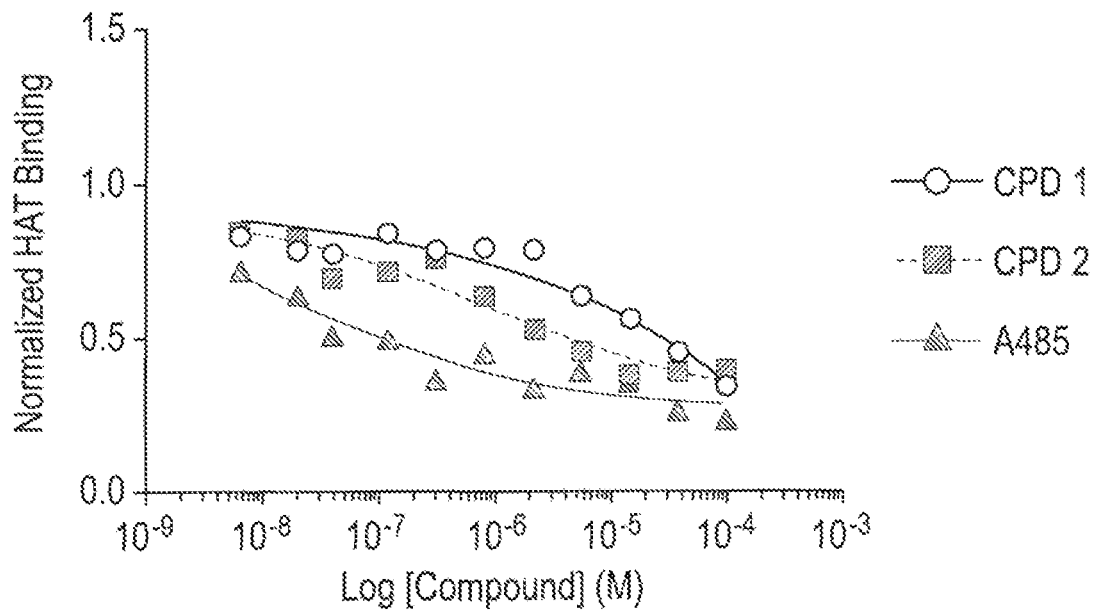
FIG. 11B is a graph that shows that CPD 1, CPD 2 and A485 (HAT inhibitor) bind the HAT (EP300) domain by AlphaScreen™ assay.
Figure 11C:
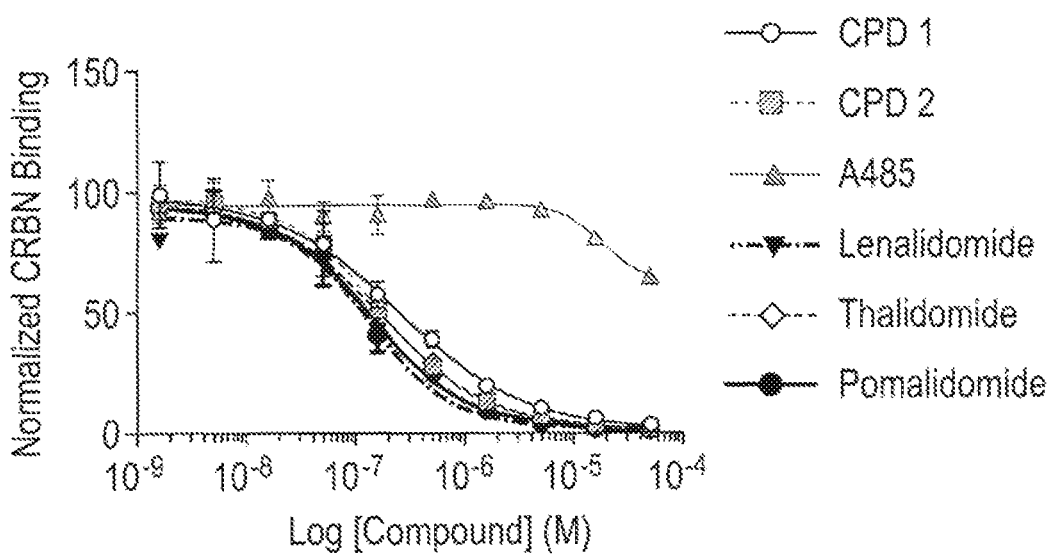
FIG. 11C is a graph that shows that CPD 1, CPD 2, lenalidomide, thalidomide, and pomalidomide bind the cereblon (CRBN) by AlphaScreen™ assay. As expected, no binding was observed with A485.

The results, illustrated in FIG. 11A-FIG. 11C, show inventive degrader CPD 1 bound both CRBN (FIG. 11C) and HAT domain (FIG. 11B).

Example 33: CPD 1 is a CRBN-Dependent Degrader Molecule

CPD 1 was tested in CRBN knockout (k/o) Kelly cell lines. The experimental protocol is the same as in Example 24.

Figure 12A:
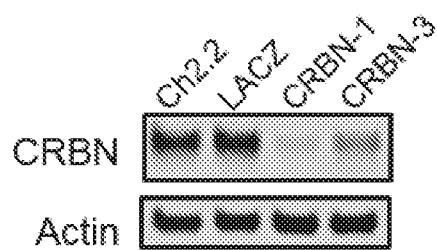
FIG. 12A is an immunoblot that shows CRBN levels in Ch2.2, LACZ and CRBN knock/out cell lines.
Figure 12B:
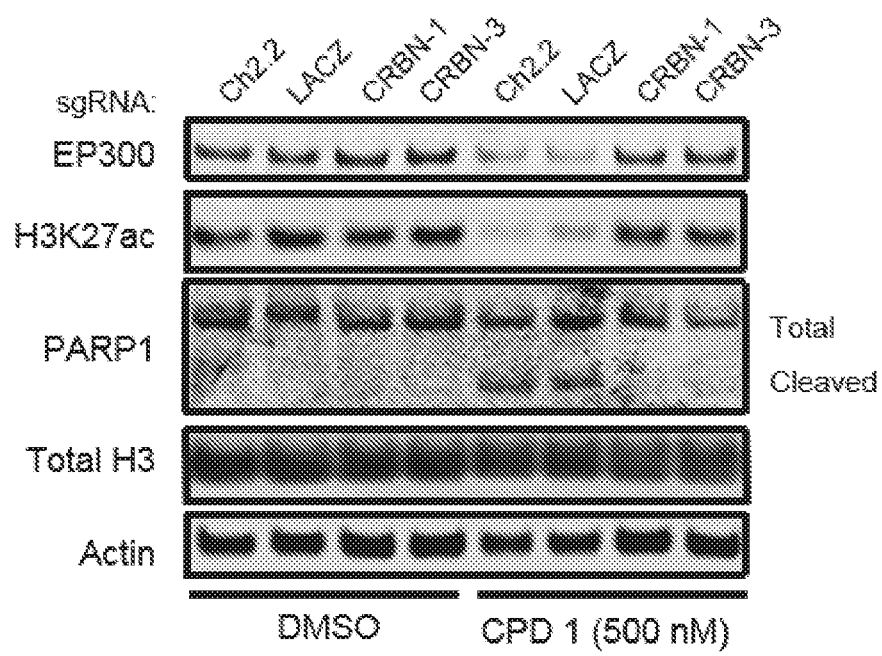
FIG. 12B is an immunoblot that shows EP300 degradation and CBP, H3K27Ac, and total H3 levels after treating Ch2.2, LACZ and CRBN knock/out cell lines with CPD 1 (500 nM).
Figure 12C:
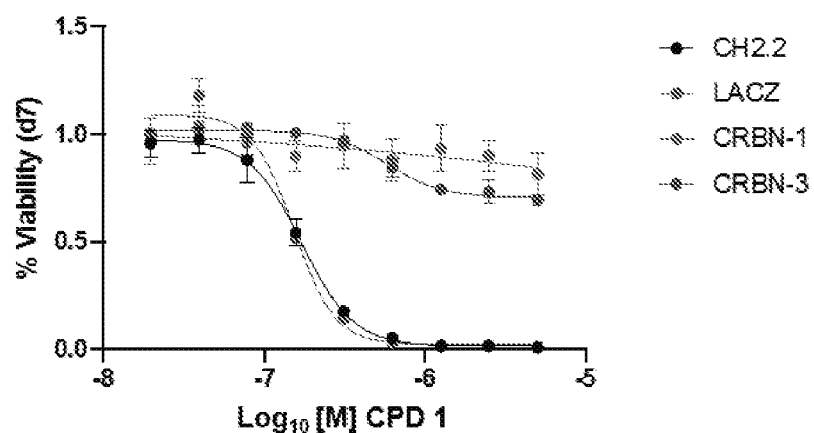
FIG. 12C is a graph that shows cell viability in Ch2.2, LACZ and CRBN knock/out cell lines after treatment with different concentrations (μM) of CPD1.
Figure 12D:
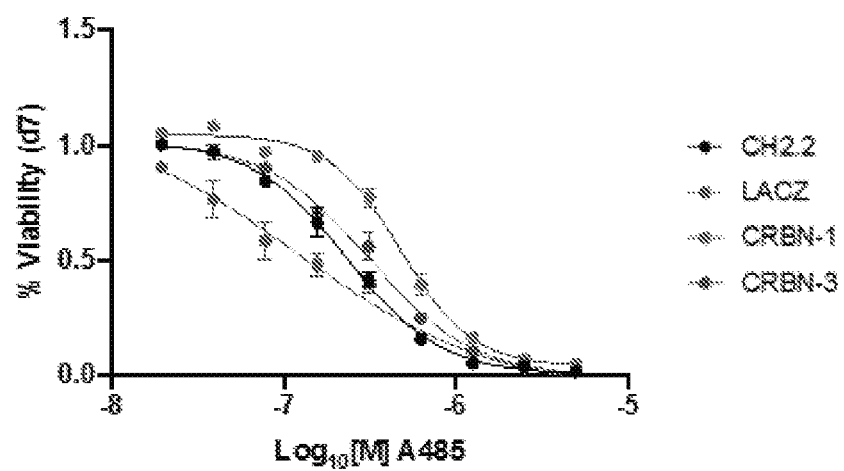
FIG. 12D is a graph that shows cell viability in Ch2.2, LACZ and CRBN knock/out cell lines after treatment with different concentrations (μM) of A485.

The results, illustrated in FIG. 12A-FIG. 12D, show CPD 1 did not degrade EP300 or CBP in the CRBN k/o lines (CRBN-1 and CRBN-3), which confirmed that EP300 degradation by inventive compounds is CRBN-dependent. Cell growth inhibition curves in FIG. 12C and FIG. 12D showed that CPD 1 did not affect CRBN k/o cell lines.

Example 34: In Vivo Study in CD1 Mice with CPD 1

Figure 6A:
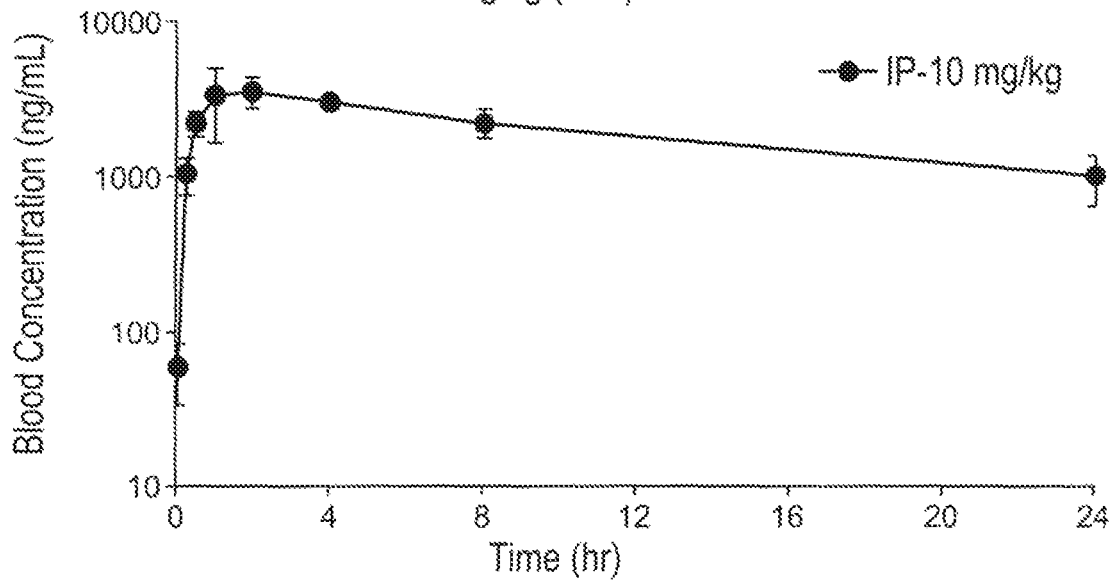
FIG. 6A is graph that shows the time profile of CPD 1 after an intraperitoneal (IP) injection dose at 10 mg/kg (n=3) in male CD1 mice. The compound concentration in animal blood was measured by LCMS/MS through a series bleeding at different time points. The data shows the compound Cmax 5 µM in blood and half-life (13 hours). A-485 half life is 0.7 h in mice.

CPD 1 was tested in mice for maximum tolerated dose (MTD) (FIG. 6A). The mice were treated with 10 mg/kg (mpk), 20 mpk, and 40 mpk with 4 mice in each group. The compound was also tested in human CRBN knock in mice, the blood samples were collected after 21 day treatment. All the tested blood samples were normal.

Figure 13A:
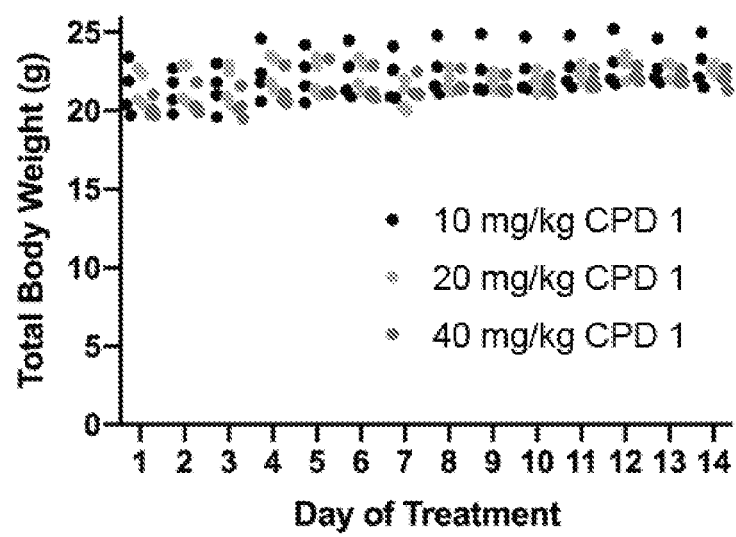
FIG. 13A is a graph that shows the change in total body weight in mice treated with 10 mg/kg, 20 mg/kg, and 40 mg/kg over 14 days.
Figure 13B:
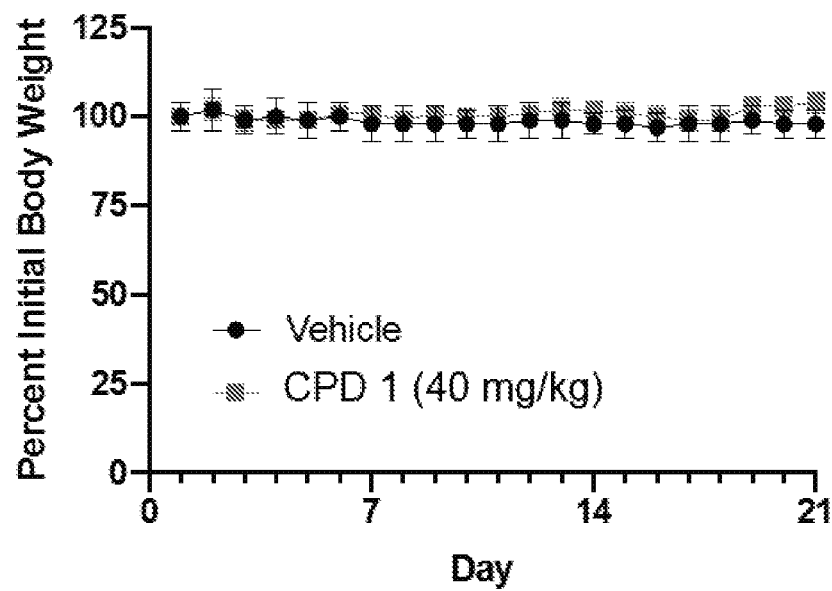
FIG. 13B is a graph that shows the change in percent initial body weight in mice treated with 40 mg/kg over 21 days.
Figure 13C:
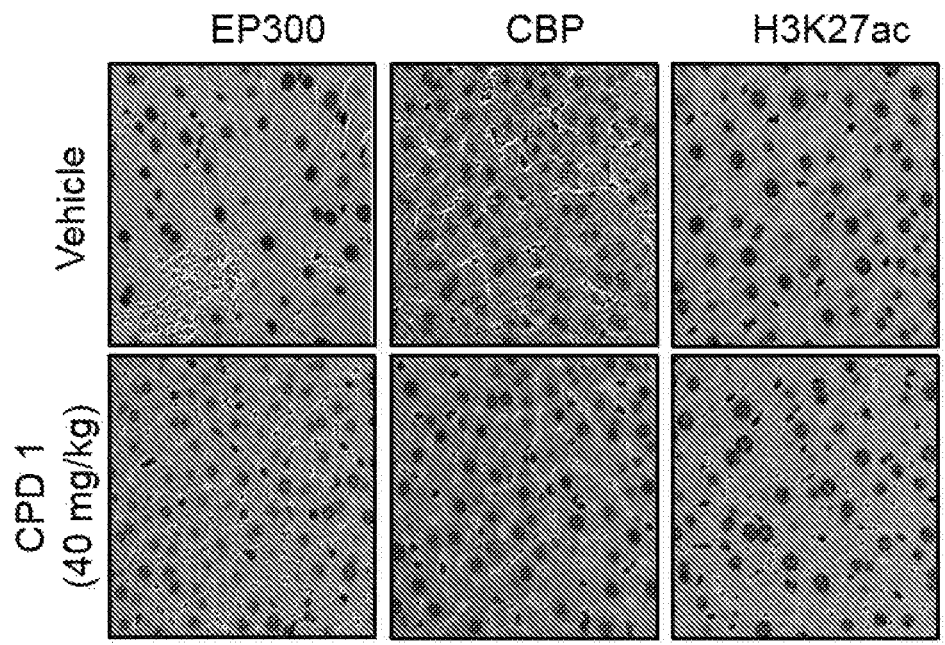
FIG. 13C is an image that shows the immunohistochemistry (IHC) staining results of a mouse liver from the maximum tolerated dose (MTD) study with CPD 1.

The results, illustrated in FIG. 13A-FIG. 13C, show that no weight loss was observed in the mice, which indicated that CPD1 was well tolerated the in vivo study. Also, no toxicity was observed in humanized CRBN$^{1391V}$ mice (FIG. 13C).

Blood samples were taken from mice treated daily with 40 mpk intraperitoneal injection (IP) after 14 days. The results are summarized in Table 2. The blood sample measurements indicated that CPD 1 was not toxic to the mice.

Immunohistochemistry (IHC) staining was used to examine a liver from MTD study. Staining showed the liver tissue had EP300 knockout with 14-day treatment in normal mice with 40 mpk (FIG. 13C). A drop in P300 levels was observed in vivo. No changes in CBP and H3K27Ac levels were observed.

Example 35: CPD 1 has Anti-Tumor Activity In Vivo

The xenograft model of Kelly cell lines was used to assess the in vivo efficacy. The Kelly cells were implanted 2 M into animals. The treatment started with day 10 at 40 mpk IP.

Figure 14A:
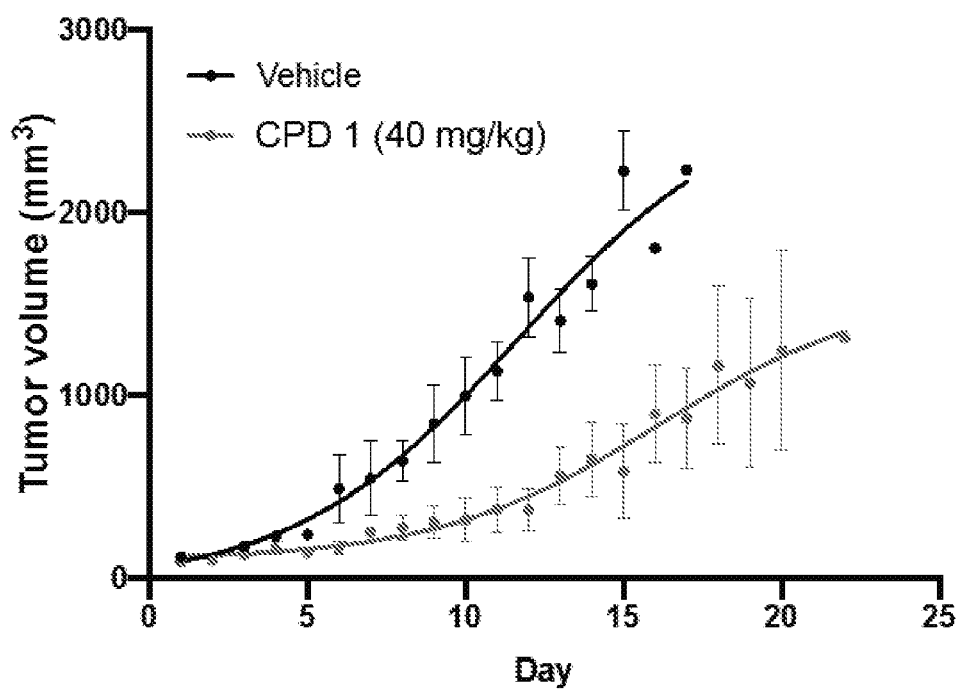
FIG. 14A is a graph that shows percent survival in mice treated with 40 mg/kg over time (day).
Figure 14B:
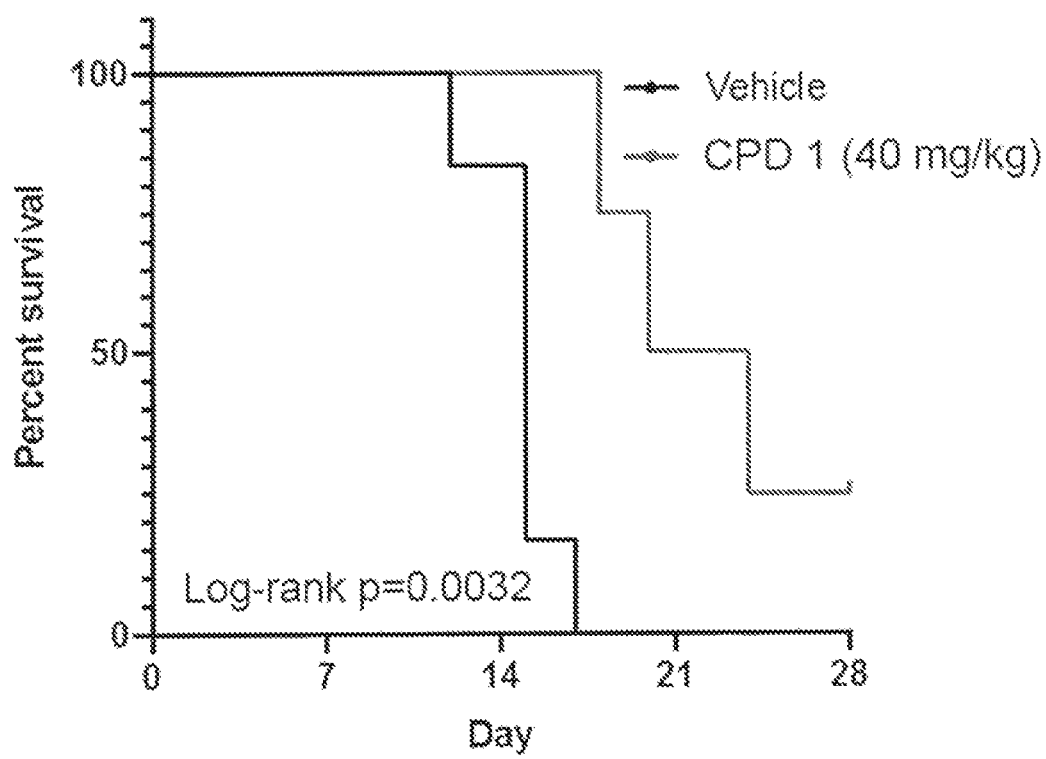
FIG. 14B is a graph that shows percent survival in mice treated with 40 mg/kg over time (day).

The results, illustrated in FIG. 14A-FIG. 14B, show that CPD 1 reduced tumor progression and extended the survival of animals.

Example 36: Cellular Potency and On-Target Effect of EP300 Degraders Assessment

To report the on-target protein degradation, a high-throughput flow cytometry-based degradation assay is used to assess EP300 degradation in cells. EP300 is cloned into an EGFP reporter system. Using FRT/Flp recombination, EP300 is expressed as an EGFP fusion, followed by a P2A site and mCherry or mCardinal as a normalization marker to express EP300-EGFP fusion protein and a RFP reporter at comparable and stable levels.

A 96-well flow cytometry setup is used to measure target protein degradation with single cell resolution as loss in EGFP to RFP signal (Lu et al., Chem. Biol. 22(6):755-63 (2015); Winter et al., Science 348(6241):1376-81 (2015); Zengerle et al., ACS Chem. Biol. 10(8):1770-7 (2015); Winter et al., Mol. Cell. 67(1):5-18 (2017)). This assay demonstrates increased sensitivity and robustness compared to other methods, and the 96-well flow cytometry setup allows full $IC_{50}$ profiling for large numbers of molecules. In parallel, we will develop a similar IKZF1 reporting cell line to monitor IKZF1 degradation to evaluate the specificity of putative EP300 degraders (Kronke et al., Science 343(6168): 301-5 (2014); Lu et al., Science 343(6168):305-9 (2014).

To demonstrate the requirement of CRBN for EP300 degradation in a cellular context, isogenic NB line, Kelly cells that have an engineered knockout of CRBN by CRISPR/Cas9 technology, are generated (Winter et al., Science 348(6241):1376-81 (2015); Winter et al., Mol. Cell.

TABLE 2

In vivo study blood analysis.

| Parameter | Vehicle | CPD 1 (40 mg/kg) | Normal Range | p |
|---|---|---|---|---|
| WBC (K/µL) | 3.86 (2.9-4.18) | 3.46 (1.36-6.56) | 1.8-10.7 | NS |
| Neutrophils (K/µL) | 1.37 (0.89-1.9) | 1.2 (0.39-3.01) | 0.1-2.4 | NS |
| Lymphocytes (K/µL) | 1.78 (1.35-1.95) | 1.80 (0.86-2.47) | 0.9-9.3 | NS |
| Monocytes (K/µL) | 0.43 (0.27-0.47) | 0.35 (0.09-0.71) | 0.0-0.4 | NS |
| Eosinophils (K/µL) | 0.12 (0.06-0.36) | 0.10 (0.01-0.3) | 0.0-0.2 | NS |
| Basophils (K/µL) | 0.03 (0.01-0.11) | 0.02 (0-0.07) | 0.0-0.2 | NS |
| Hemoglobin (g/dL) | 14.8 (12.2-17) | 13.35 (11.4-15.3) | 11.0-15.1 | NS |
| Hematocrit (%) | 46.8 (40-52.8) | 41.2 (33-50.3) | 35.1-45.4 | NS |
| Platelet (K/µL) | 904 (351-1088) | 528 (192-1071) | 592-2972 | NS |
| Creatinine | 0.16 (0.15-0.19) | 0.17 (0.15-0.22) | NR | NS |
| Albumin | 3.8 (2.7-4.6) | 3.2 (2.8-4.0) | NR | NS |
| AST | 57.5 (27-148) | 37 (23-64) | NR | NS |
| ALT | 92.5 (26-184) | 54 (47-198) | NR | NS |
| ALP | 24 (10-38) | 51 (28-62) | NR | NS |
| GGTP | 5 (5-46) | 5 (5) | NR | NS |

67(1):5-18 (2017)). WT Kelly and Kelly CRBN−/− cells are incubated with increasing concentrations of EP300 degraders and visualize EP300 protein degradation by immunoblotting. Proliferation and viability are also scored in this cell line to determine whether or not there is off-target toxicity that could impede cell growth. Together with immunoblotting of EP300, CBP and IKZF in the treated cell lines, this cellular system is used to identify additional potent and selective EP300 degraders.

Example 37: EP300 Degrader Function in Cellular Models of NB Assessment

Additional EP300 degraders with the most promising biochemical activity and on-target cellular activity ("Potent and selective compounds/molecules") are profiled in a panel of NB cell lines. Degradation of EP300 in NB lines (Kelly) is studied in dose- and time-ranging studies, by immunoblot analyses versus appropriate inactive controls (A-485, CBP30 and lenalidomide). Effects on viability is assessed in panel of MLL-r leukemic cell lines (CellTiter-Glo®; Promega™) again as compared to A-485. Effects on global H3K27 acetylation is assessed by immunoblot. Lead molecules are used in the cellular characterization method described below.

To critically assess the mechanism of degrader-induced EP300 degradation, CP300 degradation in NB cells is first tested with A-485 and phthalimides alone as negative controls. CRBN level in NB is also evaluated. Next, the requirements for degradation on proteasome function, EP300 binding and CRBN binding, is performed using competitive compounds and gene-editing strategies, as described (Winter et al., Science 348(6241):1376-81 (2015)). To corroborate the cellular requirement of CRBN binding, E3 complex activation, and proteasome function for effective EP300 degradation, Kelly and BEC2 cells is pretreated separately with carfilzomib (a proteasome inhibitor), MLN4924 (a Nedd8 activating enzyme inhibitor), or lenalidomide (a CRBN binder) prior to treatment with putative EP300 degraders.

An unbiased, proteome-wide approach is used to assess the cellular consequences of lead EP300 degrader treatment on protein stability in NB cell lines. Multiplexed quantitative mass spectrometry-based proteomics is used to evaluate the specificity and consequences of EP300 degrader treatment in NB cells (McAlister et al., Anal. Chem. 84(17): 7469-78 (2012); McAlister et al., Anal. Chem. 86(14): 7150-8 (2014)). Kelly and BEC2 cells are treated with putative EP300 degraders or DMSO for 24 h. A 24-h incubation was selected to capture primary, immediate consequences of small-molecule action and to mitigate expected, confounding effects on suppressed transactivation of EP300 target genes. Specificity for EP300 degradation is prioritized over potency coupled with off-target effects (e.g., degradation of CRBN neo-substrate IKZF1 Kronke et al., Science 343(6168):301-5 (2014); Lu et al., Science 343 (6168):305-9 (2014)). All these evaluations are used to finalize the candidate for in vivo study.

Example 38: Optimization of PK Properties of EP300 Degraders for In Vivo Study

To accurately assess the translational potential of EP300 degraders in vivo, PK properties of lead EP300 degraders are optimized. For example, CPD 1 was evaluated for its PK properties, such as half-life and maximum tolerable dose (MTD) (FIG. 6A, see, Example 34). Novel EP300 degraders are generated with good potency and selectivity utilizing the A-485 scaffold. Lead compounds are generated in large quantities for in vivo PK and efficacy studies.

Example 39: Characterization of the Effects of EP300 Degradation on Gene Expression, Chromatin Occupancy, Histone Modifications in Comparison to EP300 Inhibitor A comprehensive molecular assessment of the effects of EP300 degradation on NB cells is accomplished using transcriptional profiling via RNA-seq and chromatin assessment via ChIP-seq and ATAC-seq. A comprehensive molecular assessment of the effects of these compounds on chromatin is performed using transcriptional profiling via RNA-seq and epigenomic profiling via ChIP-seq. Specifically, kinetic studies of transcriptional response are done at 0, 6, and 24 h of cells treated with A485 or our lead EP300 degrader in resistant lines. Effects on EP300/CBP protein localization, enhancer activity (H3K27ac), and promoter integrity (H3K4me3) are studied at 0 h, 6 h, and 24 h following treatment, by ChIP-seq, and Chem-seq. Accessible chromatin and potential cis-regulator elements are determined prior to and following drug response by ATAC-seq. Integration of these datasets tests the hypothesis that degradation of EP300 does not only inhibit its enzymatic activity but also abrogates its non-enzymatic functions leading to collapse of the EP300 driven gene expression programs that have not previously been exposed to EP300 inhibitors.

Example 40: Assessment of Anti-Tumor Effects of EP300 Degraders as Compared with EP300 Inhibitors In Vitro Newly developed EP300 degraders are used to thoroughly investigate EP300 degradation versus enzymatic inhibition in vitro in NB. A panel of human NB cells in dose response format with A-485 and EP300 degraders in a head-to-head comparison (CellTiter-Glo®). Additionally, cell growth over time, EP300 protein degradation and H3K79 methylation levels are assessed via immunoblotting and cell cycle/cell death via flow cytometric analysis.

Example 41: Assessment of EP300 Degradation in Combination with Standard of Care Agents or Other Inhibitors as a Combination Approach in NB Synergy in vitro on NB cells is determined through assessment of cellular proliferation via standard approaches (CellTiter-Glo®). A robotic pinning system that allows titration of two different compounds at multiple concentrations of each to a plate of cultured cells is used. Following 48-72 h incubation, cell viability is determined by ATP content (CellTiter-Glo®), on a multilabel plate reader. Results are be plotted in the CompuSyn package according to the method described in Chou et al., Adv. Enzyme Regul. 22:27-55 (198) to determine whether there is an additive or synergistic effect of the agents. At combination doses that appear to synergize, apoptosis vs. cell cycle arrest is determined via Annexin V staining and assessment of DNA content. In all experiments, EP300 protein levels is assessed via immunoblotting to ensure protein degradation.

Figure 6B:
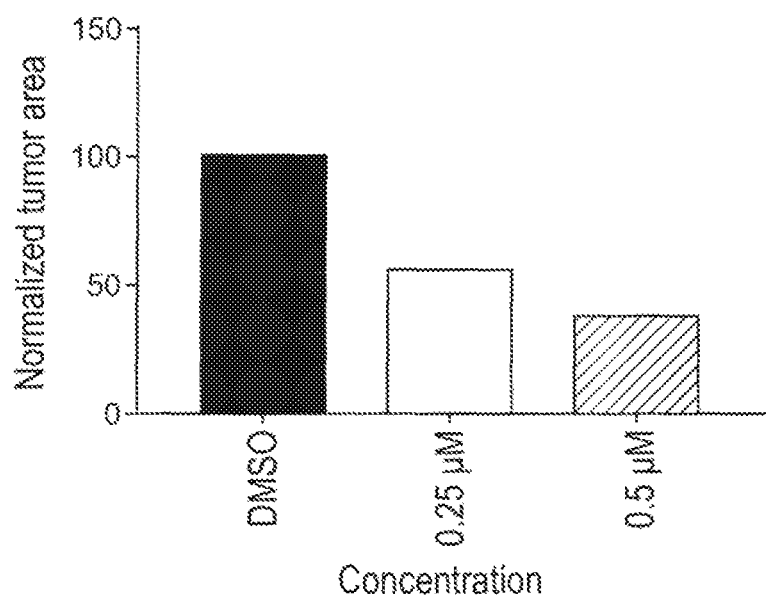
FIG. 6B is a graph that shows tumor growth inhibition in an NB zebra fish model at 0.25 µM and 0.5 µM CPD 1. No toxicity was observed in both PK and zebra fish study.

Example 42: Assessment of the Toxicity of EP300 Degrader and Inhibitor in Zebrafish and Mice Maximum tolerance dose (MTD) of each candidate was determined in zebrafish embryos. 3-day-old zebrafish embryos were exposed to different drug concentrations and monitored for adverse health effects. Treatment doses were then selected by determining the highest concentrations that did not result in adverse morphological and behavioral effects. Experiments were first carried out with compound CPD 1 as a guide in the further design of MTD assessment of lead EP300 degraders (FIG. 6B). The MTD of the degrader is also determined in mice in the similar manor. Briefly, mice were dosed with test compounds and blood and plasma is isolated at specific intervals post-administration (0.083, 0.25, 0.5, 1, 2, 4, 8, 12, and 24 h) and quantified for the presence of test article by LC/MS/MS (n=5 mice/compound). In vivo mouse PK experiments were used to determine these parameters and inform iterative rounds of medicinal chemistry for optimization of EP300 degraders (FIG. 6A). As degraders have a relatively large molecular weight, the proper formulation is investigated to increase the solubility and stability of the degraders for in vivo study. Together, these parameters, including the established MTD, are used to guide the in vivo study design, such as administration method, dosing, and schedule for the following experiment. The information obtained was also used to guide the degrader optimization conducted in Example 36.

Example 43: Evaluation of Compounds in Zebrafish Models, and Mouse PDX Models

In vivo efficacies of A-485 and degrader CPD 1 are compared in zebrafish xenograft models of NB. First, human NB cells are stably transfected with EGFP for visualization. These cells are then transplanted into 2-day-old zebrafish embryos via yolk and intravenous injection as previously described. (Haldi et al., Angiogenesis 9(3):139-51 (2016); He et al., J. Pathology 227(4):431-45 (2012); Tulotta et al., Methods Mol. Biol. 1451:155-69 (2016)). One day later, zebrafish embryos transplanted with fluorescent human NB cells are arrayed in 24-well plate and treated with the test drugs. Twelve recipient fish are exposed to each individual degraders and inhibitors added to the fish water at the MTD, as well as the DMSO control. After 5 days of treatment, in vivo cell proliferation, cell growth and invasion are analyzed using fluorescent (Tulotta et al., Methods Mol. Biol. 1451: 155-69 (2016)) and compared across the groups. Welch's t-test is used to address the inhomogeneity of variance. The drugs showing significant tumor suppression are further analyzed at a range of concentrations. To elucidate cellular mechanisms underlying the tumor suppression by active drugs or drug combinations, treated NB cells are analyzed for cell proliferation (by immunohistochemistry for PCNA and phosphorylated histone H3), cell survival and apoptosis (by TUNEL and anti-caspase 3 staining), senescence (by beta-galactosidase staining) and autophagy (by lysosome staining). PD effects on EP300 protein levels, H3K27 Acetylation, the MYCN level, and gene expression by qRT-PCR are performed on NB cells isolated from dissociated zebrafish embryos after 0, 1, 2, 3, 4 and 5 days of treatment.

Next, in vivo efficacy of A-485 and lead EP300 degraders are compared in NB (Kelly) xenotransplant model by injecting 1×106 cells each into thirty 6-8 week-old NOD-SCID-IL2Rnull (NSG) mice. These mice start manifesting clinical symptoms 2-3 weeks after transplantation. After we have confirmed engraftment, animals are separated into either an efficacy or pharmacodynamics (PD) cohort (3 per arm for PD studies, 5 per arm for efficacy studies). Both cohorts are dosed by intraperitoneal (IP) injection at MTD per day of A485 or degrader daily. A control group receive IP injection of the vehicle determined in formulation study of Example 10. All animals are weighed to assess toxicity and tumor size will be measured every three days. Efficacy (survival) is determined after 21 days of drug treatment followed by a 7-day drug holiday. Animals assessed for PD are dosed for 14 days and euthanized following the completion of infusion. At the completion of the study, animals are euthanized and tissue collected. A femur, part of the spleen, part of the liver, and any enlarged lymph nodes are fixed in 10% formalin for histologic examination. PD effects on EP300 protein levels, H3K27 acetylation, and gene expression by qRT-PCR are performed. The EP300 degrader that performed well in xenotransplant studies is used to perform similar experiments in NB PDX models. Thirty 6-8 week-old NSG mice are injected with 1×106 human PDX cells (secondary transplant). Mice are monitored for engraftment of tumor as described above. Engrafted mice are also divided into treatment cohorts (3 per arm for PD studies, 5 per are for efficacy studies) to be treated with vehicle, a EP300 degrader, or A-485 (administered as described above). All analysis are performed as described above. In total, these studies are performed on 3-5 distinct PDXs.

Example 44: Assessment of EP300 Degrader in Combination for NB Treatment in PDX Models PDX models are used to evaluate the combination effect of EP300 degrader with identified EP300 inhibitors. These experiments are performed similar to those described in Example 42, except that animals will be randomized into four treatment cohorts of 8 mice each (3 per arm for PD studies, 5 per are for efficacy studies): vehicle, EP300 degrader, second inhibitor, or degrader/inhibitor.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A bifunctional compound having a structure represented by formula I:

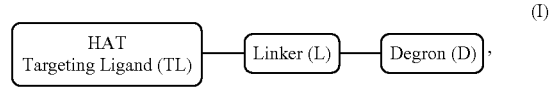

(I)

pharmaceutically acceptable salt or stereoisomer thereof, wherein the HAT targeting ligand has a structure represented by any one of structures TL-1 b to TL-1f:

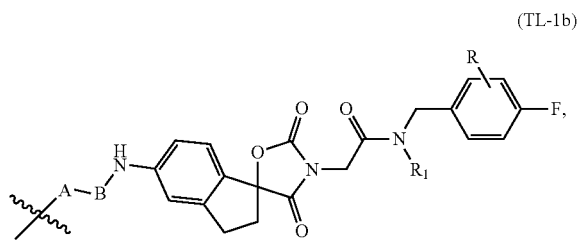
(TL-1b)

wherein A is CH₂, NH or O; B is CH₂ or CO; R is H, halo, CN, CF₃, alkyl or alkoxy; R₁ is

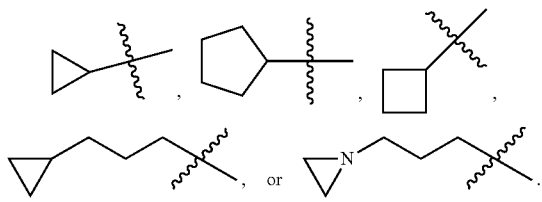

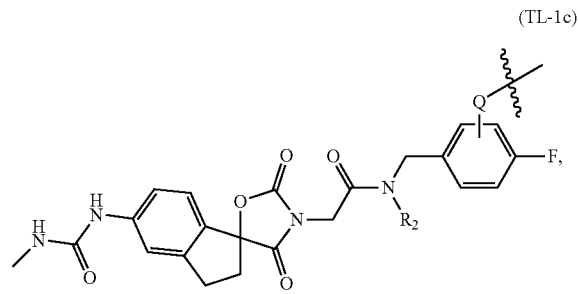
(TL-1c)

wherein

Q is CH₂, O, N, CO, C(O)O, C(O)N, CH₂N, CH₂C(O), CH₂C(O)O, CH₂C(O)N, or CH₂CH₂N, and R₂ is

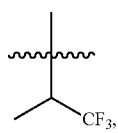

a C₃-C₅ carbocyclic or alkcarbocyclic group or a 3-5 membered N-heterocyclic or alkN-heterocyclic group, and wherein the alk group is a C1-C10 alkyl group;

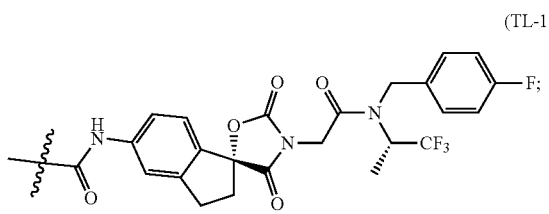
(TL-1d)

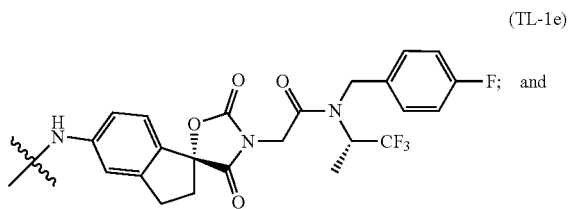
(TL-1e)

and

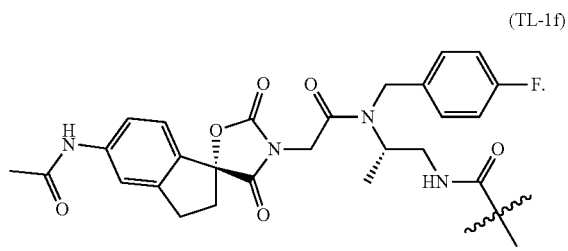
(TL-1f)

the linker represents a moiety that covalently connects the degron and the targeting ligand, and comprises an alkylene chain or a polyethylene glycol chain, either of which may be interrupted by, and/or terminate (at either or both termini) at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)₂—, —OS(O)—, —S(O)O—, —S(O)—, —OS(O)₂—, —S(O)₂O—, —N(R')S(O)₂—, —S(O)₂N(R')—, —N(R')S(O)—, —S(O)N(R')—, —N(R')S(O)₂N(R')—, —N(R')S(O)N(R')—, C₃-C₁₂ carbocyclene, 3- to 12-membered heterocyclene, 5- to 12-membered heteroarylene or any combination thereof, wherein R' is H or C₁-C₆ alkyl, wherein the interrupting and the one or both terminating groups may be the same or different; and the degron binds cereblon (CRBRN) and is represented by structure D1:

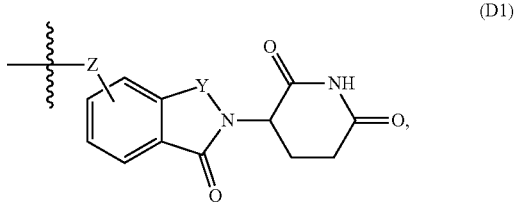
(D1)

wherein Y is CH₂ or CO; and

Z is NH, O, or OCH₂CO and the squiggle (v) represents the point of attachment for the linker, or the degron binds von Hippel Landau tumor suppressor (VHL) and is represented by a structure selected from the group consisting of:

(D2-a)
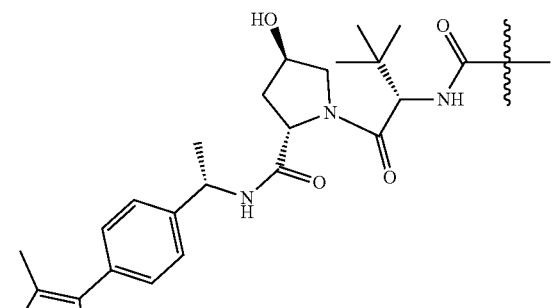
;
(D2-b)
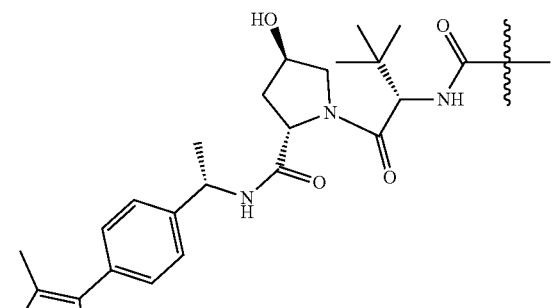
;
(D2-c)
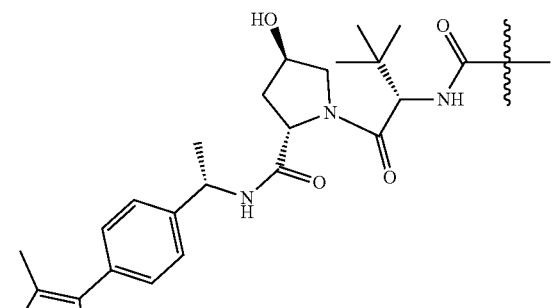
,
wherein Y' is a bond, N, O or C;
(D2-d)
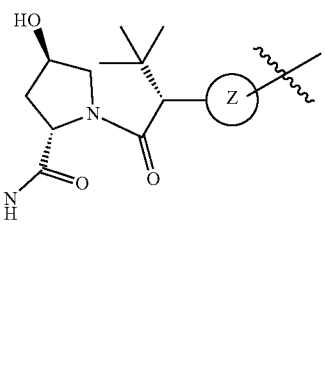
,
wherein Z is a $C_5$-$C_6$ carbocyclic or a $C_5$-$C_6$ heterocyclic group; and
(D2-e)
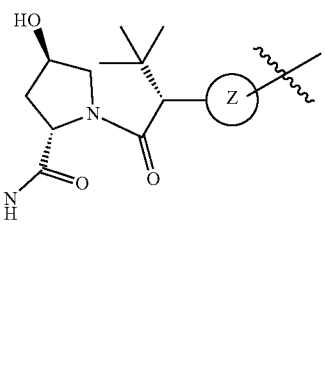
.
2. The bifunctional compound of claim 1, which is represented by any one of structures I-1b to Ib-1f:
(I-1b)
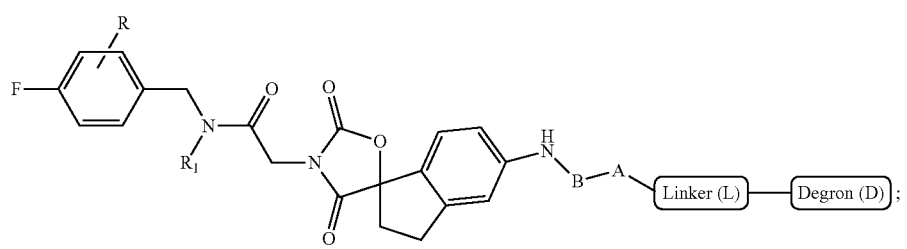
;

-continued (I-1c)
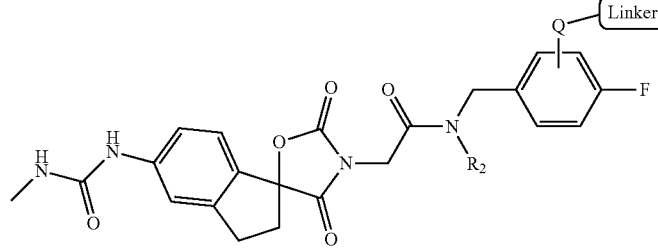

(I-1d)
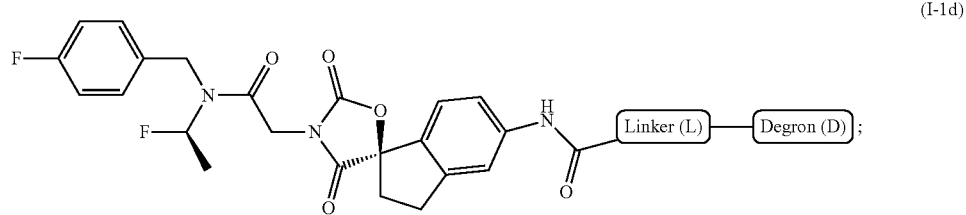

(I-1d)
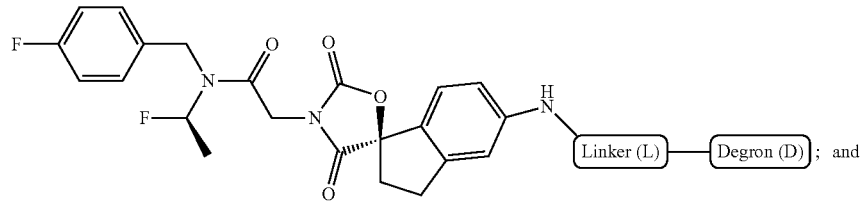

(I-1f)
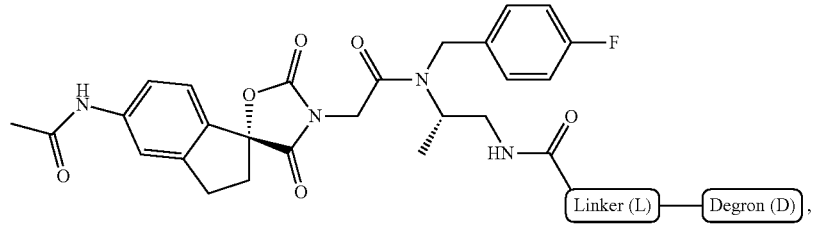

or a pharmaceutically acceptable salt or stereoisomer thereof.

3. A bifunctional compound having a structure represented by formula I:

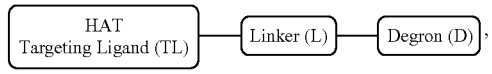 (I)

pharmaceutically acceptable salt or stereoisomer thereof, wherein the HAT targeting ligand has a structure represented by any one of structures TL-1 and TL-1a to TL-1f:

(TL-1)
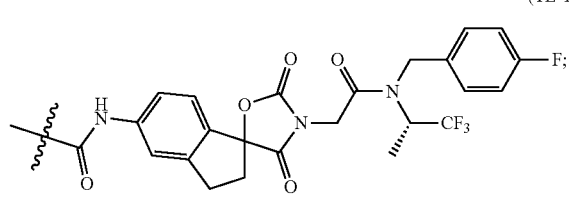

(TL-1a)
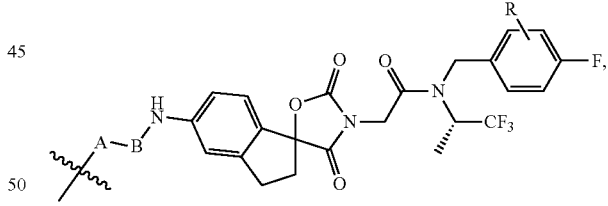

wherein A is $CH_2$, NH or O; B is $CH_2$ or CO; and R is H, halo, CN, $CF_3$, alkyl or alkoxy;

(TL-1b)
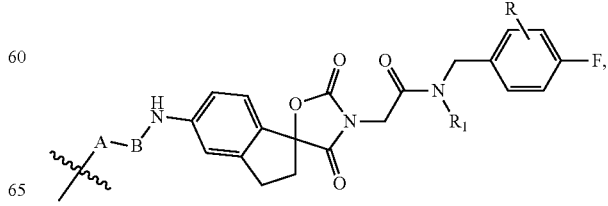

wherein A is $CH_2$, NH or O; B is $CH_2$ or CO; R is H, halo, CN, $CF_3$, alkyl or alkoxy; $R_1$ is a $C_3$-$C_5$ carbocyclic or alkcarbocyclic group or a 3-5 membered N-heterocyclic or alkN-heterocyclic group, and wherein the alk group is a $C_1$-$C_{10}$ alkyl group;

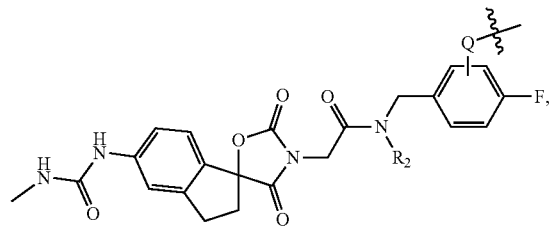
(TL-1c)

wherein

Q is $CH_2$, O, N, CO, C(O)O, C(O)N, $CH_2N$, $CH_2C(O)$, $CH_2C(O)O$, $CH_2C(O)N$, or $CH_2CH_2N$, and $R_2$ is

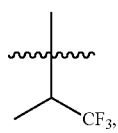

a $C_3$-$C_5$ carbocyclic or alkcarbocyclic group or a 3-5 membered N-heterocyclic or alkN-heterocyclic group, and wherein the alk group is a $C_1$-$C_{10}$ alkyl group;

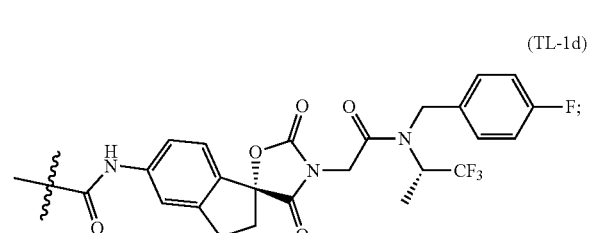
(TL-1d)

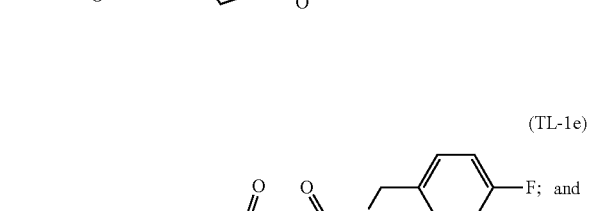
(TL-1e)

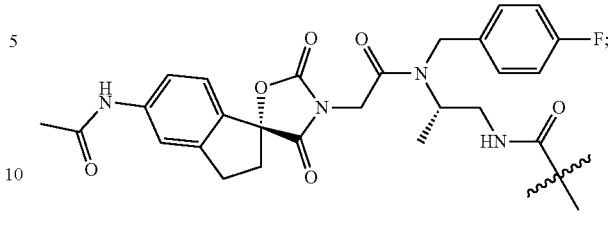
(TL-1f)

wherein the linker is represented by structure L10:

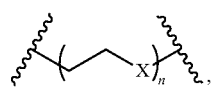
(L10)

wherein X is $CH_2$, NH, NMe, or O; and n is an integer from 0 to 11; and the degron binds cereblon (CRBRN) and is represented by structure D1:

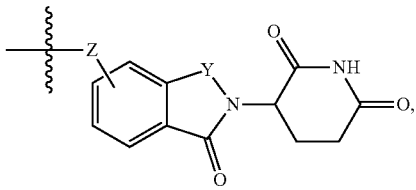
(D1)

wherein Y is $CH_2$ or CO; and

Z is NH, O, or $OCH_2CO$ and the squiggle(s) represents the point of attachment for the linker, or the degron binds von Hippel Landau tumor suppressor (VHL) and is represented by a structure selected from the group consisting of:

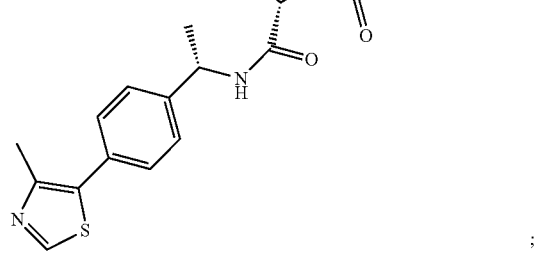
(D2-a)

(D2-b)
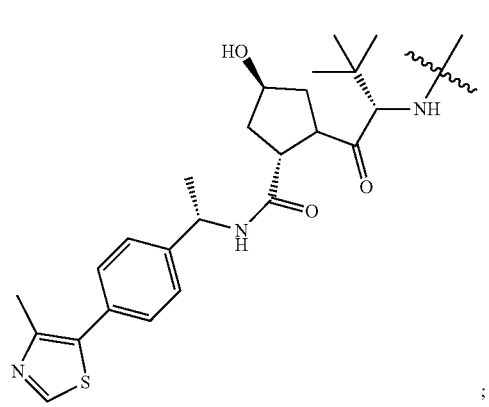
;
(D2-c)
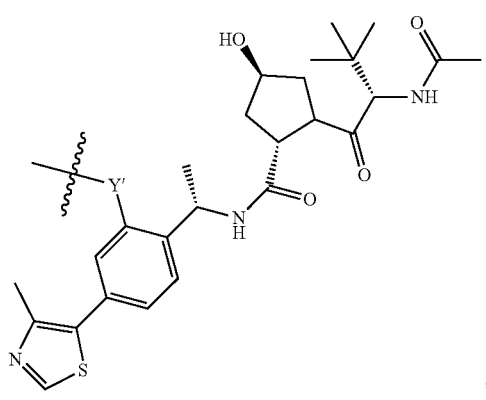
,
wherein Y' is a bond, N, O or C;
(D2-d)
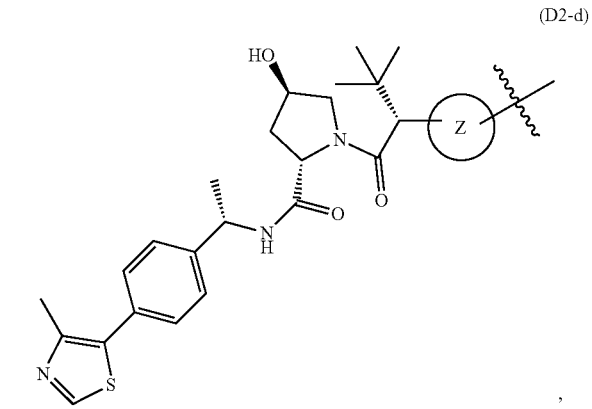
,
wherein Z is a $C_5$-$C_6$ carbocyclic or a $C_5$-$C_6$ heterocyclic group; and
(D2-e)
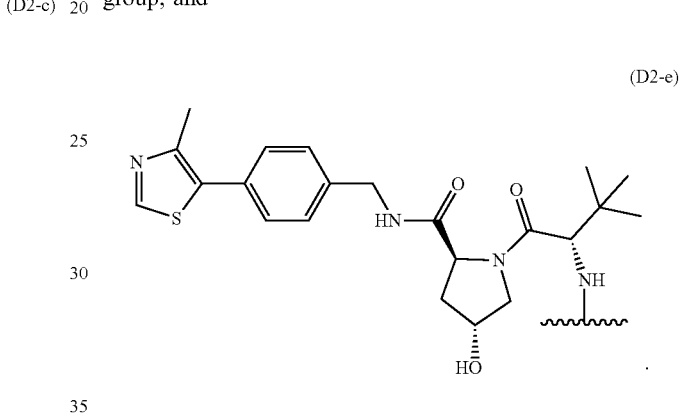
.
4. The bifunctional compound of claim 1, wherein the linker is represented by any one of structures L11 to L26:
(L11) (L12)
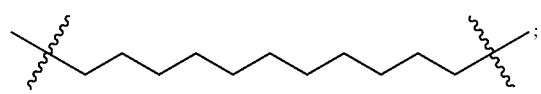
(L13) (L14)
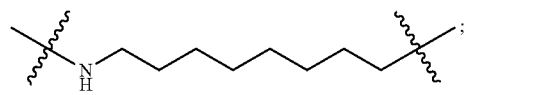
(L15) (L16)
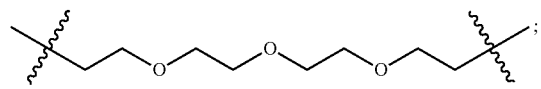
(L17) (L18)
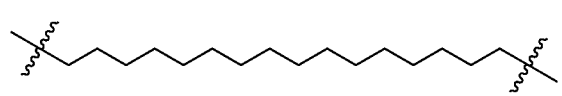
(L19)
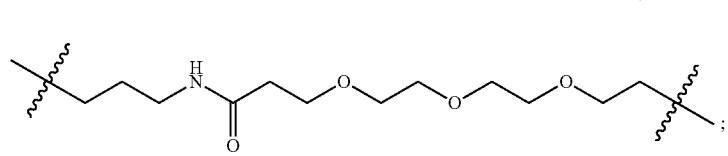

-continued
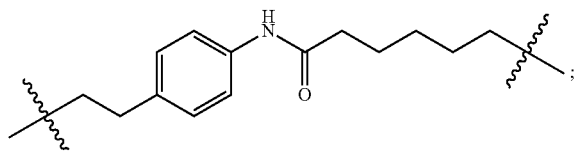
(L20)
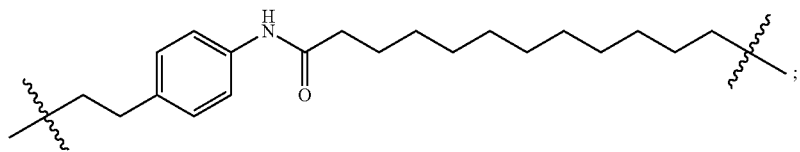
(L21)
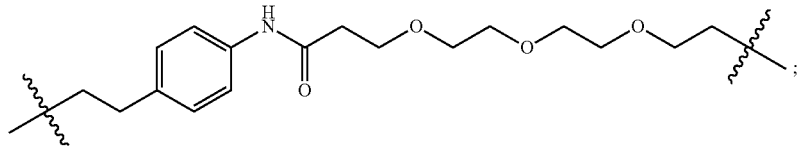
(L22)
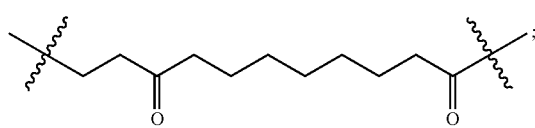
(L23)
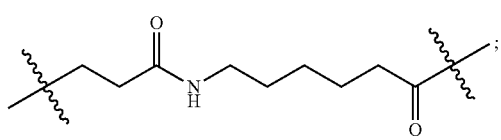
(L24)
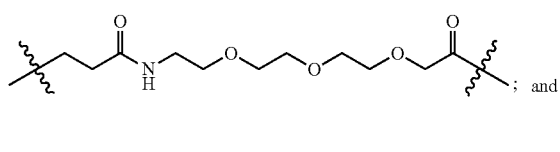
(L25)
; and
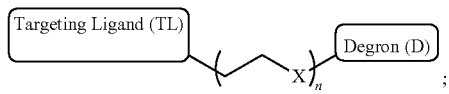
(L26)
.
5. A bifunctional compound, which is represented by any one of structures I-2 to I-12:
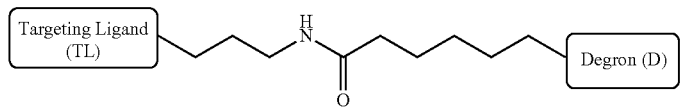
(I-2)
wherein X is CH$_2$, NH, NMe, or O; and n is an integer from 0 to 11;
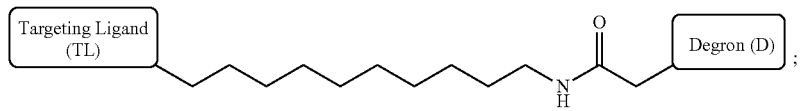
(I-3)
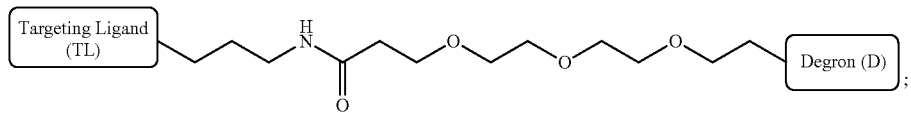
(I-4)

-continued
(I-5)
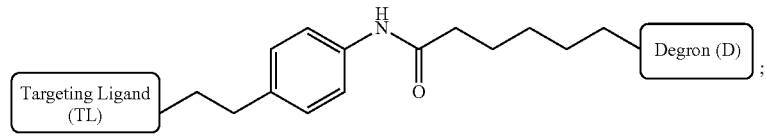
(I-6)
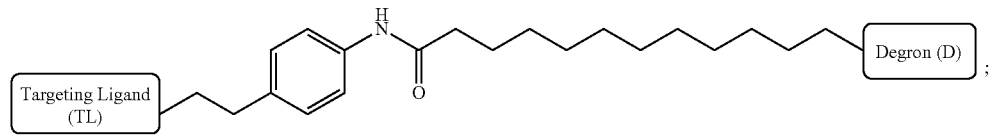
(I-7)
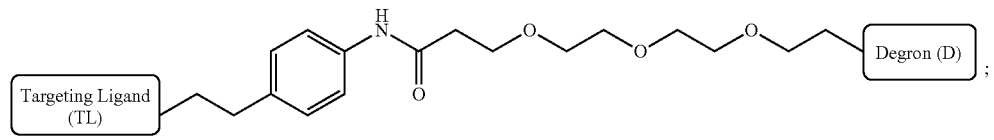
(I-8)
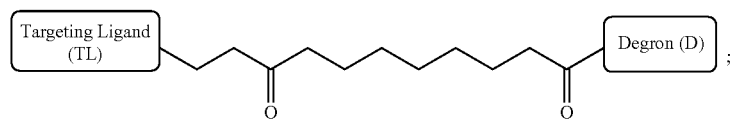
(I-9)
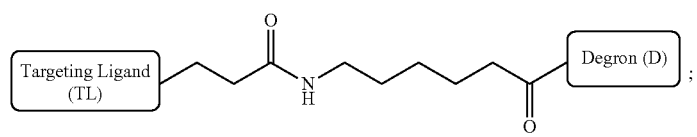
(I-10)
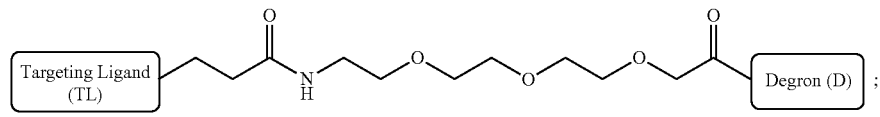
(I-11)
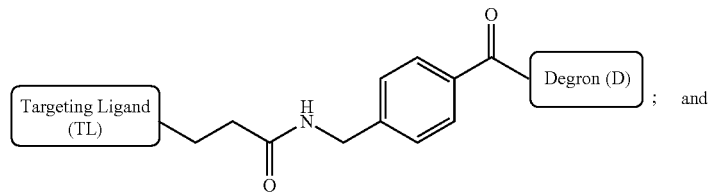
; and
or a pharmaceutically acceptable salt or stereoisomer thereof,
wherein the Targeting Ligand (TL) is a EP300 targeting ligand and has a structure represented by any one of structures TL-1 and TL-1a to TL-1f:
-continued
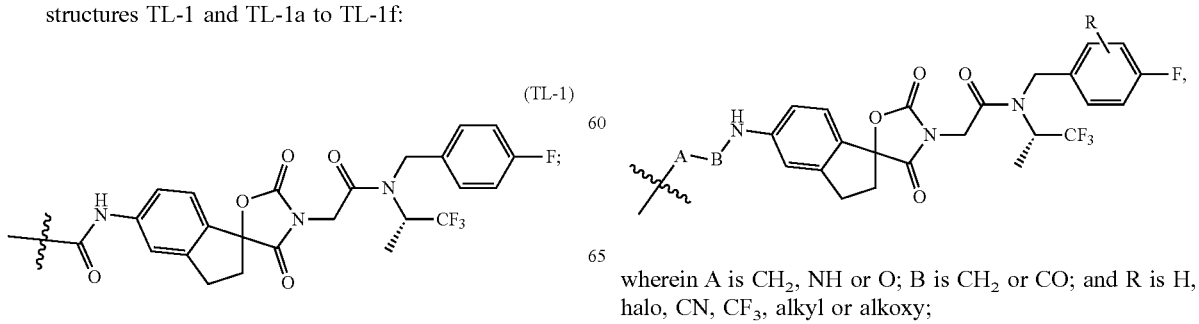
wherein A is CH$_2$, NH or O; B is CH$_2$ or CO; and R is H, halo, CN, CF$_3$, alkyl or alkoxy;

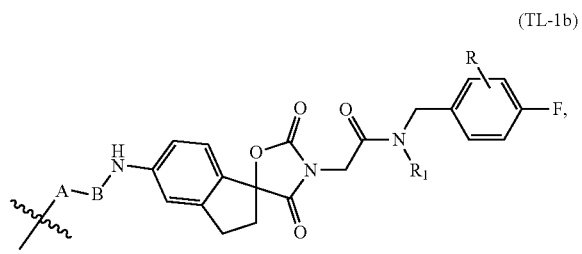
(TL-1b)

wherein A is $CH_2$, NH or O; B is $CH_2$ or CO; R is H, halo, CN, $CF_3$, alkyl or alkoxy; $R_1$ is a C3-C5 carbocyclic or alkcarbocyclic group or a 3-5 membered N-heterocyclic or alkN-heterocyclic group, and wherein the alk group is a C1-C10 alkyl group;

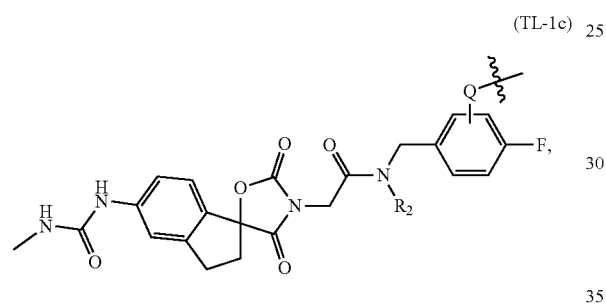
(TL-1c)

wherein

Q is $CH_2$, O, N, CO, C(O)O, C(O)N, $CH_2N$, $CH_2C(O)$, $CH_2C(O)O$, $CH_2C(O)N$, or $CH_2CH_2N$, and $R_2$ is

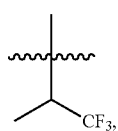

a $C_3$-$C_5$ carbocyclic or alkcarbocyclic group or a 3-5 membered N-heterocyclic or alkN-heterocyclic group, and wherein the alk group is a $C_1$-$C_{10}$ alkyl group;

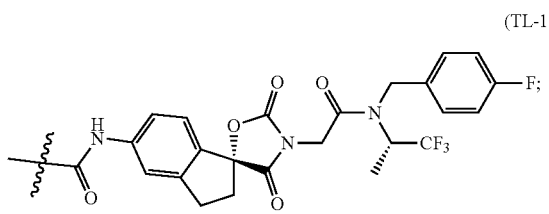
(TL-1d)

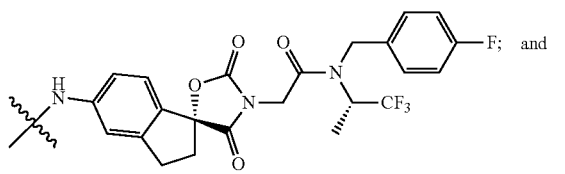
(TL-1e)

and

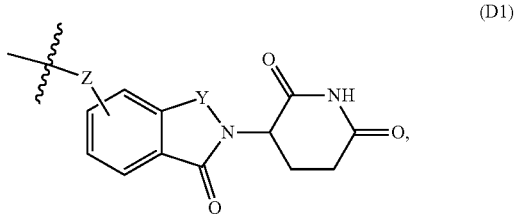
(TL-1f)

the degron binds cereblon (CRBRN) and is represented by structure D1:

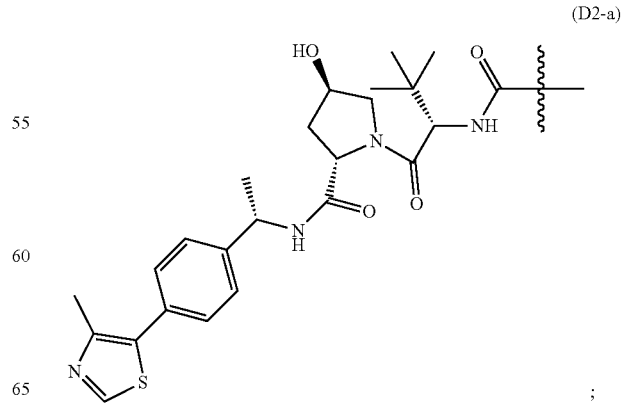
(D1)

wherein Y is $CH_2$ or CO; and

Z is NH, O, or $OCH_2CO$ and the squiggle (S represents the point of attachment for the linker, or the degron binds von Hippel Landau tumor suppressor (VHL) and is represented by a structure selected from the group consisting of:

(D2-a)

;

-continued
(D2-b)
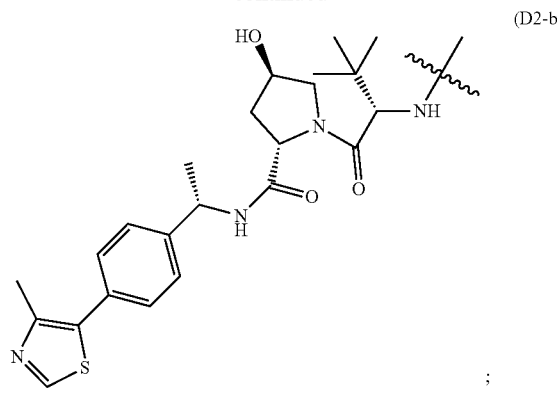
(D2-d)
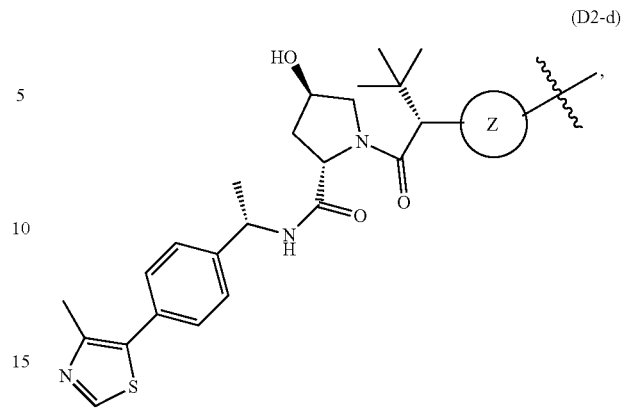
wherein Z is a $C_5$-$C_6$ carbocyclic or a $C_5$-$C_6$ heterocyclic group; and
(D2-c)
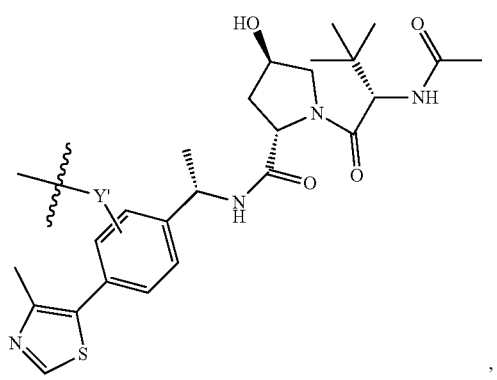
wherein Y' is a bond, N, O or C;
(D2-e)
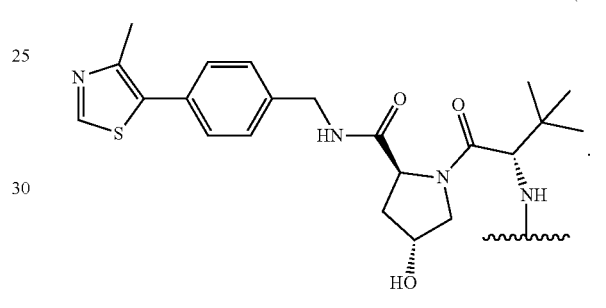
6. A bifunctional compound, which is represented by a structure selected from the group consisting of:
(TL1-L10)
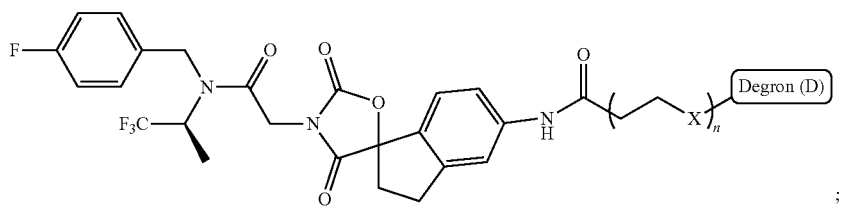
(TL1a-L10)
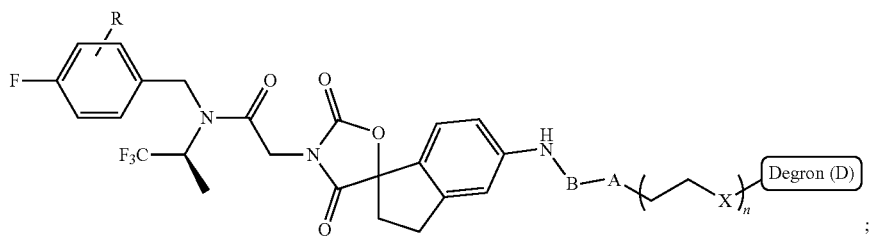

-continued
(TL1b-L10)
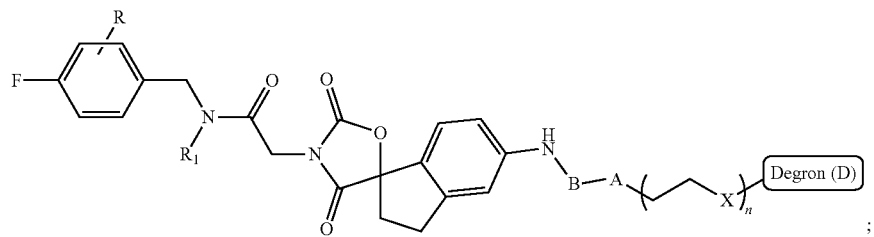
(TL1c-L10)
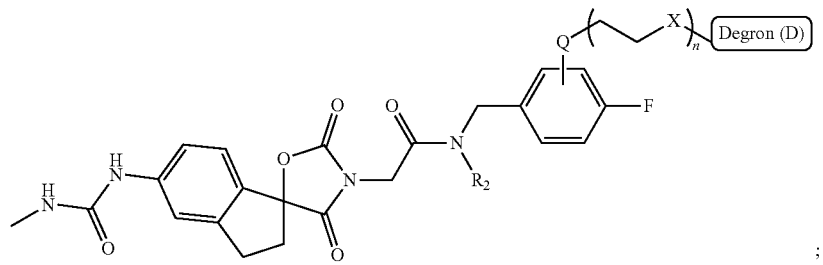
(TL1d-L10)
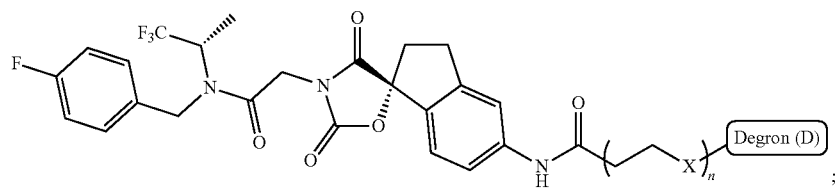
(TL1e-L10)
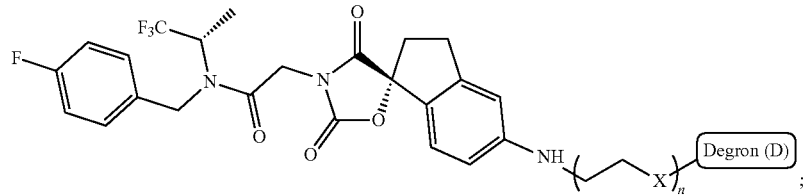
(TL1f-L10)
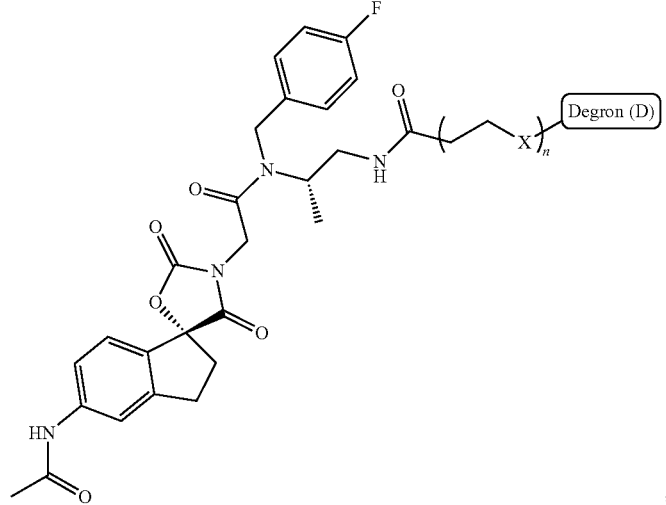

-continued
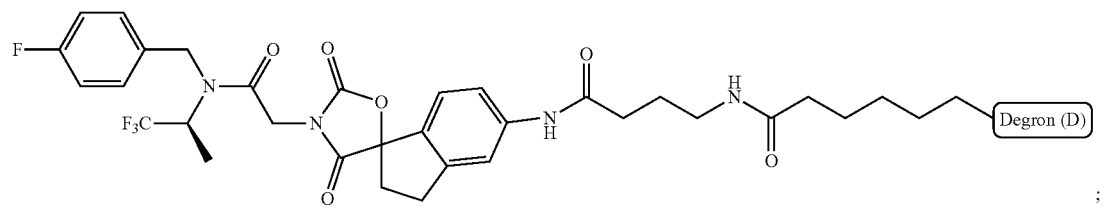
(TL1-L16)
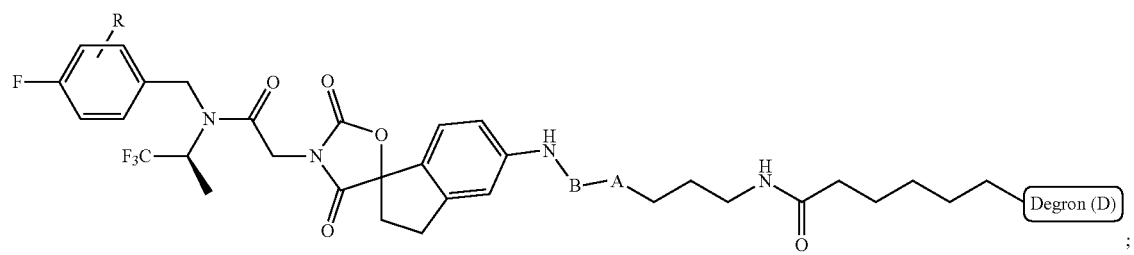
(TL1a-L16)
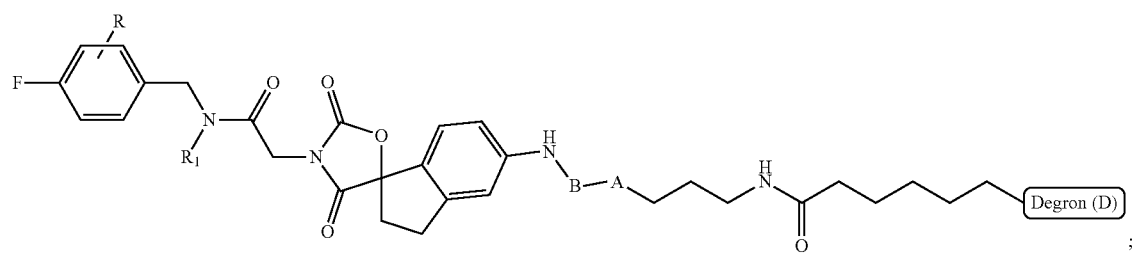
(TL1b-L16)
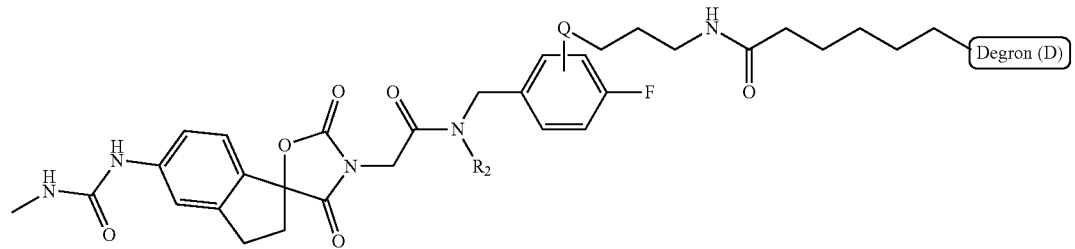
(TL1c-L16)
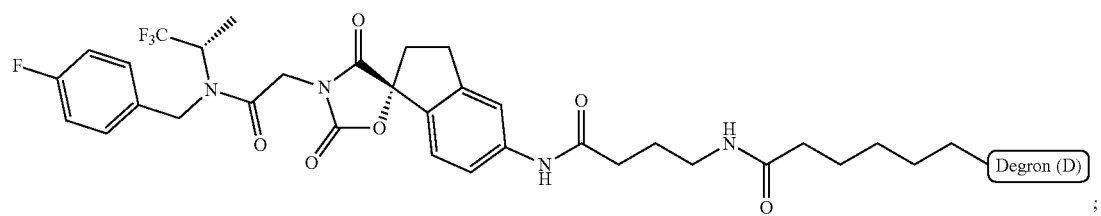
(TL1d-L16)
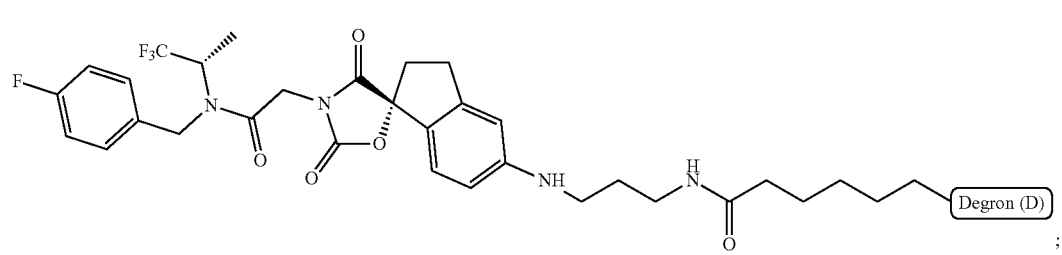
(TL1e-L16)

-continued
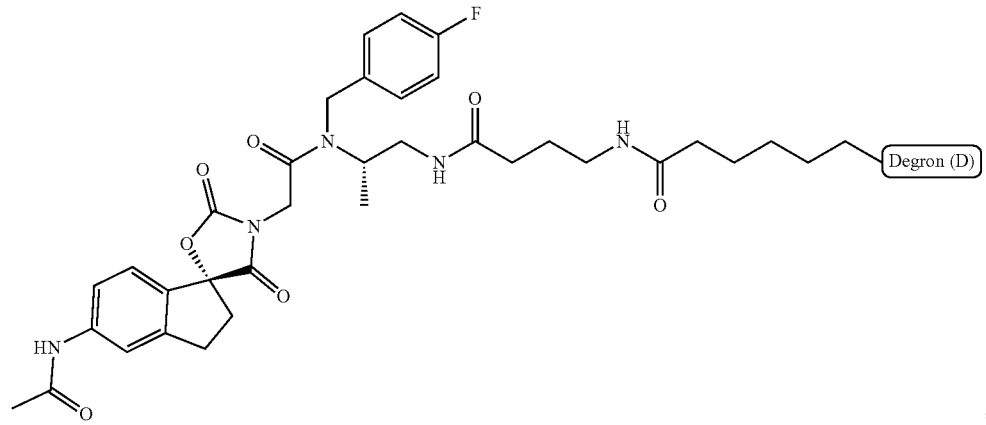
(TL1f-L16)
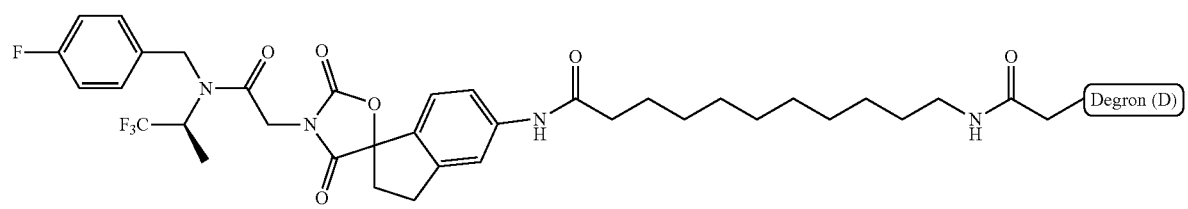
(TL1-L18)
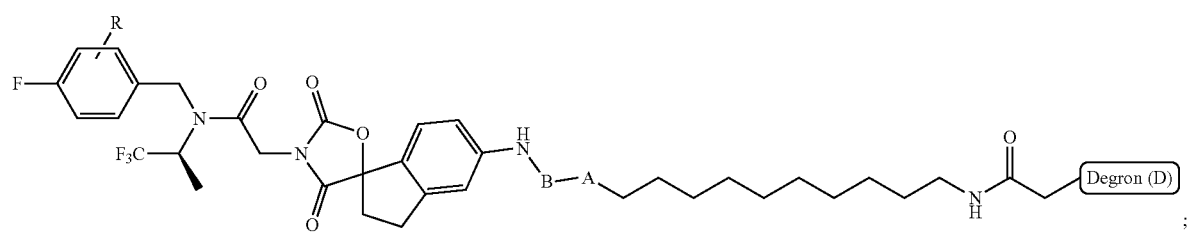
(TL1a-L18)
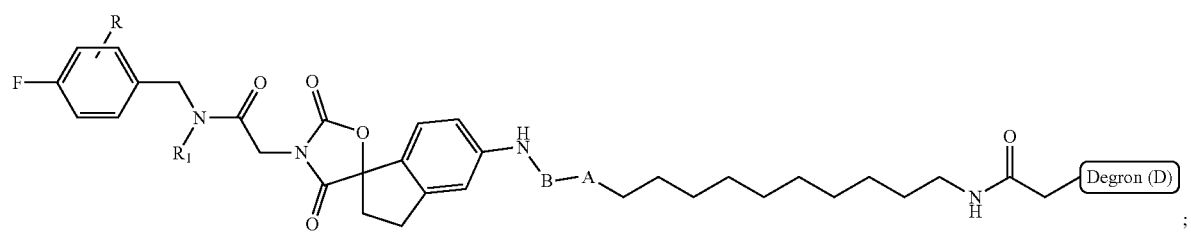
(TL1b-L18)
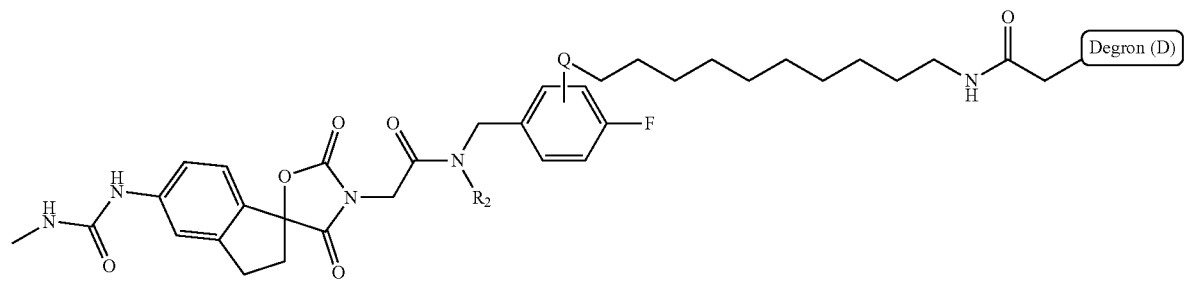
(TL1c-L18)

-continued
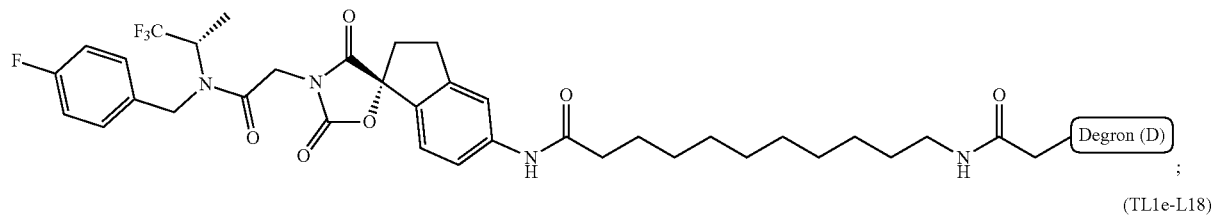
(TL1d-L18)
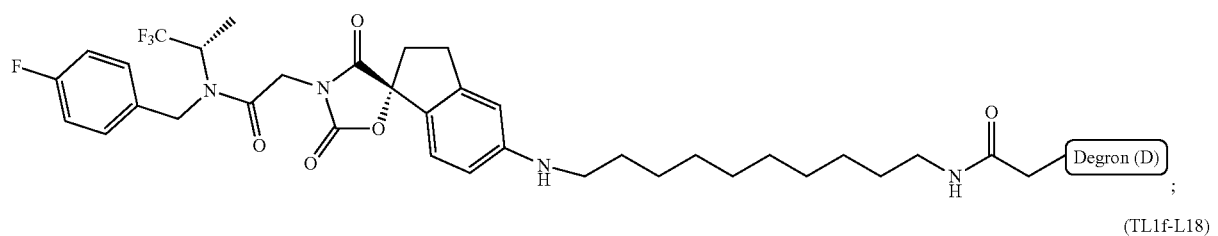
(TL1e-L18)
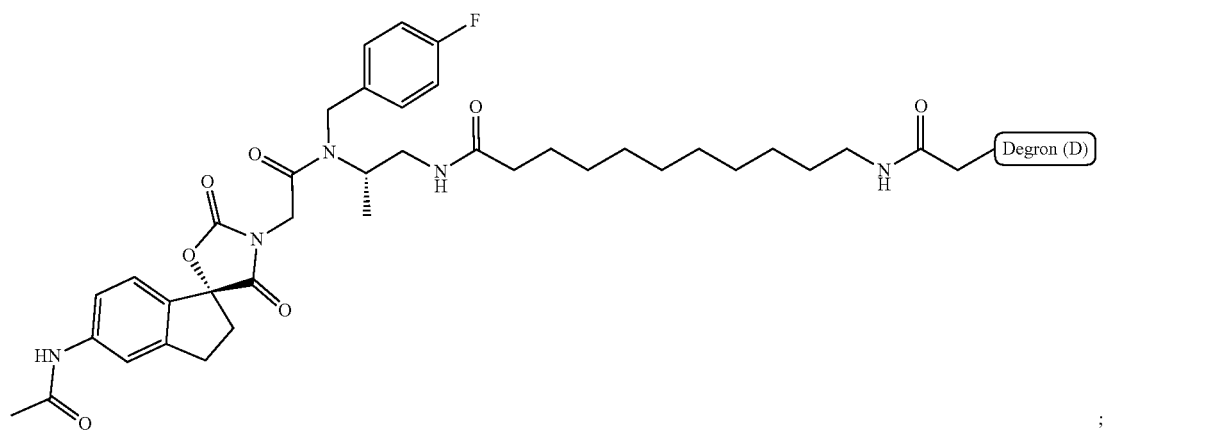
(TL1f-L18)
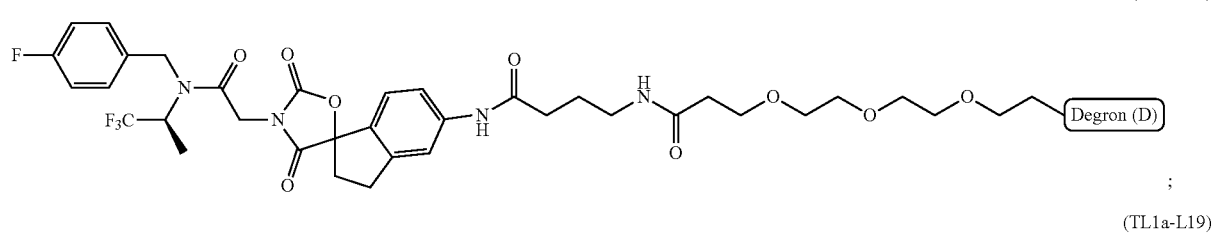
(TL1-L19)
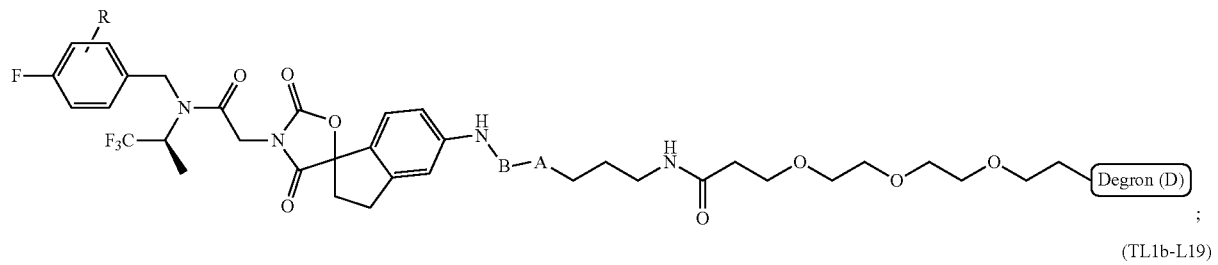
(TL1a-L19)
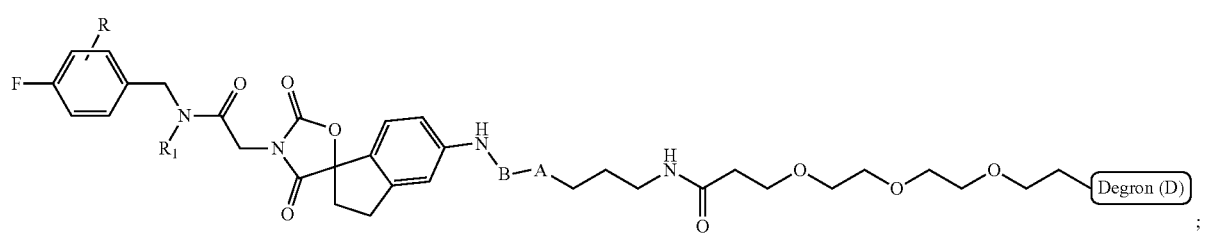
(TL1b-L19)

-continued
(TL1c-L19)
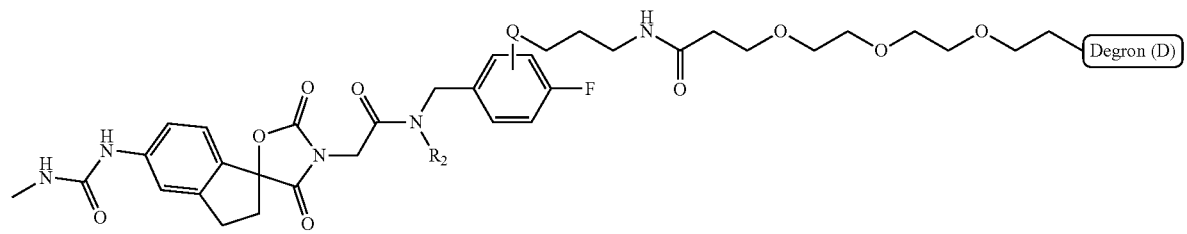
;
(TL1d-L19)
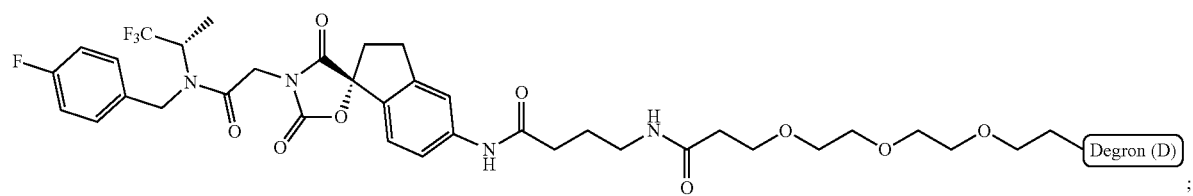
;
(TL1e-L19)
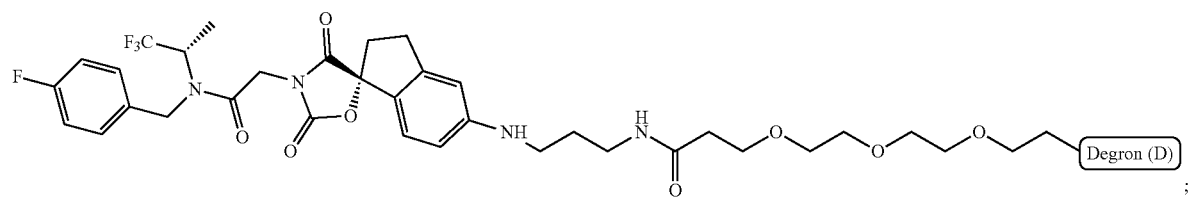
;
(TL1f-L19)
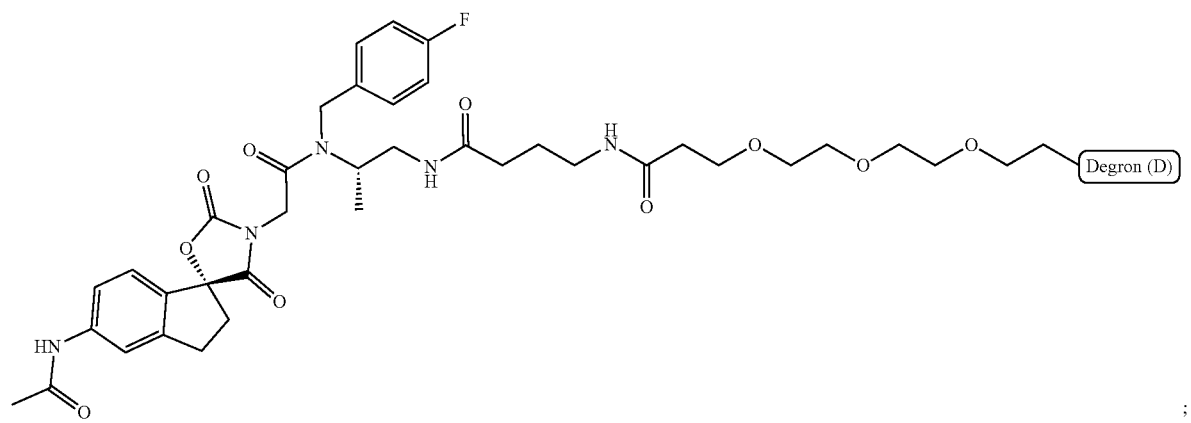
;
(TL1-L20)
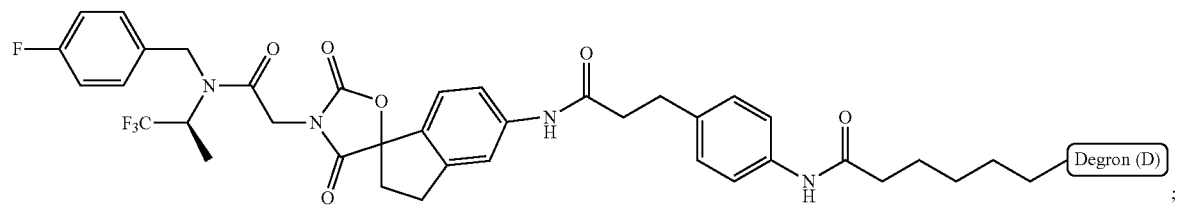
;

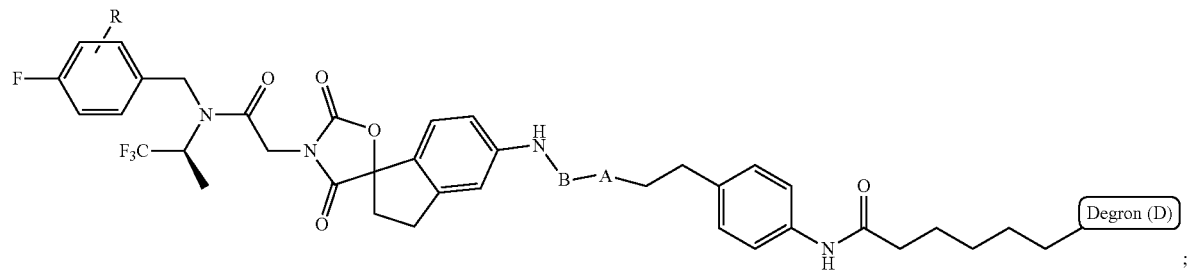
(TL1a-L20)
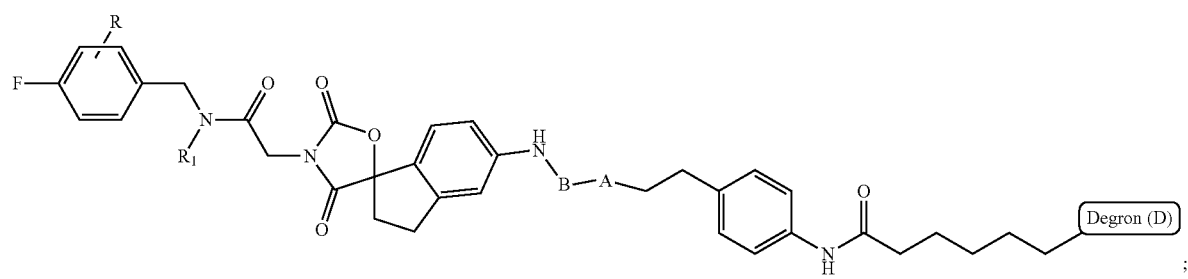
(TL1b-L20)
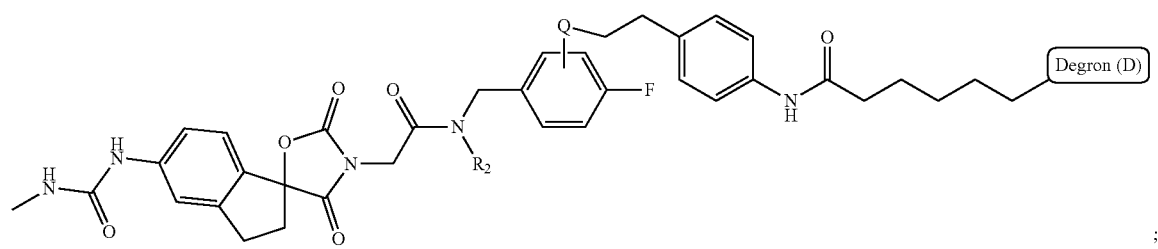
(TL1c-L20)
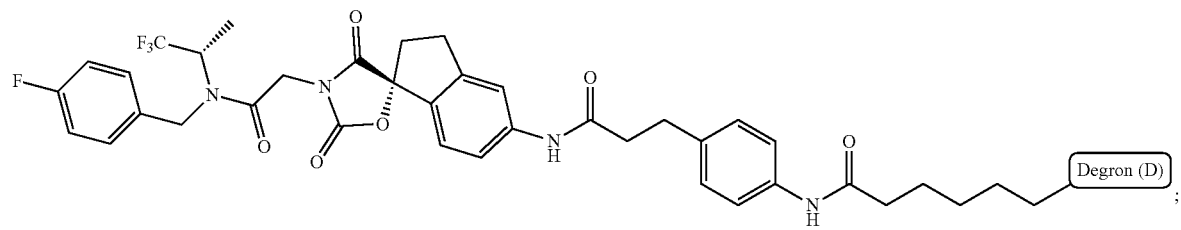
(TL1d-L20)
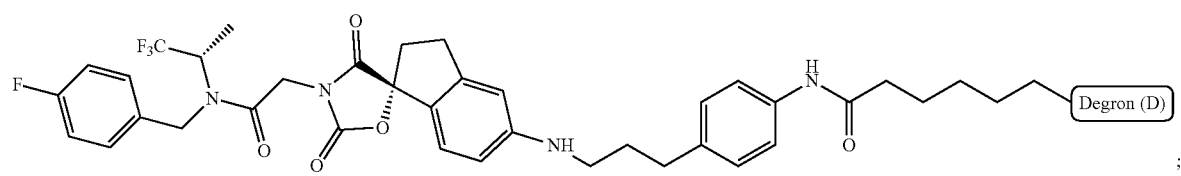
(TL1e-L20)

-continued
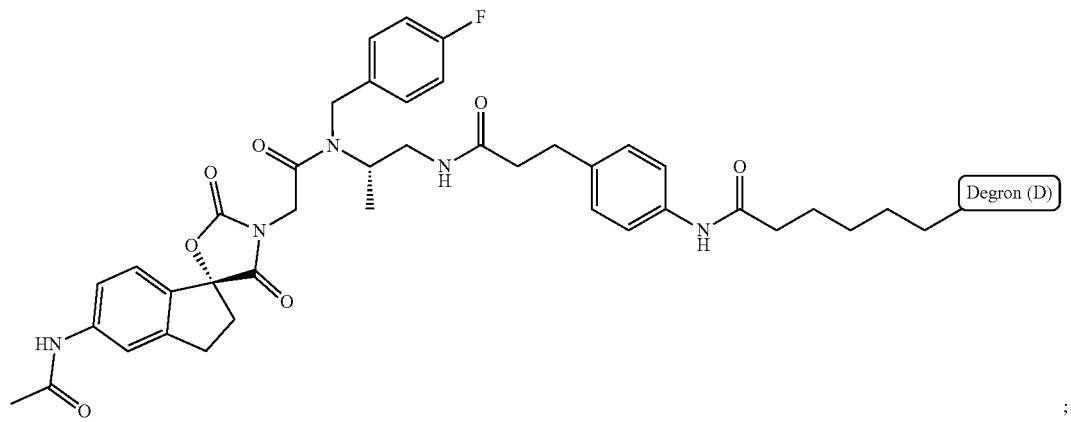
(TL1f-L20)
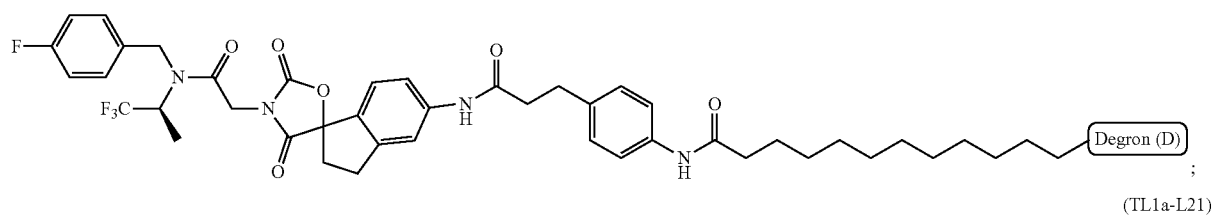
(TL1-L21)
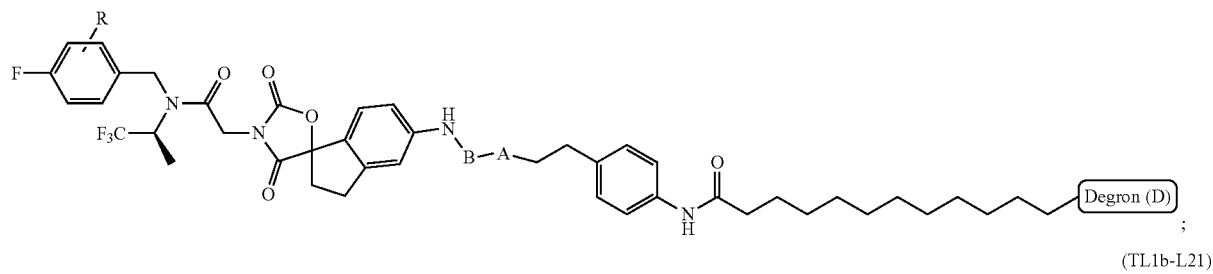
(TL1a-L21)
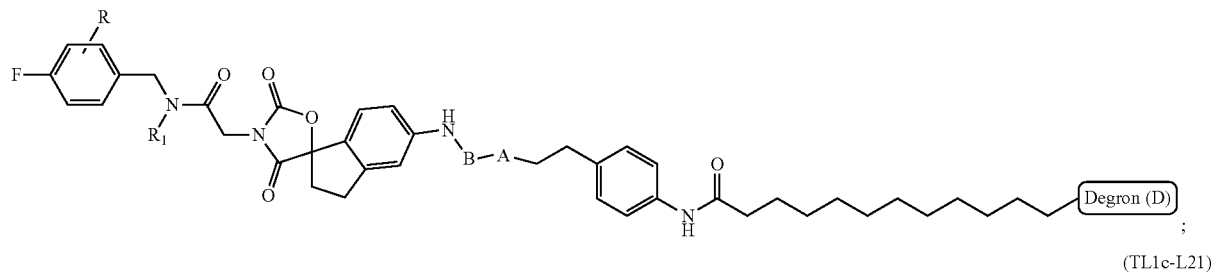
(TL1b-L21)
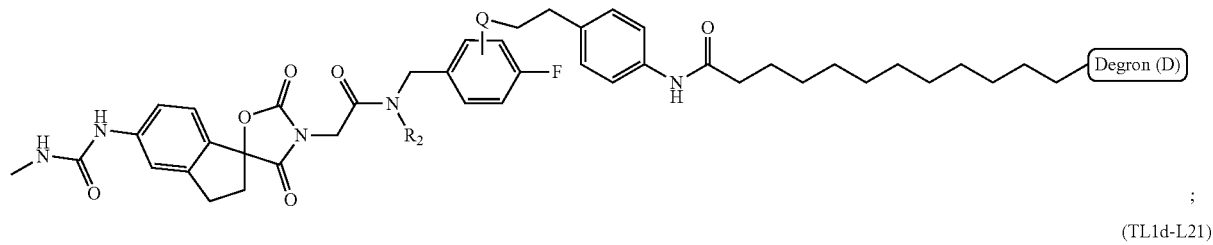
(TL1c-L21)
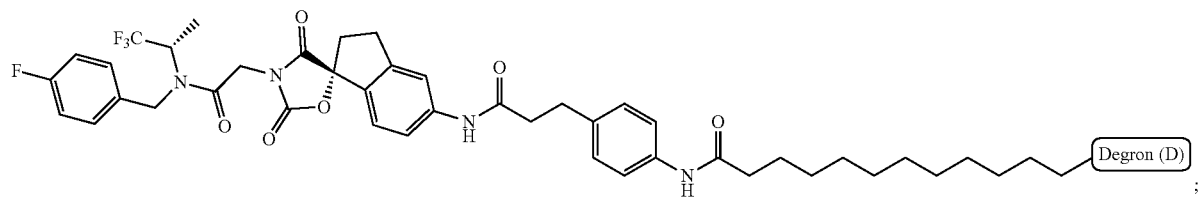
(TL1d-L21)

-continued
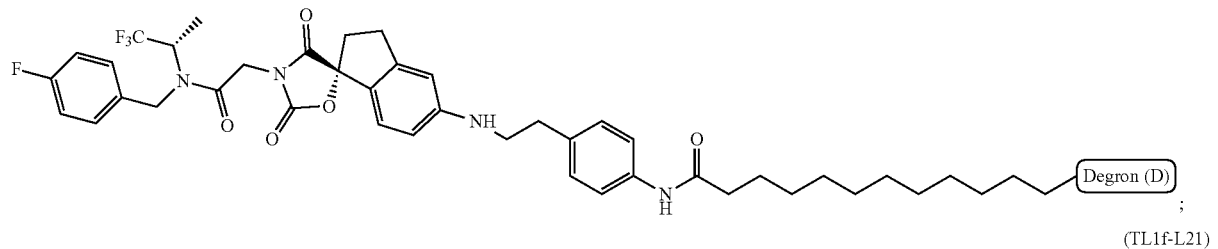
(TL1e-L21)
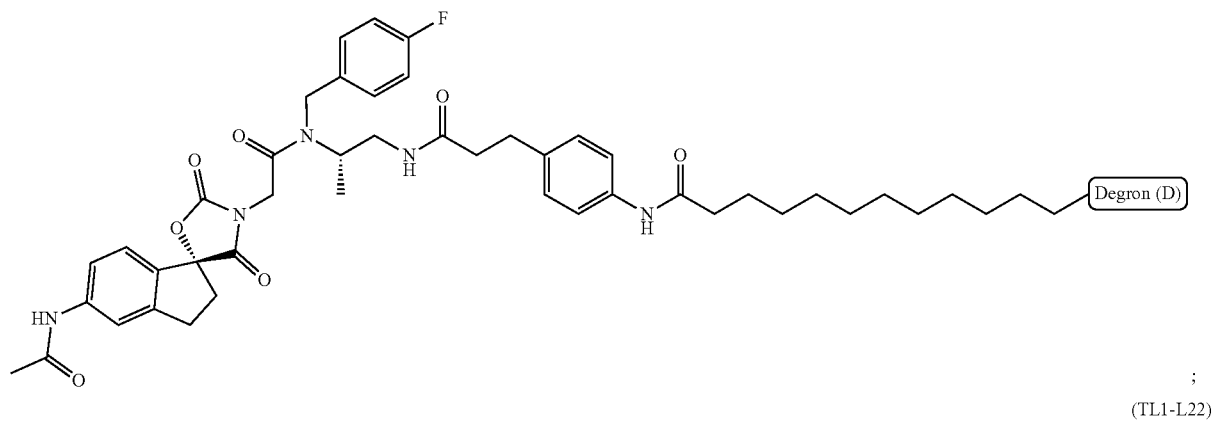
(TL1f-L21)
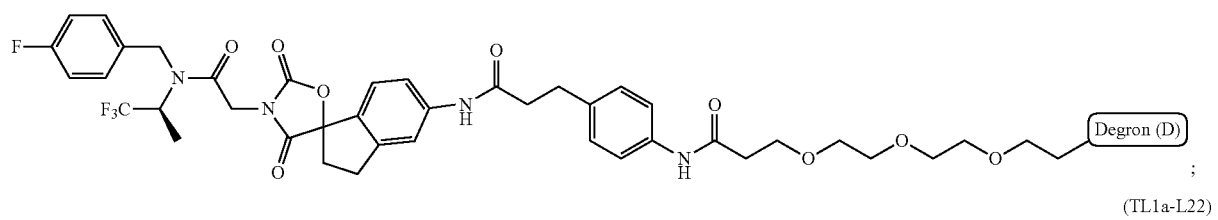
(TL1-L22)
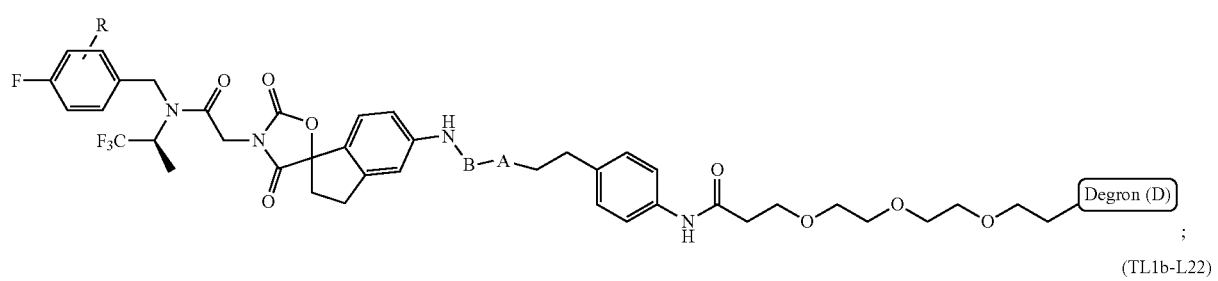
(TL1a-L22)
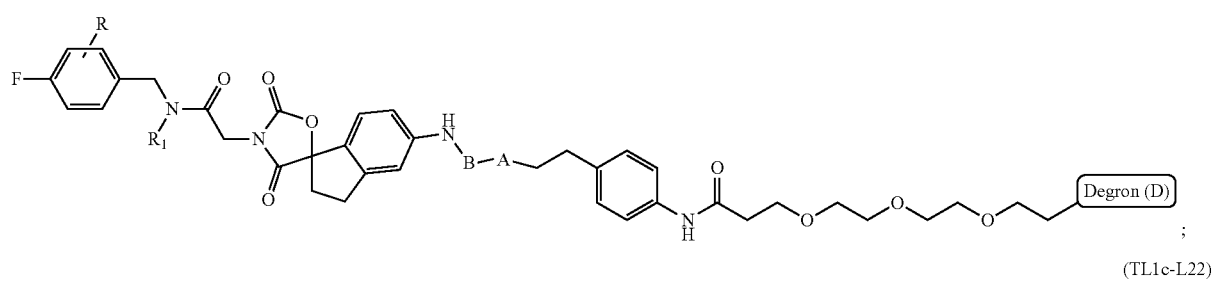
(TL1b-L22)
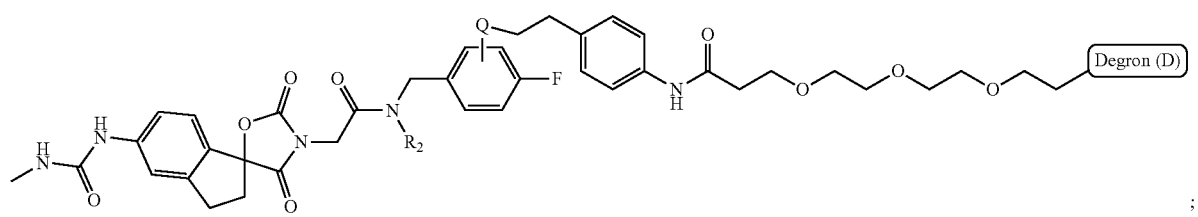
(TL1c-L22)

(TL1d-L22)
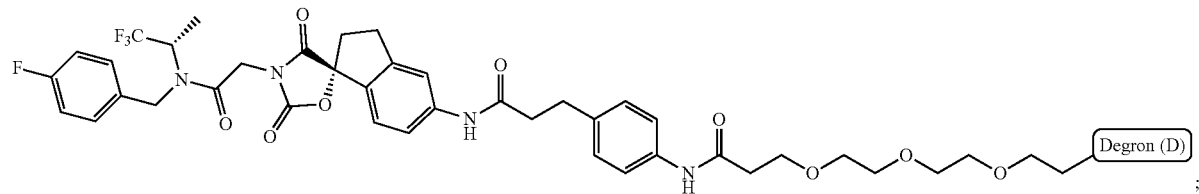
(TL1e-L22)
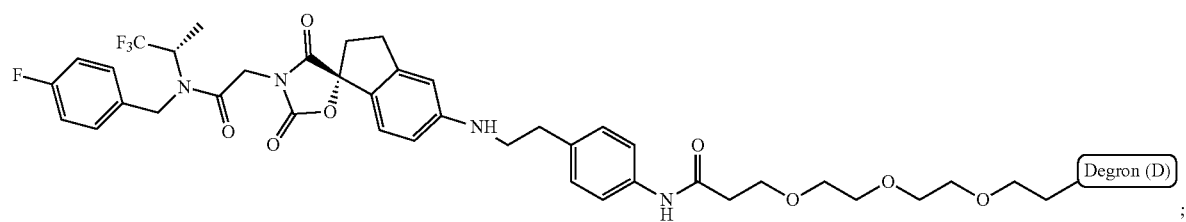
(TL1f-L22)
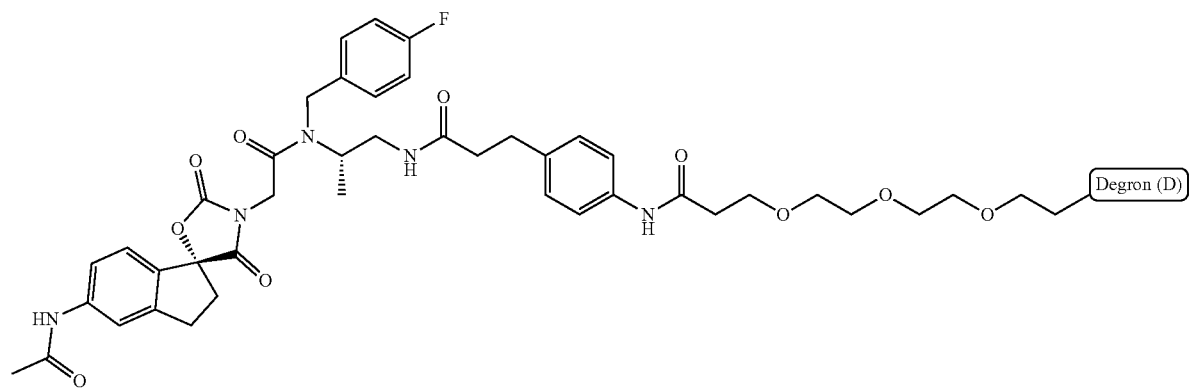
(TL1-L23)
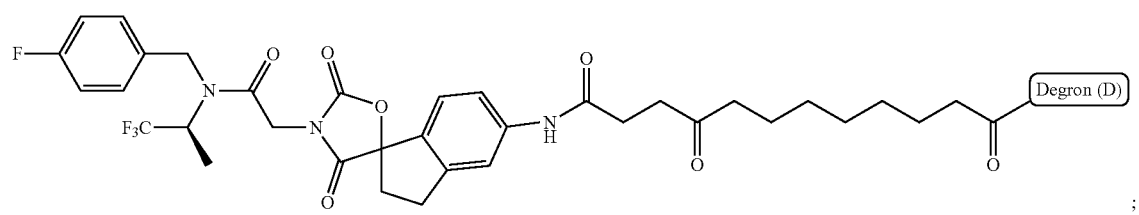
(TL1a-L23)
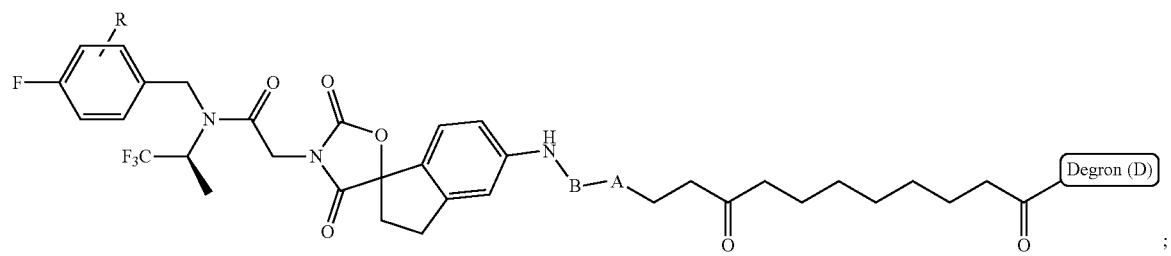

-continued
(TL1b-L23)
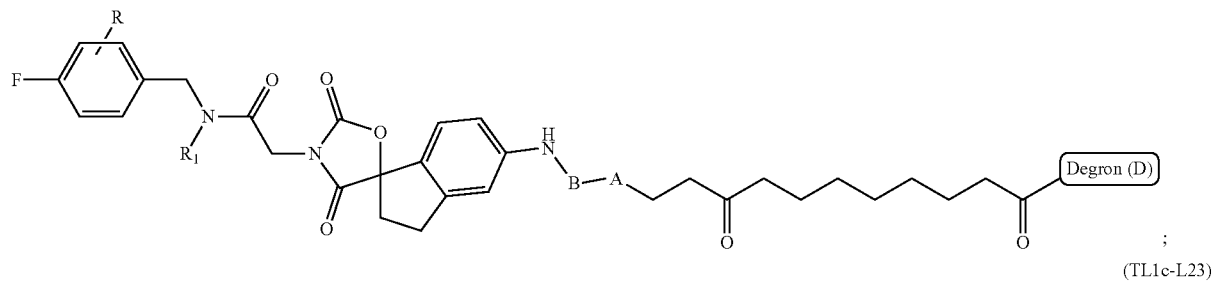
(TL1c-L23)
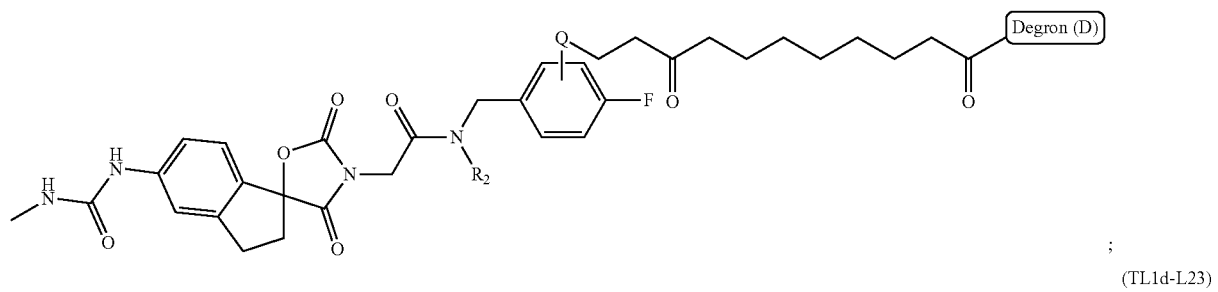
(TL1d-L23)
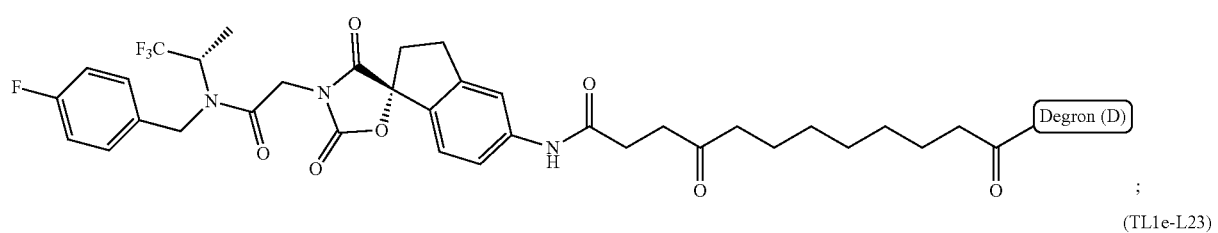
(TL1e-L23)
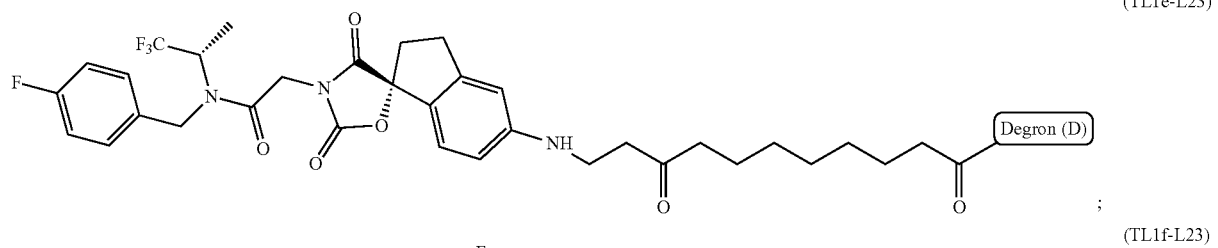
(TL1f-L23)
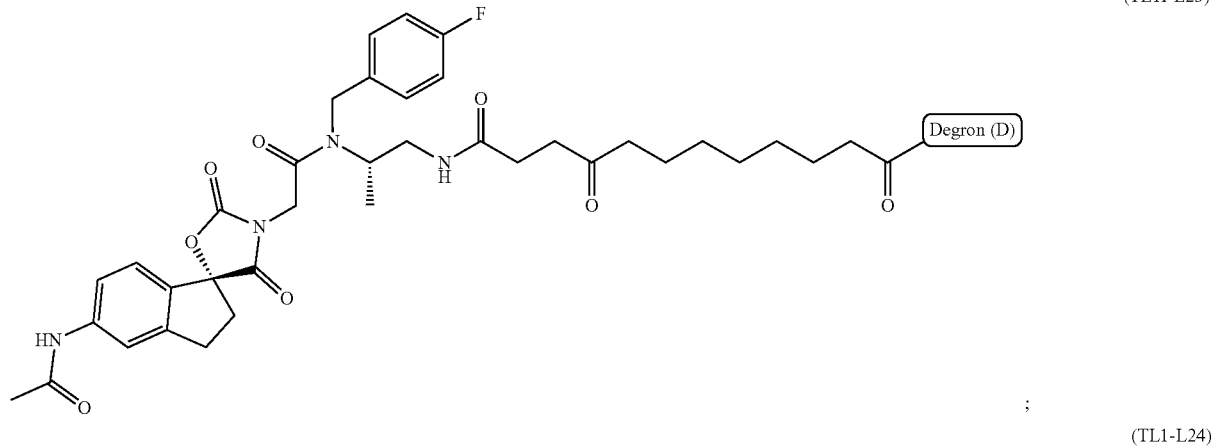
(TL1-L24)
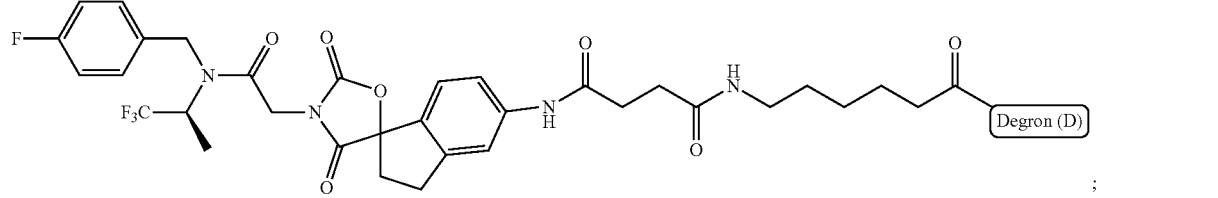

(TL1a-L24)
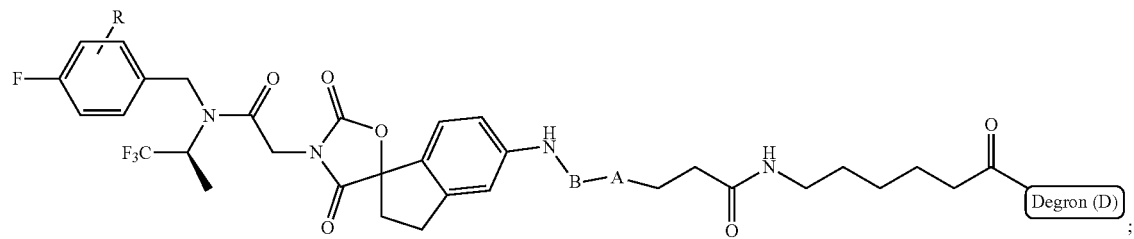
(TL1b-L24)
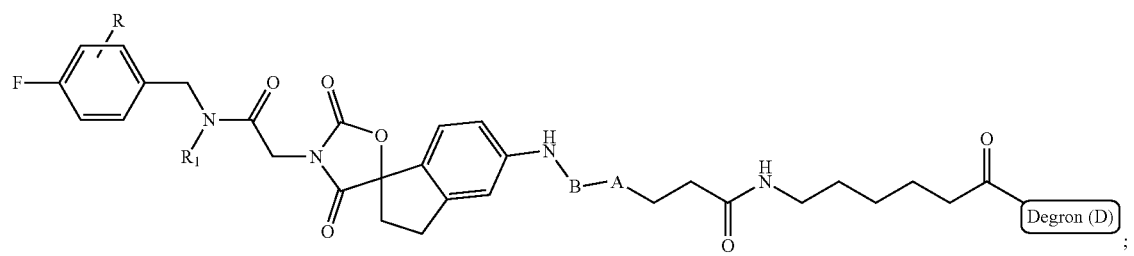
(TL1c-L24)
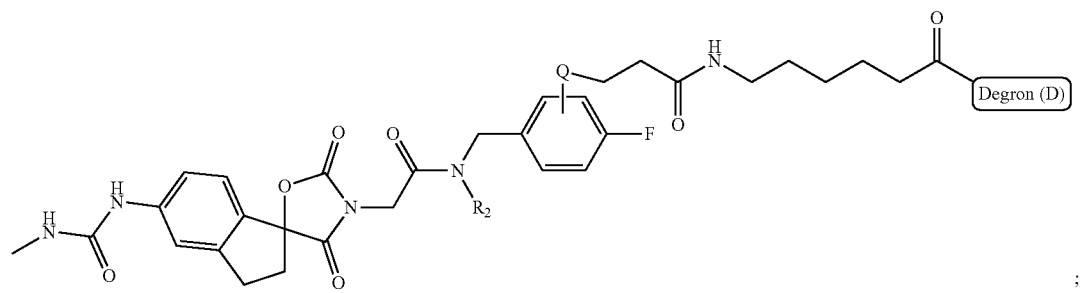
(TL1d-L24)
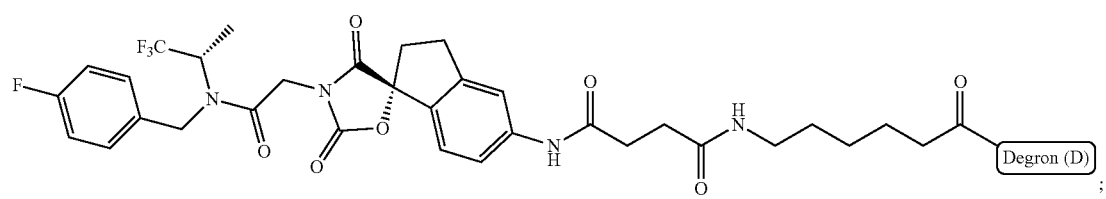
(TL1e-L24)
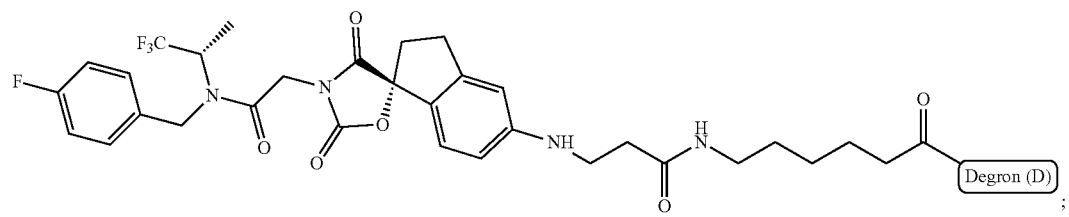

(TL1f-L24)
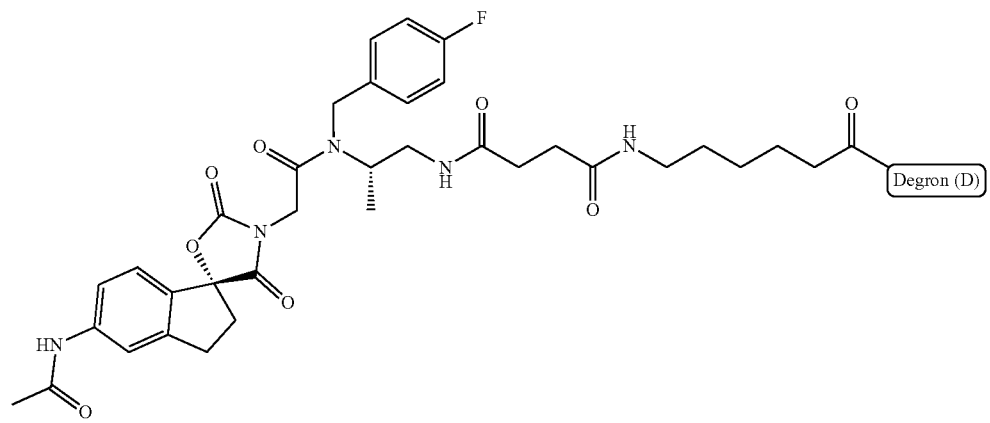
(TL1-L25)
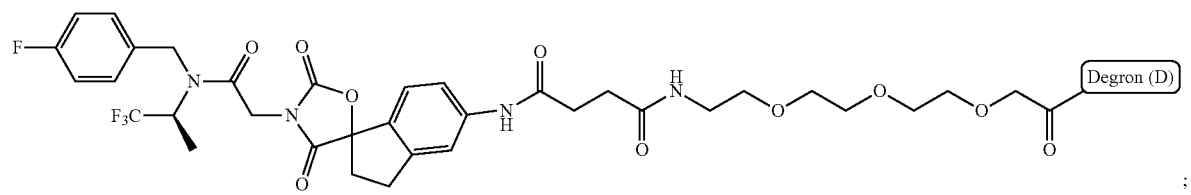
(TL1a-L25)
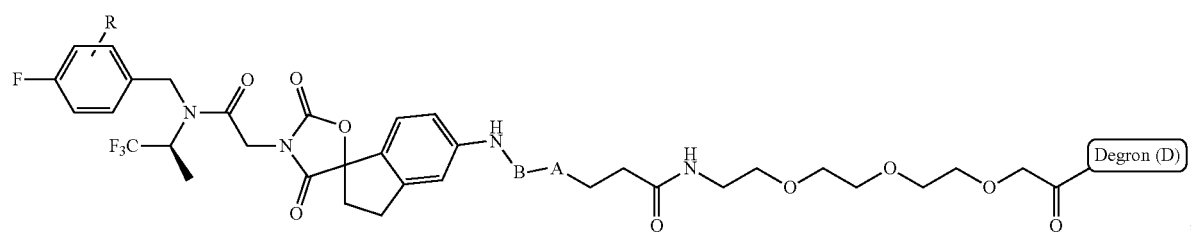
(TL1b-L25)
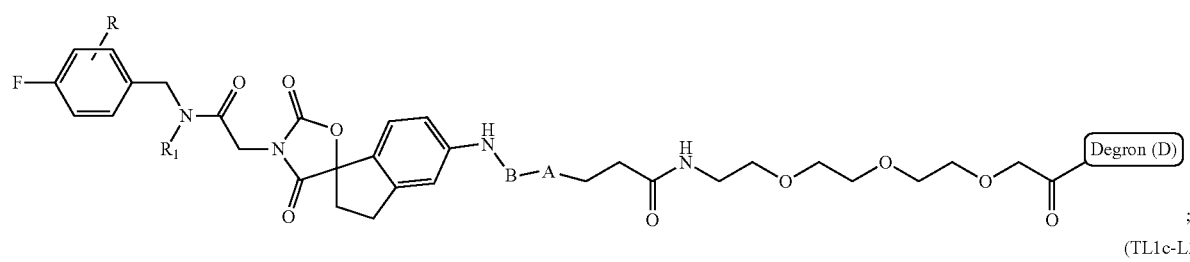
(TL1c-L25)
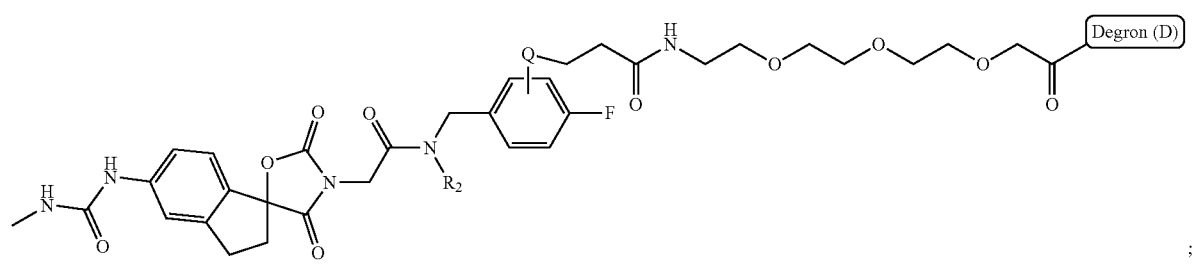
(TL1d-L25)
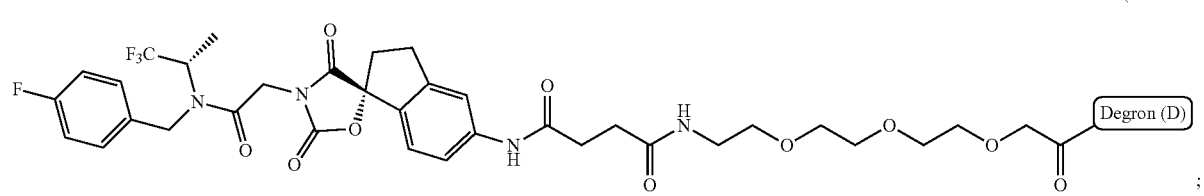

-continued
(TL1e-L25)
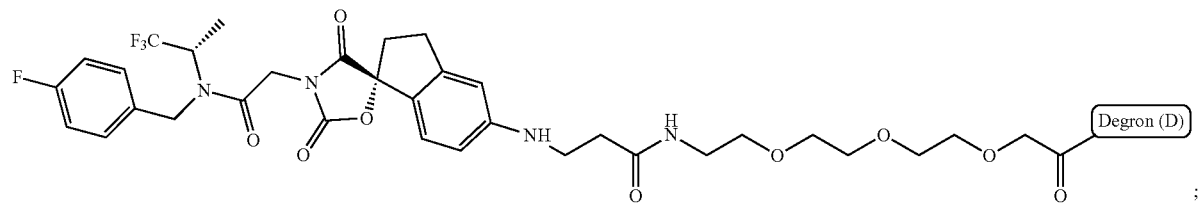
(TL1f-L25)
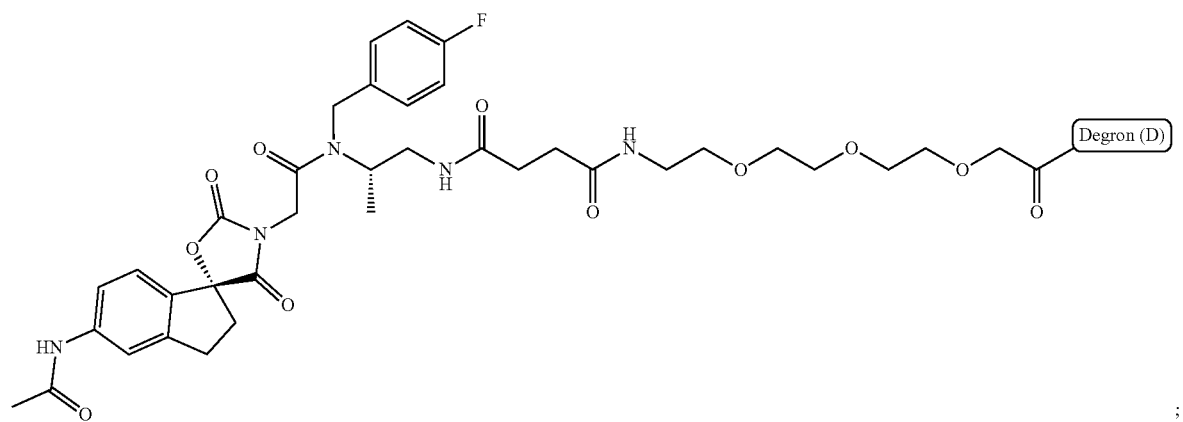
(TL1-L26)
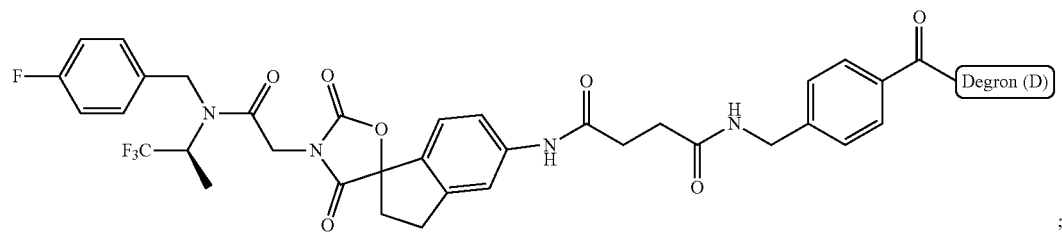
(TL1a-L26)
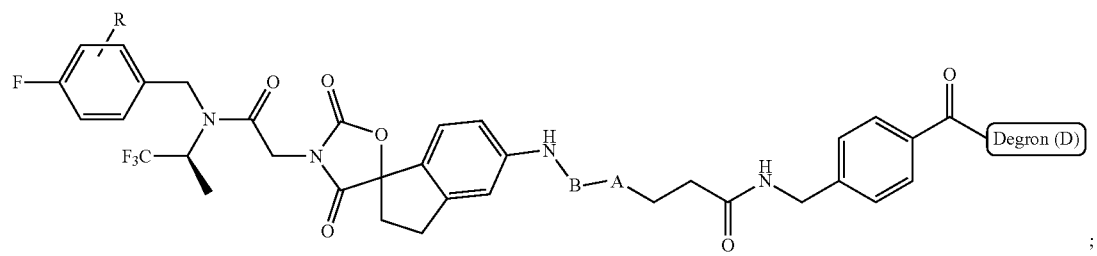
(TL1b-L26)
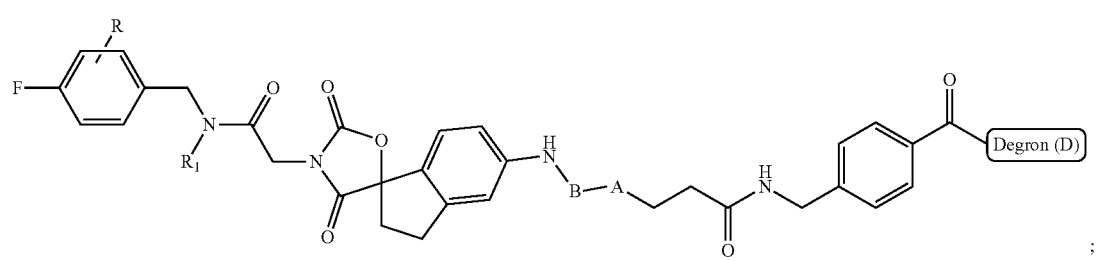

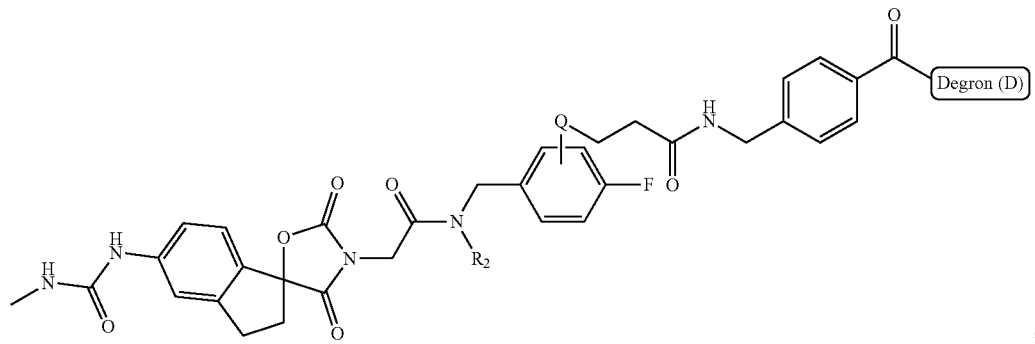

(TL1c-L26)

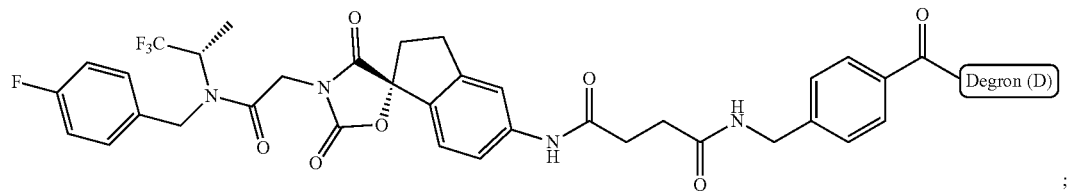

(TL1d-L26)

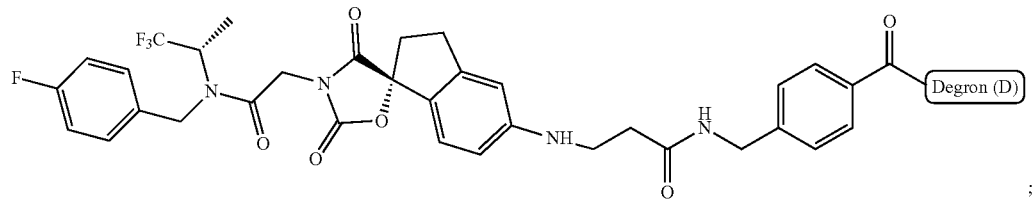

(TL1e-L26)

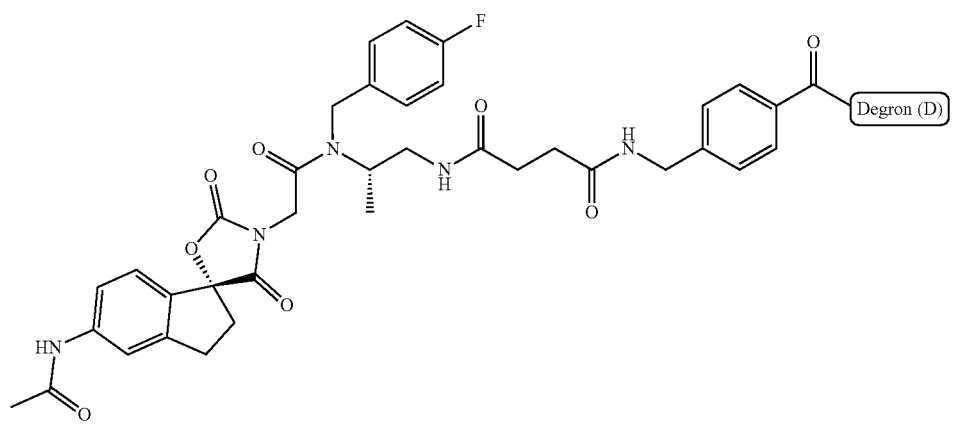

(TL1f-L26)

or a pharmaceutically acceptable salt or stereoisomer thereof, wherein X is CH$_2$, NH, NMe, or O; and n is an integer from 0 to 11;

wherein A is CH$_2$, NH or O;

B is CH$_2$ or CO; and R is H, halo, CN, CF$_3$, alkyl or alkoxy;

R is H, halo, CN, CF$_3$, alkyl or alkoxy;

R$_1$ is a C3-C5 carbocyclic or alkcarbocyclic group or a 3-5 membered N-heterocyclic or alkN-heterocyclic group, and wherein the alk group is a C1-C10 alkyl group;

Q is CH$_2$, O, N, CO, C(O)O, C(O)N, CH$_2$N, CH$_2$C(O), CH$_2$C(O)O, CH$_2$C(O)N, or CH$_2$CH$_2$N;

and R$_2$ is

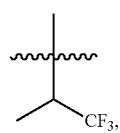 [SMILES: *C(C)C(F)(F)F]

a C3-C5 carbocyclic or alkcarbocyclic group or a 3-5 membered N-heterocyclic or alkN-heterocyclic group, and wherein the alk group is a C1-C10 alkyl group; and the degron binds cereblon (CRBRN) and is represented by structure D1:

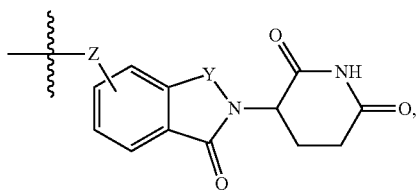

(D1)

wherein Y is CH$_2$ or CO; and

Z is NH, O, or OCH$_2$CO and the squiggle ($\sim$) represents the point of attachment for the linker, or the degron binds von Hippel Landau tumor suppressor (VHL) and is represented by a structure selected from the group consisting of:

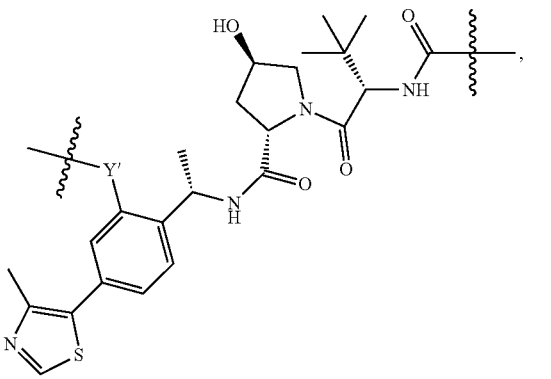

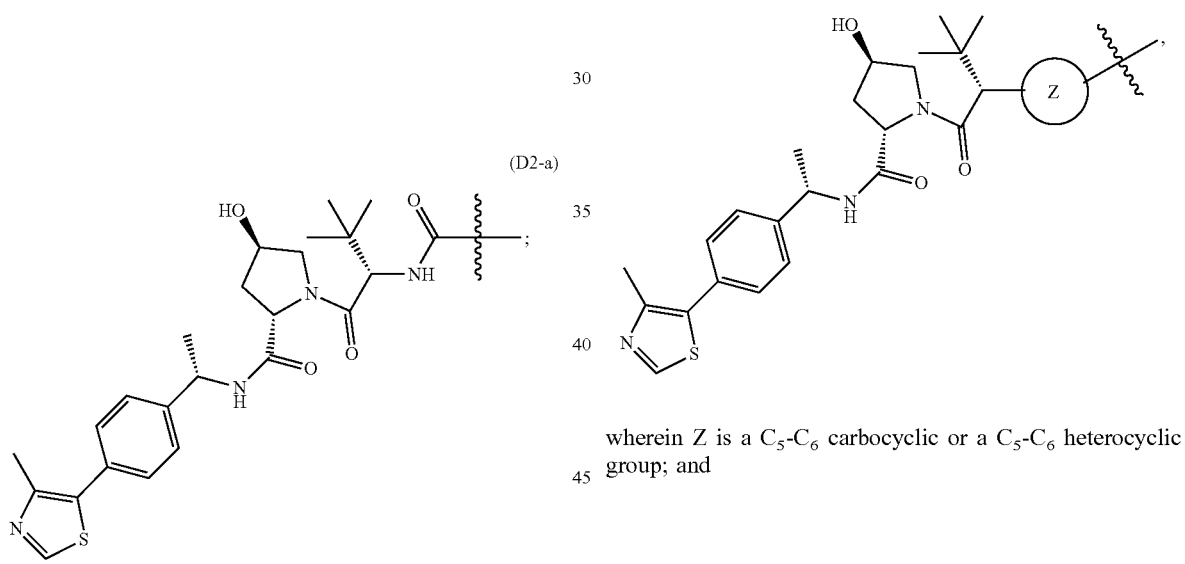

wherein Y' is a bond, N, O or C;

wherein Z is a C$_5$-C$_6$ carbocyclic or a C$_5$-C$_6$ heterocyclic group; and

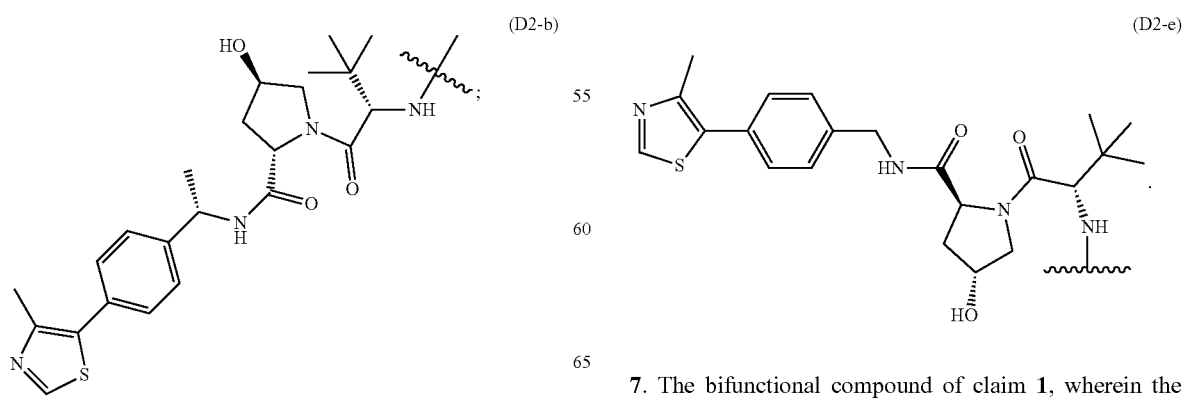

7. The bifunctional compound of claim 1, wherein the degron is represented by structure D1:

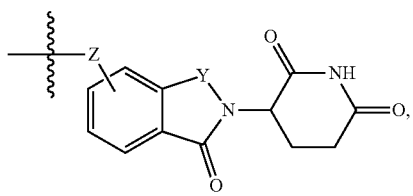
(D1)

wherein Y is CH₂ or CO;

and Z is NH, O, or OCH₂CO and the squiggle (⌇) represents the point of attachment for the linker and EP300 targeting moiety.

8. The bifunctional compound of claim 6, wherein the degron is represented by structure D1-a:

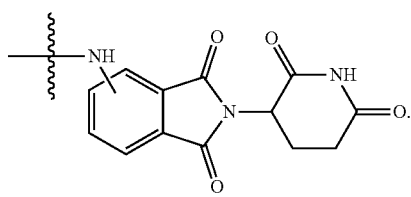
(D1-a)

9. The bifunctional compound of claim 1, wherein the degron is represented by a structure selected from the group consisting of:

(D2-a)

(D2-b)

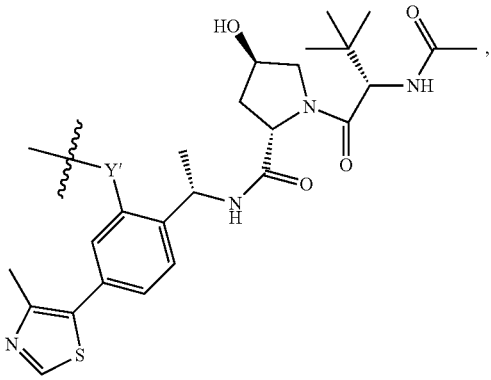
(D2-c)

wherein Y' is a bond, N, O or C;

(D2-d)

wherein Z is a C₅-C₆ carbocyclic or a C₅-C₆ heterocyclic group; and (D2-e)

10. A pharmaceutical composition comprising a therapeutically effective amount of the bifunctional compound of formula (I) or pharmaceutically acceptable salt or stereoisomer of claim 1, and a pharmaceutically acceptable carrier.

11. The pharmaceutical composition of claim 10, which is in the form of a tablet or capsule.

12. The bifunctional compound of claim 1, which is represented by any one of structures 1, 3, 5-9, 15-18 and 23:

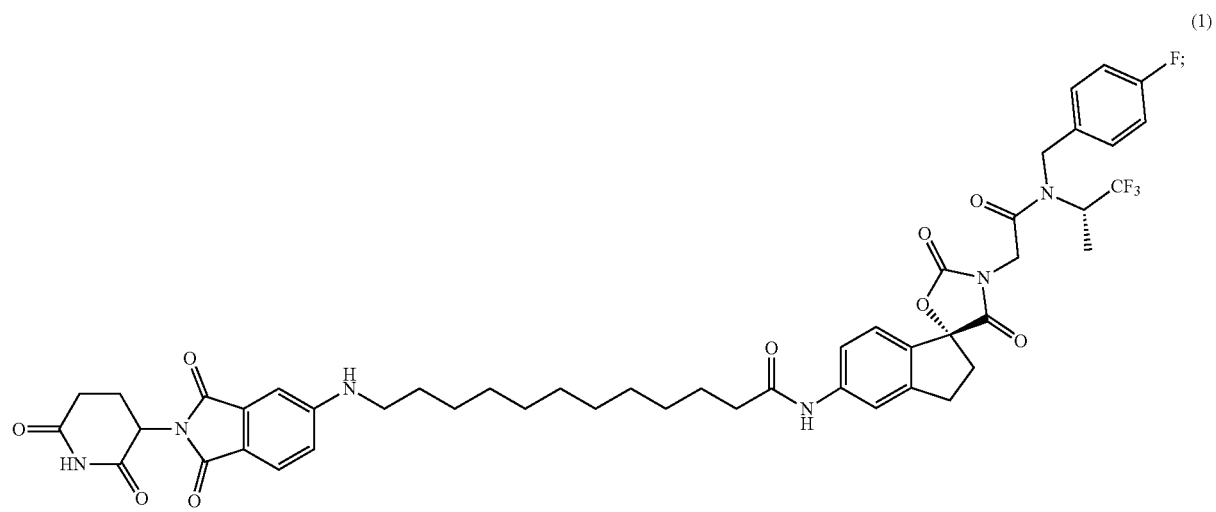
(1)
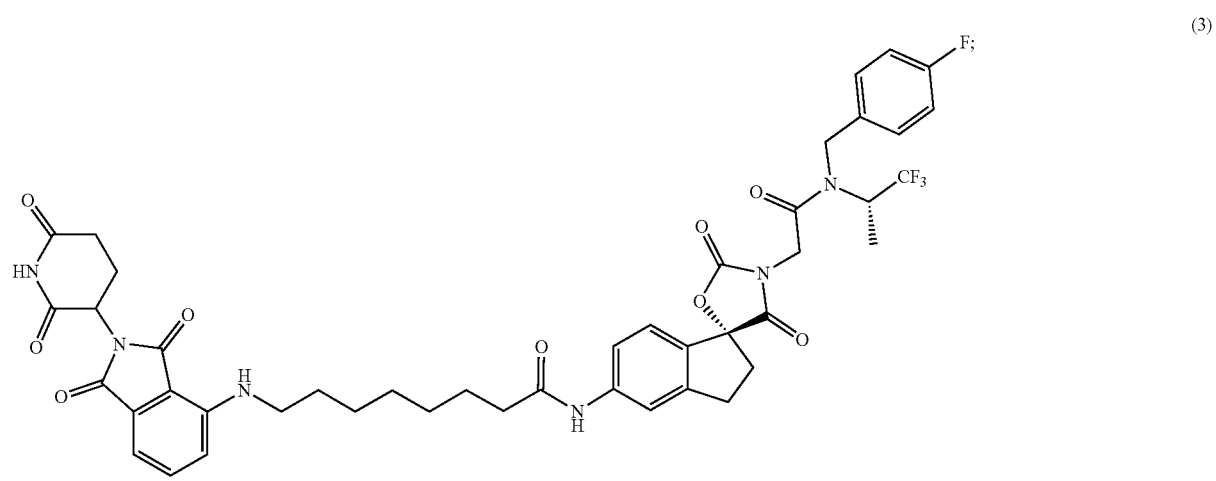
(3)
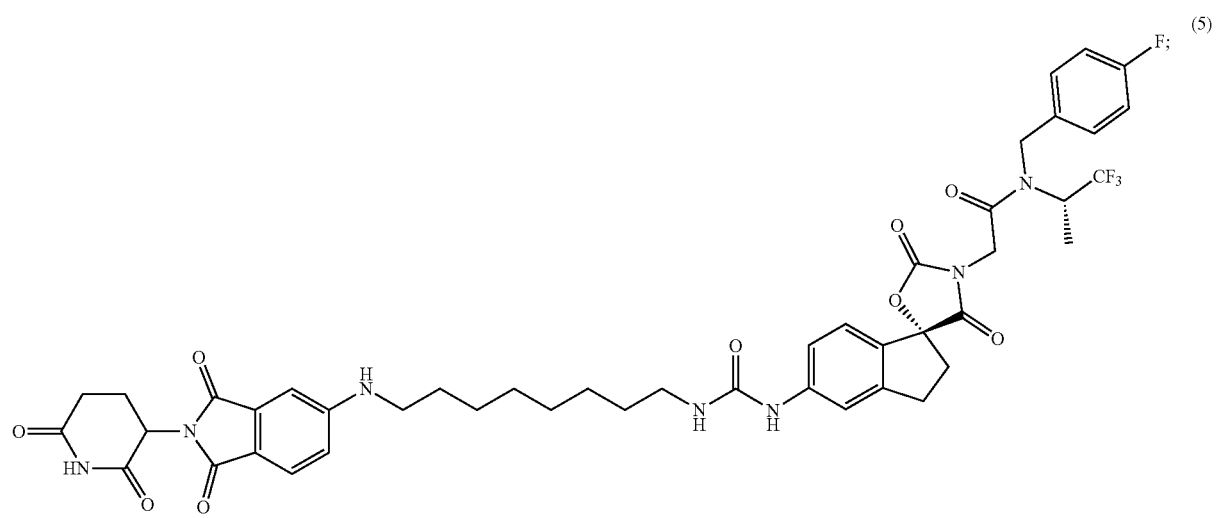
(5)

-continued
(6)
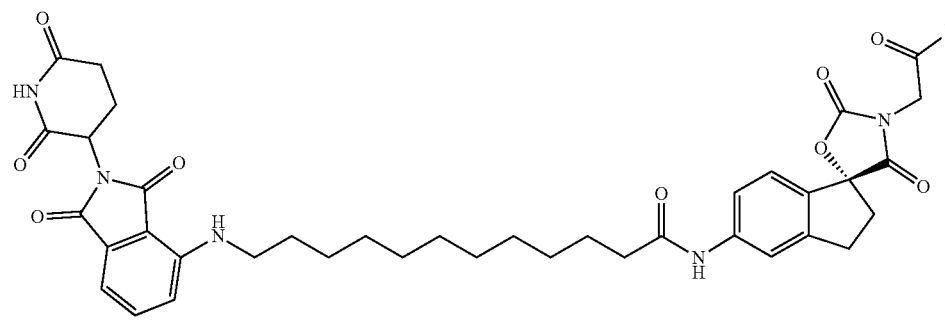
(7)
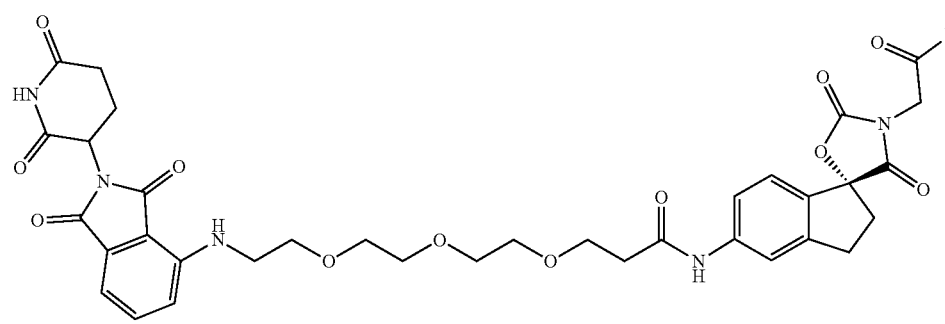
(8)
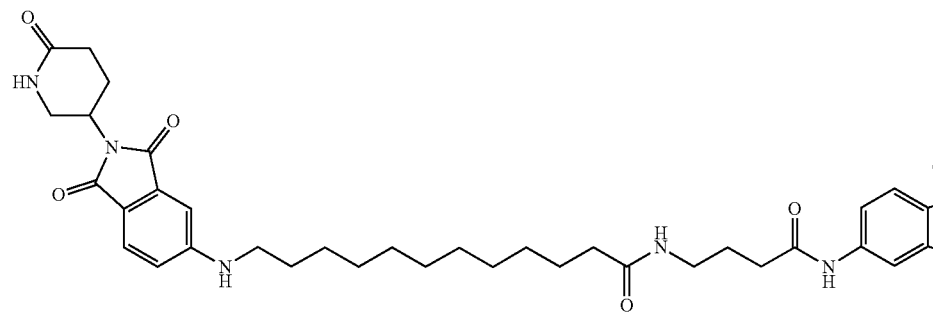

-continued
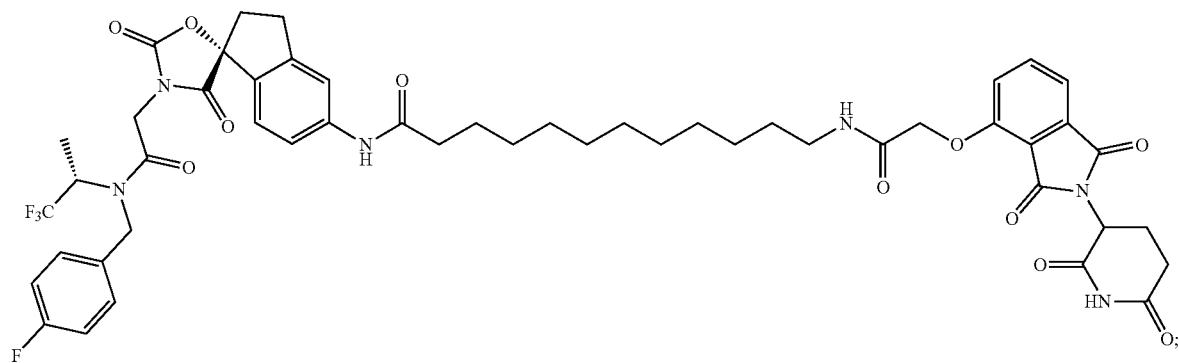
(9)
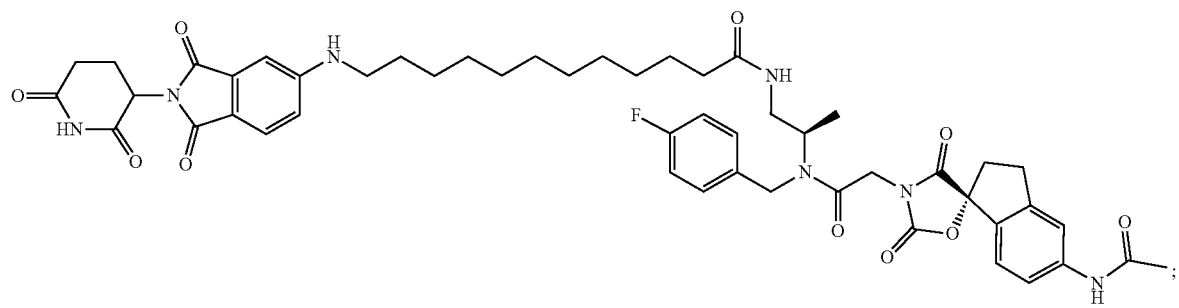
(15)
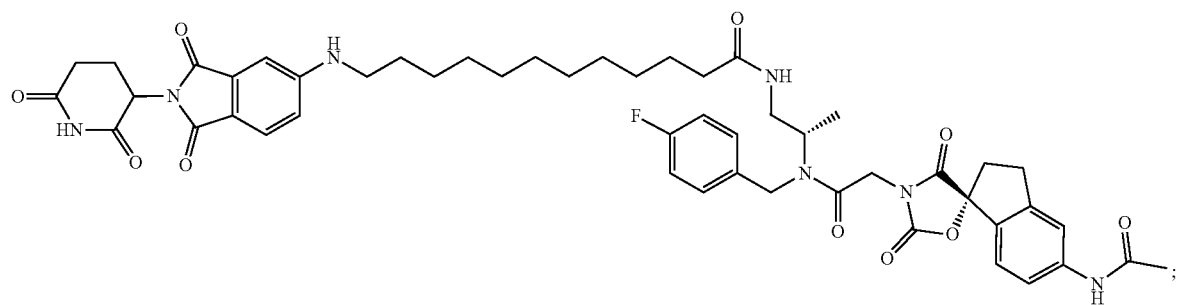
(16)
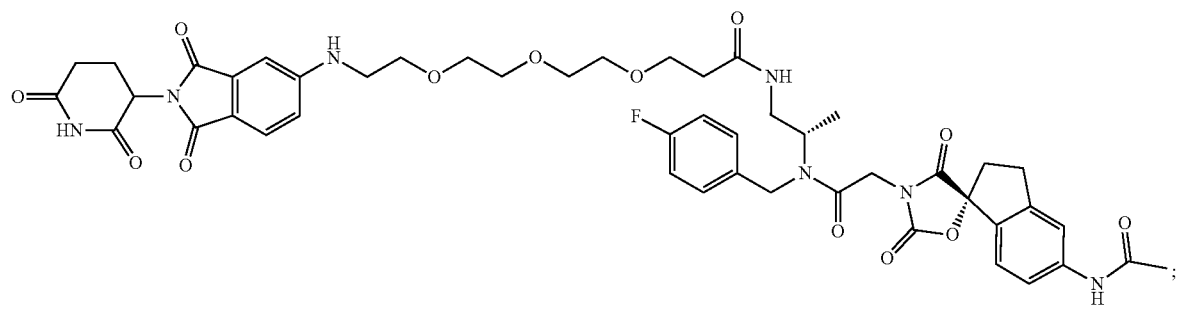
(17)

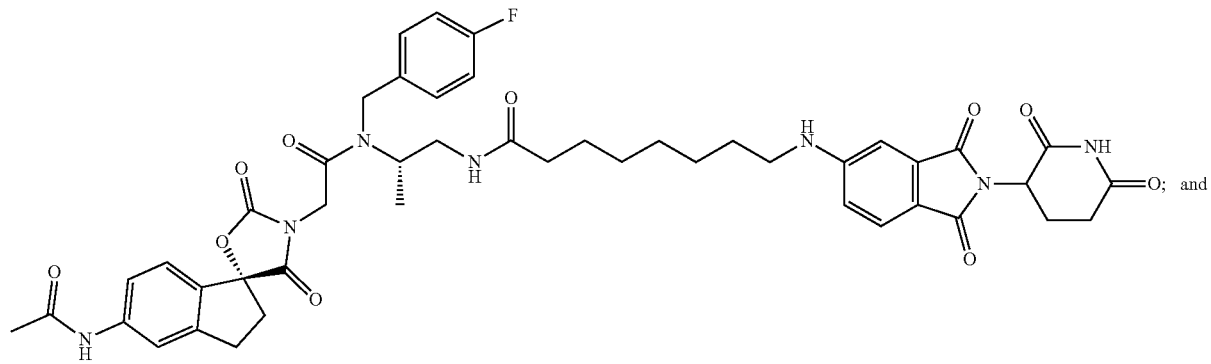
(18)
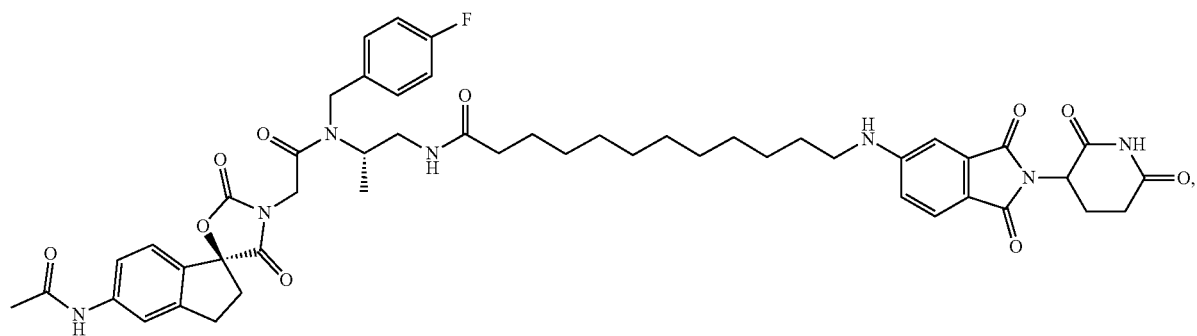
(23)
and pharmaceutically acceptable salts and stereoisomers thereof.
13. The bifunctional compound of claim 3, which is represented by structure 4:
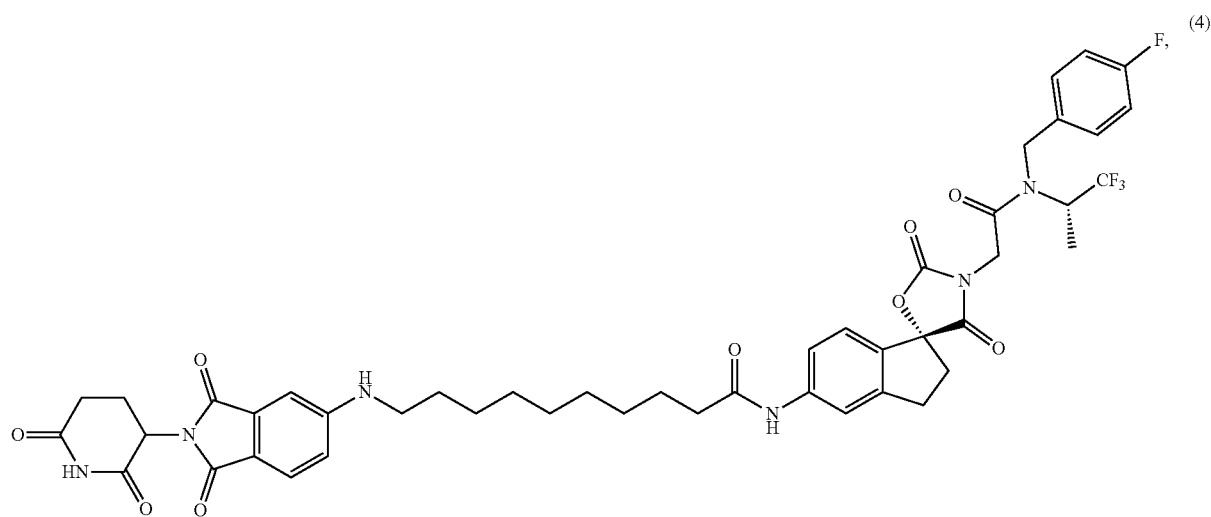 [SMILES: C[C@H](N(Cc1ccc(F)cc1)C(=O)CN1C(=O)O[C@@]2(CCc3cc(NC(=O)CCCCCCCCCNc4ccc5c(c4)C(=O)N(C4CCC(=O)NC4=O)C5=O)ccc32)C1=O)C(F)(F)F]
(4)
and pharmaceutically acceptable salts and stereoisomers thereof.

14. The bifunctional compound of claim 5, which is represented by any one of structures 10, 12, 14 and 19-22:
(12)
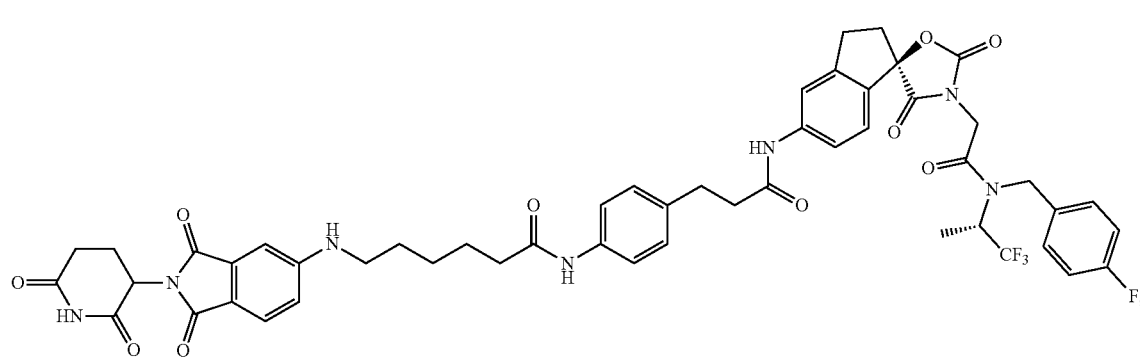
(14)
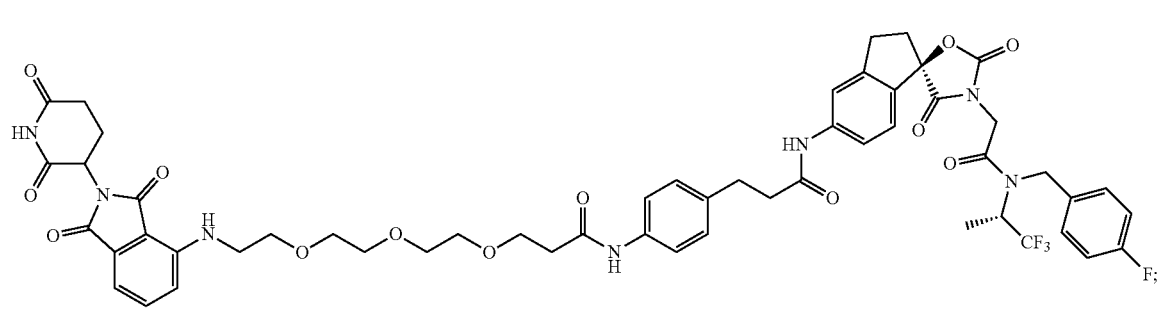
(19)
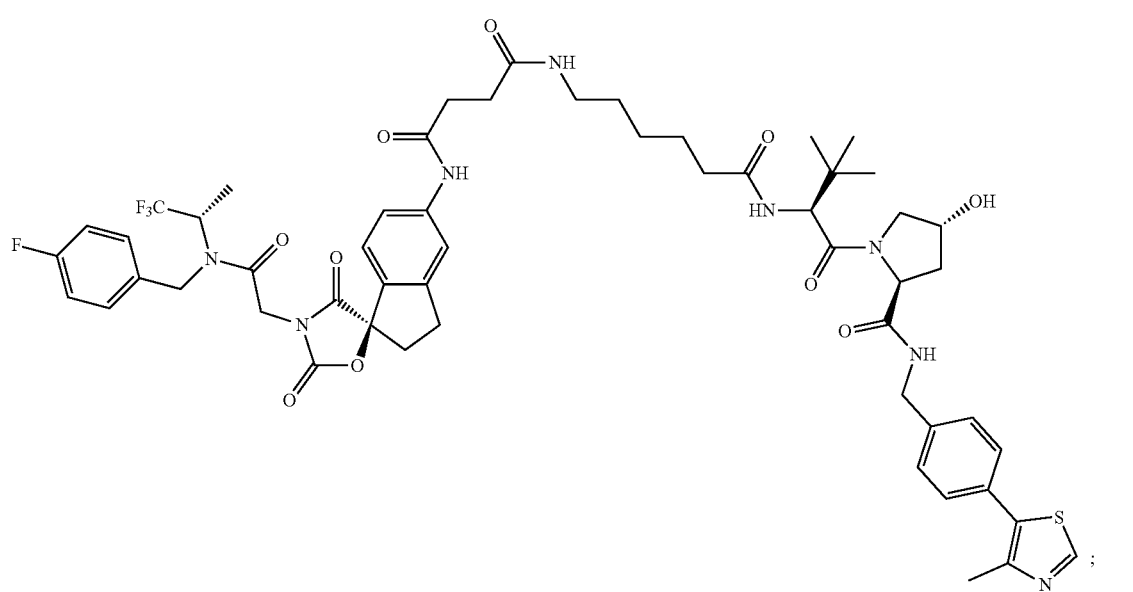
(20)
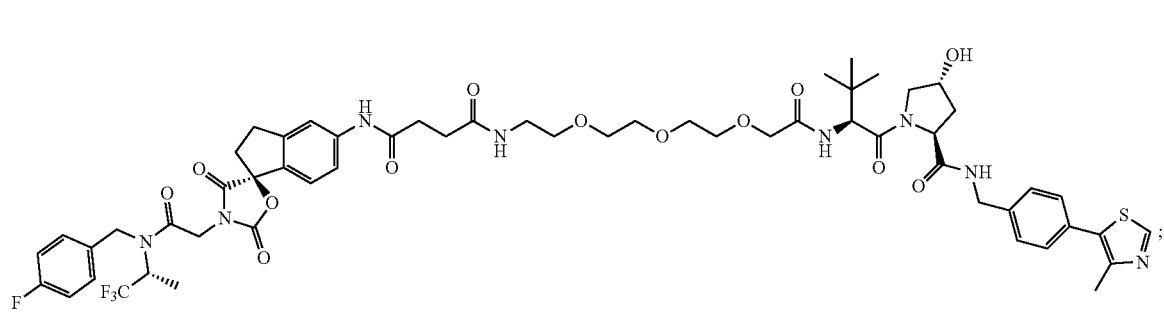

-continued
(21)
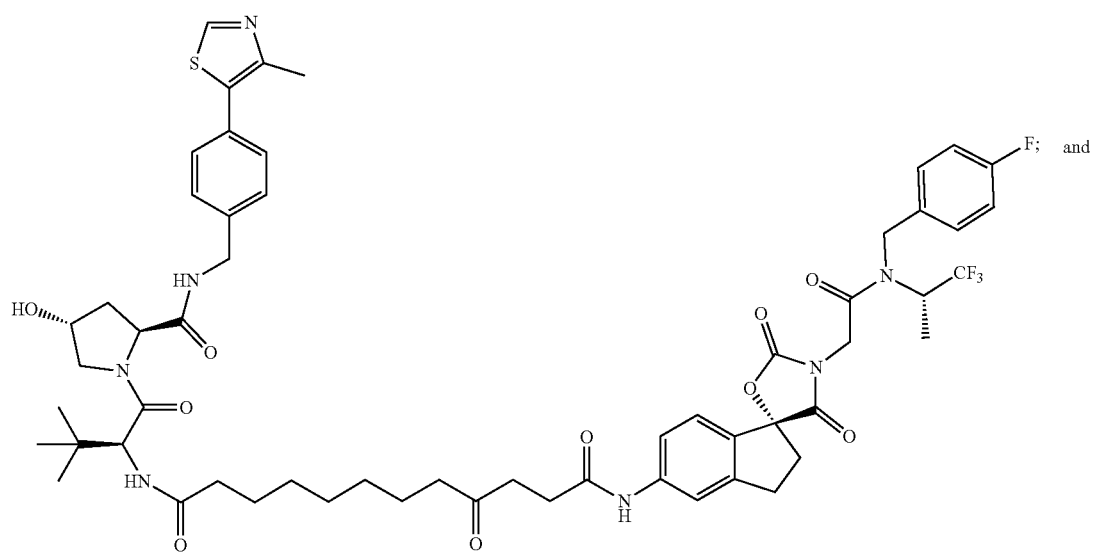
(22)
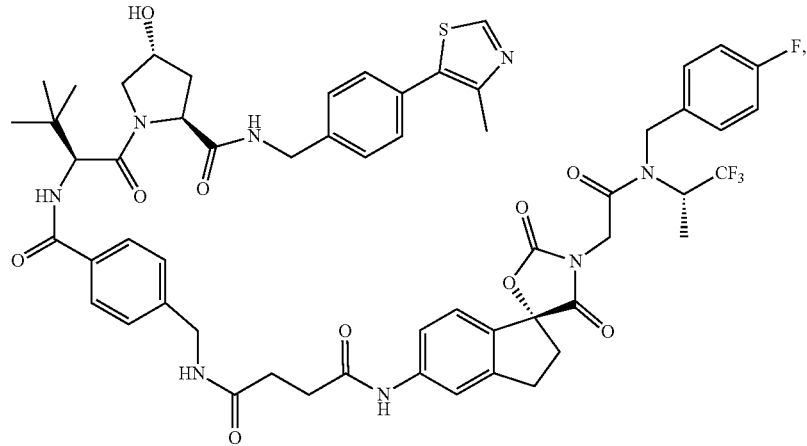
and pharmaceutically acceptable salts and stereoisomers thereof.
15. The bifunctional compound of claim 6, which is represented by structure 11 or 13:
(11)
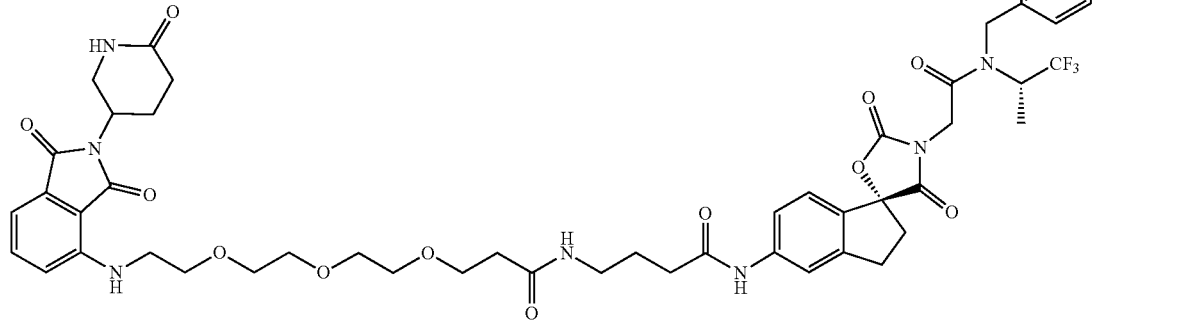

(13)

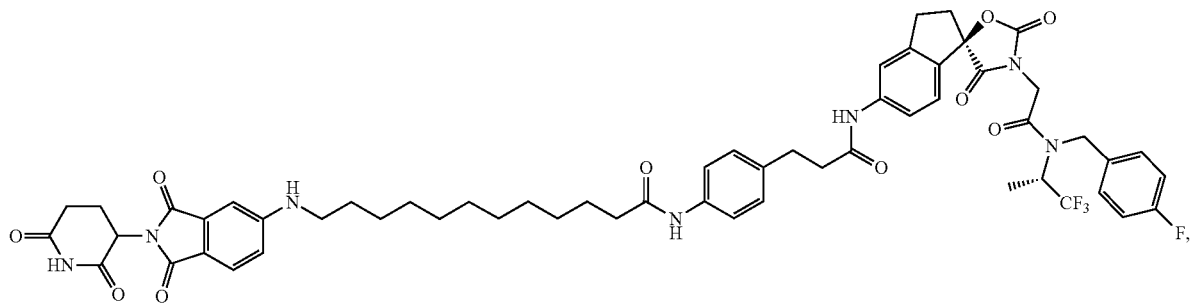

and pharmaceutically acceptable salts and stereoisomers thereof.

16. A pharmaceutical composition comprising a therapeutically effective amount of the bifunctional compound of formula (I) or pharmaceutically acceptable salt or stereoisomer of claim 3, and a pharmaceutically acceptable carrier.

17. The pharmaceutical composition of claim 16, which is in the form of a tablet or capsule.

18. A pharmaceutical composition comprising a therapeutically effective amount of the bifunctional compound or pharmaceutically acceptable salt or stereoisomer of claim 5, and a pharmaceutically acceptable carrier.

19. The pharmaceutical composition of claim 18, which is in the form of a tablet or capsule.

20. A pharmaceutical composition comprising a therapeutically effective amount of the bifunctional compound or pharmaceutically acceptable salt or stereoisomer of claim 6, and a pharmaceutically acceptable carrier.

21. The pharmaceutical composition of claim 20, which is in the form of a tablet or capsule.

22. A method of treating a disease or disorder involving dysregulated EP300 activity, comprising administering a therapeutically effective amount of the bifunctional compound of formula (I) or a pharmaceutically acceptable salt or stereoisomer thereof of claim 1, to a subject in need thereof.

23. The method of claim 22, wherein the disease or disorder is an EP300-dependent and a MYC-family dependent cancer.

24. The method of claim 22, wherein the disease or disorder is high-risk neuroblastoma (NB).

25. The method of claim 22, wherein the disease or disorder is acute myeloid leukemia (AML), multiple myeloma (MM), or diffuse large B cell lymphoma.

26. The method of claim 22, the disease or disorder is a solid tumor selected from melanoma, rhabdomyosarcoma, colon cancer, rectum cancer, stomach cancer, breast cancer, and pancreatic cancer.

27. The method of claim 24, wherein the method further comprises administering the therapeutically effective amount of the bifunctional compound of formula I, or a pharmaceutically acceptable salt or stereoisomer thereof, to the subject, in combination with a therapeutically effective amount of an additional anti-NB agent.

28. The method of claim 22, wherein the therapeutically effective amount of the bifunctional compound of formula I or a pharmaceutically acceptable salt or stereoisomer thereof, is administered orally to a subject in the form of a tablet or capsule.

29. The method of claim 22, wherein the therapeutically effective amount of the bifunctional compound of formula I or a pharmaceutically acceptable salt, or stereoisomer thereof, is administered parenterally to the subject in the form of a liquid.

30. The method of claim 22, wherein the bifunctional compound of formula (I) is administered to the subject in the form of a salt.

\* \* \* \* \*